United States Patent
Foley et al.

(10) Patent No.: US 10,538,596 B2
(45) Date of Patent: Jan. 21, 2020

(54) CXCR4 BINDING MOLECULES AND METHODS OF USE THEREOF

(71) Applicant: AdAlta Limited, Bundoora, Victoria (AU)

(72) Inventors: Michael Foley, Coburg (AU); Andrew Pow, Burlingame, CA (US); Katherine Griffiths, Etham North (AU); Samantha Cobb, South Yarra (AU); Katerina Viduka, Greensborough (AU)

(73) Assignee: Adalta Limited, Bundoora (AU)

(*) Notice: Subject to any disclaimer, the term of this patent is extended or adjusted under 35 U.S.C. 154(b) by 0 days.

(21) Appl. No.: 15/542,060

(22) PCT Filed: Jan. 8, 2016

(86) PCT No.: PCT/AU2016/050005
§ 371 (c)(1),
(2) Date: Nov. 2, 2017

(87) PCT Pub. No.: WO2016/109872
PCT Pub. Date: Jul. 14, 2016

(65) Prior Publication Data
US 2018/0072816 A1 Mar. 15, 2018

(30) Foreign Application Priority Data
Jan. 9, 2015 (AU) .............................. 2015900054

(51) Int. Cl.
| *C07K 17/02* | (2006.01) |
|---|---|
| *G01N 33/574* | (2006.01) |
| *G01N 33/569* | (2006.01) |
| *C07K 16/18* | (2006.01) |
| *C07K 16/28* | (2006.01) |
| *A61K 38/22* | (2006.01) |
| *A61K 39/00* | (2006.01) |

(52) U.S. Cl.
CPC .......... *C07K 17/02* (2013.01); *A61K 38/2228* (2013.01); *C07K 16/18* (2013.01); *C07K 16/2866* (2013.01); *G01N 33/56988* (2013.01); *G01N 33/574* (2013.01); *A61K 2039/505* (2013.01); *C07K 2317/31* (2013.01); *C07K 2317/34* (2013.01); *C07K 2317/56* (2013.01); *C07K 2317/569* (2013.01); *C07K 2317/76* (2013.01); *C07K 2317/92* (2013.01); *G01N 2333/521* (2013.01); *G01N 2800/285* (2013.01); *G01N 2800/323* (2013.01)

(58) Field of Classification Search
CPC ..................................................... C07K 17/02; C07K 16/2866; C07K 2317/31; C07K 2317/34; C07K 2317/56; C07K 2317/76; C07K 2317/92; A61K 38/2228; A61K 2039/505; G01N 33/574; G01N 2333/521
See application file for complete search history.

(56) References Cited

U.S. PATENT DOCUMENTS

| 2010/0136584 A1 | 6/2010 | Bhatt |
| 2011/0044988 A1 | 2/2011 | Bernhagen et al. |

FOREIGN PATENT DOCUMENTS

WO WO 2005/118629 A1 12/2005

OTHER PUBLICATIONS

Paul, WE. Fundamental Immunology, 3rd ed. Raven Press, NY, Chap. 9, pp. 292-295, 1993.*
Rudikoff S. et al. Proc. Natl. Acad. Sci. USA, 79:1979-1983, 1982.*
Colman, PM. Research in Immunology, Elsevier, NY, 145(1):33-36, 1994.*
Jaehnichen et al., "CXCR4 Nanobodies (VHH-Based Single Variable Domains) Potently Inhibit Chemotaxis and HIV-1 Replication and Mobilize Stem Cells," (2010), PNAS 107(47):20565-20570.
Ramsey and McAlpine, "Halting Metastasis through CXCR4 Inhibition," (2013), Bioorg. Med. Chem. Lett. 23:20-25, Elsevier Ltd.
Griffiths, Katherine et al.: *"i-bodies, Human Single Domain Antibodies That Antagonize Chemokine Receptor CXCR4"*, Journal of Biological Chemistry, vol. 291, No. 24, Apr. 1, 2016, pp. 12641-12657, XP055478828.
Supplementary European Search Report dated Jun. 8, 2018, regarding EP 16 73 4863.

* cited by examiner

*Primary Examiner* — Robert S Landsman
(74) *Attorney, Agent, or Firm* — DLA Piper LLP (US)

(57) ABSTRACT

The present disclosure relates to polypeptides (also referred to herein as CXCR4 binding molecules or polypeptides) that are directed against the G-coupled protein receptor CXCR4, also known as Fusin or CD184. The invention also relates to nucleic acids encoding such polypeptides; to methods for preparing such polypeptide; to compositions, and in particular to pharmaceutical compositions that comprise such polypeptides and to uses of such polypeptides for therapeutic or diagnostic purposes.

10 Claims, 44 Drawing Sheets

Specification includes a Sequence Listing.

1 26 33 79 88 97

A LQVDIVPSQGEISVGESKFFLCQVAG DAKDKD ISWFSPNGEKLTPNQQRISVVWNDDSSSTLTIYNANIDDAGIYKCVV TGEDGSES EATVNVKIFQ (SEQ ID NO:1)

B LQVDIVPSQGEISVGESKFFLCA'B'AG XXXXXX ISWFSPNGEKLTPNQQRISVVWNDDSSSTLTIYNANIDDAGIYKCVV Y'n EATVNVKIFQ (SEQ ID NO:2)

C LQVDIVPSQGEISVGESKFFLCQVAG SGSDIR ISWFSPNGEKLTPNQQRISVVWNDDSSSTLTIYNANIDDAGIYKCVV YRTGGYRHRALVLG EATVNVKIFQ (SEQ ID NO:11)

D ZMLQVDIVPSQGEISVGESKFFLCA'B'AG S$X_1$S$X_2X_3$R ISWFSPNGEKLTPNQQRISVVWNDDSSSTLTIYNANIDDAGIYKCVV $Y'_1$R$Y'_2$G$Y'_3$YRHR$Y'_4$L$Y'_5$LG EATVNVKIFQ (SEQ ID NO:39)

A

B

C

ADCX99-FH

D

ADCX6

E

ADCX306

F

ADCX668

SEQUENCE LISTING

```
<160> NUMBER OF SEQ ID NOS: 105

<210> SEQ ID NO 1
<211> LENGTH: 97
<212> TYPE: PRT
<213> ORGANISM: Homo sapiens
```

<400> SEQUENCE: 1

Leu Gln Val Asp Ile Val Pro Ser Gln Gly Glu Ile Ser Val Gly Glu
1               5                   10                  15

Ser Lys Phe Phe Leu Cys Gln Val Ala Gly Asp Ala Lys Asp Lys Asp
                20                  25                  30

Ile Ser Trp Phe Ser Pro Asn Gly Glu Lys Leu Thr Pro Asn Gln Gln
                35                  40                  45

Arg Ile Ser Val Val Trp Asn Asp Asp Ser Ser Thr Leu Thr Ile
50                  55                  60

Tyr Asn Ala Asn Ile Asp Asp Ala Gly Ile Tyr Lys Cys Val Val Thr
65                  70                  75                  80

Gly Glu Asp Gly Ser Glu Ser Glu Ala Thr Val Asn Val Lys Ile Phe
                85                  90                  95

Gln

<210> SEQ ID NO 2
<211> LENGTH: 90
<212> TYPE: PRT
<213> ORGANISM: Artificial Sequence
<220> FEATURE:
<223> OTHER INFORMATION: Synthetic

<400> SEQUENCE: 2

Leu Gln Val Asp Ile Val Pro Ser Gln Gly Glu Ile Ser Val Gly Glu
1               5                   10                  15

Ser Lys Phe Phe Leu Cys Ala Ala Ala Asx Ala Ala Ala Gly Ile Ser
                20                  25                  30

Trp Phe Ser Pro Asn Gly Glu Lys Leu Thr Pro Asn Gln Gln Arg Ile
            35                  40                  45

Ser Val Val Trp Asn Asp Asp Ser Ser Ser Thr Leu Thr Ile Tyr Asn
        50                  55                  60

Ala Asn Ile Asp Asp Ala Gly Ile Tyr Lys Cys Val Val Tyr Ala Ala
65                  70                  75                  80

Glu Ala Thr Val Asn Val Lys Ile Phe Gln
                85                  90

<210> SEQ ID NO 3
<211> LENGTH: 97
<212> TYPE: PRT
<213> ORGANISM: Bos taurus

<400> SEQUENCE: 3

Leu Gln Val Asp Ile Val Pro Ser Gln Gly Glu Ile Ser Val Gly Glu
1               5                   10                  15

Ser Lys Phe Phe Leu Cys Gln Val Ala Gly Asp Ala Lys Asp Lys Asp
                20                  25                  30

Ile Ser Trp Phe Ser Pro Asn Gly Glu Lys Leu Thr Pro Asn Gln Gln
                35                  40                  45

Arg Ile Ser Val Val Trp Asn Asp Asp Ser Ser Thr Leu Thr Ile
50                  55                  60

Tyr Asn Ala Asn Ile Asp Asp Ala Gly Ile Tyr Lys Cys Val Val Thr
65                  70                  75                  80

Ala Glu Asp Gly Thr Glu Ser Glu Ala Thr Val Asn Val Lys Ile Phe
                85                  90                  95

Gln

```
<210> SEQ ID NO 4
<211> LENGTH: 97
<212> TYPE: PRT
<213> ORGANISM: Mus musculus

<400> SEQUENCE: 4

Leu Gln Val Asp Ile Val Pro Ser Gln Gly Glu Ile Ser Val Gly Glu
1               5                   10                  15

Ser Lys Phe Phe Leu Cys Gln Val Ala Gly Asp Ala Lys Asp Lys Asp
            20                  25                  30

Ile Ser Trp Phe Ser Pro Asn Gly Glu Lys Leu Ser Pro Asn Gln Gln
        35                  40                  45

Arg Ile Ser Val Val Trp Asn Asp Asp Ser Ser Thr Leu Thr Ile
    50                  55                  60

Tyr Asn Ala Asn Ile Asp Asp Ala Gly Ile Tyr Lys Cys Val Val Thr
65                  70                  75                  80

Ala Glu Asp Gly Thr Gln Ser Glu Ala Thr Val Asn Val Lys Ile Phe
                85                  90                  95

Gln

<210> SEQ ID NO 5
<211> LENGTH: 97
<212> TYPE: PRT
<213> ORGANISM: Rattus rattus

<400> SEQUENCE: 5

Leu Gln Val Asp Ile Val Pro Ser Gln Gly Glu Ile Ser Val Gly Glu
1               5                   10                  15

Ser Lys Phe Phe Leu Cys Gln Val Ala Gly Asp Ala Lys Asp Lys Asp
            20                  25                  30

Ile Ser Trp Phe Ser Pro Asn Gly Glu Lys Leu Ser Pro Asn Gln Gln
        35                  40                  45

Arg Ile Ser Val Val Trp Asn Asp Asp Ser Ser Thr Leu Thr Ile
    50                  55                  60

Tyr Asn Ala Asn Ile Asp Asp Ala Gly Ile Tyr Lys Cys Val Val Thr
65                  70                  75                  80

Ala Glu Asp Gly Thr Gln Ser Glu Ala Thr Val Asn Val Lys Ile Phe
                85                  90                  95

Gln

<210> SEQ ID NO 6
<211> LENGTH: 97
<212> TYPE: PRT
<213> ORGANISM: Gallus gallus

<400> SEQUENCE: 6

Leu Gln Val Asp Ile Val Pro Ser Gln Gly Glu Ile Ser Val Gly Glu
1               5                   10                  15

Ser Lys Phe Phe Leu Cys Gln Val Ala Gly Glu Ala Lys Tyr Lys Asp
            20                  25                  30

Ile Ser Trp Phe Ser Pro Asn Gly Glu Lys Leu Thr Pro Asn Gln Gln
        35                  40                  45

Arg Ile Ser Val Val Arg Asn Asp Asp Phe Ser Ser Thr Leu Thr Ile
    50                  55                  60

Tyr Asn Ala Asn Ile Asp Asp Ala Gly Ile Tyr Lys Cys Val Val Ser
65                  70                  75                  80

Ser Val Glu Glu Gly Asp Ser Glu Ala Thr Val Asn Val Lys Ile Phe
```

Gln

<210> SEQ ID NO 7
<211> LENGTH: 94
<212> TYPE: PRT
<213> ORGANISM: Xenopus laevis

<400> SEQUENCE: 7

Leu Glu Val Asn Ile Val Pro Asp Gln Gly Glu Ile Ser Leu Gly Glu
1               5                   10                  15

Ser Lys Phe Phe Leu Cys Gln Val Ser Gly Glu Ala Thr Asp Ile Ser
            20                  25                  30

Trp Tyr Ser Pro Thr Gly Glu Lys Leu Leu Asn Gln Gln Gln Ile Ser
        35                  40                  45

Val Val Lys Asn Asp Glu Tyr Thr Ser Thr Leu Thr Ile Tyr Asn Val
    50                  55                  60

Ser Ser Gln Asp Ala Gly Ile Tyr Lys Cys Val Ala Ser Ser Glu Thr
65                  70                  75                  80

Glu Gly Glu Ser Glu Gly Thr Val Asn Leu Lys Ile Tyr Gln
                85                  90

<210> SEQ ID NO 8
<211> LENGTH: 94
<212> TYPE: PRT
<213> ORGANISM: Xenopus laevis

<400> SEQUENCE: 8

Leu Glu Val Asn Ile Val Pro Asp Gln Gly Glu Ile Ser Leu Gly Glu
1               5                   10                  15

Ser Lys Phe Phe Leu Cys Gln Val Ser Gly Glu Ala Thr Asp Ile Ser
            20                  25                  30

Trp Tyr Ser Pro Thr Gly Glu Lys Leu Val Thr Gln Gln Gln Ile Ser
        35                  40                  45

Val Val Arg Ser Asp Asp Tyr Thr Ser Thr Leu Thr Ile Tyr Asn Ala
    50                  55                  60

Ser Ser Gln Asp Ala Gly Ile Tyr Lys Cys Val Ala Ser Asn Glu Ala
65                  70                  75                  80

Glu Gly Glu Ser Glu Gly Thr Val Asn Leu Lys Ile Tyr Gln
                85                  90

<210> SEQ ID NO 9
<211> LENGTH: 93
<212> TYPE: PRT
<213> ORGANISM: Homo sapiens

<400> SEQUENCE: 9

Leu Gln Val Thr Ile Ser Leu Ser Lys Val Glu Leu Ser Val Gly Glu
1               5                   10                  15

Ser Lys Phe Phe Thr Cys Thr Ala Ile Gly Glu Pro Glu Ser Ile Asp
            20                  25                  30

Trp Tyr Asn Pro Gln Gly Glu Lys Ile Ile Ser Thr Gln Arg Val Val
        35                  40                  45

Val Gln Lys Glu Gly Val Arg Ser Arg Leu Thr Ile Tyr Asn Ala Asn
    50                  55                  60

Ile Glu Asp Ala Gly Ile Tyr Arg Cys Gln Ala Thr Asp Ala Lys Gly
65                  70                  75                  80

```
Gln Thr Gln Glu Ala Thr Val Val Leu Glu Ile Tyr Gln
            85                  90

<210> SEQ ID NO 10
<211> LENGTH: 93
<212> TYPE: PRT
<213> ORGANISM: Mus musculus

<400> SEQUENCE: 10

Leu Gln Val Thr Ile Ser Leu Ser Lys Val Glu Leu Ser Val Gly Glu
1               5                   10                  15

Ser Lys Phe Phe Thr Cys Thr Ala Ile Gly Glu Pro Glu Ser Ile Asp
            20                  25                  30

Trp Tyr Asn Pro Gln Gly Glu Lys Ile Ile Ser Thr Gln Arg Val Met
        35                  40                  45

Leu Gln Lys Glu Gly Val Arg Ser Arg Leu Thr Ile Tyr Asn Ala Asn
    50                  55                  60

Ile Glu Asp Ala Gly Ile Tyr Arg Cys Gln Ala Thr Asp Ala Lys Gly
65                  70                  75                  80

Gln Thr Gln Glu Ala Thr Val Val Leu Glu Ile Tyr Gln
            85                  90

<210> SEQ ID NO 11
<211> LENGTH: 103
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: ADCX-99 protein sequence

<400> SEQUENCE: 11

Leu Gln Val Asp Ile Val Pro Ser Gln Gly Glu Ile Ser Val Gly Glu
1               5                   10                  15

Ser Lys Phe Phe Leu Cys Gln Val Ala Gly Ser Gly Ser Asp Ile Arg
            20                  25                  30

Ile Ser Trp Phe Ser Pro Asn Gly Glu Lys Leu Thr Pro Asn Gln Gln
        35                  40                  45

Arg Ile Ser Val Val Trp Asn Asp Asp Ser Ser Thr Leu Thr Ile
    50                  55                  60

Tyr Asn Ala Asn Ile Asp Asp Ala Gly Ile Tyr Lys Cys Val Val Tyr
65                  70                  75                  80

Arg Thr Gly Gly Tyr Arg His Arg Ala Leu Val Leu Gly Glu Ala Thr
            85                  90                  95

Val Asn Val Lys Ile Phe Gln
            100

<210> SEQ ID NO 12
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: ADCX_99 CDR1 protein sequence

<400> SEQUENCE: 12

Ser Gly Ser Asp Ile Arg
1               5
```

```
<210> SEQ ID NO 13
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: ADCX-99 CDR3 protein sequence

<400> SEQUENCE: 13

Tyr Arg Thr Gly Gly Tyr Arg His Arg Ala Leu Val Leu Gly
1               5                   10

<210> SEQ ID NO 14
<211> LENGTH: 100
<212> TYPE: PRT
<213> ORGANISM: Artificial Sequence
<220> FEATURE:
<223> OTHER INFORMATION: Synthetic

<400> SEQUENCE: 14

Leu Gln Val Asp Ile Val Pro Ser Gln Gly Glu Ile Ser Val Gly Glu
1               5                   10                  15

Ser Lys Phe Phe Leu Cys Gln Val Ala Gly His Leu Glu Val Arg Ser
            20                  25                  30

Ile Ser Trp Phe Ser Pro Asn Gly Glu Lys Leu Thr Pro Asn Gln Gln
        35                  40                  45

Arg Ile Ser Val Val Trp Asn Asp Asp Ser Ser Thr Leu Thr Ile
    50                  55                  60

Tyr Asn Ala Asn Ile Asp Asp Ala Gly Ile Tyr Lys Cys Val Val Glu
65                  70                  75                  80

Gln Arg Gly Arg Ser Gln Ser Tyr Phe Ser Glu Ala Thr Val Asn Val
                85                  90                  95

Lys Ile Phe Gln
            100

<210> SEQ ID NO 15
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: protein sequence encoding ADCX-272 CDR1

<400> SEQUENCE: 15

His Leu Glu Val Arg Ser
1               5

<210> SEQ ID NO 16
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: protein sequence encoding ADCX-272 CDR3

<400> SEQUENCE: 16

Glu Gln Arg Gly Arg Ser Gln Ser Tyr Phe Ser
1               5                   10
```

<210> SEQ ID NO 17
<211> LENGTH: 99
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: protein sequence encoding ADCX-6

<400> SEQUENCE: 17

Leu Gln Val Asp Ile Val Pro Ser Gln Gly Glu Ile Ser Val Gly Glu
1               5                   10                  15

Ser Lys Phe Phe Leu Cys Gln Val Ala Gly Leu Thr Ser Leu Glu Gly
            20                  25                  30

Ile Ser Trp Phe Ser Pro Asn Gly Glu Lys Leu Thr Pro Asn Gln Gln
        35                  40                  45

Arg Ile Ser Val Val Trp Asn Asp Asp Ser Ser Thr Leu Thr Ile
    50                  55                  60

Tyr Asn Ala Asn Ile Asp Asp Ala Gly Ile Tyr Lys Cys Val Val Glu
65                  70                  75                  80

Asp His Pro Gln Tyr Ser Lys Met Glu Glu Ala Thr Val Asn Val Lys
                85                  90                  95

Ile Phe Gln

<210> SEQ ID NO 18
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: protein sequence encoding ADCX-6 CDR1

<400> SEQUENCE: 18

Leu Thr Ser Leu Glu Gly
1               5

<210> SEQ ID NO 19
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: protein sequence encoding ADCX-6 CDR3

<400> SEQUENCE: 19

Glu Asp His Pro Gln Tyr Ser Lys Met Glu
1               5                   10

<210> SEQ ID NO 20
<211> LENGTH: 99
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: protein sequence encoding ADCX-54

<400> SEQUENCE: 20

Leu Gln Val Asp Ile Val Pro Ser Gln Gly Glu Ile Ser Val Gly Glu

```
                1               5                  10                 15
Ser Lys Phe Phe Leu Cys Gln Val Ala Gly Arg Thr Ile Ile Val Glu
                20                 25                 30

Ile Ser Trp Phe Ser Pro Asn Gly Glu Lys Leu Thr Pro Asn Gln Gln
                35                 40                 45

Arg Ile Ser Val Val Trp Asn Asp Asp Ser Ser Thr Leu Thr Ile
        50                 55                 60

Tyr Asn Ala Asn Ile Asp Asp Ala Gly Ile Tyr Lys Cys Val Val Val
 65                 70                 75                 80

Leu Ser Ile Arg Gly Lys Trp Glu Leu Glu Ala Thr Val Asn Val Lys
                85                 90                 95

Ile Phe Gln

<210> SEQ ID NO 21
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: protein sequence encoding ADCX-54 CDR1

<400> SEQUENCE: 21

Arg Thr Ile Ile Val Glu
1               5

<210> SEQ ID NO 22
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: protein sequence encoding ADCX-54 CDR3

<400> SEQUENCE: 22

Val Leu Ser Ile Arg Gly Lys Trp Glu Leu
1               5                  10

<210> SEQ ID NO 23
<211> LENGTH: 103
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: protein sequence encoding ADCX-LS

<400> SEQUENCE: 23

Leu Gln Val Asp Ile Val Pro Ser Gln Gly Glu Ile Ser Val Gly Glu
1               5                  10                 15

Ser Lys Phe Phe Leu Cys Gln Val Ala Gly Ile Ala Tyr Phe Ser Thr
                20                 25                 30

Ile Ser Trp Phe Ser Pro Asn Gly Glu Lys Leu Thr Pro Asn Gln Gln
                35                 40                 45

Arg Ile Ser Val Val Trp Asn Asp Asp Ser Ser Thr Leu Thr Ile
        50                 55                 60

Tyr Asn Ala Asn Ile Asp Asp Ala Gly Ile Tyr Lys Cys Val Val Gln
 65                 70                 75                 80
```

```
Val Ser Asp His Pro Glu Ala Gly Ile Leu Trp Arg Gly Glu Ala Thr
            85                  90                  95

Val Asn Val Lys Ile Phe Gln
            100

<210> SEQ ID NO 24
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: protein sequence encoding ADCX-LS CDR1

<400> SEQUENCE: 24

Ile Ala Glu Phe Ser Thr
1               5

<210> SEQ ID NO 25
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: protein sequence encoding ADCX-LS CDR3

<400> SEQUENCE: 25

Gln Val Ser Asp His Pro Glu Ala Gly Ile Leu Trp Arg Gly
1               5                   10

<210> SEQ ID NO 26
<211> LENGTH: 99
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: protein sequence encoding ADCX-668

<400> SEQUENCE: 26

Leu Gln Val Asp Ile Val Pro Ser Gln Gly Glu Ile Ser Val Gly Glu
1               5                   10                  15

Ser Lys Phe Phe Leu Cys Gln Val Ala Gly Thr Ile Trp Tyr Glu Gln
            20                  25                  30

Ile Ser Trp Phe Thr Pro Asn Gly Glu Lys Leu Thr Pro Asn Gln Gln
        35                  40                  45

Arg Ile Ser Val Val Trp Asn Asp Asp Ser Ser Thr Leu Thr Ile
    50                  55                  60

Tyr Asn Ala Asn Ile Asp Asp Ala Gly Ile Tyr Lys Cys Val Val Trp
65                  70                  75                  80

Thr Arg Pro Val Thr Ser Ser Met His Glu Ala Thr Val Asn Val Lys
                85                  90                  95

Ile Phe Gln

<210> SEQ ID NO 27
<211> LENGTH: 6
<212> TYPE: PRT
<213> ORGANISM: Artificial Sequence
<220> FEATURE:
<223> OTHER INFORMATION: Synthetic
<220> FEATURE:
```

```
<221> NAME/KEY: misc_feature
<223> OTHER INFORMATION: protein sequence encoding ADCX-668 CDR1

<400> SEQUENCE: 27

Thr Ile Trp Tyr Glu Gln
1               5

<210> SEQ ID NO 28
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: protein sequence encoding ADCX-668 CDR3

<400> SEQUENCE: 28

Trp Thr Arg Pro Val Thr Ser Ser Met His
1               5                   10

<210> SEQ ID NO 29
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: protein sequence encoding ADCX306

<400> SEQUENCE: 29

Leu Gln Val Asp Ile Val Pro Ser Gln Gly Glu Ile Ser Val Gly Glu
1               5                   10                  15

Ser Lys Phe Phe Leu Cys Gln Val Ala Gly Phe Gln Glu Trp Val Asn
            20                  25                  30

Trp Phe Ser Pro Asn Gly Glu Lys Leu Thr Pro Asn Gln Gln Arg Ile
        35                  40                  45

Ser Val Val Trp Asn Asp Asp Ser Ser Ser Thr Leu Thr Ile Tyr Asn
    50                  55                  60

Ala Asn Ile Asp Asp Ala Gly Ile Tyr Lys Cys Val Val Thr Met Pro
65                  70                  75                  80

His Thr Leu Asn Asn Leu Asp Val Arg Thr Glu Ala Thr Val Asn Val
                85                  90                  95

Lys Ile Phe Gln
            100

<210> SEQ ID NO 30
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: protein sequence encoding ADCX306  CDR1

<400> SEQUENCE: 30

Phe Gln Glu Trp Val Asn
1               5

<210> SEQ ID NO 31
<211> LENGTH: 13
<212> TYPE: PRT
<213> ORGANISM: Artificial Sequence
```

<220> FEATURE:
<223> OTHER INFORMATION: Synthetic
<220> FEATURE:
<221> NAME/KEY: misc_feature
<223> OTHER INFORMATION: protein sequence encoding ADCX306 CDR3

<400> SEQUENCE: 31

Thr Met Pro His Thr Leu Asn Asn Leu Asp Val Arg Thr
1               5                   10

<210> SEQ ID NO 32
<211> LENGTH: 309
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: nucleotide sequence encoding ADCX-99

<400> SEQUENCE: 32
ctgcaagtag atattgtgcc gagccagggc gaaattagcg tgggcgaaag caaattttc         60 ttatgccagg tggcgggctc tgggagtgat attcggatca gctggtttag cccgaacggt        120
gaaaaactga ccccgaatca gcaacgtatc agcgttgtgt ggaacgatga tagctctagt        180
accctgacga tttacaatgc gaacattgat gacgcgggca tttataaatg cgtggtatat        240
aggacggggg ggtatcgtca tcgtgctctt gtgctggggg aagccaccgt taatgtgaaa        300
atcttcag                                                                309

<210> SEQ ID NO 33
<211> LENGTH: 300
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: nucleotide sequence encoding ADCX-272

<400> SEQUENCE: 33
ctgcaagtag atattgtgcc gagccagggc gaaattagcg tgggcgaaag caaattttc         60 ttatgccagg tggcgggcca tttgtaggtg aggtcgatca gctggtttag cccgaacggt        120
gaaaaactga ccccgaatca gcaacgtatc agcgttgtgt ggaacgatga tagctctagt        180
accctgacga tttacaatgc gaacattgat gacgcgggca tttataaatg cgtggtagag        240
cagcgggggc ggtcgcagtc ttattttcg gaagccaccg ttaatgtgaa aatctttcag        300

<210> SEQ ID NO 34
<211> LENGTH: 297
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: nucleotide sequence encoding ADCX-6

<400> SEQUENCE: 34
ctgcaagtgg acattgtccc gagccagggt gagatttcgg tgggcgagtc caagttctt         60 ctgtgtcaag ttgccggtct gaccagcctg gaaggtatta gctggttcag cccgaacggc        120
gaaaaactga cgccaaatca gcagcgtatt agcgtcgttt ggaatgacga ctctagcagc        180
accttgacga tctacaacgc gaacatcgat gatgcgggta tctataagtg cgttgtcgag        240

```
gatcacccgc aatacagcaa aatggaagag gcaaccgtta atgtgaaaat ctttcag      297
```

<210> SEQ ID NO 35
<211> LENGTH: 297
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: nucleotide sequence encoding ADCX-54

<400> SEQUENCE: 35

```
ctgcaagtag atattgtgcc gagccagggc gaaattagcg tgggcgaaag caaattttc    60
ttatgccagg tggcgggccg gacgattatt gtgtagatca gctggtttag cccgaacggt  120
gaaaaactga ccccgaatca gcaacgtatc agcgttgtgt ggaacgatga tagctctagt  180
accctgacga tttacaatgc gaacattgat gacgcgggca tttataaatg cgtggtagtg  240
ctgtctattc ggggtaagtg gtagctggaa gccaccgtta atgtgaaaat ctttcag     297
```

<210> SEQ ID NO 36
<211> LENGTH: 309
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: nucleotide sequence encoding ADCX-LS

<400> SEQUENCE: 36

```
ctgcaagtag atattgtgcc gagccagggc gaaattagcg tgggcgaaag caaattttc    60
ttatgccagg tggcgggcat tgcttatttt agtactatca gctggtttag cccgaacggt  120
gaaaaactga ccccgaatca gcaacgtatc agcgttgtgt ggaacgatga tagctctagt  180
accctgacga tttacaatgc gaacattgat gacgcgggca tttataaatg cgtggtacag  240
gtttcggatc atccgtaggc gggtattttg tggcggggtg aagccaccgt taatgtgaaa  300
atctttcag                                                          309
```

<210> SEQ ID NO 37
<211> LENGTH: 297
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: nucleotide sequence encoding ADCX-668

<400> SEQUENCE: 37

```
ctgcaagttg acattgtgcc gagccagggc gaaattagcg tgggcgaaag caaattttc    60
ttatgccagg tggcgggcac tatttggtat tagcagatca gctggtttac cccgaacggt  120
gaaaaactga ccccgaatca gcaacgtatc agcgttgtgt ggaacgatga tagctctagt  180
accctgacga tttacaatgc gaacattgat gacgcgggca tttataaatg cgtggtatgg  240
acgcgtcctg ttacttcttc gatgcatgaa gccaccgtta atgtgaaaat ctttcag     297
```

<210> SEQ ID NO 38
<211> LENGTH: 300
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: nucleotide sequence encoding ADCX306

<400> SEQUENCE: 38

Cys Thr Gly Cys Ala Ala Gly Thr Gly Ala Cys Ala Thr Thr Gly
1               5                   10                  15

Thr Gly Cys Cys Gly Ala Gly Cys Cys Ala Ala Gly Gly Cys Gly Ala
            20                  25                  30

Gly Ala Thr Thr Thr Cys Cys Gly Thr Cys Gly Gly Cys Gly Ala Gly
            35                  40                  45

Ala Gly Cys Ala Ala Ala Thr Thr Cys Thr Thr Thr Cys Thr Gly Thr
        50                  55                  60

Gly Thr Cys Ala Gly Gly Thr Thr Gly Cys Gly Gly Thr Thr Thr
65                  70                  75                  80

Thr Cys Ala Ala Gly Ala Ala Thr Gly Gly Thr Cys Ala Ala Thr
            85                  90                  95

Thr Gly Gly Thr Thr Cys Thr Cys Cys Gly Ala Ala Thr
                100                 105                 110

Gly Thr Gly Ala Ala Ala Gly Cys Thr Gly Ala Cys Gly Cys Cys
            115                 120                 125

Gly Ala Ala Cys Cys Ala Gly Cys Ala Gly Cys Ala Thr Thr
        130                 135                 140

Ala Gly Cys Gly Thr Thr Gly Thr Ala Thr Gly Gly Ala Ala Thr Gly
145                 150                 155                 160

Ala Thr Gly Ala Cys Ala Gly Cys Ala Gly Cys Ala Gly Cys Ala Cys
                165                 170                 175

Cys Cys Thr Gly Ala Cys Gly Ala Thr Cys Thr Ala Cys Ala Ala Cys
            180                 185                 190

Gly Cys Ala Ala Ala Cys Ala Thr Cys Gly Ala Cys Gly Ala Thr Gly
            195                 200                 205

Cys Cys Gly Gly Thr Ala Thr Cys Thr Ala Thr Ala Ala Gly Thr Gly
210                 215                 220

Cys Gly Thr Thr Gly Thr Cys Ala Cys Cys Ala Thr Gly Cys Cys Ala
225                 230                 235                 240

Cys Ala Cys Ala Cys Cys Thr Gly Ala Ala Cys Ala Ala Thr Cys
            245                 250                 255

Thr Gly Gly Ala Thr Gly Thr Cys Gly Thr Ala Cys Cys Gly Ala
            260                 265                 270

Gly Gly Cys Gly Ala Cys Thr Gly Thr Gly Ala Ala Cys Gly Thr Gly
            275                 280                 285

Ala Ala Ala Ala Thr Cys Thr Thr Cys Cys Ala Gly
            290                 295                 300

<210> SEQ ID NO 39
<211> LENGTH: 101
<212> TYPE: PRT
<213> ORGANISM: Artificial Sequence
<220> FEATURE:
<223> OTHER INFORMATION: Synthetic

<400> SEQUENCE: 39

Glx Leu Gln Val Asp Ile Val Pro Ser Gln Gly Glu Ile Ser Val Gly
1               5                   10                  15

Glu Ser Lys Phe Phe Leu Cys Ala Asx Ala Gly Ser Ser Arg Ile Ser

```
                    20                  25                  30

Trp Phe Ser Pro Asn Gly Glu Lys Leu Thr Pro Asn Gln Gln Arg Ile
            35                  40                  45

Ser Val Val Trp Asn Asp Asp Ser Ser Thr Leu Thr Ile Tyr Asn
 50                  55                  60

Ala Asn Ile Asp Asp Ala Gly Ile Tyr Lys Cys Val Val Tyr Arg Tyr
 65                  70                  75                  80

Gly Tyr Tyr Arg His Arg Tyr Leu Tyr Leu Gly Glu Ala Thr Val Asn
                85                  90                  95

Val Lys Ile Phe Gln
            100

<210> SEQ ID NO 40
<211> LENGTH: 103
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: protein sequence encoding AM3-114 CDR1

<400> SEQUENCE: 40

Leu Gln Val Asp Ile Val Pro Tyr Gln Gly Glu Ile Ser Val Gly Glu
 1               5                  10                  15

Ser Lys Phe Phe Leu Cys Gln Val Ala Gly Ser Leu Ser Gly Ile Arg
            20                  25                  30

Ile Ser Trp Phe Ser Pro Asn Gly Glu Lys Leu Thr Pro Asn Gln Gln
            35                  40                  45

Arg Ile Ser Val Val Trp Asn Asp Asp Ser Ser Thr Leu Thr Ile
 50                  55                  60

Tyr Asn Ala Asn Ile Asp Asp Ala Gly Ile Tyr Lys Cys Val Val Trp
 65                  70                  75                  80

Arg Thr Gly Gly Tyr Arg His Arg Tyr Leu Val Leu Gly Glu Ala Thr
                85                  90                  95

Val Asn Val Lys Ile Phe Gln
            100

<210> SEQ ID NO 41
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: protein sequence encoding AM3-114 CDR1

<400> SEQUENCE: 41

Ser Leu Ser Gly Ile Arg
 1               5

<210> SEQ ID NO 42
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: protein sequence encoding AM3-114 CDR3

<400> SEQUENCE: 42
```

```
Trp Arg Thr Gly Gly Tyr Arg His Arg Tyr Leu Val Leu Gly
1               5                   10
```

<210> SEQ ID NO 43
<211> LENGTH: 314
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: nucleotide sequence encoding AM3-114

<400> SEQUENCE: 43

```
atggcgctgc aggtggatat tgtgccgagc cagggcgaaa ttagcgtggg cgaaagcaaa    60
ttttttctgt gccaggtggc gggcagcctg agcggcattc gtattagctg gtttagcccg   120
aacggcgaaa aactgacccc gaaccagcag cgtattagcg tggtgtggaa cgatgatagc   180
agcagcaccc tgaccattta taacgcgaac attgatgatg cgggcattta taaatgcgtg   240
gtgtggcgta ccggcggcta tcgtcatcgt tatctggtgc tgggcgaagc gaccgtgaac   300
gtgaaaattt ttca                                                    314
```

<210> SEQ ID NO 44
<211> LENGTH: 103
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: protein sequence encoding AM3-920

<400> SEQUENCE: 44

```
Leu Gln Val Asp Ile Val Pro Ser Gln Gly Glu Ile Ser Val Gly Glu
1               5                   10                  15

Ser Lys Phe Phe Leu Cys Gln Val Ala Gly Ser Gly Ser Gly Ile Arg
            20                  25                  30

Ile Ser Trp Phe Ser Pro Asn Gly Glu Lys Leu Thr Pro Asn Gln Gln
        35                  40                  45

Arg Ile Ser Val Val Trp Asn Asp Asp Ser Ser Thr Leu Thr Ile
    50                  55                  60

Tyr Asn Ala Asn Ile Asp Asp Ala Gly Ile Tyr Lys Cys Val Val Trp
65                  70                  75                  80

Arg Thr Gly Gly Tyr Arg His Arg Tyr Leu Val Leu Gly Glu Ala Thr
                85                  90                  95

Val Asn Val Lys Ile Phe Gln
            100
```

<210> SEQ ID NO 45
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: protein sequence encoding AM3-920 CDR1

<400> SEQUENCE: 45

```
Ser Gly Ser Gly Ile Arg
1               5
```

```
<210> SEQ ID NO 46
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: protein sequence encoding AM3-920 CDR3

<400> SEQUENCE: 46

Trp Arg Thr Gly Gly Tyr Arg His Arg Tyr Leu Val Leu Gly
1               5                   10

<210> SEQ ID NO 47
<211> LENGTH: 313
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: nucleotide sequence encoding AM3-920

<400> SEQUENCE: 47
atggcgctgc aggtggatat tgtgccgagc cagggcgaaa ttagcgtggg cgaaagcaaa      60
ttttttctgt gccaggtggc gggcagcggc agcggcattc gtattagctg gtttagcccg     120
aacggcgaaa aactgacccc gaaccagcag cgtattagcg tggtgtggaa cgatgataca     180
gcagcaccct gaccatttat aacgcgaaca ttgatgatgc gggcatttat aaatgcgtgg     240
tgtggcgtac cggcggctat cgtcatcgtt atctggtgct gggcgaagcg accgtgaacg     300
tgaaaatttt tca                                                       313

<210> SEQ ID NO 48
<211> LENGTH: 103
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: protein sequence encoding AM4-1121

<400> SEQUENCE: 48

Leu Gln Val Asp Ile Val Pro Ser Gln Gly Glu Ile Ser Val Gly Glu
1               5                   10                  15

Ser Lys Phe Phe Leu Cys Gln Val Ala Gly Ser Lys Ser Gly Ile Arg
            20                  25                  30

Ile Ser Trp Phe Ser Pro Asn Gly Glu Lys Leu Thr Pro Asn Gln Gln
        35                  40                  45

Arg Ile Ser Val Val Trp Asn Asp Asp Ser Ser Thr Leu Thr Ile
    50                  55                  60

Tyr Asn Ala Asn Ile Asp Asp Ala Gly Ile Tyr Lys Cys Val Val
65                  70                  75                  80

Arg Thr Gly Gly Tyr Arg His Arg Tyr Leu Arg Leu Gly Glu Ala Thr
                85                  90                  95

Val Asn Val Lys Ile Phe Gln
            100

<210> SEQ ID NO 49
<211> LENGTH: 6
<212> TYPE: PRT
```

```
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: protein sequence encoding AM4-1121 CDR1

<400> SEQUENCE: 49

Ser Lys Ser Gly Ile Arg
1               5

<210> SEQ ID NO 50
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: protein sequence encoding AM4-1121 CDR3

<400> SEQUENCE: 50

Tyr Arg Thr Gly Gly Tyr Arg His Arg Tyr Leu Arg Leu Gly
1               5                   10

<210> SEQ ID NO 51
<211> LENGTH: 313
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: nucleotide sequence encoding AM4-1121

<400> SEQUENCE: 51
atggcgctgc aggtggatat tgtgccgagc cagggcgaaa ttagcgtggg cgaaagcaaa      60
ttttttctgt gccaggtggc gggcagcaaa agcggcattc gtattagctg gtttagcccg     120
aacggcgaaa aactgacccc gaaccagcag cgtattagcg tggtgtggaa cgatgataca     180
gcagcaccct gaccatttat aacgcgaaca ttgatgatgc gggcatttat aaatgcgtgg     240
tgtatcgtac cggcggctat cgtcatcgtt atctgcgtct gggcgaagcg accgtgaacg     300
tgaaaatttt tca                                                        313

<210> SEQ ID NO 52
<211> LENGTH: 103
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: protein sequence encoding AM4-613

<400> SEQUENCE: 52

Leu Gln Val Asp Ile Val Pro Ser Gln Gly Glu Ile Ser Val Gly Glu
1               5                   10                  15

Ser Lys Phe Phe Leu Cys Gln Val Ala Gly Ser Lys Ser Asp Val Arg
            20                  25                  30

Ile Ser Trp Phe Ser Pro Asn Gly Glu Lys Leu Thr Pro Asn Gln Gln
        35                  40                  45

Arg Ile Ser Val Val Trp Asn Asp Asp Ser Ser Thr Leu Thr Ile
    50                  55                  60

Tyr Asn Ala Asn Ile Asp Asp Ala Gly Ile Tyr Lys Cys Val Val Trp
```

```
                65                  70                  75                  80
Arg Thr Gly Gly Tyr Arg His Arg Tyr Leu Val Leu Gly Glu Ala Thr
                        85                  90                  95

Val Asn Val Lys Ile Phe Gln
                100

<210> SEQ ID NO 53
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: protein sequence encoding AM4-613 CDR1

<400> SEQUENCE: 53

Ser Lys Ser Asp Val Arg
1               5

<210> SEQ ID NO 54
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: protein sequence encoding AM4-613 CDR3

<400> SEQUENCE: 54

Trp Arg Thr Gly Gly Tyr Arg His Arg Tyr Leu Val Leu Gly
1               5                   10

<210> SEQ ID NO 55
<211> LENGTH: 313
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: nucleotide sequence encoding AM4-613

<400> SEQUENCE: 55

Ala Thr Gly Gly Cys Gly Cys Thr Gly Cys Ala Gly Gly Thr Gly Gly
1               5                   10                  15

Ala Thr Ala Thr Thr Gly Thr Gly Cys Cys Gly Ala Gly Cys Cys Ala
                20                  25                  30

Gly Gly Gly Cys Gly Ala Ala Ala Thr Thr Ala Gly Cys Gly Thr Gly
            35                  40                  45

Gly Gly Cys Gly Ala Ala Ala Gly Cys Ala Ala Thr Thr Thr Thr
        50                  55                  60

Thr Thr Cys Thr Gly Thr Gly Cys Cys Ala Gly Thr Gly Gly Cys
65                  70                  75                  80

Gly Gly Gly Cys Ala Gly Cys Ala Ala Ala Gly Cys Gly Ala Thr
                85                  90                  95

Gly Thr Gly Cys Gly Thr Ala Thr Thr Ala Gly Cys Thr Gly Gly Thr
                100                 105                 110

Thr Thr Ala Gly Cys Cys Cys Gly Ala Ala Cys Gly Gly Cys Gly Ala
            115                 120                 125

Ala Ala Ala Ala Cys Thr Gly Ala Cys Cys Cys Cys Gly Ala Ala Cys
                130                 135                 140
```

```
Cys Ala Gly Cys Ala Gly Cys Gly Thr Ala Thr Ala Gly Cys Gly
145                 150                 155                 160

Thr Gly Gly Thr Gly Thr Gly Gly Ala Ala Cys Gly Ala Thr Gly Ala
                165                 170                 175

Thr Ala Cys Ala Gly Cys Ala Gly Cys Ala Cys Cys Thr Gly Ala
            180                 185                 190

Cys Cys Ala Thr Thr Thr Ala Thr Ala Ala Cys Gly Cys Gly Ala Ala
            195                 200                 205

Cys Ala Thr Thr Gly Ala Thr Gly Ala Thr Gly Cys Gly Gly Gly Cys
        210                 215                 220

Ala Thr Thr Thr Ala Thr Ala Ala Ala Thr Gly Cys Gly Thr Gly Gly
225                 230                 235                 240

Thr Gly Thr Gly Gly Cys Gly Thr Ala Cys Cys Gly Cys Gly Gly
                245                 250                 255

Cys Thr Ala Thr Cys Gly Thr Cys Ala Thr Cys Gly Thr Thr Ala Thr
            260                 265                 270

Cys Thr Gly Gly Thr Gly Cys Thr Gly Gly Gly Cys Gly Ala Ala Gly
        275                 280                 285

Cys Gly Ala Cys Cys Gly Thr Gly Ala Ala Cys Gly Thr Gly Ala Ala
        290                 295                 300

Ala Ala Thr Thr Thr Thr Thr Cys Ala
305                 310
```

<210> SEQ ID NO 56  
<211> LENGTH: 102  
<212> TYPE: PRT  
<213> ORGANISM: Artificial Sequence  
<220> FEATURE:  
<223> OTHER INFORMATION: Synthetic  
<220> FEATURE:  
<221> NAME/KEY: misc_feature  
<223> OTHER INFORMATION: protein sequence encoding AM3-523

<400> SEQUENCE: 56

```
Leu Gln Val Asp Ile Val Pro Ser Gln Gly Glu Ile Ser Val Gly Glu
1               5                   10                  15

Ser Lys Phe Phe Leu Cys Gln Val Ala Gly Ser Gly Ser His Met Arg
            20                  25                  30

Ile Ser Trp Phe Ser Pro Asn Gly Glu Lys Leu Thr Pro Asn Gln Gln
        35                  40                  45

Arg Ile Ser Val Val Trp Asn Asp Asp Ser Ser Thr Leu Thr Ile
50                  55                  60

Tyr Asn Ala Asn Ile Asp Asp Ala Gly Ile Tyr Lys Cys Val Val Trp
65                  70                  75                  80

Val Gly Gly Tyr Arg His Arg Ala Leu Val Leu Gly Glu Ala Thr Val
                85                  90                  95

Asn Val Lys Ile Phe Gln
            100
```

<210> SEQ ID NO 57  
<211> LENGTH: 6  
<212> TYPE: PRT  
<213> ORGANISM: Artificial Sequence  
<220> FEATURE:  
<223> OTHER INFORMATION: Synthetic  
<220> FEATURE:  
<221> NAME/KEY: misc_feature  
<223> OTHER INFORMATION: protein sequence encoding AM3-523 CDR1

<400> SEQUENCE: 57

Ser Gly Ser His Met Arg
1               5

<210> SEQ ID NO 58
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: protein sequence encoding AM3-523 CDR3

<400> SEQUENCE: 58

Trp Arg Val Gly Gly Tyr Arg His Arg Ala Leu Val Leu Gly
1               5                  10

<210> SEQ ID NO 59
<211> LENGTH: 314
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: nucleotide sequence encoding AM3-523

<400> SEQUENCE: 59
atggcgctgc aggtggatat tgtgccgagc cagggcgaaa ttagcgtggg cgaaagcaaa      60
ttttttctgt gccaggtggc gggcagcggc agccatatgc gtattagctg gtttagcccg     120
aacggcgaaa aactgacccc gaaccagcag cgtattagcg tggtgtggaa cgatgatagc     180
agcagcaccc tgaccattta taacgcgaac attgatgatg cgggcattta taaatgcgtg     240
gtgtggcgtg tgggcggcta tcgtcatcgt gcgctggtgc tgggcgaagc gaccgtgaac     300
gtgaaaattt ttca                                                       314

<210> SEQ ID NO 60
<211> LENGTH: 103
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: protein sequence encoding AM4-661

<400> SEQUENCE: 60

Leu Gln Val Asp Ile Val Pro Ser Gln Gly Glu Ile Ser Val Gly Glu
1               5                   10                  15

Ser Lys Phe Phe Leu Cys Gln Val Ala Gly Ser Lys Ser Asp Phe Arg
            20                  25                  30

Ile Ser Trp Phe Ser Pro Asn Gly Glu Lys Leu Thr Pro Asn Gln Gln
        35                  40                  45

Arg Ile Ser Val Val Trp Asn Asp Asp Ser Ser Thr Leu Thr Ile
    50                  55                  60

Tyr Asn Ala Asn Ile Asp Asp Ala Gly Ile Tyr Lys Cys Val Val Tyr
65                  70                  75                  80

Arg Thr Gly Gly Tyr Arg His Arg Tyr Leu Val Leu Gly Glu Ala Thr
                85                  90                  95

Val Asn Val Lys Ile Phe Gln
            100

```
<210> SEQ ID NO 61
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: protein sequence encoding AM4-661 CDR1

<400> SEQUENCE: 61

Ser Lys Ser Asp Phe Arg
1               5

<210> SEQ ID NO 62
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: protein sequence encoding AM4-661 CDR3

<400> SEQUENCE: 62

Tyr Arg Thr Gly Gly Tyr Arg His Arg Tyr Leu Val Leu Gly
1               5                   10

<210> SEQ ID NO 63
<211> LENGTH: 314
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: nucleotide sequence encoding AM4-661

<400> SEQUENCE: 63
atggcgctgc aggtggatat tgtgccgagc cagggcgaaa ttagcgtggg cgaaagcaaa     60
ttttttctgt gccaggtggc gggcagcaaa agcaacattc gtattagctg gtttagcccg    120
aacggcgaaa aactgacccc gaaccagcag cgtattagcg tggtgtggaa cgatgatagc    180
agcagcaccc tgaccattta taacgcgaac attgatgatg cgggcattta taatgcgtg     240 gtgtatcgta ccggcggcta tcgtcatcgt tatctgaaac tgggcgaagc gaccgtgaac    300
gtgaaaattt ttca                                                      314

<210> SEQ ID NO 64
<211> LENGTH: 103
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: protein sequence encoding AM3-466

<400> SEQUENCE: 64

Leu Gln Val Asp Ile Val Pro Ser Gln Gly Glu Ile Ser Val Gly Glu
1               5                   10                  15

Ser Lys Phe Phe Leu Cys Gln Val Ala Gly Ser Gly Ser His Gln Arg
            20                  25                  30

Ile Ser Trp Phe Ser Pro Asn Gly Glu Lys Leu Thr Pro Asn Gln Gln
        35                  40                  45
```

```
Arg Ile Ser Val Val Trp Asn Asp Asp Ser Ser Ser Thr Leu Thr Ile
        50                  55                  60

Tyr Asn Ala Asn Ile Asp Asp Ala Gly Ile Tyr Lys Cys Val Val Trp
 65                  70                  75                  80

Arg Thr Gly Ala Tyr Arg His Arg Ala Leu Val Leu Gly Glu Ala Thr
                85                  90                  95

Val Asn Val Lys Ile Phe Gln
            100
```

<210> SEQ ID NO 65
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: protein sequence encoding AM3-466 CDR1

<400> SEQUENCE: 65

```
Ser Gly Ser His Gln Arg
1               5
```

<210> SEQ ID NO 66
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: protein sequence encoding AM3-466 CDR3

<400> SEQUENCE: 66

```
Trp Arg Thr Gly Ala Tyr Arg His Arg Ala Leu Val Leu Gly
1               5                   10
```

<210> SEQ ID NO 67
<211> LENGTH: 314
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: nucleotide sequence encoding AM3-466

<400> SEQUENCE: 67

```
Ala Thr Gly Gly Cys Gly Cys Thr Gly Cys Ala Gly Gly Thr Gly Gly
1               5                   10                  15

Ala Thr Ala Thr Thr Gly Thr Gly Cys Cys Gly Ala Cys Cys Ala
            20                  25                  30

Gly Gly Gly Cys Gly Ala Ala Ala Thr Thr Ala Gly Cys Gly Thr Gly
                35                  40                  45

Gly Gly Cys Gly Ala Ala Ala Gly Cys Ala Ala Thr Thr Thr Thr
        50                  55                  60

Thr Thr Cys Thr Gly Thr Gly Cys Cys Ala Gly Gly Thr Gly Gly Cys
65                  70                  75                  80

Gly Gly Gly Cys Ala Gly Cys Gly Gly Cys Ala Gly Cys Cys Ala Thr
                85                  90                  95

Cys Ala Gly Cys Gly Thr Ala Thr Thr Ala Gly Cys Thr Gly Gly Thr
            100                 105                 110
```

Thr Thr Ala Gly Cys Cys Cys Gly Ala Ala Cys Gly Cys Gly Ala
            115                 120                 125

Ala Ala Ala Ala Cys Thr Gly Ala Cys Cys Cys Gly Ala Ala Cys
    130                 135                 140

Cys Ala Gly Cys Ala Gly Cys Gly Thr Ala Thr Ala Gly Cys Gly
145                 150                 155                 160

Thr Gly Gly Thr Gly Thr Gly Ala Ala Cys Gly Ala Thr Gly Ala
                165                 170                 175

Thr Ala Gly Cys Ala Gly Cys Ala Gly Cys Ala Cys Cys Thr Gly
            180                 185                 190

Ala Cys Cys Ala Thr Thr Thr Ala Thr Ala Ala Cys Gly Cys Gly
        195                 200                 205

Ala Cys Ala Thr Thr Gly Ala Thr Gly Ala Thr Gly Cys Gly Gly
    210                 215                 220

Cys Ala Thr Thr Thr Ala Thr Ala Ala Ala Thr Gly Cys Gly Thr Gly
225                 230                 235                 240

Gly Thr Gly Thr Gly Gly Cys Gly Thr Ala Cys Cys Gly Gly Cys Gly
                245                 250                 255

Cys Gly Thr Ala Thr Cys Gly Thr Cys Ala Thr Cys Gly Thr Gly Cys
            260                 265                 270

Gly Cys Thr Gly Gly Thr Gly Cys Thr Gly Gly Gly Cys Gly Ala Ala
        275                 280                 285

Gly Cys Gly Ala Cys Cys Gly Thr Gly Ala Ala Cys Gly Thr Gly Ala
    290                 295                 300

Ala Ala Ala Thr Thr Thr Thr Cys Ala
305                 310

<210> SEQ ID NO 68
<211> LENGTH: 103
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: protein sequence encoding AM5-245

<400> SEQUENCE: 68

Leu Gln Val Asp Ile Val Pro Ser Gln Gly Glu Ile Ser Val Gly Glu
1               5                   10                  15

Ser Lys Phe Phe Leu Cys Gln Ala Ala Gly Ser Gly Ser His Ile Arg
            20                  25                  30

Ile Ser Trp Phe Ser Pro Asn Gly Glu Lys Leu Thr Pro Asn Gln Gln
        35                  40                  45

Arg Ile Ser Val Val Trp Asn Asp Asp Ser Ser Thr Leu Thr Ile
    50                  55                  60

Tyr Asn Ala Asn Ile Asp Asp Ala Gly Ile Tyr Lys Cys Val Val Trp
65                  70                  75                  80

Arg Thr Gly Gly Tyr Arg His Arg Ala Leu Val Leu Gly Glu Ala Thr
                85                  90                  95

Val Asn Val Lys Ile Phe Gln
            100

<210> SEQ ID NO 69
<211> LENGTH: 6
<212> TYPE: PRT
<213> ORGANISM: Artificial Sequence
<220> FEATURE:

```
<223> OTHER INFORMATION: Synthetic
<220> FEATURE:
<221> NAME/KEY: misc_feature
<223> OTHER INFORMATION: protein sequence encoding AM5-245 CDR1

<400> SEQUENCE: 69

Ser Gly Ser His Ile Arg
1               5

<210> SEQ ID NO 70
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: protein sequence encoding AM5-245 CDR3

<400> SEQUENCE: 70

Trp Arg Thr Gly Gly Tyr Arg His Arg Ala Leu Val Leu Gly
1               5                  10

<210> SEQ ID NO 71
<211> LENGTH: 314
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: nucleotide sequence encoding AM5-245

<400> SEQUENCE: 71
atggcgctgc aggtggatat tgtgccgagc cagggcgaaa ttagcgtggg cgaaagcaaa      60 tttttctgt  gccaggcggc gggcagcggc agccatattc gtattagctg gtttagcccg     120
aacggcgaaa aactgacccc gaaccagcag cgtattagcg tggtgtggaa cgatgatagc     180
agcagcaccc tgaccattta taacgcgaac attgatgatg cgggcattta taaatgcgtg     240
gtgtggcgta ccggcggcta tcgtcatcgt gcgctggtgc tgggcgaagc gaccgtgaac     300
gtgaaaattt ttca                                                      314

<210> SEQ ID NO 72
<211> LENGTH: 103
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: protein sequence encoding AM4-272

<400> SEQUENCE: 72

Leu Gln Val Asp Ile Val Pro Ser Gln Gly Glu Ile Ser Val Gly Glu
1               5                  10                  15

Ser Lys Phe Phe Leu Cys Gln Val Ala Gly Ser Tyr Ser Asp Tyr Arg
                20                  25                  30

Ile Ser Trp Phe Ser Pro Asn Gly Glu Lys Leu Thr Pro Asn Gln Gln
            35                  40                  45

Arg Ile Ser Val Val Trp Asn Asp Asp Ser Ser Thr Leu Thr Ile
        50                  55                  60

Tyr Asn Ala Asn Ile Asp Asp Ala Gly Ile Tyr Lys Cys Val Val Tyr
65                  70                  75                  80
```

Arg Ile Gly Gly Tyr Arg His Arg Tyr Leu Val Leu Gly Glu Ala Thr
            85                  90                  95

Val Asn Val Lys Ile Phe Gln
            100

<210> SEQ ID NO 73
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: protein sequence encoding AM4-272 CDR1

<400> SEQUENCE: 73

Ser Tyr Ser Asp Tyr Arg
1               5

<210> SEQ ID NO 74
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: protein sequence encoding AM4-272 CDR3

<400> SEQUENCE: 74

Tyr Arg Ile Gly Gly Tyr Arg His Arg Tyr Leu Val Leu Gly
1               5                   10

<210> SEQ ID NO 75
<211> LENGTH: 300
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: nucleotide sequence encoding AM4-272

<400> SEQUENCE: 75
ctgcaagtag atattgtgcc gagccagggc gaaattagcg tgggcgaaag caaatttttc      60
ttatgccagg tggcgggcca tttgtaggtg aggtcgatca gctggtttag cccgaacggt     120
gaaaaactga ccccgaatca gcaacgtatc agcgttgtgt ggaacgatga tagctctagt     180
accctgacga tttacaatgc gaacattgat gacgcgggca tttataaatg cgtggtagag     240
cagcgggggc ggtcgcagtc ttatttttcg gaagccaccg ttaatgtgaa aatctttcag     300

<210> SEQ ID NO 76
<211> LENGTH: 103
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: protein sequence encoding AM4-746

<400> SEQUENCE: 76

Leu Gln Val Asp Ile Val Pro Ser Gln Gly Glu Ile Ser Val Gly Glu
1               5                   10                  15

Ser Lys Phe Phe Leu Cys Gln Val Ala Gly Ser Lys Ser Asn Ile Arg
            20                  25                  30

```
Ile Ser Trp Phe Ser Pro Asn Gly Glu Lys Leu Thr Pro Asn Gln Gln
        35                  40                  45

Arg Ile Ser Val Val Trp Asn Asp Asp Ser Ser Thr Leu Thr Ile
    50                  55                  60

Tyr Asn Ala Asn Ile Asp Asp Ala Gly Ile Tyr Lys Cys Val Val Tyr
65                  70                  75                  80

Arg Thr Gly Gly Tyr Arg His Arg Tyr Leu Lys Leu Gly Glu Ala Thr
                85                  90                  95

Val Asn Val Lys Ile Phe Gln
            100
```

```
<210> SEQ ID NO 77
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: protein sequence encoding AM4-746 CDR1

<400> SEQUENCE: 77

Ser Lys Ser Asn Ile Arg
1               5
```

```
<210> SEQ ID NO 78
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: protein sequence encoding AM4-746 CDR3

<400> SEQUENCE: 78

Tyr Arg Thr Gly Gly Tyr Arg His Arg Tyr Leu Lys Leu Gly
1               5                   10
```

```
<210> SEQ ID NO 79
<211> LENGTH: 314
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: nucleotide sequence encoding AM4-746

<400> SEQUENCE: 79
atggcgctgc aggtggatat tgtgccgagc cagggcgaaa ttagcgtggg cgaaagcaaa      60
ttttttctgt gccaggtggc gggcagcaaa agcaacattc gtattagctg gtttagcccg     120
aacggcgaaa aactgacccc gaaccagcag cgtattagcg tggtgtggaa cgatgatagc     180
agcagcaccc tgaccattta taacgcgaac attgatgatg cgggcattta taaatgcgtg     240
gtgtatcgta ccggcggcta tcgtcatcgt tatctgaaac tgggcgaagc gaccgtgaac     300
gtgaaaattt ttca                                                       314
```

```
<210> SEQ ID NO 80
<211> LENGTH: 243
<212> TYPE: PRT
<213> ORGANISM: Artificial Sequence
<220> FEATURE:
```

<223> OTHER INFORMATION: Synthetic
<220> FEATURE:
<221> NAME/KEY: misc_feature
<223> OTHER INFORMATION: protein sequence encoding AM3-114-Im7-FH-SA21
      dual specificity ibody

<400> SEQUENCE: 80

```
Met Ala Leu Gln Val Asp Ile Val Pro Ser Gln Gly Glu Ile Ser Val
1               5                   10                  15

Gly Glu Ser Lys Phe Phe Leu Cys Gln Val Ala Gly Ser Leu Ser Gly
            20                  25                  30

Ile Arg Ile Ser Trp Phe Ser Pro Asn Gly Glu Lys Leu Thr Pro Asn
        35                  40                  45

Gln Gln Arg Ile Ser Val Val Trp Asn Asp Ser Ser Ser Thr Leu
    50                  55                  60

Thr Ile Tyr Asn Ala Asn Ile Asp Asp Ala Gly Ile Tyr Lys Cys Val
65                  70                  75                  80

Val Trp Arg Thr Gly Gly Tyr Arg His Arg Tyr Leu Val Leu Gly Glu
                85                  90                  95

Ala Thr Val Asn Val Lys Ile Phe Gln Gly Gly Gly Ser Glu Leu
            100                 105                 110

Lys Asn Ser Ile Ser Asp Tyr Thr Glu Ala Glu Phe Val Gln Leu Leu
            115                 120                 125

Lys Glu Ile Glu Lys Glu Asn Val Ala Ala Thr Asp Asp Val Leu Asp
    130                 135                 140

Val Leu Leu Glu His Phe Val Lys Ile Thr Glu His Pro Asp Gly Thr
145                 150                 155                 160

Asp Leu Ile Tyr Tyr Pro Ser Asp Asn Arg Asp Asp Ser Pro Glu Gly
                165                 170                 175

Ile Val Lys Glu Ile Lys Glu Trp Arg Ala Ala Asn Gly Lys Pro Gly
            180                 185                 190

Phe Lys Gln Gly Gly Gly Gly Ser Asp Tyr Lys Asp Asp Asp
    195                 200                 205

Lys Gly Ser Gly His His His His His His Gly Gly Gly Gly
    210                 215                 220

Ser Arg Leu Ile Glu Asp Ile Cys Leu Pro Arg Trp Gly Cys Leu Trp
225                 230                 235                 240

Glu Asp Asp
```

<210> SEQ ID NO 81
<211> LENGTH: 732
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: nucleotide sequence encoding
      AM3-114-Im7-FH-SA21 dual specificity ibody

<400> SEQUENCE: 81

```
atggccctgc aagtcgacat cgttccgtca caaggtgaaa tcagcgtggg tgagtccaaa      60
ttctttctgt gccaggtcgc aggcagcctg agcggtatcc gtattagctg gttcagcccg     120
aatggcgaaa agctgacgcc gaaccagcag cgtatctctg tggtttggaa cgacgacagc     180
agcagcaccc tgaccatcta taacgccaat attgatgatg caggcattta caaatgtgtg     240
gtgtggcgca ccggtggtta ccgccaccgt tacctggttt tgggcgaggc gacggtcaat     300
```

```
gttaagattt tccaaggtgg cggtggtagc gagctgaaga actccatcag cgactatacc    360
gaagcggaat tgttcagtt gctgaaagaa attgagaaag aaaatgtcgc ggccactgat    420
gacgtcttag acgtgctgct ggagcatttt gttaagatca ccgagcaccc ggacggtacg    480
gatctcatct actatcctag cgataaccgc gacgattctc cagagggcat tgtcaaagaa    540
attaaggaat ggcgtgctgc aaatggtaaa ccgggtttca acagggtgg tggtggcggc     600 agcgactaca aagatgatga cgacaagggt agcggccacc atcaccacca tcatcaccac    660
ggcggcggcg gctcgcgttt gattgaagat atctgcctgc cgcgttgggg ttgtctgtgg    720
gaggacgatt aa                                                       732
```

<210> SEQ ID NO 82
<211> LENGTH: 105
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: amino acid sequence encoding 21H5 i-body

<400> SEQUENCE: 82

```
Leu Gln Val Asp Ile Val Pro Ser Gln Gly Glu Ile Ser Val Gly Glu
1               5                   10                  15

Ser Lys Phe Phe Leu Cys Gln Val Ala Gly Asp Ala Lys Asp Lys Asp
            20                  25                  30

Ile Ser Trp Phe Ser Pro Asn Gly Glu Lys Leu Thr Pro Asn Gln Gln
        35                  40                  45

Arg Ile Ser Val Val Trp Asn Asp Asp Ser Ser Thr Leu Thr Ile
    50                  55                  60

Tyr Asn Ala Asn Ile Asp Asp Ala Gly Ile Tyr Lys Cys Val Val Thr
65                  70                  75                  80

Gly Ser Asp Ala Met Ser Asn Tyr Ser Tyr Pro Ile Ser Glu Ser Glu
                85                  90                  95

Ala Thr Val Asn Val Lys Ile Phe Gln
            100                 105
```

<210> SEQ ID NO 83
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: amino acid sequence encoding AM4-774 CDR1

<400> SEQUENCE: 83

```
Ser Lys Ser Val Ile Arg
1               5
```

<210> SEQ ID NO 84
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: amino acid sequence encoding AM4-774 CDR3

<400> SEQUENCE: 84

```
Tyr Arg Thr Gly Gly Tyr Arg His Arg Tyr Leu Val Leu Gly
1               5                   10
```

<210> SEQ ID NO 85
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: amino acid sequence encoding AM4-208 CDR1

<400> SEQUENCE: 85

```
Ser Lys Ser Glu Ile Arg
1               5
```

<210> SEQ ID NO 86
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: amino acid sequence encoding AM4-208 CDR3

<400> SEQUENCE: 86

```
Tyr Arg Thr Gly Gly Tyr Arg His Arg Tyr Leu Val Leu Gly
1               5                   10
```

<210> SEQ ID NO 87
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: amino acid sequence encoding AM4-1088 CDR1

<400> SEQUENCE: 87

```
Ser Lys Ser Asp Phe Arg
1               5
```

<210> SEQ ID NO 88
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: amino acid sequence encoding AM4-1088 CDR3

<400> SEQUENCE: 88

```
Arg Thr Gly Gly Tyr Arg His Arg Tyr Leu Lys Leu Gly
1               5                   10
```

<210> SEQ ID NO 89
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: amino acid sequence encoding AM4-239 CDR1

<400> SEQUENCE: 89

```
Ala Tyr Ser Asp Ile Arg
1               5
```

<210> SEQ ID NO 90
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: amino acid sequence encoding AM4-239 CDR3

<400> SEQUENCE: 90

```
Tyr Arg Thr Gly Gly Tyr Arg His Arg Tyr Leu Val Leu Gly
1               5                   10
```

<210> SEQ ID NO 91
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: amino acid sequence encoding AM3-32 CDR1

<400> SEQUENCE: 91

```
Ser Gly Ser Gly Ile Thr
1               5
```

<210> SEQ ID NO 92
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: amino acid sequence encoding AM3-32 CDR3

<400> SEQUENCE: 92

```
Trp Arg Thr Gly Val Tyr Arg His Arg Ala Leu Val Leu Gly
1               5                   10
```

<210> SEQ ID NO 93
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: amino acid sequence encoding AM4-757 CDR1

<400> SEQUENCE: 93

```
Ser Lys Ser Ala Ile Arg
1               5
```

<210> SEQ ID NO 94
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: amino acid sequence encoding AM4-757 CDR3

```
<400> SEQUENCE: 94

Tyr Arg Thr Gly Ser Tyr Arg His Arg Tyr Leu Val Leu Gly
1               5                   10

<210> SEQ ID NO 95
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: amino acid sequence encoding AM4-386 CDR1

<400> SEQUENCE: 95

Ile Thr Ser Glu Gly His
1               5

<210> SEQ ID NO 96
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: amino acid sequence encoding AM4-386 CDR3

<400> SEQUENCE: 96

Glu Thr Thr Val Phe Asn Glu Val Met Arg Leu Gly Asn Gly Ala His
1               5                   10                  15

Val Tyr

<210> SEQ ID NO 97
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: amino acid sequence encoding AM4-352 CDR1

<400> SEQUENCE: 97

Ser Lys Asp Asp Ile Arg
1               5

<210> SEQ ID NO 98
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: amino acid sequence encoding AM4-352 CDR3

<400> SEQUENCE: 98

Tyr Arg Thr Gly Gly Tyr Arg His Arg Tyr Leu Val Leu Gly
1               5                   10

<210> SEQ ID NO 99
<211> LENGTH: 6
<212> TYPE: PRT
<213> ORGANISM: Artificial Sequence
<220> FEATURE:
<223> OTHER INFORMATION: Synthetic
<220> FEATURE:
```

```
<221> NAME/KEY: misc_feature
<223> OTHER INFORMATION: amino acid sequence encoding AM3-182 CDR1

<400> SEQUENCE: 99

Val Gly Asn His Ile Arg
1               5

<210> SEQ ID NO 100
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: amino acid sequence encoding AM3-182 CDR3

<400> SEQUENCE: 100

Trp Arg Ala Gly Gly Tyr Arg His Arg Ala Leu Val Leu Gly
1               5                   10

<210> SEQ ID NO 101
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: amino acid sequence encoding AM4-203 CDR1

<400> SEQUENCE: 101

Ser Tyr Gly Asp Ile Arg
1               5

<210> SEQ ID NO 102
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: amino acid sequence encoding AM4-203 CDR3

<400> SEQUENCE: 102

Tyr Arg Thr Gly Gly Trp Arg His Arg Tyr Leu Val Leu Gly
1               5                   10

<210> SEQ ID NO 103
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: amino acid sequence encoding AM5-95 CDR1

<400> SEQUENCE: 103

Ser Gly Ser His Ile Arg
1               5

<210> SEQ ID NO 104
<211> LENGTH: 14
<212> TYPE: PRT
<213> ORGANISM: Artificial Sequence
<220> FEATURE:
<223> OTHER INFORMATION: Synthetic
```

```
<220> FEATURE:
<221> NAME/KEY: misc_feature
<223> OTHER INFORMATION: amino acid sequence encoding AM5-95 CDR3

<400> SEQUENCE: 104

Trp Arg Thr Gly Gly Tyr Arg His Arg Ala Leu Val Leu Gly
1               5                   10

<210> SEQ ID NO 105
<211> LENGTH: 352
<212> TYPE: PRT
<213> ORGANISM: Homo sapiens

<400> SEQUENCE: 105

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
                20                  25                  30

Asn Ala Asn Phe Asn Lys Ile Phe Leu Pro Thr Ile Tyr Ser Ile Ile
            35                  40                  45

Phe Leu Thr Gly Ile Val Gly Asn Gly Leu Val Ile Leu Val Met Gly
        50                  55                  60

Tyr Gln Lys Lys Leu Arg Ser Met Thr Asp Lys Tyr Arg Leu His Leu
65                  70                  75                  80

Ser Val Ala Asp Leu Leu Phe Val Ile Thr Leu Pro Phe Trp Ala Val
                85                  90                  95

Asp Ala Val Ala Asn Trp Tyr Phe Gly Asn Phe Leu Cys Lys Ala Val
                100                 105                 110

His Val Ile Tyr Thr Val Asn Leu Tyr Ser Ser Val Leu Ile Leu Ala
                115                 120                 125

Phe Ile Ser Leu Asp Arg Tyr Leu Ala Ile Val His Ala Thr Asn Ser
        130                 135                 140

Gln Arg Pro Arg Lys Leu Leu Ala Glu Lys Val Val Tyr Val Gly Val
145                 150                 155                 160

Trp Ile Pro Ala Leu Leu Leu Thr Ile Pro Asp Phe Ile Phe Ala Asn
                165                 170                 175

Val Ser Glu Ala Asp Asp Arg Tyr Ile Cys Asp Arg Phe Tyr Pro Asn
                180                 185                 190

Asp Leu Trp Val Val Phe Gln Phe Gln His Ile Met Val Gly Leu
        195                 200                 205

Ile Leu Pro Gly Ile Val Ile Leu Ser Cys Tyr Cys Ile Ile Ile Ser
        210                 215                 220

Lys Leu Ser His Ser Lys Gly His Gln Lys Arg Lys Ala Leu Lys Thr
225                 230                 235                 240

Thr Val Ile Leu Ile Leu Ala Phe Phe Ala Cys Trp Leu Pro Tyr Tyr
                245                 250                 255

Ile Gly Ile Ser Ile Asp Ser Phe Ile Leu Leu Glu Ile Ile Lys Gln
                260                 265                 270

Gly Cys Glu Phe Glu Asn Thr Val His Lys Trp Ile Ser Ile Thr Glu
                275                 280                 285

Ala Leu Ala Phe Phe His Cys Cys Leu Asn Pro Ile Leu Tyr Ala Phe
        290                 295                 300

Leu Gly Ala Lys Phe Lys Thr Ser Ala Gln His Ala Leu Thr Ser Val
305                 310                 315                 320
```

```
Ser Arg Gly Ser Ser Leu Lys Ile Leu Ser Lys Gly Lys Arg Gly Gly
                325                 330             335

His Ser Ser Val Ser Thr Glu Ser Glu Ser Ser Phe His Ser Ser
            340             345             350
```

CXCR4 BINDING MOLECULES AND METHODS OF USE THEREOF

RELATED APPLICATIONS AND INCORPORATION BY REFERENCE

All documents cited or referenced herein, and all documents cited or referenced in herein cited documents, together with any manufacturer's instructions, descriptions, product specifications, and product sheets for any products mentioned herein or in any document incorporated by reference herein, are hereby incorporated herein by reference in their entirety.

This application is a 35 USC § 371 National Stage application of International Application No. PCT/AU2016/050005 filed Jan. 8, 2016, now pending; which claims the benefit under 35 USC § 119(a) to Australia Application Serial No. 2015900054 filed Jan. 9, 2015, now expired. The disclosure of each of the prior applications is considered part of and is incorporated by reference in the disclosure of this application.

The entire content of the electronic submission of the sequence listing is incorporated by reference in its entirety for all purposes.

FIELD OF THE INVENTION

The present disclosure relates to polypeptides (also referred to herein as CXCR4 binding molecules or polypeptides) that are directed against the G-coupled protein receptor CXCR4, also known as Fusin or CD184. The invention also relates to nucleic acids encoding such polypeptides; to methods for preparing such polypeptide; to compositions, and in particular to pharmaceutical compositions that comprise such polypeptides and to uses of such polypeptides for therapeutic or diagnostic purposes.

BACKGROUND OF THE INVENTION

Chemokines (chemoattractant cytokines) are a family of structurally and functionally related small proteins that direct migration of cells (e.g., leukocytes and/or lymphocytes and/or stem cells and/or neurons) in addition to controlling other biological processes, such as angiogenesis, morphogenesis, autoimmunity, tumor growth and metastasis. Chemokines are grouped into families based on the presence and relative position of amino terminal cysteine residues (e.g. CC, CXC, $CX_3C$ and C chemokines). Generally, the biological activity of a chemokine is mediated by a cell surface receptor, in particular a 7-transmembrane-domain G protein-coupled receptor (GPCR). The chemokine receptors are grouped and named according to the family of chemokine(s) to which they bind.

One member of the CXCR family is CXCR4 that is predominantly expressed on lymphocytes and that activates chemotaxis. CXCR4, also called fusin, is an alpha-chemokine receptor specific for stromal-derived-factor-1 (SDF-1, also called CXCL12), a molecule endowed with potent chemotactic activity for lymphocytes.

CXCR4 plays a role in embryogenesis, homeostasis, fibrosis and inflammation. The CXCR4/SDF-1 pathway has been implicated in organ vascularisation, as well as in the immune and hematopoietic systems (Tachibana K et al. (1998) Nature 393:591-594). Drugs that block the CXCR4 receptor appear to be capable of "mobilising" hematopoietic stem cells into the blood stream as peripheral blood stem cells. CXCR4 has also been shown to function as a co-receptor for T lymphorophic HIV-1 isolates (Geng Y et al. (1996) Science 272:872-877). CXCR4 has also been shown to be expressed on a wide variety of cancer cell types and to be involved in stimulating the metastatic process in many different neoplasms (Murphy P M (20001) N. Eng. J. Med. 345:833-835).

G-protein coupled receptors are currently the most important class of therapeutic targets, and antibodies directed against them are highly sought for therapeutic, diagnostic and research purposes. Despite substantial interest in these targets, high-quality antibodies or binding agents against membrane proteins have been challenging to generate using conventional means.

Binding agents to CXCR4 have previously been described, including whole antibodies (e.g. Medarex), antibody fragments and single-domain antibodies (Ablynx), however the present binding agents provide an alternative construct which alleviates some of the drawbacks of antibodies, for example, Fc-mediated effects as well as high production costs, low stability and their large size, which reduce their utility for tumor penetration. The binding agents of the present invention provide an alternative to small molecule agents such as Plerixafor (Mozobil or AMD3100) which is currently indicated for peripheral blood stem cell mobilisation in combination with granulocyte colony stimulating factor (G-CSF) in patients with non-Hodgkins' lymphoma (NHL) and multiple myeloma (MM).

SUMMARY OF THE INVENTION

The present disclosure relates to CXCR4 binding molecules or polypeptides, referred to as "i-bodies" in the examples described herein. These i-bodies bind to native human CXCR4 expressed on a cell surface. The i-bodies of the present disclosure can be used to modulate, and in particular inhibit or prevent CXCR4 mediated signalling and/or to modulate the biological pathways in which CXCR4 is involved and/or to modulate the biological mechanisms, responses and effects associated with such signalling. As such, the i-bodies of the present disclosure can be used for the prevention and treatment of CXCR4-related diseases and disorders.

It will be appreciated that CXCR4 binding molecules or i-bodies of the present disclosure provide advantages over other binding agents such as traditional antibodies. Like traditional antibodies, the i-bodies of the present disclosure are able to bind to their target with high affinity and high specificity but their smaller size and stability are advantageous when compared to traditional therapeutic antibodies, polypeptides or peptides. I-bodies are also more stable molecules than conventional antibodies which leads to alternative routes of administration and to lower dose form, less frequent dosage, and less side effects. I-bodies are also smaller in size and therefore can penetrate tissues, organs and areas such as the bone matrix and micro-tumor environment that other large proteins may not be able to penetrate. I-bodies also have a long CDR3 binding loop that is able to penetrate grooves and clefts unlike traditional monoclonal antibodies. The i-bodies of the present disclosure are able to bind deep into the pocket of the CXCR4 G-protein coupled receptor (GPCR).

Due to their relatively small size, the i-body is ideally suited for tailoring half life which will have advantages when used as an imaging agent or in the delivery of a required dose for a set period of time. As a small polypeptide, the i-body also provides the delivery of a pay-load to the target through conjugation to the identified polypeptide.

Additionally, the inventors have found that the CXCR4 binding polypeptides/i-bodies of the present disclosure have features that distinguish them over other inhibitor/antagonist CXCR4 binding molecules known in the art. In particular, the CXCR4 binding polypeptides/i-bodies of the present disclosure do not cause stem cell mobilisation. Additionally, the CXCR4 binding polypeptides/i-bodies of the present disclosure do not inhibit calcium flux.

The present disclosure provides a polypeptide which comprises a scaffold region and complementarity determining regions (CDR1 and CDR3) contained therein, wherein the scaffold region comprises a sequence which has at least 75% identity to the scaffold region defined by amino acids 1 to 26, 33 to 79 and 88 to 97 of SEQ ID NO:1 and wherein the CDR1 and CDR3 region defined by amino acids 27 to 32 and 80-87 respectively of SEQ ID NO:1 are modified by amino acid addition or substitution therein and wherein the polypeptide binds to human CXCR4.

In one example, the polypeptide comprises the sequence set forth in SEQ ID NO:2 (FIG. 1B) or the sequence set forth in SEQ ID NO:2 or the sequence set forth in SEQ ID NO:2 comprising between 1 and 5 amino acid additions or substitution therein.

In one example, the CDR1 region consists of a random sequence of six consecutive amino acid residues (designed XXXXXX in FIG. 1B) and the CDR3 region is represented by Y'n (in FIG. 1B), wherein Y is any amino acid residue and n is any number between 10 and 20 amino acids inclusive. The CDR1 and/or CDR3 regions of SEQ ID NO:2 are modified by amino acid addition and/or substitution relative to the corresponding CDR1 and/or CDR3 regions in SEQ ID NO:1.

In one example, the amino acid A' at position 23 of SEQ ID NO:2 is the amino acid glutamine (Q) or lysine (K).

In one example, the amino acid B' at position 24 of SEQ ID NO:2 is the amino acid valine (V) or alanine (A).

In one example, A' is Q and B' is V in SEQ ID NO:2.

The polypeptide may further comprise between 1 and 4 consecutive N-terminal amino acids selected from the group consisting of M, EAEA, MA or MP.

In one example, the polypeptide binds to human CXCR4. In a further example, the polypeptide is an antagonist of human CXCR4.

In one example, the polypeptide binds to human CXCR4 with an affinity of less than 50 uM, less than 20 uM, less than 10 uM, less than 1 μM, less than 850 nM, less than 700 nM, less than 600 nM, less than 500 nM, less than 300 nM, less than 100 nM, less than 50 nM, less than 25 nM, less than 20 nM, less than 15 nM, less than 10 nM, or less than 5 nM. In a particular example, the polypeptide binds to human CXCR4 with an affinity of about 700 nM. In a particular example, the polypeptide binds to human CXCR4 with an affinity of less than 700 nM.

In one example, the scaffold region comprises a sequence which has at least 80%, or at least 85%, or at least 90%, or at least 95%, or at least 97%, or at least 98%, at least 99% identity, or 100% identity to SEQ ID NO:1 at positions 1 to 26, 33-79 and 88-97.

In one example, the scaffold region comprises a sequence which has at least 80%, or at least 85%, or at least 90%, or at least 95%, or at least 97%, or at least 98%, at least 99% homology, or 100% homology to SEQ ID NO:1 at positions 1 to 26, 33-79 and 88-97.

In one example the polypeptide according to SEQ ID NO:1 or SEQ ID NO:2 is modified by one or more amino acid substitutions.

In one example the CDR1 and CDR3 region is modified by one or more amino acid substitutions. In another embodiment the CDR1 and/or CDR3 region is modified by replacement with a random loop sequence.

In one example the CDR3 region comprises or consists of a sequence having at least 70% identity, or at least 80% identity, or at least 90% identity, or at least 95% identity, or at least 97% identity, or at least 98% identity, or at least 99% identity, or 100% identity to SEQ ID NO: 13, SEQ ID NO: 16, SEQ ID NO: 19, SEQ ID NO: 22, SEQ ID NO: 25, SEQ ID NO: 28, or SEQ ID NO: 31.

In one example the CDR3 region comprises or consists of a sequence having at least 70% homology, or at least 80% homology, or at least 90% homology, or at least 95% homology, or at least 97% homology, or at least 98% homology, or at least 99% homology, or 100% homology to SEQ ID NO: 13, SEQ ID NO: 16, SEQ ID NO: 19, SEQ ID NO: 22, SEQ ID NO: 25, SEQ ID NO: 28, or SEQ ID NO: 31.

In another example, CDR3 region comprises or consists of a sequence having at least one, two, three, four, five or six substitutions within a sequence selected from SEQ ID NO: 13, SEQ ID NO: 16, SEQ ID NO: 19, SEQ ID NO: 22, SEQ ID NO: 25, SEQ ID NO: 28, or SEQ ID NO: 31.

In another example, CDR3 region comprises or consists of SEQ ID NO: 13.

In one example the CDR1 region comprises or consists of a sequence having at least 50% identity, or at least 65% identity, or at least 80% identity, or 100% identity to SEQ ID NO: 12, SEQ ID NO: 15, SEQ ID NO: 18, SEQ ID NO: 21, SEQ ID NO: 24, SEQ ID NO: 27, or SEQ ID NO: 30.

In one example the CDR1 region comprises or consists of a sequence having at least 50% homology, or at least 65% homology, or at least 80% homology, or 100% homology to SEQ ID NO: 12, SEQ ID NO: 15, SEQ ID NO: 18, SEQ ID NO: 21, SEQ ID NO: 24, SEQ ID NO: 27, or SEQ ID NO: 30.

In another example, CDR1 region comprises or consists of a sequence having at least one, two or three substitutions within SEQ ID NO: 12, SEQ ID NO: 15, SEQ ID NO: 18, SEQ ID NO: 21, SEQ ID NO: 24, SEQ ID NO: 27, or SEQ ID NO: 30.

In another example, the CDR1 region comprises or consists of SEQ ID NO: 12.

In another example, the polypeptide comprises:
(i) a CDR1 region sequence having at least 50% identity to SEQ ID NO: 12 and a CDR3 region sequence having at least 70% identity to SEQ ID NO: 13;
(ii) a CDR1 region sequence having at least 50% homology to SEQ ID NO: 12 and a CDR3 region sequence having at least 70% homology to SEQ ID NO: 13;
(iii) a CDR1 region sequence having at least 50% identity to SEQ ID NO: 15 and a CDR3 region sequence having at least 70% identity to SEQ ID NO: 16;
(iv) a CDR1 region sequence having at least 50% homology to SEQ ID NO: 15 and a CDR3 region sequence having at least 70% homology to SEQ ID NO: 16;
(v) a CDR1 region sequence having at least 50% identity to SEQ ID NO: 18 and a CDR3 region sequence having at least 70% identity to SEQ ID NO: 19;
(vi) a CDR1 region sequence having at least 50% homology to SEQ ID NO: 18 and a CDR3 region sequence having at least 70% homology to SEQ ID NO: 19;
(vii) a CDR1 region sequence having at least 50% identity to SEQ ID NO: 21 a thae CDR3 region sequence having at least 70% identity to SEQ ID NO: 22;

(viii) a CDR1 region sequence having at least 50% homology to SEQ ID NO: 21 and a CDR3 region sequence having at least 70% homology to SEQ ID NO: 22;

(ix) a CDR1 region sequence having at least 50% identity to SEQ ID NO: 24 and a CDR3 region sequence having at least 70% identity to SEQ ID NO: 25;

(x) a CDR1 region sequence having at least 50% homology to SEQ ID NO: 24 and a CDR3 region sequence having at least 70% homology to SEQ ID NO: 25;

(xi) a CDR1 region having at least 50% identity to SEQ ID NO: 27 and a CDR3 region sequence having at least 70% identity to SEQ ID NO: 28;

(xii) a CDR1 region sequence having at least 50% homology to SEQ ID NO: 27 and a CDR3 region sequence having at least 70% homology to SEQ ID NO: 28;

(xiii) a CDR1 region sequence having at least 50% identity to SEQ ID NO: 30 and a CDR3 region sequence having at least 70% identity to SEQ ID NO: 31; or (xiv) a CDR1 region sequence having at least 50% homology to SEQ ID NO: 30 and a CDR3 region sequence having at least 70% homology to SEQ ID NO: 31.

In one example, the polypeptide comprises a sequence that has at least 80% identity, at least 90% identity, or at least 95% identity, or at least 97% identity, or at least 98% identity, or at least 99% identity to SEQ ID NO: 11, SEQ ID NO: 14, SEQ ID NO: 17, SEQ ID NO: 20, SEQ ID NO: 23, SEQ ID NO: 26, or SEQ ID NO: 29.

In one example, the polypeptide comprises a sequence that has at least 70% homology, or at least 80% homology, or at least 90% homology, or at least 95% homology, or at least 98% homology, or at least 99% homology to SEQ ID NO: 11, SEQ ID NO: 14, SEQ ID NO: 17, SEQ ID NO: 20, SEQ ID NO: 23, SEQ ID NO: 26, or SEQ ID NO: 29.

In one example, the polypeptide comprises a sequence set forth in any one of SEQ ID NO: 11, SEQ ID NO: 14, SEQ ID NO: 17, SEQ ID NO: 20, SEQ ID NO: 23, SEQ ID NO: 26, or SEQ ID NO: 29.

In one example the polypeptide comprises one, two, three, four, five, six, seven, eight, nine or ten substitutions within the sequence selected from the group consisting of SEQ ID NO: 11, SEQ ID NO: 14, SEQ ID NO: 17, SEQ ID NO: 20, SEQ ID NO: 23, SEQ ID NO: 26, SEQ ID NO: 29, SEQ ID NO:40, SEQ ID NO:44, SEQ ID NO:48, SEQ ID NO:52, SEQ ID NO:56, SEQ ID NO:60, SEQ ID NO:64, SEQ ID NO:68, SEQ ID NO:72, or SEQ ID NO: 76.

In one example the polypeptide comprises or consists of SEQ ID NO: 11.

In a further example, polypeptide comprises a CDR1 region comprising a sequence represented by the formula $SX_1SX_2X_3R$ wherein $X_1$ is G, K, L or Y;
$X_2$ is D, H, G or N; and
$X_3$ is I, V, M, F, Q or Y;

or a conservative amino acid substitution thereof.

In one example, the CDR1 region comprises or consists of the sequence set forth in any one of SEQ ID NO: 41, SEQ ID NO: 45, SEQ ID NO: 49, SEQ ID NO: 53, SEQ ID NO:57, SEQ ID NO:61, SEQ ID NO:65, SEQ ID NO:69, SEQ ID NO: 73, or SEQ ID NO:77.

In one example, the polypeptide comprises a CDR3 region comprises a sequence represented by the formula $Y'_1RY'_2GY'_3YRHRY'_4LY'_5LG$ wherein.

$Y'_1$ is Y or W;
$Y'_2$ is T, V or I;
$Y'_3$ is G or A;
$Y'_4$ is A or Y; and
$Y'_5$ is V, R or K;

or a conservative amino acid substitution thereof.

In one example, the CDR3 region comprises or consists of the sequence set forth in any one of SEQ ID NO: 42, SEQ ID NO: 46, SEQ ID NO: 50, SEQ ID NO: 54, SEQ ID NO: 58, SEQ ID NO: 62, SEQ ID NO: 66, SEQ ID NO: 70, SEQ ID NO: 74, or SEQ ID NO: 78.

In another example, the polypeptide comprises a sequence at least 70% identical to a sequence selected from the group consisting of SEQ ID NO: 40, SEQ ID NO: 44, SEQ ID NO: 48, SEQ ID NO: 52, SEQ ID NO: 56, SEQ ID NO: 60, SEQ ID NO: 64, SEQ ID NO: 68, SEQ ID NO: 72 or SEQ ID NO: 76.

In another example, the polypeptide comprises a sequence at least 75%, 80%, 85%, 87%, 90%, 93%, 95%, 98%, or 99% identical to a sequence selected from the group consisting of SEQ ID NO: 40, SEQ ID NO: 44, SEQ ID NO: 48, SEQ ID NO: 52, SEQ ID NO: 56, SEQ ID NO: 60, SEQ ID NO: 64, SEQ ID NO: 68, SEQ ID NO: 72 or SEQ ID NO: 76.

In another example, the polypeptide comprises a sequence represented by the sequence

```
                                          (SEQ ID NO: 39)
ZLQVDIVPSQGEISVGESKFFLCA'B'AGSX₁SX₂X₃RISWFSPNGEK

LTPNQQRISVVWNDDSSSTLTIYNANIDDAGIYKCVVY'₁RY'₂GY'₃

YRHRY'₄LY'₅LGEATVNVKIFQ
``` wherein
A' is Q or K;
B' is V or A;
$X_1$ is G, K, L or Y;
$X_2$ is D, H, G or N;
$X_3$ is I, V, M, F, Q or Y;
$Y'_1$ is Y or W;
$Y'_2$ is T, V or I;
$Y'_3$ is G or A;
$Y'_4$ is A or Y; and
$Y'_5$ is V, R or K;

or a conservative amino acid substitution thereof; and
Z is an amino acid(s) selected from M, EAEA, MA or MP or is absent.

In another example, the polypeptide comprises or consists of the sequence set forth in any one of SEQ ID NO: 40, SEQ ID NO: 44, SEQ ID NO: 48, SEQ ID NO: 52, SEQ ID NO: 56, SEQ ID NO: 60, SEQ ID NO: 64, SEQ ID NO: 68, SEQ ID NO: 72 or SEQ ID NO: 76.

In another example, the polypeptide comprises or consists of the sequence set forth in SEQ ID NO: 40.

In one example, the $K_D$ of the polypeptide for human CXCR4 is between about 0.01 nM to about 700 nM, such as between about 0.05 nM to about 500 nM, for example between about 0.1 nM to about 100 nM, for example between about 1 nM to about 50 nM, between about 5 nM to about 30 nM, between about 10 nM to about 20 nM or between about 3 nM to about 16 nM, In another example, the polypeptide binds to human CXCR4 with an affinity between 3 nM and 10 nM. In another example, the polypeptide binds to human CXCR4 with an affinity between 3 nM and 5 nM.

In one example, the $K_D$ is assessed by immobilizing the human CXCR4 and assessing binding of the polypeptide to the immobilized human CXCR4 using surface plasmon resonance. In one example, the assessment of binding of the polypeptide is to immobilised CXCR4 lipoparticles.

An exemplary polypeptide of the disclosure has a $K_D$ of about 5 nM (e.g., +/−1 nM) for human CXCR4.

In another example, the association rate (Ka) is between about $1\times10^4 M^{-1}s^{-1}$ to about $10\times10^5 M^{-1}s^{-1}$, for example between about $5\times10^4 M^{-1}s^{-1}$ to about $8.5\times10^5 M^{-1}s^{-1}$, for example, between about $1\times10^4 M^{-1}s^{-1}$ to about $6\times10^5 M^{-1}s^{-1}$, for example between $6\times10^5 M^{-1}s^{-1}$ to $1\times10^6 M^{-1}s^{-1}$. In one example, the Ka is assessed by immobilizing the human CXCR4 and assessing binding of the molecule to the immobilized human CXCR4 using surface plasmon resonance.

In another example, the dissociation rate (Kd) is between about $0.005 M^{-1}s^{-1}$ to about $0.9 M^{-1}s^{-1}$, for example between about $0.02 M^{-1}s^{-1}$ to about $0.7 M^{-1}s^{-1}$, for example between about $0.2 M^{-1}s^{-1}$ and $0.55 M^{-1}s^{-1}$.

An exemplary polypeptide of the disclosure has a $K_a$ of about $1.297\times10^6 M^{-1}s^{-1}$. A further exemplary binding polypeptide of the disclosure has a $K_d$ of about $0.00629 M^{-1}s^{-1}$. In one example, the Ka and Kd are assessed by immobilizing a lipoparticle expressing human CXCR4 and assessing binding of the polypeptide to the immobilized lipoparticle expressing human CXCR4 using surface plasmon resonance.

Residues involved in the binding of the polypeptides of the present disclosure to CXCR4 have been determined and are disclosed herein. In one example, the disclosure provides a CXCR4 binding polypeptide as described herein, that binds to one or more core residues of human CXCR4 selected from the group consisting of E32, Y184, F189, W195, D262 and L266 or combinations of any of these. In another example, the residue is selected from the group consisting of E32K, Y184S, F189L, W195R, D262G and L266H or a combination of any of these. In another example, the disclosure provide a CXCR4 binding polypeptide as described herein that binds to one or more residues of CXCR4 selected from the group consisting of C28, V112, D193, P191, E268 and E288 or combinations of any of these. In another example, the residue is selected from the group consisting of C28W, V112A, D193G, P191T, E268K and E288G or a combination of any of these. The amino acid residues being substituted are numbered according to the canonical sequence of human CXCR4 having Uniprot sequence identifier number P61073-1 (SEQ ID NO: 105).

The CXCR4 binding polypeptides contact the same residues that have been shown to be responsible for the binding of small molecules such as AMD3100 indicating that the CXCR4 binding polypeptides can penetrate deep into the CXCR4 binding pocket. In a particular example, the polypeptide binds to the D262 position of CXCR4.

The polypeptide of the present disclosure can generally be used to modulate CXCR4 mediated signalling, and/or to modulate the biological pathways in which CXCR4 is involved, and/or to modulate the biological mechanisms, responses and effects associated with such signalling or these pathways.

In one example, the polypeptide can be used to modulate (i.e. inhibit, prevent, stimulate or boost) one or more of the following activities:
  (i) calcium flux in cells expressing CXCR4;
  (ii) cAMP in cells expressing CXCR4;
  (iii) β-arrestin signalling in cells expressing CXCR4;
  (iv) apoptosis in cells expressing CXCR4;
  (v) cell proliferation of cells expressing CXCR4;
  (vi) metastasis of cells expressing CXCR4;
  (vii) CXCR4 induced angiogenesis; and
  (viii) migration of cells expressing CXCR4.

In one example, tumor cell proliferation may be increased or decreased by at least 30% preferably at least 50% or at least 60%, or 70% or 75%, or 80% or 90% or more, compared to the differentiation and or proliferation of tumor cells under the same condition without the presence of the polypeptide.

In one example, the polypeptide can be used to inhibit tumor cell proliferation in a tumor cell proliferation assay with an $IC_{50}$ of less than 600 nM, less than 500 nM, less than 200 nM, less than 100 nM, less than 50 nM, less than 25 nM, less that 10 nM or less than 5 nM. In one example, the tumor cell proliferation assay is a 5-bromo-2'-deoxyuridine cell proliferation or CTG (CellTiter-Glo®) assay. In another example, the inhibition of tumor cell proliferation is determined by way of MTT assay.

In one example, induction of apoptosis in cells expressing CXCR4 by the polypeptide of the present disclosure can be measured by caspase assay, tunnel and DNA fragmentation assay, cell permeability assay, annexin V assay, protein cleavage assay and mitochondrial and ATP/ADP assay. Such assays will be familiar to persons skilled in the art.

In one example, the polypeptide of the present disclosure can be used inhibit metastases of CXCR4⁺ tumor cells, for example in a metastatic breast cancer model with cells expressing CXCR4, for example MDA-MB-231 or MDA-MB-468 cells.

Accordingly, the present disclosure also provides a method of inhibiting metastasis of a cancer cell expressing CXCR4.

In one example, the polypeptide of present disclosure can be used to inhibit SDF-1 induced migration of cells expressing CXCR4, for example in CEM, MDA-MB-231, MDA-MB-468, PC3 and Ramos cells.

In one example, the polypeptide of the present disclosure can be used to inhibit angiogenesis, which can be measured in a capillary tube formation assay, for example with HUVEC cells or MDA-MB-231 cells.

In one example, the polypeptide of the present disclosure is used in the treatment or prevention of a CXCR4-related disease or disorder in a subject.

The human CXCR4 to which the polypeptide binds may be in monomeric, dimeric or multimeric form. For example, the human CXCR4 may be in the form of a heterodimer. Examples of CXCR heterodimers that have been described include CXCR4/CXCR7 (Levoye et al Blood 2009 113; 6085-6093), CXCR4/CCR2 (Sohy et al J Biol Chem. 2007 282; 30062-30069), CXCR4/β2AR (β2 adrenergic receptor) (La Rocca et al J Cardiovasc Pharmacol. 2010 56; 548-559), CXCR4/CCR5 (Sohy et al J Biol Chem. 2009 284; 31270-31279), CXCR4/DOR (Delta opiod receptor) (Pello et al Eur. J. Immunol. 2008 38; 537-549). CXCR4 has also been shown to interact with the T cell receptor (Kremer et al J. Immunol. 2011 187; 1440-1447). These dimers can modulate the SDF-1 induced signaling outcomes and the i-body antagonists described may also alter the signaling consequences as compared to the CXCR4 as a monomer.

In one example, the polypeptide of the present disclosure binds to a transmembrane or other domain which influences the structure of CXCR4.

In another example, the polypeptide of the present disclosure specifically binds to any suitable extracellular part, region, domain, loop or extracellular epitope of CXCR4. In one example, the polypeptide specifically binds to one of the extracellular parts of the transmembrane domains or to one of the extracellular loops that links the transmembrane domains.

In another example the polypeptide of the disclosure is PEGylated.

The present disclosure also provides a nucleic acid molecule encoding a polypeptide described herein.

In one example the nucleic acid molecule comprises a sequence that has at least 80% identity, at least 90% identity, or at least 95% identity, or at least 97% identity, or at least 98% identity, or at least 99% identity, or 100% identity to any one of SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 43, SEQ ID NO: 47, SEQ ID NO: 51, SEQ ID NO: 55, SEQ ID NO: 59, SEQ ID NO: 63, SEQ ID NO: 67, SEQ ID NO: 71, SEQ ID NO: 75, or SEQ ID NO: 79.

In one example the nucleic acid molecule comprises a sequence that has at least 80% homology, at least 90% homology, or at least 95% homology, or at least 97% homology, or at least 98% homology, or at least 99% homology, or 100% homology to any one of SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 43, SEQ ID NO: 47, SEQ ID NO: 51, SEQ ID NO: 55, SEQ ID NO: 59, SEQ ID NO: 63, SEQ ID NO: 67, SEQ ID NO: 71, SEQ ID NO: 75, or SEQ ID NO: 79.

In one example, the nucleic acid molecule encodes a polypeptide selected from the group consisting of SEQ ID NO: 40, SEQ ID NO: 44, SEQ ID NO: 48, SEQ ID NO: 52, SEQ ID NO: 56, SEQ ID NO: 60, SEQ ID NO: 64, SEQ ID NO: 68, SEQ ID NO: 72, or SEQ ID NO: 76.

The present disclosure also provides an expression construct comprising a nucleic acid molecule described herein.

The present disclosure also provides a host cell comprising the nucleic acid molecule or expression construct described herein.

The present disclosure also provides a method of producing a polypeptide of the present disclosure which comprises culturing a host cell under conditions enabling expression of the polypeptide and recovering the polypeptide.

The present disclosure also provides a conjugate (e.g. immunoconjugate) comprising a polypeptide described herein and an agent.

The agent may be, for example, a therapeutic agent, a toxin, a detectable label or an agent which extends the half life of the polypeptide. In one example, the agent is polyethylene glycol (PEG). In another example, the agent is a consecutive sequence of Pro-Ala-Ser (PAS).

In one example the agent which extends the half life of the polypeptide binds to a serum protein (e.g. albumin) or an Fc portion of an immunoglobulin.

In another example the polypeptide of the invention may be linked to a toxin or cytotoxic drug for delivery to cells such as tumour cells.

In another example the polypeptide of the invention may be linked to a label such as a radioisotope.

The present disclosure also provides a multimer comprising two or more polypeptides described herein. The polypeptides may comprise the same or different amino acid sequences. For example, in its simplest form, at least two polypeptides are directly linked via a suitable linker or sequence or spacer. For example, the linker or spacer can be between 1 and 50 amino acids. For example, a suitable linker is a GS9 linker or GS15 linker or a GS20 linker.

The present disclosure also provides for multivalent or multispecific polypeptides (including bi-specific polypeptides). In one example the disclosure provides a polypeptide of the present disclosure linked to a polypeptide directed to a target other than CXCR4, including by not limited to, human serum albumin to increase half-life, CD3, CD64, CD16 or CD89 to redirect and activate any circulating T cells against tumors. In a particular example, the multispecific polypeptide is a bi-specific polypeptide which binds to CXCR4 and human serum albumin (HSA), the polypeptide comprising the sequence of SEQ ID NO:80.

The present disclosure also provides a pharmaceutical composition comprising a polypeptide or a conjugate or a multimer as described herein and an acceptable carrier.

The present disclosure also provides a polypeptide, a conjugate or a multimer according to the present disclosure for use in the treatment or prevention of a CXCR4-related disease or disorder, the polypeptide comprising a sequence selected from the group consisting of SEQ ID NO: 11, SEQ ID NO:14, SEQ ID NO:17, SEQ ID NO:20, SEQ ID NO:23, SEQ ID NO:26, SEQ ID NO:29, SEQ ID NO: 40, SEQ ID NO: 44, SEQ ID NO: 48, SEQ ID NO: 52, SEQ ID NO: 56, SEQ ID NO: 60, SEQ ID NO: 64, SEQ ID NO: 68, SEQ ID NO: 72, or SEQ ID NO: 76.

In one example the polypeptide of the present disclosure binds specifically to human CXCR4.

The present disclosure also provides a method of preventing or treating a CXCR4-related disease or disorder or a disease or disorder associated with CXCR4 signalling or a pathway or mechanism in which CXCR4 is involved, comprising administering to a subject in need thereof a polypeptide or a conjugate or a multimer of the present disclosure.

In one example, the polypeptide comprises a sequence selected from the group consisting of SEQ ID NO: 11, SEQ ID NO:14, SEQ ID NO:17, SEQ ID NO:20, SEQ ID NO:23, SEQ ID NO:26, SEQ ID NO:29, SEQ ID NO: 40, SEQ ID NO: 44, SEQ ID NO: 48, SEQ ID NO: 52, SEQ ID NO: 56, SEQ ID NO: 60, SEQ ID NO: 64, SEQ ID NO: 68, SEQ ID NO: 72, or SEQ ID NO: 76.

Diseases or disorders amenable to treatment with the polypeptide, nucleic acid molecule, conjugate or multimer of the present disclosure include cancers (for example, hematopoietic cancers: CLL, AML, ALL, MM, NHL; solid tumors: breast cancer, lung cancer, brain tumors; stromal chemoresistance of tumors; leukemia and other cancers), viral infections (e.g. HIV/AIDS, West Nile Virus encephalitis), inflammatory disease (e.g. rheumatoid arthritis, asthma, systemic lupus erythematosus; neuro-inflammatory diseases), fibrosis, for example, lung (pulmonary fibrosis), systemic sclerosis, kidney disease (diabetic nephropathy, FSGS as examples), liver, eye (uveitis, AMD, diabetic retinopathy); immune deficiency disorders; multiple sclerosis, and stroke. Tissue and wound healing including scarring, burns, or radiation induced burns.

In one particular example, the CXCR4-related disease or disorder is fibrosis. In a further example, the disorder is idiopathic pulmonary fibrosis (IPF). In another particular example, the CXCR4-related disease or disorder is kidney disease.

In another example, the CXCR4-related disease or disorder is multiple sclerosis.

In another example, the CXCR4-related disease or disorder is atherosclerosis.

In another example, the CXCR4-related disease or disorder is HIV.

The polypeptide of the present disclosure may or may not cause stem cell mobilisation. In one example, the present disclosure also provides a method for peripheral blood stem cell mobilisation, comprising administering to a subject in need thereof a polypeptide, nucleic acid molecule, conjugate or multimer of the present disclosure. In one example, the peripheral blood stem cells are used for autologous stem cell transplantation. In one example, the subject in need thereof has multiple myeloma, acute myeloid leukemia or non-Hodgkin's lymphoma. In a further example, the stem cells are CD34+ cells.

In general, antibodies directed to CXCR4 have been shown to mobilise stem cells which is not desirable for a therapeutic approach in some indications. The polypeptides of the present disclosure do not substantially cause stem cell mobilisation. In one example, mobilisation of stem cells is reduced by a polypeptide of the present disclosure by at least 50%, at least 60%, at least 70%, at least 80% or at least 90% compared to the control AMD3100.

In another example, the polypeptide does not substantially inhibit calcium flux.

The present disclosure also provides a functional fragment of a CXCR4 binding polypeptide described herein. In one example, the functional fragment comprises the CDR3 sequence of a CXCR4 binding molecule described herein. By "functional fragment" we mean a fragment which binds to human CXCR4 with an affinity which is substantially similar or improved when compared to the full length polypeptide from which it is derived, and which inhibits or prevents CXCR4 mediated signalling. Preferably, the fragment binds to one or more core residues of human CXCR4 selected from the group consisting of E32, Y184, F189, W195, D262 and L266 or combinations of any of these.

In a further example, the functional fragment comprises a sequence selected from the group consisting of SEQ ID NO: 13, SEQ ID NO: 16, SEQ ID NO: 19, SEQ ID NO: 22, SEQ ID NO: 25, SEQ ID NO: 28, SEQ ID NO: 31, SEQ ID NO: 42, SEQ ID NO: 46, SEQ ID NO: 50, SEQ ID NO: 54, SEQ ID NO: 58, SEQ ID NO: 62, SEQ ID NO: 66, SEQ ID NO: 70, SEQ ID NO: 74, or SEQ ID NO: 78.

The present disclosure further provides a peptide mimetic based on a CXCR4 binding polypeptide described herein or a portion thereof, such as a CDR3 sequence of a CXCR4 binding polypeptide described herein. The peptide mimetic may be based on, or derived from a sequence selected from the group consisting of SEQ ID NO: 13, SEQ ID NO: 16, SEQ ID NO: 19, SEQ ID NO: 22, SEQ ID NO: 25, SEQ ID NO: 28, SEQ ID NO: 31, SEQ ID NO: 42, SEQ ID NO: 46, SEQ ID NO: 50, SEQ ID NO: 54, SEQ ID NO: 58, SEQ ID NO: 62, SEQ ID NO: 66, SEQ ID NO: 70, SEQ ID NO: 74, or SEQ ID NO: 78. The present disclosure also contemplates compositions comprising one or more mimetic peptides for use in treating a CXCR4 related disease or disorder, in particular a CXCR4 related disease or disorder described herein.

The present disclosure additionally provides the polypeptide or the nucleic acid or the expression construct, or the cell or the composition of the present disclosure for use in the treatment or prophylaxis of a CXCR4-related disease or disorder.

The present disclosure additionally provides for use of the polypeptide or the nucleic acid or the expression construct or the cell or the composition of the present disclosure in medicine.

The present disclosure also provides use of a polypeptide or the nucleic acid or the expression construct or the cell or the composition of the present disclosure for the treatment or prophylaxis of a CXCR4-related disease or disorder.

In one particular example, the CXCR4-related disease or disorder is fibrosis. In another particular example, the CXCR4-related disease or disorder is lung fibrosis. In another example it is liver fibrosis. In another example it is a fibrosis related condition of the eye. In another example it is skin fibrosis. In yet another example it is kidney fibrosis.

The present disclosure additionally provides for use of the polypeptide or the nucleic acid or the expression construct or the cell of the present disclosure in the manufacture of a medicament for the treatment or prophylaxis of a CXCR4-related disease or condition.

The polypeptide of the present disclosure can also be used in a diagnostic format.

The present disclosure therefore additionally provides a method for detecting CXCR4 in a sample obtained from a subject, the method comprising contacting a sample with the polypeptide of the disclosure such that a CXCR4-polypeptide complex forms and detecting the complex, wherein detecting the complex is indicative of CXCR4 in the sample. In one example, the sample is from a subject suffering from CXCR4-related disease or condition. In a further example, the sample is a biological sample.

The present disclosure also provides a method for detecting a complex of CXCR4 binding polypeptide bound to human CXCR4 in a subject or in a sample obtained from a subject, the method comprising allowing said complex to form and detecting the formed complex. In one example, the human CXCR4 may be a dimer, trimer or multimer. Methods of detecting forming complexes will be familiar to persons skilled in the art. Examples include western blot analysis or surface plasmon resonance (biacore). Alternatively, fluorescent based methods may be used where the formation of the complex results in a fluorescently detectable signal being produced which may or may not be quantified.

The present disclosure also provides a complex of a CXCR4 binding polypeptide of the disclosure bound to human CXCR4. The human CXCR4 portion of the complex may be in the form of a dimer, trimer or multimer.

The present disclosure additionally provides a method for diagnosing a CXCR4-related disease or disorder in a subject, the method comprising performing the method described herein for detecting CXCR4 in a sample from the subject, wherein detection of CXCR4 in the sample is indicative of the disease or disorder.

In one example, the method comprises determining the level of CXCR4 in the sample, wherein an increased or decreased level of CXCR4 in the sample compared to a control sample is indicative of the disease or disorder.

The present disclosure additionally provides a method for localizing and/or detecting and/or diagnosing and/or prognosing a CXCR4-related disease or disorder, the method comprising detecting in vivo the polypeptide of the present disclosure bound to CXCR4, if present, wherein the polypeptide is conjugated to a detectable tag.

In one example, the method additionally comprises administering the polypeptide to the subject.

In one example of any method of treatment/prophylaxis/diagnosis/prognosis described herein the CXCR4 related disease or disorder is a cancer, viral infection (e.g. HIV), inflammatory disease, neuro-inflammatory diseases; fibrosis, immune deficiency disorder; multiple sclerosis, hot flash or stroke. In a further example, the CXCR4 related disease or disorder is fibrosis, cancer or inflammation.

The term "subject" according to the present disclosure is intended to include human and non-human animals. Non-human animals include all vertebrates, e.g., mammals and non-mammals, such as non-human primates, sheep, dogs, cats, cows, horses, chickens, amphibians, and reptiles.

BRIEF DESCRIPTION OF THE FIGURES

FIGS. 2-1 and 2-2 show surface plasmon resonance (SPR; Biacore) affinities for (A) ADCX-306 (22.5 uM), (B) ADCX-272 (1.6 uM), and (C) ADCX-668 (42 uM).

FIGS. 3-1 to 3-3 shows β-arrestin activity for ADCX-99 (with Flag, Histidine (FH) and with IM7-FH protein tag), ADCX-6, ADCX-306, ADCX-668 and ADCX-272 at various concentrations as indicated. All i-bodies demonstrated some degree of inhibition of β-arrestin.

FIGS. 7-1 and 7-2 show 90 individual i-bodies from the affinity-matured mutant library of i-body ADCX-99. The affinity matured i-bodies were tested for binding to CXCR4 positive lipoparticles (A) and to CCR5 positive lipoparticles (B). Binding of the affinity matured i-bodies to CXCR4 and CCR5 positive lipoparticles is compared to binding of the wild-type i-body ADCX-99 (last two columns) and to the positive control i-body ADCX-272, and negative control i-body ADR-3.

FIGS. 16-1 to 16-3 show binding affinity as determined by flow cytometry of i-body AM3-114 to various cell lines that do not express CXCR4 T47D (A), and that express CXCR4 at various levels, including: Namalwa (B), MOLP8 (C), MOLT4 (D), Jurkat (E), CCRF-CEM (F), A498 (G), Ramos (H), NCI-H69 (I) and HL-60 (J). All cell lines were tested with i-body concentrations of 10, 1 and 0.001 µM and in addition Namalwa cells (B) were tested with i-bodies at 4.7, 2.1, 0.47, 0.21, 0.1 and 0.01 µM.

FIGS. 19-1 and 19-2 show CXCR4 i-body induced apoptosis of Ramos cells. AM3-114 (AD-114), AM4-272 (AD-272), AM3-523 (AD-523) i-bodies bound to Ramos cells and induced apoptosis as assessed by double staining of annexin V and propidium iodide (top left quadrant in each of the flow cytometry traces). Untreated cells acted a negative control and thapsigargin is a well-described inducer of apoptosis (19-1). Quantitation of the flow cytometry traces is shown in the graphical form (19-2).

FIGS. 23-1 and 23-2 show inhibition of HIV with PEGylated (30 KDa and 2×20 KDa PEG) and non-PEGylated CXCR4 i-bodies AM3-114 and AM4-746. CXCR4 i-bodies block infection of three strains of HIV in a dose-dependent manner (A). The CXCR4 i-bodies are unable to block infection of a CCR5 dependent strain of HIV (B).

FIGS. 31-1 to 31-3 show the effect of i-bodies (AM3-114, AM4-272, AM3-523), CXCR4 small molecule antagonist AMD3100 and negative control i-body 21H5 in inhibiting human IPF lung fibroblast invasion. Relative wound densities (%) of IPF lung fibroblast lines in the presence of i-bodies. Fibroblasts from normal lung (A), from slow IPF progressor (B) and from a rapid IPF progressor (C). Arrows indicate i-body AM3-114 which specifically inhibited migration of IPF lung fibroblasts (B and C), i-body AM4-272 inhibited fast progressor fibroblasts (C) but neither i-body had any effect on normal lung fibroblasts (A). AMD3100 and the negative control i-body 21H5 had no effect on any of these cell lines.

KEY TO SEQUENCE LISTING

Figure 2:
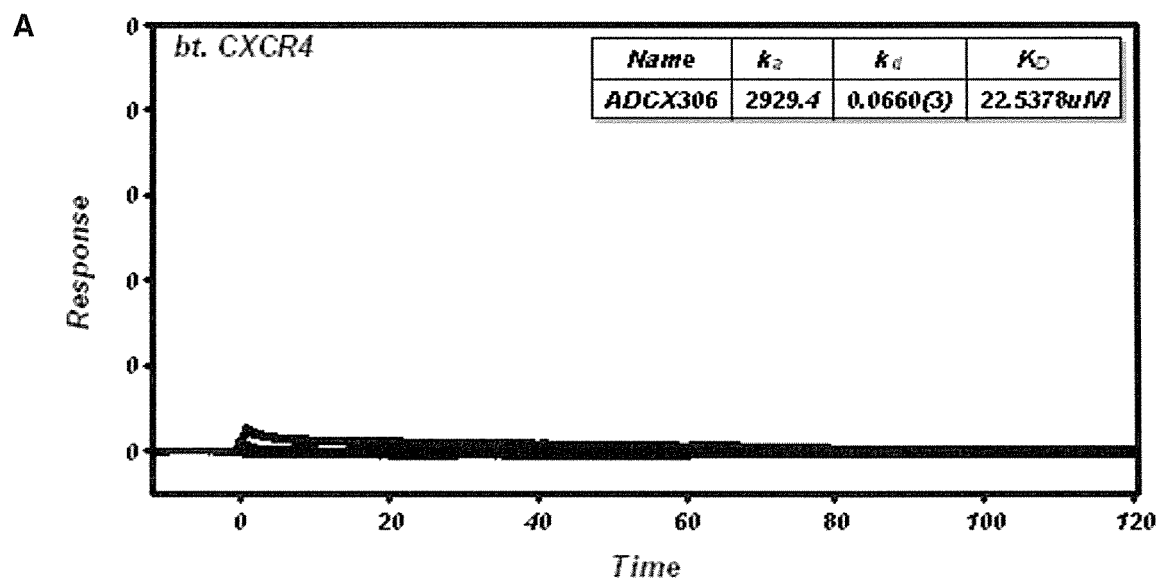

SEQ ID NO 1: amino acid sequence encoding *Homo sapiens* NCAM domain 1
SEQ ID NO: 2 amino acid sequence encoding i-body scaffold.
SEQ ID NO: 3 amino acid sequence encoding *Bos taurus* NCAM domain 1
SEQ ID NO: 4 amino acid sequence encoding *Mus musculus* NCAM domain 1
SEQ ID NO: 5 amino acid sequence encoding *Rat rattus* NCAM domain 1
SEQ ID NO: 6 amino acid sequence encoding *Gallus gallus* NCAM domain 1
SEQ ID NO: 7 amino acid sequence encoding *Xenopus laevis* NCAM2 domain 1
SEQ ID NO: 8 amino acid sequence encoding *Xenopus laevis* NCAM1 domain 1
SEQ ID NO: 9 amino acid sequence encoding *Homo sapiens* NCAM2 domain 1
SEQ ID NO: 10 amino acid sequence encoding *Mus musculus* NCAM2 domain 1
SEQ ID NO: 11 amino acid sequence encoding ADCX-99
SEQ ID NO: 12 amino acid sequence encoding ADCX-99 CDR1
SEQ ID NO: 13 amino acid sequence encoding ADCX-99 CDR3
SEQ ID NO: 14 amino acid sequence encoding ADCX-272
SEQ ID NO: 15 amino acid sequence encoding ADCX-272 CDR1
SEQ ID NO: 16 amino acid sequence encoding ADCX-272 CDR3
SEQ ID NO: 17 amino acid sequence encoding ADCX-6
SEQ ID NO: 18 amino acid sequence encoding ADCX-6 CDR1
SEQ ID NO: 19 amino acid sequence encoding ADCX-6 CDR3
SEQ ID NO: 20 amino acid sequence encoding ADCX-54
SEQ ID NO: 21 amino acid sequence encoding ADCX-54 CDR1
SEQ ID NO: 22 amino acid sequence encoding ADCX-54 CDR3
SEQ ID NO: 23 amino acid sequence encoding ADCX-LS
SEQ ID NO: 24 amino acid sequence encoding ADCX-LS CDR1
SEQ ID NO: 25 amino acid sequence encoding ADCX-LS CDR3
SEQ ID NO: 26 amino acid sequence encoding ADCX-668
SEQ ID NO: 27 amino acid sequence encoding ADCX-668 CDR1
SEQ ID NO: 28 amino acid sequence encoding ADCX-668 CDR3
SEQ ID NO: 29 amino acid sequence encoding ADCX-306

SEQ ID NO: 30 amino acid sequence encoding ADCX-306 CDR1
SEQ ID NO: 31 amino acid sequence encoding ADCX-306 CDR3
SEQ ID NO: 32 nucleotide sequence encoding ADCX-99
SEQ ID NO: 33 nucleotide sequence encoding ADCX-272
SEQ ID NO: 34 nucleotide sequence encoding ADCX-6
SEQ ID NO: 35 nucleotide sequence encoding ADCX-54
SEQ ID NO: 36 nucleotide sequence encoding ADCX-LS
SEQ ID NO: 37 nucleotide sequence encoding ADCX-668
SEQ ID NO: 38 nucleotide sequence encoding ADCX-306
SEQ ID NO: 39 consensus amino acid sequence of affinity matured i-bodies.
SEQ ID NO: 40 amino acid sequence encoding AM3-114
SEQ ID NO: 41 amino acid sequence encoding AM3-114 CDR1
SEQ ID NO: 42 amino acid sequence encoding AM3-114 CDR3
SEQ ID NO: 43 nucleotide sequence encoding AM3-114
SEQ ID NO: 44 amino acid sequence encoding AM3-920
SEQ ID NO: 45 amino acid sequence encoding AM3-920 CDR1
SEQ ID NO: 46 amino acid sequence encoding AM3-920 CDR3
SEQ ID NO: 47 nucleotide sequence encoding AM3-920
SEQ ID NO: 48 amino acid sequence encoding AM4-1121
SEQ ID NO: 49 amino acid sequence encoding AM4-1121 CDR1
SEQ ID NO: 50 amino acid sequence encoding AM4-1121 CDR3
SEQ ID NO: 51 nucleotide sequence encoding AM4-1121
SEQ ID NO: 52 amino acid sequence encoding AM4-613
SEQ ID NO: 53 amino acid sequence encoding AM4-613 CDR1
SEQ ID NO: 54 amino acid sequence encoding AM4-613 CDR3
SEQ ID NO: 55 nucleotide sequence encoding AM4-613
SEQ ID NO: 56 amino acid sequence encoding AM3-523
SEQ ID NO: 57 amino acid sequence encoding AM3-523 CDR1
SEQ ID NO: 58 amino acid sequence encoding AM3-523 CDR3
SEQ ID NO: 59 nucleotide sequence encoding AM3-523
SEQ ID NO: 60 amino acid sequence encoding AM4-661
SEQ ID NO: 61 amino acid sequence encoding AM4-661 CDR1
SEQ ID NO: 62 amino acid sequence encoding AM4-661 CDR3
SEQ ID NO: 63 nucleotide sequence encoding AM4-661
SEQ ID NO: 64 amino acid sequence encoding AM3-466
SEQ ID NO: 65 amino acid sequence encoding AM3-466 CDR1
SEQ ID NO: 66 amino acid sequence encoding AM3-466 CDR3
SEQ ID NO: 67 nucleotide sequence encoding AM3-466
SEQ ID NO: 68 amino acid sequence encoding AM5-245
SEQ ID NO: 69 amino acid sequence encoding AM5-245 CDR1
SEQ ID NO: 70 amino acid sequence encoding AM5-245 CDR3
SEQ ID NO: 71 nucleotide sequence encoding AM5-245
SEQ ID NO: 72 amino acid sequence encoding AM4-272
SEQ ID NO: 73 amino acid sequence encoding AM4-272 CDR1
SEQ ID NO: 74 amino acid sequence encoding AM4-272 CDR3
SEQ ID NO: 75 nucleotide sequence encoding AM4-272
SEQ ID NO: 76 amino acid sequence encoding AM4-746
SEQ ID NO: 77 amino acid sequence encoding AM4-746 CDR1
SEQ ID NO: 78 amino acid sequence encoding AM4-746 CDR3
SEQ ID NO: 79 nucleotide sequence encoding AM4-746
SEQ ID NO: 80 amino acid sequence encoding AM3-114-Im7-FH-SA21 dual specificity i-body
SEQ ID NO:81 nucleotide sequence encoding AM3-114-Im7-FH-SA21 dual specificity i-body
SEQ ID NO:82 amino acid sequence encoding 21H5 i-body
SEQ ID NO:83 amino acid sequence encoding AM4-774 CDR1
SEQ ID NO:84 amino acid sequence encoding AM4-774 CDR3
SEQ ID NO:85 amino acid sequence encoding AM4-208 CDR1
SEQ ID NO:86 amino acid sequence encoding AM4-208 CDR3
SEQ ID NO:87 amino acid sequence encoding AM4-1088 CDR1
SEQ ID NO:88 amino acid sequence encoding AM4-1088 CDR3
SEQ ID NO:89 amino acid sequence encoding AM4-239 CDR1
SEQ ID NO:90 amino acid sequence encoding AM4-239 CDR3
SEQ ID NO:91 amino acid sequence encoding AM3-32 CDR1
SEQ ID NO:92 amino acid sequence encoding AM3-32 CDR3
SEQ ID NO:93 amino acid sequence encoding AM4-757 CDR1
SEQ ID NO:94 amino acid sequence encoding AM4-757 CDR3
SEQ ID NO:95 amino acid sequence encoding AM4-386 CDR1
SEQ ID NO:96 amino acid sequence encoding AM4-386 CDR3
SEQ ID NO:97 amino acid sequence encoding AM4-352 CDR1
SEQ ID NO:98 amino acid sequence encoding AM4-352 CDR3
SEQ ID NO:99 amino acid sequence encoding AM3-182 CDR1
SEQ ID NO:100 amino acid sequence encoding AM3-182 CDR3
SEQ ID NO:101 amino acid sequence encoding AM4-203 CDR1
SEQ ID NO:102 amino acid sequence encoding AM4-203 CDR3
SEQ ID NO:103 amino acid sequence encoding AM5-95 CDR1
SEQ ID NO:104 amino acid sequence encoding AM5-95 CDR3
SEQ ID NO:105 amino acid sequence encoding human CXCR4

DETAILED DESCRIPTION

General

The term "and/or", e.g., "X and/or Y" shall be understood to mean either "X and Y" or "X or Y" and shall be taken to provide explicit support for both meanings or for either meaning.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present disclosure is not to be limited in scope by the specific embodiments described herein, which are intended for the purpose of exemplification only. Functionally-equivalent products, compositions and methods are clearly within the scope of the disclosure, as described herein.

Any example herein shall be taken to apply mutatis mutandis to any other example unless specifically stated otherwise.

Selected Definitions

The term "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein, the term "affinity" refers to the strength of binding of a single molecule to its ligands and is typically expressed as the equilibrium dissociation constant ($K_D$) for the reversible binding of two agents. It is determined by the ratio of $K_{off}/K_{on}$, between the i-body or CXCR4 binding polypeptide of the present disclosure and CXCR4. $K_D$ and affinity are inversely related. The $K_D$ value relates to the concentration of i-body or CXCR4 binding polypeptide and so the lower the KD value (lower concentration), the higher the affinity of the antibody. Affinity of an i-body or CXCR4 binding polypeptide of the present disclosure to CXCR4 can be, for example, from about 100 nanomolar (nM) to about 0.1 nM, from about 100 nM to about 1 picomolar (pM), or from about 100 nM to about 1 femtomolar (fM) or more.

As used herein, the term "binds" in reference to the interaction of a CXCR4 binding molecule or polypeptide with a target means that the interaction is dependent upon the presence of a particular structure (e.g., an antigenic determinant or epitope) on the target. For example, a CXCR4 binding molecule or polypeptide recognizes and binds to a specific protein structure rather than to proteins generally.

As used herein, the term "conservative amino acid substitution" refers to grouping of amino acids on the basis of certain common properties. A functional way to define common properties between individual amino acids is to analyse the normalised frequencies of amino acid changes between corresponding proteins of homologous organisms. According to such analysis, groups of amino acids may be defined where amino acids within a group exchange preferentially with each other, and therefore resemble each other most in their impact on the overall protein structure (Schulz G E and RH Schirmer, Principles of Protein Structure, Springer-Verlag). Examples of amino acid groups defined in this manner include:

(i) charged groups, consisting of Glu, Asp, Lys, Arg and His,
(ii) aromatic groups consisting of Phe, Tyr and Trp,
(iii) nitrogen ring group consisting of His and Trp,
(iv) slightly polar group consisting of Met and Cys etc.

As used herein, the term "CXCR4-related disease or condition" shall be taken to mean disease and disorders that can be prevented and/or treated, respectively, by suitably administering to a subject in need thereof (i.e. having the disease or disorder or at least one symptom thereof and/or at risk of attracting or developing the disease or disorder) of either a CXCR4 binding molecule or a polypeptide or composition of the present disclosure and/or of a known active principle active against CXCR4 or a biological pathway or mechanism in which CXCR4 is involved. The term CXCR4 related disease or condition also includes CXCR4-mediated diseases or disorders.

As used herein, the term "homology" describes a mathematically based comparison of sequence similarities which is used to identify genes or proteins with similar functions or motifs. The polypeptide sequences of the present disclosure may be used as a "query sequence" to perform a search against public databases to, for example, identify other family members, related sequences or homologs. Such searches can be performed using BLAST programs (Altschul et al (1990) J. Mo. Biol. 215:403-10). To obtain gapped alignments for comparison purposes, Gapped BLAST can be utilised a described in Altschul et al (1997) Nuc Acids Res. 25(17):3389-3402.

As used herein, the term "identity" means the percentage of identical nucleotide or amino acid residues at corresponding portions in two or more sequences when sequences are aligned to maximise sequence matching, i.e. taking into account gaps and insertions. Identity can be readily calculated using known methods, including, but not limited to those described in Computational Molecular Biology, Lesk A M ed. Oxford University Press New York, 1988; Computer Analysis of Sequence data, Part I Griffin A M and Griffin H G eds., Humana Press, New Jersey, 1994; Sequence analysis in molecular biology, von Heinje G, Academic Press, New Jersey, 1994). Methods to determine identity are designed to give the largest match between the sequences tested. Moreover, methods to determined identity are codified in publicly available computer programs. Computer program methods to determine identity between two sequence include, but are not limited to, the GCG program package, BLASTP, BLASTN and FASTA. The well known Smith Waterman algorithm may also be used to determine identity.

As used herein, the terms "treating", "treat" or "treatment" include administering a therapeutically effective amount of the polypeptide, nucleic acid molecule, conjugate or multimer of the present disclosure sufficient to reduce or eliminate at least one symptom of a specified disorder. In one example, the treatment involves administering a therapeutically effective amount of the polypeptide, nucleic acid molecule, conjugate or multimer to treat or prevent a CXCR4-related disease or disorder. In one example, treatment also refers to prophylactic treatment.

As used herein, the terms "preventing", "prevent" or "prevention" include administering a therapeutically effective amount of the polypeptide, nucleic acid molecule, conjugate or multimer of the present disclosure sufficient to stop or hinder the development of at least one symptom of a specified disorder.

As used herein, the term "specifically binds" or "binds specifically" shall be taken to mean a CXCR4 binding molecule or polypeptide of the disclosure reacts or associates more frequently, more rapidly, with greater duration and/or with greater affinity with a particular target or cell expressing CXCR4 than it does with alternative targets or cells. More particularly, the CXCR4 binding molecule or polypeptide binds with greater affinity to a target or cell expressing CXCR4 than it does to other chemokine receptors, for example CCR5, CXCR7 or CCR7. For example, a CXCR4 binding molecule or polypeptide that specifically binds to a target binds that target with greater affinity (e.g. 2 fold, 10 fold, 20 fold or 40 fold or 60 fold or 80 fold to 100 fold or 150 fold or 200 fold greater affinity), avidity, more readily, and/or with greater duration than it binds to other GPCRs, e.g., to other GPCRs that are similar in structure or sequence. A polypeptide which binds specifically to CXCR4 may demonstrate some cross-reactivity with other chemokine receptors or affinity related molecules but only to the extent that such cross-reactivity does not substantially modulate a biological mechanism response or effect of CXCR4 binding.

As used herein, reference to a "similar" level of binding will be understood to mean that a CXCR4 binding molecule or polypeptide binds to a target at a level within about 30% or 25% or 20% of the level at which it binds to another target. This term can also mean that one binding molecule or polypeptide binds to a target at a level within about 30% or 25% or 20% of the level at which another binding molecule or polypeptide binds to the same target.

The term "substantially" as used herein in the context of binding, refers to a polypeptide that binds to CXCR4 at a level within about 15%, or 10% or 5% of the level at which it binds to another target. This term can also mean that one binding molecule or polypeptide binds to a target at a level within about 5% or 4% or 3% of the level at which another binding molecule or polypeptide binds to the same target.

The term "random loop sequence" as used herein refers to a portion of a peptide sequence that extends either from or between a β-strand conformation or β-strand conformations of an intermediate (I-SET) domain. Loop regions are typically free of extended β-strand conformations. Loop region 4 is analogous to a conventional CDR1 loop. Loop region 8 is analogous to a conventional CDR3 loop.

As used herein, the term "complementarity determining regions" (syn. CDRs; i.e., CDR1, CDR2, and CDR3) refers to the amino acid residues within an immunoglobulin superfamily domain, the presence of which are major contributors to specific antigen binding.

The term "scaffold" or "i-body scaffold" as used herein is intended to refer to the sequence represented by the scaffold regions of the i-SET human NCAM1 Immunoglobulin (Ig) domain 1 (SEQ ID NO:1) defined by amino acids 1 to 26, 33 to 79 and 88 to 97.

The term "isolated" as used herein in the context of isolated polypeptide or isolated binding polypeptide refers to a protein or recombinant or synthetic origin or some combination thereof, which by virtue of its origin or source of derivation the protein is not associated with proteins found in nature, is free of other proteins from the same source, is expressed by a cell from a different species or does not occur in nature.

The term "therapeutically effective amount" refers to an amount of therapeutic agent that when administered alone or in combination with another therapeutic agent to a cell, tissue or subject is effective to prevent or ameliorate the disease condition or the progression of the disease.

The term "peptide mimetic" or "peptidomimetic" means a peptide-like molecule that is able to serve as a model for a peptide substrate upon which it is structurally based. Such peptidomimetics include chemically modified peptides, peptide-like molecules containing non-naturally occurring amino acids, and peptoids, which are peptide-like molecules resulting from oligomeric assembly of N-substituted glycines (see, for example, Goodman and Ro, Peptidomimetics for Drug Design, in BURGER'S MEDICINAL CHEMISTRY AND DRUG DISCOVERY Vol. 1 (ed. M. E. Wolff; John Wiley & Sons 1995), pages 803-861).

A variety of peptide mimetics are known in the art including, for example, peptide-like molecules which contain a constrained amino acid, a non-peptide component that mimics peptide secondary structure, or an amide bond isostere. A peptide mimetic that contains a constrained, non-naturally occurring amino acid can include, for example, an α-methylated amino acid; an α,α-dialkyl-glycine or α-aminocycloalkane carboxylic acid; an Nα-Cα cyclized amino acid; an Nα-methylated amino acid; a β- or γ-amino cycloalkane carboxylic acid; an α,β-unsaturated amino acid; a β,β-dimethyl or β-methyl amino acid; a β-substituted-2,3-methano amino acid; an NCδ or Cα-Cδ cyclized amino acid; or a substituted proline or another amino acid mimetic.

In addition, a peptide mimetic which mimics peptide secondary structure can contain, for example, a nonpeptidic β-turn mimic; γ-turn mimic; mimic of β-sheet structure; or mimic of helical structure, each of which is well known in the art. A peptide mimetic also can be a peptide-like molecule which contains, for example, an amide bond isostere such as a retro-inverso modification; reduced amide bond; methylenethioether or methylenesulfoxide bond; methylene ether bond; ethylene bond; thioamide bond; trans-olefin or fluoroolefin bond; 1,5-disubstituted tetrazole ring; ketomethylene or fluoroketomethylene bond or another amide isostere. One skilled in the art understands that these and other peptidomimetic components are encompassed within the meaning of the term "peptide imetic" as used herein. The term "polypeptide" or "peptide" shall include peptidomimetics unless expressly indicated otherwise.

I-Body Scaffold and CXCR4 Binding Molecules

The present disclosure provides a binding polypeptide (or "i-body"), which comprises a scaffold with modified CDR1 and CDR3 regions. In one example the scaffold region comprises Domain 1 of human NCAM1 as shown in SEQ ID NO:1 or a related domain sequence that has at least 45% identity thereto or at least 75% homology excluding CDR1 and CDR3 regions as highlighted.

NCAM (or Neural Cell Adhesion Molecule) is a glycoprotein of the I-SET domains or intermediate-set domains from the Immunoglobulin (Ig) superfamily. The extracellular domain of NCAM consists of five immunoglobulin-like (Ig) domains followed by two fibronectin type III (FNIII) domains.

Related domain sequences include SEQ ID NO's 3, 4, 5, 6 and 8 which show cow, mouse, rat, chicken and frog NCAM 1 domain sequences respectively and SEQ ID NO's 7, 9 and 10 which show frog, human and mouse NCAM 2 domain sequences respectively.

The sequence identity between these related domains is as follows:

| NCBI REF | Score | E value | | |
|---|---|---|---|---|
| P13591.3\|NCAM1_HUMAN RecName: NCAM | 200 | 5e-60 | Identity (100%) | SEQ ID NO: 1 |
| P31836.1\|NCAM1_BOVIN RecName: NCAM | 197 | 6e-59 | Identity (98%) | SEQ ID NO: 3 |
| P13595.3\|NCAM1_MOUSE RecName: NCAM | 195 | 2e-57 | Identity (95%) | SEQ ID NO: 4 |
| P13596.1\|NCAM1_RAT RecName: NCAM | 192 | 3e-57 | Identity (95%) | SEQ ID NO: 5 |
| P13590.3\|NCAM1_CHICK RecName: NCAM | 175 | 2e-50 | Identity (89%) | SEQ ID NO: 6 |
| P36335.1\|NCA12_XENLA RecName: NCAM | 130 | 1e-34 | Identity (68%) | SEQ ID NO: 7 |
| P16170.1\|NCA11_XENLA RecName: NCAM | 130 | 1e-34 | Identity (68%) | SEQ ID NO: 8 |
| O15394.2\|NCAM2_HUMAN RecName: NCAM | 87.8 | 8e-20 | Identity (51%) | SEQ ID NO: 9 |
| O35136.1\|NCAM2_MOUSE RecName: NCAM | 86.3 | 3e-19 | Identity (47%) | SEQ ID NO: 10 |

The sequence homology between these related domains is as follows:

| | |
|---|---|
| sp\|P13591.3\|NCAM1_HUMAN RecName: NCAM | Sequence homology (100%) SEQ ID NO: 1 |
| sp\|P31836.1\|NCAM1_BOVIN RecName: NCAM | Sequence homology (100%) SEQ ID NO: 3 |
| sp\|P13595.3\|NCAM1_MOUSE RecName: NCAM | Sequence homology (99%) SEQ ID NO: 4 |
| sp\|P13596.1\|NCAM1_RAT RecName: NCAM | Sequence homology (99%) SEQ ID NO: 5 |
| sp\|P13590.3\|NCAM1_CHICK RecName: NCAM | Sequence homology (98%) SEQ ID NO: 6 |
| sp\|P36335.1\|NCA12_XENLA RecName: NCAM | Sequence homology (89%) SEQ ID NO: 7 |
| sp\|P16170.1\|NCA11_XENLA RecName: NCAM | Sequence homology (89%) SEQ ID NO: 8 |
| sp\|O15394.2\|NCAM2_HUMAN RecName: NCAM | Sequence homology (74%) SEQ ID NO: 9 |
| sp\|O35136.1\|NCAM2_MOUSE RecName: NCAM | Sequence homology (74%) SEQ ID NO: 10 |

Domain 1 of human NCAM has been produced as a recombinant polypeptide in a bacterial expression system (Frei et al. (1992) *J. Cell Biol.* 118:177-194).

The present disclosure describes modifications introduced into an i-body scaffold in the CDR1 and/or CDR3 regions, which have been shown to alter the binding properties of the domain (or "i-body"). In particular, the inventors have developed modified i-body amino acids and polypeptides which surprisingly are able to bind to CXCR4 with high affinity and specificity and inhibit or reduce CXCR4-induced cell migration. In particular, the CXCR4 binding polypeptides or i-bodies of the present disclosure are useful in inhibiting cancer metastasis, anti-inflammatory and fibrosis related diseases.

Accordingly the present disclosure provides a number of polypeptides which bind to CXCR4 which comprise the i-body scaffold acid sequence, wherein the CDR1 or CDR3 region of the i-body scaffold have been modified and wherein the molecule binds to human CXCR4 with an affinity of less than 50 uM, less than 40 μM, less than 20 μM, less than 10 uM, less than 1 uM, less than 700 nM, less than 600 nM, less than 500 nM, less than 400 nM, less than 300 nM, less than 200 nM, less than 100 nM, less than 50 nM, less than 10 nM, or less than 5 nM or less than 1 nM.

In one embodiment the entire CDR1 and/or CDR3 regions of the polypeptide are replaced with a random loop sequence.

For example, the CDR1 loop region of the polypeptide may be replaced with a loop region having the sequence as shown in SEQ ID NO: 12, SEQ ID NO:15, SEQ ID NO:18, SEQ ID NO:21, SEQ ID NO:24, SEQ ID NO: 27, SEQ ID NO: 30, SEQ ID NO: 41, SEQ ID NO: 45, SEQ ID NO: 49, SEQ ID NO: 53, SEQ ID NO: 57, SEQ ID NO:61, SEQ ID NO:65, SEQ ID NO:69, SEQ ID NO:73, or SEQ ID NO:77 or a sequence having at least 50% identity thereto.

For example, the CDR1 loop region of the polypeptide may be replaced with a loop region having the sequence as shown in SEQ ID NO: 12, SEQ ID NO:15, SEQ ID NO:18, SEQ ID NO:21, SEQ ID NO:24, SEQ ID NO: 27, SEQ ID NO: 30, SEQ ID NO: 41, SEQ ID NO: 45, SEQ ID NO: 49, SEQ ID NO: 53, SEQ ID NO: 57, SEQ ID NO: 61, SEQ ID NO: 65, SEQ ID NO: 69, SEQ ID NO: 73, or SEQ ID NO: 77 or a sequence having at least 50% homology thereto.

In another example, the CDR3 loop region of the polypeptide may be replaced with a loop region having the sequence as shown in SEQ ID NO: 13, SEQ ID NO: 16, SEQ ID NO: 19, SEQ ID NO: 22, SEQ ID NO: 25, SEQ ID NO: 28, SEQ ID NO: 31, SEQ ID NO: 42, SEQ ID NO: 46, SEQ ID NO: 50, SEQ ID NO: 54, SEQ ID NO: 58, SEQ ID NO: 62, SEQ ID NO: 66, SEQ ID NO: 70, SEQ ID NO: 74, or SEQ ID NO: 78, a sequence having at least 70% identity thereto.

In another example, the CDR3 loop region of the polypeptide may be replaced with a loop region having the sequence as shown in SEQ ID NO: 13, SEQ ID NO: 16, SEQ ID NO: 19, SEQ ID NO: 22, SEQ ID NO: 25, SEQ ID NO: 28, SEQ ID NO: 31, SEQ ID NO: 42, SEQ ID NO: 46, SEQ ID NO: 50, SEQ ID NO: 54, SEQ ID NO: 58, SEQ ID NO: 62, SEQ ID NO: 66, SEQ ID NO:70, SEQ ID NO: 74, or SEQ ID NO: 78 a sequence having at least 70% homology thereto.

In one example the polypeptide comprises a sequence that has at least 80% identity, at least 90% identity, or at least 95% identity, or at least 97% identity, or at least 98% identity, or at least 99% identity to identity to SEQ ID NO: 11, SEQ ID NO: 14, SEQ ID NO: 17, SEQ ID NO: 20, SEQ ID NO: 23, SEQ ID NO: 26, SEQ ID NO: 29, SEQ ID NO: 40, SEQ ID NO: 44, SEQ ID NO: 48, SEQ ID NO: 52 or SEQ ID NO: 56, SEQ ID NO:60, SEQ ID NO: 64, SEQ ID NO: 68, SEQ ID NO: 72, or SEQ ID NO: 76.

In one example the polypeptide comprises a sequence that has at least 80% homology, at least 90% homology, or at least 95% homology, or at least 97% homology, or at least 98% homology, or at least 99% homology to SEQ ID NO: 11, SEQ ID NO: 14, SEQ ID NO: 17, SEQ ID NO: 20, SEQ ID NO: 23, SEQ ID NO: 26, SEQ ID NO: 29, SEQ ID NO: 40, SEQ ID NO: 44, SEQ ID NO: 48, SEQ ID NO: 52 or SEQ ID NO: 56, SEQ ID NO:60, SEQ ID NO: 64, SEQ ID NO: 68, SEQ ID NO: 72, or SEQ ID NO: 76.

In one example the polypeptide comprises or consists of SEQ ID NO: 11, SEQ ID NO: 14, SEQ ID NO: 17, SEQ ID NO: 20, SEQ ID NO: 23, SEQ ID NO: 26, SEQ ID NO: 29, SEQ ID NO: 40, SEQ ID NO: 44, SEQ ID NO: 48, SEQ ID NO: 52 or SEQ ID NO: 56, SEQ ID NO:60, SEQ ID NO: 64, SEQ ID NO: 68, SEQ ID NO: 72, or SEQ ID NO: 76.

In one example the polypeptide comprises or consists of SEQ ID NO: 11 comprising one, two, three, four, five, six, seven, eight, nine or ten amino acid substitutions.

In one example the polypeptide comprises or consists of SEQ ID NO: 11.

The present disclosure also provides a nucleic acid molecule encoding a polypeptide described herein.

In one example the nucleic acid molecule comprises a sequence that has at least 80% identity, at least 90% identity, or at least 95% identity, or at least 97% identity, or at least 98% identity, or at least 99% identity or 100% identity to any one of SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 43, SEQ ID NO: 47, SEQ ID NO: 51, SEQ ID NO: 55, SEQ ID NO: 59, SEQ ID NO: 63, SEQ ID NO: 67, SEQ ID NO: 71, SEQ ID NO: 75, or SEQ ID NO: 79.

In one example the nucleic acid molecule comprises a sequence that has at least 80% homology, at least 90% homology, or at least 95% homology, or at least 97% homology, or at least 98% homology, or at least 99% homology or 100% homology to any one of SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 43, SEQ ID NO: 47, SEQ ID NO: 51, SEQ ID NO: 55, SEQ ID NO: 59, SEQ ID NO: 63, SEQ ID NO: 67, SEQ ID NO: 71, SEQ ID NO: 75, or SEQ ID NO: 79.

The % identity of a polypeptide or polynucleotide is determined by GAP (Needleman and Wunsch, 1970) analysis (GCG program) with a gap creation penalty=5, and a gap extension penalty=0.3. The query sequence is at least 50 residues in length, and the GAP analysis aligns the two sequences over a region of at least 50 residues. For example, the query sequence is at least 100 residues in length and the GAP analysis aligns the two sequences over a region of at least 100 residues. In one example, the two sequences are aligned over their entire length.

For purposes of the present disclosure, alignments of sequences and calculation of homology scores are done using a Needleman-Wunsch alignment (i.e. global alignment), useful for both protein and DNA alignments. The default scoring matrices BLOSUM50 and the identity matrix are used for protein and DNA alignments respectively. The penalty for the first residue in a gap is −12 for proteins and −16 for DNA, white the penalty for additional residues in a gap is −2 for proteins and −4 for DNA. Alignment is from the FASTA package version v20u6 (W. R. Pearson and D. J. Lipman (1988), "Improved Tools for Biological Sequence Analysis", PNAS 85:2444-2448, and W. R. Pearson (1990) "Rapid and Sensitive Sequence Comparison with FASTP and FASTA", Methods in Enzymology, 183:63-98).

The present disclosure contemplates variant forms of binding protein of the disclosure. For example, such a variant binding protein comprises one or more conservative amino acid substitutions compared to a sequence set forth herein. In some examples, the binding protein comprises 10 or fewer, e.g., 9 or 8 or 7 or 6 or 5 or 4 or 3 or 2 or 1 conservative amino acid substitutions. A "conservative amino acid substitution" is one in which the amino acid residue is replaced with an amino acid residue having a similar side chain and/or hydropathicity and/or hydrophilicity.

Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine). Hydropathic indices are described, for example in Kyte and Doolittle (1982) and hydrophylic indices are described in, e.g., U.S. Pat. No. 4,554,101.

The present disclosure also contemplates non-conservative amino acid changes. For example, of particular interest are substitutions of charged amino acids with another charged amino acid and with neutral or positively charged amino acids. In some examples, the binding protein comprises 10 or fewer, e.g., 9 or 8 or 7 or 6 or 5 or 4 or 3 or 2 or 1 non-conservative amino acid substitutions.

A variant form of a CXCR4 binding protein described herein retains the ability to bind to CXCR4. Methods for determining specific binding to CXCR4 are described herein.

Affinity Maturation

In a further example, a polypeptide of the disclosure is affinity matured to produce an i-body capable of binding to CXCR4 with increased affinity, specificity or activity or to produce an i-body with increased expression or solubility. For example, the sequence encoding the polypeptide of the disclosure is mutated such that one or more amino acid substitutions is introduced. The resulting variant polypeptide is then screened for binding to CXCR4, e.g., in a competitive assay, screened for increase in specificity to other chemokine receptors (for example CCR10, CCR2, CCR3, CCR4, CCR5, CCR6, CCR7, CCR8, CCR9, CX3CR1, CXCR1, CXCR2, CXCR3, CXCR5, CXCR6, CXCR7, CCR1, XCR1; see FIG. 9), or screened for increase in expression or increase in solubility (see FIG. 7) or screened via affinity assays as described below for increases in affinity to CXCR4.

There are several protocols for affinity maturation of polypeptides and proteins. These include DNA shuffling (Stemmer Proc Natl Acad Sci USA. (1994); 91(22):10747-10751), error-prone PCR (Hawkins et al. (1992) J. Mol. Biol., 226; 889-896 and Henderson et al. (2007) Structure 15:1452-66) and bacterial mutator cells (Irving et al. (1996) Immunotechnology 2:127-43.3) that randomise the whole scaffold, as well as more targeted methods such as doped oligonucleotide mutagenesis (Hermes et al. (1989) Gene, 84; 143-1514). Ribosome display coupled with error-prone RNA dependent RNA polymerase from Qbeta bacteriophage has also been used to affinity mature single domains, binding proteins and polypeptides (Kopsidas et al, (2006) Immunology Letters 107 163-168).

The polypeptides according to the disclosure may be soluble secreted proteins or may be presented as a fusion protein on the surface of a cell, or particle (e.g., a phage or other virus, a ribosome or a spore). Exemplary phage display methods are described, for example, in U.S. Pat. Nos. 5,821,047; 6,248,516 and 6,190,908. Phage display particles produced using these methods are then screened to identify a displayed binding protein having a conformation sufficient for binding to CXCR4 or an improved binder to CXCR4.

Apparent affinities can be determined by methods such as an enzyme linked immunosorbent assay (ELISA) or any other technique familiar to one of skill in the art. Avidities can be determined by methods such as a Scatchard analysis or any other technique familiar to one of skill in the art.

Another technique for measuring apparent binding affinity familiar to those of skill in the art is a surface plasmon resonance technique (analyzed on a BIACORE 2000 system) (Liljeblad, et al., Glyco. J. 2000, 17:323-329). Standard measurements and traditional binding assays are described by Heeley, R. P, Endocr. Res. 2002, 28:217-229.

In one example, an affinity matured i-body of the present disclosure specifically binds to human CXCR4 with a greater binding affinity (e.g. at least about 5 times, at least about 10 times, at least about 50 times, at least about 100 times, at least about 500 times, or at least about 1000 times greater) than the binding affinity of the non-affinity matured i-body.

Protein Production

In one example, a polypeptide of the disclosure is produced by culturing a cell line, e.g., an *E. Coli* cell line under conditions sufficient to produce the protein, e.g., as described herein and/or as is known in the art.

Recombinant Expression

In the case of a recombinant protein, nucleic acid encoding same is placed into one or more expression constructs, e.g., expression vector(s), which is/are then transfected into host cells, such as cells that can produce a disulphide bridge or bond, such as bacterial cells including *E. coli* cells, yeast cells, insect cells, or mammalian cells. Exemplary mammalian cells include simian COS cells, Chinese Hamster Ovary (CHO) cells, or myeloma cells that do not otherwise produce immunoglobulin protein. Exemplary bacterial cells include BL21(DE3), BL21(DE3)-pLysS, Tuner, Tuner pLysS, Origami, Origami B, Origami B pLysS, Rosetta, AD494, HMS174 which are all available form Novagen.

Molecular cloning techniques to achieve these ends are known in the art and described, for example in Ausubel F M (1987) Current Protocols in Molecular Biology. New York. N.Y., John Wiley & Sons or Sambrook, Fritsch and Maniatis Molecular Cloning: a laboratory manual Cold Spring Harbor N.Y. Cold Spring Harbor Laboratory Press. A wide variety of cloning and in vitro amplification methods are suitable for the construction of recombinant nucleic acids.

Following isolation, the nucleic acid encoding a protein of the disclosure is inserted into an expression construct or replicable vector for further cloning (amplification of the DNA) or for expression in a cell-free system or in cells. For example, the nucleic acid is operably linked to a promoter.

As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid, e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid to which it is operably linked. Exemplary promoters can contain additional copies of one or more specific regulatory elements to further enhance expression and/or alter the spatial expression and/or temporal expression of said nucleic acid.

As used herein, the term "operably linked to" means positioning a promoter relative to a nucleic acid such that expression of the nucleic acid is controlled by the promoter.

Cell free expression systems are also contemplated by the present disclosure. For example, a nucleic acid encoding a CXCR4 binding polypeptide is operably linked to a suitable promoter, e.g., a T7, T5 or SP6 promoter, and the resulting expression construct exposed to conditions sufficient for transcription and translation. Typical expression vectors for in vitro expression or cell-free expression have been described and include, but are not limited to the TNT T7 and TNT T3 systems (Promega), the pEXP1-DEST and pEXP2-DEST vectors (Invitrogen).

Many vectors for expression in cells are available. The vector components generally include, but are not limited to, one or more of the following: a signal sequence, a sequence encoding a polypeptide of the present disclosure (e.g., derived from the information provided herein), an enhancer element, a promoter, and a transcription termination sequence. The skilled artisan will be aware of suitable sequences for expression of a protein. Vectors can be plasmids, viral e.g. phage or phagemid as appropriate. Many known techniques and protocols for manipulation of nucleic acid, for example, in the preparation of nucleic acid constructs, mutagenesis, introduction of DNA into cells and gene expression and analysis of protein are described in for example, Ausubel F M (1987) Current Protocols in Molecular Biology. New York. N.Y., John Wiley & Sons. A wide variety of host/expression vector combinations can be employed in expressing the i-body DNA segues of the disclosure. Useful expression vectors, for example, can consist of segments of chromosomal, non-chromosomal and synthetic DNA sequences. Suitable vectors include derivatives of SV40 and known bacterial plasmids, e.g., *E. coli* plasmids col E1, Perl, Pbr322, Pmb9 and their derivatives, plasmids such as RP4; phage DNAs, e.g., the numerous derivatives of phage \ e.g., NM989, and other phage DNA, e.g., M13 and filamentous single stranded phage DNA; yeast plasmids such as the 2u plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Exemplary signal sequences include prokaryotic secretion signals (e.g., DsbA, pelB, alkaline phosphatase, penicillinase, Ipp, or heat-stable enterotoxin II), yeast secretion signals (e.g., invertase leader, α factor leader, or acid phosphatase leader) or mammalian secretion signals (e.g., herpes simplex gD signal).

Exemplary leader peptides include those active in prokaryotes (such as PelB, OmpA, PIII, DsbA, TorT, TolB, phoA promoter, β-lactamase and lactose promoter systems, alkaline phosphatase, a tryptophan (trp) promoter system, and hybrid promoters such as the tac promoter).

Suitable bacterial promoters include the *E. coli* lacI and lacZ promoters, the T3 and T7, T5 promoters, the gpt promoter, the lambda PR and PL promoters and the trp promoter. Eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

Exemplary promoters active in mammalian cells include cytomegalovirus immediate early promoter (CMV-IE), human elongation factor 1-α promoter (EF1), small nuclear RNA promoters (U1a and U1b), α-myosin heavy chain promoter, Simian virus 40 promoter (SV40), Rous sarcoma virus promoter (RSV), Adenovirus major late promoter, β-actin promoter; hybrid regulatory element comprising a CMV enhancer/β-actin promoter or an immunoglobulin promoter or active fragment thereof. Examples of useful mammalian host cell lines are monkey kidney CV1 line transformed by SV40 (COS-7, AUSTRALIAN CELL BANK CRL 1651); human embryonic kidney line (293 or 293 cells subcloned for growth in suspension culture; baby hamster kidney cells (BHK, AUSTRALIAN CELL BANK CCL 10); or Chinese hamster ovary cells (CHO).

Typical promoters suitable for expression in yeast cells such as for example a yeast cell selected from the group comprising *Pichia pastoris, Saccharomyces cerevisiae* and *S. pombe*, include, but are not limited to, the ADH1 promoter, the GAL1 promoter, the GAL4 promoter, the CUP1 promoter, the PHO5 promoter, the nmt promoter, the RPR1 promoter, or the TEF1 promoter.

Means for introducing the isolated nucleic acid molecule or a gene construct comprising same into a cell for expression are known to those skilled in the art. The technique used for a given cell depends on the known successful techniques. Means for introducing recombinant DNA into cells include microinjection, transfection mediated by DEAE-dextran, transfection mediated by liposomes such as by using lipofectamine (Gibco, MD, USA) and/or cellfectin (Gibco, MD, USA), PEG-mediated DNA uptake, electroporation, viral transduction (e.g., using a lentivirus) and microparticle bombardment such as by using DNA-coated tungsten or gold particles (Agracetus Inc., WI, USA) amongst others.

In some cases it is useful to express a protein, polypeptide or peptide in insoluble form, particularly when the polypeptide of interest is rather short, normally soluble, and/or subject to proteolytic degradation within the host cell. Production of the protein in insoluble form both facilitates simple recovery and protects the polypeptide from the undesirable proteolytic degradation. One means to produce the polypeptide in insoluble form is to recombinantly produce the polypeptide as part of an insoluble fusion protein by including in the fusion construct at least one peptide tag (i.e., an inclusion body tag) that induces inclusion body formation. Typically, the fusion protein is designed to include at least one cleavable peptide linker so that the polypeptide of interest can be subsequently recovered from the fusion protein. The fusion protein may be designed to include a plurality of inclusion body tags, cleavable peptide linkers, and regions encoding the polypeptide of interest.

Fusion proteins comprising a peptide tag that facilitate the expression of insoluble proteins are well known in the art. Typically, the tag portion of the chimeric or fusion protein is large, increasing the likelihood that the fusion protein will be insoluble. Example of large peptide tags typically used include, but are not limited to chloramphenicol acetyltransferase (Dykes et al., Eur. J. Biochem., 174:411 (1988), . beta.-galactosidase (Schellenberger et al., Int. J. Peptide Protein Res., 41:326 (1993); Shen et al., Proc. Nat. Acad. Sci. USA 281:4627 (1984); and Kempe et al., Gene, 39:239 (1985)), glutathione-S-transferase (Ray et al., Bio/Technology, 11:64 (1993) and Hancock et al. (WO94/04688)), the N-terminus of L-ribulokinase (U.S. Pat. No. 5,206,154 and Lai et al., Antimicrob. Agents & Chemo., 37:1614 (1993), bacteriophage T4 gp55 protein (Gramm et al., Bio/Technology, 12:1017 (1994), bacterial ketosteroid isomerase protein (Kuliopulos et al., J. Am. Chem. Soc. 116:4599 (1994), ubiquitin (Pilon et al., Biotechnol. Prog., 13:374-79 (1997), bovine prochymosin (Naught et al., Biotechnol. Bioengineer. 57:55-61 (1998), and bactericidal/permeability-increasing protein ("BPI"; Better, M. D. and Gavit, P D., U.S. Pat. No. 6,242,219). The art is replete with specific examples of this technology, see for example U.S. Pat. No. 6,613,548, describing fusion protein of a proteinaceous tag and a soluble protein and subsequent purification from cell lysate; U.S. Pat. No. 6,037,145, teaching a tag that protects the expressed chimeric protein from a specific protease; U.S. Pat. No. 5,648,244, teaching the synthesis of a fusion protein having a tag and a cleavable linker for facile purification of the desired protein; and U.S. Pat. Nos. 5,215,896; 5,302,526; 5,330,902; and US 2005221444, describing fusion tags containing amino acid compositions specifically designed to increase insolubility of the chimeric protein or peptide.

Shorter inclusion body tags have recently been developed from the *Zea mays* zein protein (U.S. patent application Ser. No. 11/641,936), the *Daucus carota* cystatin (U.S. patent application Ser. No. 11/641,273), and an amyloid-like hypothetical protein from *Caenorhabditis elegans* (U.S. patent application Ser. No. 11/516,362; each hereby incorporated by reference in their entirety) The use of short inclusion body tags increases the yield of the target peptide produced within the recombinant host cell.

Also provided herein is a recombinant host cell which comprises one or more polynucleotide constructs. A polynucleotide encoding an i-body of the present disclosure is encompassed herein as are methods of production of i-bodies which method comprises expression from a polynucleotide. Expression can be achieved, for example, by culturing under appropriate conditions recombinant host cells containing the polynucleotide.

The host cells used to produce the binding molecule or polypeptide of this disclosure may be cultured in a variety of media, depending on the cell type used. Commercially available media such as Ham's FIO (Sigma), Minimal Essential Medium ((MEM), (Sigma), RPMI-1640 (Sigma), and Dulbecco's Modified Eagle's Medium ((DMEM), Sigma) are suitable for culturing mammalian cells. Media for culturing other cell types discussed herein are known in the art.

It will be understood that not all vectors, expression control sequences and hosts will function equally well to express the DNA sequences. Neither will all hosts function equally well with the same expression system. However, one skilled in the art will be able to select the proper vectors, expression control sequences, and hosts without undue experimentation to accomplish the desired expression without departing from the scope of this application. For example, in selecting a vector, the host must be considered because the vector must function in it. The vector's copy number, the ability to control that copy number, and the expression of any other proteins encoded by the vector, such as antibiotic markers, will also be considered.

The present disclosure also provides a host cell containing one or more polynucleotides as disclosed herein. The present disclosure also provides a method of introducing such one or more polynucleotides into a host cell by any suitable technique as described above.

Once the polynucleotide has been introduced into the host cell, expression of the polynucleotide can occur, e.g. by culturing host cells under conditions for expression of one or more polypeptides from one or more polynucleotides.

A polynucleotide encoding an i-body of the present disclosure can be prepared recombinantly/synthetically, in addition to, or rather than cloning. The polynucleotide can be designed with the appropriate codons for the CXCR4 binding polypeptide. In general, one will select preferred codons for an intended host if the sequence will be used for expression. The complete polynucleotide can be assembled from overlapping oligonucleotides prepared by standard methods and assembled into a complete coding sequence.

See, e.g., Edge, Nature, 292:756 (1981); Nambair et al., Science, 223:1299 (1984); Jay et al., J. Biol. Chem., 259: 6311 (1984).

Isolation of Proteins

A CXCR4 binding molecule or polypeptide or i-body of the present disclosure can be isolated or purified.

Methods for purifying a polypeptide of the disclosure are known in the art and/or described herein.

When using recombinant techniques, the polypeptide of the disclosure can be produced intracellularly, in the periplasmic space, or directly secreted into the medium. If the protein is produced intracellularly, as a first step, the particulate debris, either host cells or lysed fragments, is removed, for example, by centrifugation or ultrafiltration. Where the protein is secreted into the medium, supernatants from such expression systems can be first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The protein prepared from the cells can be purified using, for example, ion exchange, hydroxyapatite chromatography, hydrophobic interaction chromatography, gel electrophoresis, dialysis, affinity chromatography (e.g., protein A affinity chromatography or protein G chromatography), heat, or any combination of the foregoing. These methods are known in the art and described, for example in WO99/57134.

The skilled artisan will also be aware that a polypeptide of the disclosure can be modified to include a tag to facilitate purification or detection, e.g., a poly-histidine tag, e.g., a hexa-histidine tag, or a influenza virus hemagglutinin (HA) tag, or a Simian Virus 5 (V5) tag, or a FLAG tag, or a glutathione S-transferase (GST) tag. For example, the tag is a hexa-his tag. The resulting protein is then purified using methods known in the art, such as, affinity purification. For example, a protein comprising a hexa-his tag is purified by contacting a sample comprising the protein with nickel-nitrilotriacetic acid (Ni-NTA) that specifically binds a hexa-his tag immobilized on a solid or semi-solid support, washing the sample to remove unbound protein, and subsequently eluting the bound protein. Alternatively, or in addition a polypeptide, ligand or antibody that binds to a tag is used in an affinity purification method.

Conjugates

The present disclosure also provides conjugates of CXCR4 binding molecules or polypeptides described herein. Examples of compounds to which a polypeptide of the present disclosure can be conjugated are selected from the group consisting of a radioisotope, a detectable label, a therapeutic compound, a colloid, a toxin, a nucleic acid, a peptide, a protein, a compound that increases the half life of the protein in a subject and mixtures thereof.

Exemplary therapeutic agents include, but are not limited to an anti-angiogenic agent, an anti-neovascularization and/or other vascularization agent, an anti-proliferative agent, a pro-apoptotic agent, a chemotherapeutic agent, anti-mitotic agents (eg anti-mitotic agent Auristatin, (MMAF/MMAE as per Angew. Chem. Int. Ed. 2014, 53, 1-6) or a therapeutic nucleic acid.

A toxin includes any agent that is detrimental to (e.g., kills) cells. For a description of these classes of drugs, which are known in the art, and their mechanisms of action, see Goodman et al., (1990). Additional techniques relevant to the preparation of antibody immunotoxin conjugates are provided in for instance in U.S. Pat. No. 5,194,594 and may be utilised in the present disclosure. Exemplary toxins include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. See, for example, WO93/21232.

In some examples, the CXCR4 binding molecules or polypeptides or i-bodies can be covalently or non-covalently coupled to a cytotoxin or other cell proliferation inhibiting compound, in order to localise delivery of that agent to a tumour cell. For instance, the agent can be selected from the group consisting agents, enzyme inhibitors, proliferation inhibitors, lytic agents, DNA or RNA synthesis inhibitors, membrane permeability modifiers, DNA metabolites, dichioroethylsulfide derivatives, protein production inhibitors, ribosome inhibitors, inducers of apoptosis, and neurotoxins.

Suitable chemotherapeutic agents for forming immunoconjugates of the present disclosure include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1 dehydrotestosterone, glucocorticoids, procaine, tetracaine, lidocaine, propranolol, and puromycin, antimetabolites (such as methotrexate, 6-mercaptopurine, 6 thioguanine, cytarabine, fludarabin, 5-fluorouracil, decarbazine, hydroxyurea, asparaginase, gemcitabine, cladribine), alkylating agents (such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin), antibiotics (such as dactinomycin (formerly actinomycin), bleomycin, daunorubicin (formerly daunomycin), doxorubicin, idarubicin, mithramycin, mitomycin, mitoxantrone, plicamycin, anthramycin (AMC)).

In one example, a CXCR4 binding molecule or polypeptide as described herein is conjugated or linked to another protein (e.g. Human Serum Albumin or HSA), including another CXCR4 binding molecule or polypeptide of the disclosure or a protein comprising a CDR1 and/or CDR3 region as described herein. A CXCR4 binding molecule or polypeptide as described herein may also be conjugated to another binding molecule or polypeptide which targets, for example, a tumour antigen, or a target that has the potential to redirect and activate any circulating T cells against tumors (for example CD3), or a target that is notably expressed on monocytes and macrophages and upregulated upon activation on neutrophils (for example CD64) or a target that is expressed on the surface of natural killer cells, neutrophil polymorphonuclear leukocytes, monocytes and macrophages. In one example, the binding molecule or polypeptide is a low affinity binder of IgG (for example CD16) or a target that is constitutively expressed primarily on neutrophils, monocytes, macrophages and eosinophils (for example CD89). Other proteins or conjugation partners are not excluded. Additional proteins will be apparent to the skilled artisan and include, for example, an immunomodulator or a half-life extending protein or a peptide or polypeptide or other protein that binds to serum albumin amongst others.

Exemplary serum albumin binding peptides or protein are described in US20060228364 or US20080260757.

In one example a CXCR4 binding molecule or polypeptide of the present disclosure is conjugated to an XTEN polypeptide as described in Schellenberger et al (2009) Nature Biotechnology 27(12):1186-1192.

In one example a CXCR4 binding molecule or polypeptide of the present disclosure is conjugated to a polypeptide as described in Schlapschy et al (2013) Protein Engineering, Design & Selection vol. 26 no. 8 pp. 489-501.

In one example a polypeptide of the present disclosure is conjugated to an Fc region of an immunoglobulin as described, for example, in Peters et al (2010), Blood Vol. 115 no. 10 2057-2064, Kim et al, (2009) BMB Rep. 42:212-216 and Nagashima et al (2011) J Biochem. 149: 337-346.

CXCR4 binding polypeptide conjugates (bispecific molecules) can be prepared using methods known in the art. For example, each binding specificity of the bispecific molecule can be generated separately and then conjugated to one another. When the binding specificities are proteins, polypeptides or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g., Karpovsky el al. (1984) J. Exp. Med 160 1686, Liu, M A et al. (1985) Proc. Natl. Acad. Sci. USA 82 8648). Other methods include those described in Paulus (1985) Behring Ins Mitt No 78, 1 18-132, Brennan et al. (1985) Science 229 81-83 and Glennie et al. (1987). J Immunol 39 2367-2375).

A variety of radionuclides are available for the production of radioconjugated proteins. Examples include, but are not limited to, low energy radioactive nuclei (e.g., suitable for diagnostic purposes), such as 13C, 15N, 2H, 125I, 123I, 99Tc, 43K, 52Fe, 67Ga, 68Ga, 111In and the like. For example, the radionuclide is a gamma, photon, or positron-emitting radionuclide with a half-life suitable to permit activity or detection after the elapsed time between administration and localization to the imaging site. The present disclosure also encompasses high energy radioactive nuclei (e.g., for therapeutic purposes), such as 125I, 131I, 123I, 111In, 105Rh, 153Sm, 67Cu, 67Ga, 166Ho, 177Lu, 186Re and 188Re. These isotopes typically produce high energy α- or β-particles which have a short path length. Such radionuclides kill cells to which they are in close proximity, for example neoplastic cells to which the conjugate has attached or has entered. They have little or no effect on non-localized cells and are essentially non-immunogenic. Alternatively, high-energy isotopes may be generated by thermal irradiation of an otherwise stable isotope, for example as in boron neutron-capture therapy (Guan et al., 1998). Other isotopes which may be suitable are described in Carter. (2001) Nature Reviews Cancer 1, 118-129, Goldmacher et al. (2011) Therapeutic Delivery 2; 397-416, Payne (2003) Cancer Cell 3, 207-212, Schrama et al, (2006) Nature Rev. Drug Discov. 5, 147-159, Reichert et al. (2007) Nature Reviews Drug Discovery 6; 349-356.

In another example, the protein is conjugated to a "receptor" (such as streptavidin) for utilization in cell pretargeting wherein the conjugate is administered to the patient, followed by removal of unbound conjugate from the circulation using a clearing agent and then administration of a "ligand" (e.g., avidin) that is conjugated to a therapeutic agent (e.g., a radionucleotide).

The CXCR4 binding molecules or polypeptides of the present disclosure can be modified to contain additional nonproteinaceous moieties that are known in the art and readily available. For example, the moieties suitable for derivatization of the protein are physiologically acceptable polymer, e.g., a water soluble polymer. Such polymers are useful for increasing stability and/or reducing clearance (e.g., by the kidney) and/or for reducing immunogenicity of a CXCR4 binding polypeptide of the disclosure. Non-limiting examples of water soluble polymers include, but are not limited to, polyethylene glycol (PEG), polyvinyl alcohol (PVA), or propropylene glycol (PPG).

In one example, a CXCR4 binding molecule or polypeptide as described herein comprises one or more detectable markers to facilitate detection and/or isolation. For example, the compound comprises a fluorescent label such as, for example, fluorescein (FITC), 5,6-carboxymethyl fluorescein, Texas red, nitrobenz-2-oxa-1,3-diazol-4-yl (NBD), coumarin, dansyl chloride, rhodamine, 4'-6-diamidino-2-phenylinodole (DAPI), and the cyanine dyes Cy3, Cy3.5, Cy5, Cy5.5 and Cy7, fluorescein (5-carboxyfluorescein-N-hydroxysuccinimide ester), rhodamine (5,6-tetramethyl rhodamine). The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm).

In certain examples, the i-bodies of the present disclosure can be coupled with an agent useful in imaging tumors. Such agents include: metals; metal chelators; lanthanides; lanthanide chelators; radiometals; radiometal chelators; positron-emitting nuclei; microbubbles (for ultrasound); liposomes; molecules microencapsulated in liposomes or nanosphere; monocrystalline iron oxide nanocompounds; magnetic resonance imaging contrast agents; light absorbing, reflecting and/or scattering agents; colloidal particles; fluorophores, such as near-infrared fluorophores. In many examples, such secondary functionality/moiety will be relatively large, e.g., at least 25 amu in size, and in many instances can be at least 50,100 or 250 amu in size. In certain examples, the secondary functionality is a chelate moiety for chelating a metal, e.g., a chelator for a radiometal or paramagnetic ion. In additional examples, it is a chelator for a radionuclide useful for radiotherapy or imaging procedures.

Alternatively, or in addition, the CXCR4 binding molecule or polypeptide as described herein is labelled with, for example, a fluorescent semiconductor nanocrystal (as described, for example, in U.S. Pat. No. 6,306,610).

Alternatively, or in addition, the CXCR4 binding molecule or polypeptide is labelled with, for example, a magnetic or paramagnetic compound, such as, iron, steel, nickel, cobalt, rare earth materials, neodymium-iron-boron, ferrous-chromium-cobalt, nickel-ferrous, cobalt-platinum, or strontium ferrite.

Immobilized Proteins

In one example a CXCR4 binding molecule or polypeptide of the disclosure is immobilized on a solid or semi-solid matrix. The term "immobilization" is to be understood to involve various methods and techniques to fix proteins onto specific matrices, e.g. as described in WO99/56126 or WO02/26292. For example, immobilization can serve to stabilize the proteins so that its activity is not reduced or adversely modified by biological, chemical or physical exposure, especially during storage or in single-batch use.

Various methods for immobilizing a protein on a matrix are known in the art and include crosslinking, binding to a carrier, and retention within a semi-permeable matrix.

Exemplary matrices include porous gels, aluminium oxide, bentonite, agarose, starch, nylon or polyacrylamide.

Assaying Activity of a CXCR4 Binding Molecule or Polypeptide of the Disclosure
Binding Assays The most specific and potent antibodies against G-protein coupled receptors typically target conformationally-complex epitopes formed by the tertiary structure of the proteins. The approaches used with regard to soluble protein targets are not effective for membrane spanning proteins, whose native structure depends on an intact lipid bilayer.

CXCR4 binding molecules or polypeptides of the present disclosure can be tested for binding to CXCR4 by, for example, standard flow cytometric methods. Since the CXCR4 binding molecules or polypeptides of the present disclosure preferably recognise human CXCR4 in its native conformation, binding to CXCR4 is preferably determined using an assay that utilises a reagent expressing the native conformation of CXCR4. Non-limiting examples of reagents expressing native conformation CXCR4 that can be used in the binding assays include cells that naturally express CXCR4, cells that have been transfected to express CXCR4 (e.g. R1610 cells transfected with a CXCR4 expression vector). Examples of suitable cells that express CXCR4 include MDA-MB-231, MDA-MB-468, MDA-MB-361, MDA-MB-549, Ramos, Namalwa, MOLT-4, DU-4475, DU-145, PC3, LNcaP, SW480, HT29, NCI-H69, SJSA-1-met-luc and HL-60 cells. Briefly, for the flow cytometry assay, cells expressing CXCR4 are incubated with the test CXCR4 binding molecule or polypeptide, washed, incubated with a labelled secondary reagent capable of binding to the test antibody, washed again, and subjected to analysis to detect the binding of the secondary reagent to the cells (e.g. using a FACS machine). CXCR4 molecules or polypeptides which stain cells brightly as evaluated by flow cytometry are used for further investigation. Examples of binding assays suitable for use according to the present disclosure include radioligand binding assays such as the filtration assay (PerkinElmer) or the SPA assay (PerkinElmer or GE Healthcare), or tagged ligand binding assays such as DELFIA™ TRF (PerkinElmer), LanthaScreen™ system (Invitrogen), or Tag-Lite™ system (Cisbio).

Alternatively a cell line such as a CHO cell line may be transfected with an expression vector encoding a transmembrane form of CXCR4. The transfected protein may comprise a tag, such as a myc-tag, preferably at the N-terminus, for detection using an antibody to the tag. Binding of a CXCR4 binding molecule or polypeptide of this disclosure to CXCR4 may be determined by incubating the transfected cells with the CXCR4 binding polypeptide, and detecting bound polypeptide. Binding of an antibody to the tag on the transfected protein may be used as a positive control.

A further approach for assessing binding requires the use of lipoparticles which are capable of incorporating high concentrations of target membrane proteins in their native conformations (e.g. magnetic proteoliposomes incorporating CXCR4 or liposome particles incorporating CXCR4). Such lipoprotein particles are described in, for example WO 2005/042695, WO 2011/083141, Banik et al (2009) Drug Discovery & Development 12(9):14-17; Willis S et al (2008) Biochemistry 47:6988-90. Lipoparticles are produced from mammalian cells by co-expressing the retroviral structural core polyprotein, Gag, along with a desired membrane protein (e.g. CXCR4). Gag core proteins self assemble at the plasma membrane where they bud off and capture target membrane proteins. Lipoproteins are approximately 150 nm in diameter so are readily suspended in aqueous solutions that can be used for inoculation. Because membrane proteins within lipoparticles are derived directly from the cell surface without mechanical disruption or detergents, the native structure and orientation of the membrane proteins is retained. Lipoproteins do not contain cytoplasmic proteins or inverted membrane proteins that can result in an unfocussed immune response. The lipoproteins can be immobilised onto a solid support using standard techniques and binding by the CXCR4 molecules or polypeptides according to the present disclosure analysed by surface Plasmon resonance (see for example Maynard J A et al (2009) Biotechnol J 4(11):1542-1558, Stenlund P et al (2003) Anal Biochem 316(2):243-50, Hoffman et al (2000) Proc Natl Acad Sci 97:11215-11220, WO 2005/042695).

Furthermore the lipoparticles can be mutated residue by residue to determine which residues of CXCR4 the CXCR4 binding polypeptides of the present disclosure are binding. This validates critical residues that represent amino acids whose side chains make the highest energetic contributions to the interaction between the binding CXCR4 binding polypeptide and the CXCR4 epitope (Bogan and Thorn, (1998) J. Mol. Biol. 280, 1-9; Lo Conte et al., (1999) J. Mol. Biol. 285, 2177-2198. The critical residues identified for i-body AM3-114, i-body AM4-272, and i-body AM3-523 binding were visualized on a CXCR4 dimer structure (derived from PDB ID #3ODU; Wu et al., (2010) Science 330: 1066-1071.

Another assay is an antigen binding assay, e.g., as described in Scopes In: Protein purification: principles and practice, Third Edition, Springer Verlag, 1994. Such a method generally involves labelling the CXCR4 binding molecule or polypeptide and contacting it with immobilized target or a fragment thereof, e.g., human CXCR4 or CXCR4 positive lipoparticle. Following washing to remove non-specific bound protein, the amount of label and, as a consequence, bound protein is detected. Of course, the CXCR4 binding molecule or polypeptide can be immobilized and the target labeled. Panning-type assays can also be used.

An exemplary method for determining an inhibitor of CXCR4 activity is a competitive binding assay. For example, labelled SDF-1 is added to cells expressing CXCR4 or immobilised CXCR4 positive lipoparticles either with a CXCR4 binding molecule or polypeptide or after addition of the CXCR4 binding molecule or polypeptide. Following washing to remove unbound SDF-1 and/or CXCR4 binding molecule or polypeptide, the amount of label bound to CXCR4 is detected. This is compared to the amount bound following incubation in the absence of CXCR4 binding molecule or polypeptide, and a CXCR4 binding molecule or polypeptide that reduced the amount of SDF-1 binding (i.e. bound label) is considered a CXCR4 inhibitory agent.

Binding assays can also be used to detect receptor-mediated G-protein activation (e.g. Regulation of G Protein-Coupled Receptor Function and Expression ed. Benovic J L pp 119-132 (2000) Wiley-Liss NY). Such assays include receptor-stimulated GTP binding to Gα subunits. Activation of GPCR results in GDP-GTP exchange in the Gα subunit and this exchange can be quantified and used as a direct measurement of the receptor-G protein interaction. This typically involves the use of radiolabelled guanine nucleotide with the receptor in cell free membrane preparations or artificial lipid membranes. The amount of radiolabel incorporated is used as a measure of the extent of G protein activation.

Methods for assaying antigen-binding affinity are well known in the art and also include half-maximal binding assays, competition assays, and Scatchard analysis.

Affinity Assays

Optionally, the dissociation rate constant (Kd), association rate constant (Ka) or binding constant/equilibrium dissociation constant ($K_D$, i.e., Koff/Kon) of a CXCR4 binding polypeptide is determined. These constants for a CXCR4 binding polypeptide may be measured by a radiolabeled or fluorescently-labeled CXCR4 binding assay. This assay equilibrates the CXCR4 binding polypeptide with a concentration of CXCR4 positive lipoparticles. Following washing to remove unbound CXCR4, the amount of CXCR4 binding polypeptide is determined. According to another example the constants are measured by using surface plasmon resonance assays, e.g., using BIAcore surface plasmon resonance (BIAcore, Inc., Piscataway, N.J.) with immobilized CXCR4 positive lipoparticles (WO 2005/042695).

The dissociation rate constant (Kd) is used to calculate the off rate (koff), a constant used to calculate how quickly a binding molecule dissociates from its target. A flatter slope seem in BIAcore SPR analysis indicates a slower off rate and hence stronger binding. A steeper downside means a faster off rate/weaker antibody binding.

The association rate constant (Ka) is the part of the reaction used to calculate the on rate, a constant used to characterise how quickly the binding molecule binds to its target.

The ratio of experimental measured off and on rates (Koff/Kon) is used to calculate the $K_D$ value. Most binding molecules have $K_D$ values in the low micromolar ($10^{-6}$) to nanomolar ($10^{-7}$ to $10^{-9}$) range. High affinity antibodies are generally considered to be in the low nanomolar range ($10^{-9}$) with very high affinity antibodies being in the picomolar ($10^{-12}$) range.

Functional Assays

The binding of a ligand, such as an agonist or SDF-1 to CXCR4 can result in signalling by this G protein coupled receptor, and the activity of G proteins as well as stimulating other intracellular signalling molecules. The inhibitory or stimulatory activity of a CXCR4 binding molecule or polypeptide of the present disclosure can be determined with or without a ligand in a suitable assay, as well as the assessment of the ability of the CXCR4 binding molecule or polypeptide to inhibit or stimulate the activity in the presence or absence of the ligand.

The activity of the CXCR4 receptor by the CXCR4 binding molecule or polypeptide of the present disclosure can be measured in a number of ways, for example alteration of β-arrestin modulation, alteration in intracellular $Ca^{2+}$ concentration, activation of phospholipase C, alteration in intracellular inositol triphosphate QP3 concentration, alteration in intracellular diacylglycerol (DAG) concentration, and alteration in intracellular adenosine cyclic 3',5'-monophosphate (cAMP) concentration.

G protein activity, such as hydrolysis of GTP to GDP, or later signalling event triggered by receptor binding, such as induction of rapid and transient increase in the concentration of intracellular (cytosolic) free calcium can be assayed by methods known in the art or other suitable methods (e.g. Neote et al (1993) Cell 72:415-425; Van Riper et al (1993) J. Exp. Med 177:851-856).

cAMP Assays

Activation of GPCRs by the polypeptides of the invention can be monitored by measuring the increase or decrease in intracellular cAMP with fluorescent dyes. Methods of measuring intracellular cAMP are known in the art. Assays measuring cellular levels of cAMP are dependent on the activity of adenylate cyclase, which is regulated by GPCRs coupled to $G\alpha_s$ or $G\alpha_{i/o}$ protein. Adenylate cyclase requires pre-stimulation with forskolin. In addition, to counteract the natural degradation of cAMP to AMP by phosphodiesterase (PDE) enzymes, an inhibitor of PDE (e.g. IBMX) might be required in the system during assay optimisation. Examples of useful membrane permeant dyes include acetoxymethyl ester forms of dyes that can be cleaved by intracellular esterases to form a free acid, which is no longer membrane permeant and remains trapped inside a cell. Assays designed to directly measure levels of cAMP produced upon modulation of adenylate cyclase activity by GPCRs can also be used. Such assays are based on competition between endogenous cAMP and exogenously added biotinylated cAMP. Capture of cAMP is achieved by using a specific antibody conjugated to a solid material such as a capture bead.

Radiometric assays such as the SPA cAMP assay (GE Healthcare) and the FlashPlate™ cAMP assay from Perkin-Elmer using $^{125}$I-labelled cAMP are widely used. More recently these assays have been replaced with luminescence or fluorescence based homogenous assays to avoid the use of radioactivity. A further assay is the Enzyme Fragment Complementation assay (HitHunter™) by DiscovRx. Cellular cAMP competes with cAMP labelled with a small peptide fragment of β-galactosidase for binding to an anti-cAMP antibody. The resulting free labelled cAMP complements with the enzyme fragment, producing active β-galactosidase which is detected with fluorescent or luminescent substrates. AlphaScreen™ (PerkinElmer) is a sensitive bead-based proximity chemiluminescent assay. Cellular cAMP competes with a biotinylated cAMP probe recognized by a streptavidin donor and anti-cAMP antibody-conjugated acceptor beads. Release of the biotinylated cAMP from the antibody results in the dissociation of the streptavidin donor from its acceptor, which can be measured as a decrease in the chemiluminescent signal.

In addition, fluorescence polarization (FP)-based cAMP kits are available from Perkin-Elmer, Molecular Devices and GE Healthcare. Furthermore, HTRF-based cAMP detection is available from Cisbio. With this method, novel donor (cAMP antibody labelled with europium cryptate) and acceptor (cAMP labelled with a modified allophycocyanin dye) pairs are designed to increase the stability of the signal and make this assay highly sensitive and reproducible for cAMP measurement.

More recent commercial assays, such as the cAMP-Glo™ assay (Promega) are available for modulation of GPCRs that are coupled to Ga proteins which in turn modulate adenylate cyclase. The assay is based on cAMP as a potent activator of the tetrameric, inactive cAMP-dependent protein kinase (PKA) resulting in dissociation of its cAMP-bound regulatory subunits and release of the free, active catalytic subunits. Activation of PKA can be monitored by measuring APT use in a kinase reaction with a luciferase/luciferin-based reaction. The amount of ATP consumed reflects the activation of PKA by cAMP.

β-Arrestin Recruitment Assay

Beta-arrestins are intracellular proteins that are recruited to the cell surface following activation of the GPCR. They regulate the activity of G protein-coupled receptors (GPCRs) (Luttrell et al. (2002) Journal of Cell Science, 115: 455-465). In this case by the polypeptides of the invention, resulting in desensitization and targeting of the receptor for internalization. In addition to its role in receptor desensitization, termination of G protein-coupled signalling, and internalization, β-arrestin also acts as a scaffolding protein to link activated GPCR's to additional intracellular signalling pathways such as activation of c-Src, ERK 1/2 and Akt in a G protein-independent manner. Several methods are available for measuring β-arrestin recruitment including, the TransFluor® assay (Molecular Devices) in which β-arrestin is coupled to GFP and upon receptor activation, diffuse cytoplasmic distribution of GFP changes to formation of GFP containing pits or vesicles that are visualized with high content imaging system.

Several non-imaging-based β-arrestin recruitment assays, such as Bioluminescence Resonance Energy Transfer (BRET) as described in Xu Y et al (1999) Proc Natl Acad Sci 96:151-6, PathHunter™ technology (DiscoveRx) and the Tango™ assay (Invitrogen), are available. In the BRET assay, the receptor of interest is tagged at the C-terminus with a fluorescent protein tag (such as eGFP2, GFP10 or YFP) and the β-arrestin is tagged with a Renilla luciferase (RLuc) or vice versa. Upon β-arrestin recruitment, the two tags come into close proximity and the light emitted from the RLuc reaction excites the GFP, which then emits a detectable signal at a higher wavelength. BRET is calculated as the ratio of the two emissions (GFP/RLuc).

Invitrogen's Tango™ GPCR Assay System is a platform based on a protease-activated reporter gene. β-arrestin is fused to a TEV protease, while GPCR is extended at its C-terminus with a protease cleavage site followed by the transcription factor Gal-VP16. Upon GPCR activation, protease-tagged arrestin is recruited to the receptor and the Gal-VP16 that is fused to the receptor is cleaved and enters the nucleus to regulate the transcription of a β-lactamase reporter gene. The β-lactamase catalyzes the cleavage of a modified substrate tagged with two fluorophores, and the change in FRET signal between these two fluorophores can be monitored.

The PathHunter™ assay (DiscoveRx) utilizes enzyme fragment complementation of β-galactosidase and subsequent enzymatic activity to measure receptor-β-arrestin interactions. In this assay, β-arrestin is fused to an N-terminal deletion mutant of β-galactosidase that is catalytically inactive, and GPCR is tagged at the C-terminus with a small (4 kDa) fragment derived from the deleted N-terminal sequence of β-galactosidase (ProLink™). Upon GPCR-β-arrestin interaction, the two parts of β-galactosidase are brought into proximity, which results in the activation of the enzyme, cleavage of the substrate and generation of a chemiluminescent signal.

Calcium Assays

Activation of GPCRs by the polypeptides of the invention can be monitored by measuring the increase or decrease in intracellular calcium with fluorescent dyes. The Ca2+ assay is very popular in GPCR screening owing to the availability of cell-permeable Ca2+- sensitive fluorescent dyes (such as Fluo-3 and Fluo-4) and automated realtime fluorescence plate readers, such as FLIPR™ (Molecular Device). Molecular Device also offers fluorescent dye kits, which contain proprietary quenching molecules that allow cellular loading of dye without the need of subsequent cell washing to remove excess dye. The integrated pipetting capabilities of the FLIPR™ allow ultra high-throughput screening in 384- or 1536-well format with the ability to detect agonists, antagonists, and modulators all in one assay. The use of fluorescent dyes can also be replaced by the use of $Ca^{2+-}$ sensitive biosensors. Recombinant expression of the jellyfish photoprotein aequorin, which provides an intense luminescent signal in response to elevated intracellular $Ca^{2+}$ in the presence of a coelenterazine derivative, has also been developed for functional screens of GPCRs (Eglen R M et al (2008) Assay Drug Dev Technol 6:659-71).

Additional commercial assays include the Fluo-4/Fluor-8 calcium mobilisation assay (Invitrogen), and the Tango™ GPCR assay (Life Technologies).

Chemotaxis Assays

Chemotaxis assays can also be used to assess the ability of a CXCR4 binding polypeptide of the invention to block binding of a ligand to CXCR4 and/or inhibit function associated with binding of the ligand to the receptor (Fernandis et al. (2004) Oncogene 23: 157-167). These assays are based on the functional migration of cells in vitro or in vivo induced by a compound (chemoattractant). Chemotaxis can be assessed by any suitable means, for example, in an assay utilising a 96-well chemotaxis plate, or other art recognised method for assessing chemotaxis. In one example, Jurkat cells, MDA-MB-231, MDA-MB-468, PC3, or NCI-H69 cells can be assessed for migration utilising a chemotaxis assay. For example, Jurkat cells ($5 \times 10^5$ cells in 200 ml RPMI-1640) are pre-incubated with and without the polypeptides of the invention and SDF-1 and are added to the top well of a 6.5 mm diameter, 5-mM-pore polycarbonate Transwell culture insert (Costar, Cambridge, Mass.) with 0.25% BSA. SDF-1 (fixed concentration), is added in the lower wells and cells incubated for migration at 37° C. for 4 h. Migrated cells in the lower chamber are counted with a ZM Coulter counter (Coulter Diagnostics, Hialeah, Fla.).

Proliferation Assays

The CXCR4 binding polypeptides of the present disclosure can be assessed for their ability to inhibit cell proliferation of tumor cells (e.g. tumor cells expressing surface CXCR4 such as MDA-MB-231, MDA-MB-361, MDA-MB-549, Ramos, Namalwa, MOLT-4, DU-4475, DU-145, PC3, LNcaP, SW480, HT29, NCI-H69 and HL60), or in a cell line which has been engineered to express CXCR4. The CXCR4 binding polypeptides of the present disclosure can also be assessed for their ability to inhibit cell proliferation of $CD34^+$ progenitor cells (e.g. Kahn et al. Overexpression of CXCR4 on human CD34+ progenitors increases their proliferation, migration, and NOD/SCID repopulation ((2004) Blood. 103:2942-2949). Cell proliferation assays will be known to persons skilled in the art. Examples of cell proliferation assays include the MTT Cell Proliferation Assay (ATCC), the CellTiter Aqueous Cell proliferation assay (Promega), alamarBlue Assay (Invitrogen), CyQUANT Direct Cell Proliferation assay (Life Technologies), for described in, for example WO01/081614, and U.S. Pat. No. 5,972,639.

Apoptosis Assays

The CXCR4 binding molecules or polypeptides of the present disclosure can be assessed for their ability to induce apoptosis. Apoptosis assays are available in a variety of formats which will be known to persons skilled in the art. These include:

(i) caspase assays e.g. PhiPhiLux® (OncoImmunin, Inc), caspase 3 activity assay (Roche Applied Science), caspase-Glo™ Assays (Promega), CaspACE™ Assay System (Promega), EnzChek® Caspase-3 assay kit (Invitrogen), Active Caspase-3 detection kits (Stratagene), Caspase-mediated apoptosis products (BioVision), CasPASE™ Apoptosis Assay Kit (Genentech);

(ii) Tunnel and DNA Fragmentation Assays e.g. Apoptotic DNA Ladder Kit (Roche Applied Science), Cellular DNA fragmentation ELISA (Roche Applied Science), DeadEnd™ TUNEL System (Promega), APO-BrdU™ TUNEL Assay Kit (Invitrogen), TUNEL Apoptosis Detection kit (Upstate), Apoptosis Mebstain Kit (Bechman Coulter), Nuclear-mediated apoptosis kits (BioVision), apoptotic DNA Ladder Kit (Genentech);

(iii) Cell Permeability Assays e.g. APOPercentage™ Assay (Biocolor Assays);
(iv) Annexin V assays e.g. Annexin V, Alexa Fluor® (Invitrogen), Rhodamine 110, bis-(L-aspartic acid amide), trifluoroacetic acid salt (Invitrogen), Annexin V Apoptosis kits (BioVision);
(v) Protein cleavage assays e.g. anti-poly (ADP-ribose) polymerase (Roche Applied Science), M30 CytoDEATH (Roche Applied Science);
(vi) Mitochondrial and ATP/ADP assays e.g. ApoGlow® Rapid Apoptosis Screening kit, mitochondrial membrane potential detection kit (Stratagene) and Mitochondrial-mediated apoptosis products (BioVision); and
(vii) a combination of annexin V and propidium iodide as described in the examples disclosed herein.

Angiogenesis Assays

Angiogenesis is characterised by a number of cellular events including endothelial cell migration, invasion and differentiation into capillaries. In vitro endothelial tube formation assays are used as a model for studying endothelial differentiation and modulation of endothelial tube formation by antiangiogenic agents (see for example Sharon McGonigle and Victor Shifrin Current Protocols in Pharmacology DOI: 10.1002/0471141755.ph1212s43 or Liang et al, (2007) Biochem Biophys Res Commun. August 3; 359(3): 716-722.). Typically endothelial tube formation assays are performed using human umbilical vein endothelial cells (HUVEC), HMVEC and HMEC-1 cells. The cells are plated onto a layer of Matrigel at a density of $1 \times 10^5$ cells/ml of M199 medium with 1% FBS and 200 ng/ml of CXCL12. After 18 hrs, the wells were photographed at 4× magnification and the number of their tubular networks is counted.

Receptor Dimerisation Assay

CXCR4 interacts with CXCR7, CCR5, $\beta_2$AR ($\beta_2$ adrenergic receptor), CCR2, DOR (Delta opiod receptor) and CCR7 at the plasma membrane to form a heterodimer, oligomer or even higher order complexes including homodimers with CXCR4. Compounds that specifically target GPRC heterodimers or affect receptor dimerisation may have potential to achieve specific therapeutic effects (Rozenfeld R et al (2011) Biochem J 433:11-8). Various technologies have been established to monitor receptor dimerization, including resonance energy transfer approaches (FRET or BRET).

In commonly used FRET or BRET-based approaches, donor and acceptor molecules are genetically fused to the C-terminus of GPCRs, which are overexpressed in the cells. Resonance energy transfer occurs when donor and acceptor molecules are brought into close proximity as a consequence of GPCR dimerization (reviewed in Achour L et al (2011) Methods Mol Biol 756:183-200). However, one limitation of such traditional FRET and BRET assays is that in the overexpression system, resonance energy transfer can also occur within the intracellular compartments such that it is difficult to demonstrate a specific signal resulting only from a direct interaction of proteins at the cell surface.

The GPCR dimerization assay as described in U.S. Pat. No. 8,283,127 entitled 'Detection System and Uses Therefor' covers Dimerix's Heteromer Identification Technology (HIT) assay configuration for ligand dependent identification, monitoring and screening of heteromers of any two proteins. It also covers the application of Dimerix's assay on all proximity based reporter systems.

The GPCR dimerization assay with Tag-Lite™ is a method combining TR-FRET with SNAP-Tag™ technology (Cisbio), enabling quantitative analysis of protein-protein interactions at the surface of living cells in a 96- or 384-well format. In this assay, GPCRs are tagged with either a SNAP- or CLIP-tag at the N-terminus, which can be subsequently labelled with their corresponding cell-impermeable substrates carrying appropriate TR-FRET-compatible fluorophores, typically using terbium cryptate as a donor and a green or red fluorescent molecule as an acceptor. Several possible dimer combinations exist in this assay: ¼ of the dimers contain both receptors labeled with the donor, ¼ of the dimers contain both receptors labeled with the acceptors, and ½ of the dimers contain one receptor labeled with the donor and one receptor labelled with the acceptor. Only the last fraction will emit the FRET signal.

The PathHunter™ system (DiscoveRx) is another platform that can be used for GPCR heterodimerization analysis. Cell lines utilized in the previously described PathHunter™ β-arrestin recruitment assay can be used as the starting material. In these cell lines, β-arrestin is fused to the larger portion of the β-galactosidase enzyme acceptor, and the smaller 42-amino acid ProLink™ tag is attached to one of the GPCR targets. A second untagged GPCR can be introduced into the cells and the transactivation effects of the untagged GPCR on the ProLink™-tagged GPCR can be measured by the recruitment of β-arrestin to the tagged-GPCR using PathHunter detection reagents. The transactivation strength can be estimated as a ratio between the cellular response to the agonist of the untagged GPCR and the response to the agonist of Prolink™-GPCR. The assay can be used to investigate the interaction between GPCR pairs, as well as screen for compounds that modulate GPCP activity through enhancing or disrupting GPCR heterodimerization in a 384-well format, for example CXCR4 and CXCR7, CXCR4 and CCR5 or CXCR4 and $\beta_2$AR or CXCR4 and DOR or CXCR4 and CCR2 or CXCR4 and CCR7.

Competitive Assays

Competition studies can be used to determine the ability of the CXCR4 binding molecules including the ligand SDF-1 or polypeptides (i-bodies) to compete for binding to CXCR4. Typically, the CXCR4 i-bodies are titrated in a 1:3 serial dilution series resulting in a concentration range, for example from 100 nm to 5 μM in the presence of a constant concentration of SDF-1 or FITC-labelled human anti-CXCR4 antibody (e.g. 12G5). The mixture is then added to CXCR4 expressing cells and allowed to bind. The ability of each i-body to compete with 12G5 for binding to CXCR4 expressing cells can be assessed by fluorescent cytometry and detection of FITC.

Competition studies may also be performed utilising CXCR4 containing lipoproteins (IntegraMolecular) as described in WO 2005/042695.

The ability of the i-bodies of the present disclosure to bind to a variety of different cell lines can also be examined by flow cytometry by carrying out a FACS titration. Increasing amounts of the i-body can be incubated with 100,000 cells and binding assessed by flow cytometry. The Bmax value can also be determined, which indicated approximately how many CXCR4 molecules are present on each cell. Based on the binding curves, an EC50 for i-body binding can be determined. Examples of suitable cell lines include Ramos, Raji, Namalwa, L540, DMS79, MDA-MB-231, MDA-MB-361, MDA-MB-549, MOLT-4, DU-4475, DU-145, PC3, LNcaP, SW480, HT29, NCI-H69 and HL60.

The ability of the i-bodies of the present disclosure to bind to different subsets of human peripheral blood mononuclear cells (PBMCs) can also be examined. Human PBMCs can be isolated by standard methods and the cellular subsets further isolated by FACS. Examples of cellular subsets include one or more of the following CD3+, CD20+, CD11b+, and CD14+. Binding can be assessed by flow cytometry compared to a suitable control as shown in the examples herein.

The competition assay may be performed using Iodine-125-labeled SDF-I and a cell line, which naturally express CXCR4 or CXCR4 lipoparticles. A comparison of the i-bodies on blocking SDF-I binding to the CXCR4 expressing cell line can be performed by a standard radiolabeled ligand binding assay. The i-bodies can be serially diluted 1:3 to yield a range of concentrations and then added to CXCR4 expressing cells in the presence of $^{125}$I-SDF-I with a specific activity of 2000 Ci/mmole (Amersham, catalog # EM314-25UCI). The total possible bound radiolabeled ligand can be determined by allowing the $^{125}$I-SDF-I to bind to CXCR4 expressing cells in the absence of i-bodies for 2 hours at 40° C. Non-specific binding of the radio-labeled ligand can be determined by allowing the $^{125}$I-SDF-I to bind in the presence of 1 µM unlabeled SDF-I (Peprotech, catalog #300-28A). The amount of cell-associated $^{125}$I-SDF-I is then determined by standard methods.

Alternatively unlabelled SDF-1 could be used to compete the binding of the i-body to lipoparticles overexpressing CXCR4. Binding of the i-body to these lipoparticles could be detected using an antibody to the His tag or to the FLAG tag. Increasing concentrations of SDF-1 will be added and the amount of i-body remaining bound will be measured. This can be done in an ELISA format where the CXCR4 lipoparticles are immobilised on plastic. This information will determine if the binding site of the i-body on CXCR4 is the same or near or different to the ligand SDF-1.

Protein Detection Assays

One example of the disclosure detects the presence of CXCR4 or a cell expressing same or a lipoparticle containing CXCR4 within the membrane. The amount, level or presence of a protein or cell is determined using any of a variety of techniques known to the skilled artisan such as, for example, a technique selected from the group consisting of flow cytometry, immunohistochemistry, immunofluorescence, an immunoblot, a Western blot, a dot blot, an enzyme linked immunosorbent assay (ELISA), radioimmunoassay (RIA), enzyme immunoassay, fluorescence resonance energy transfer (FRET), matrix-assisted laser desorption/ionization time of flight (MALDI-TOF), electrospray ionization (ESI), mass spectrometry (including tandem mass spectrometry, e.g. LC MS/MS), biosensor technology, evanescent fiber-optics technology or protein chip technology.

In one example the assay used to determine the amount or level of a protein is a semi-quantitative assay.

In another example the assay used to determine the amount or level of a protein is a quantitative assay.

For example, the protein is detected with an immunoassay, e.g., using an assay selected from the group consisting of, immunohistochemistry, immunofluorescence, enzyme linked immunosorbent assay (ELISA), fluorescence linked immunosorbent assay (FLISA), Western blotting, radioimmunoassay (RIA), a biosensor assay, a protein chip assay and an immunostaining assay (e.g. immunofluorescence).

Standard solid-phase ELISA or FLISA formats are particularly useful in determining the concentration of a protein from a variety of samples.

In one form, an ELISA or FLISA comprises of immobilizing a CXCR4 lipoparticle on a solid matrix, such as, for example, a membrane, a polystyrene or polycarbonate microwell, a polystyrene or polycarbonate dipstick or a glass support. A sample that includes the CXCR4 binding molecule or polypeptide of the disclosure is then brought into physical relation with the immobilised CXCR4 protein and then bound or 'captured'. The bound CXCR4 binding molecule or polypeptide is then detected using a second labelled compound that binds to a tag sequence situated on the end of the CXCR4 binding molecule or polypeptide.

It will be apparent to the skilled person that the assay formats described herein are amenable to high throughput formats, such as, for example automation of screening processes or a microarray format. Furthermore, variations of the above-described assay will be apparent to those skilled in the art, such as, for example, a competitive ELISA.

In an alternative example, a polypeptide is detected within or on a cell, using methods known in the art, such as, for example, immunohistochemistry or immunofluorescence. Methods using immunofluorescence are exemplary, as they are quantitative or at least semi-quantitative. Methods of quantitating the degree of fluorescence of a stained cell are known in the art.

Lipoparticles containing CXCR4 can be used to assess the binding of a CXCR4 binding molecule or polypeptide of the present disclosure with CXCR4. The CXCR4 protein embedded in the lipoparticle can be used in assays where soluble proteins or whole cells cannot be used, such as assays where the protein of interest (e.g. CXCR4) must be bound to a support or substrate, for example an assay using a microfluidic device e,g. a biosensor assay. In some examples a lipoprotein is attached to a surface and is then contacted with the CXCR4 binding molecule or polypeptide of the disclosure and the biosensor detects the binding of the CXCR4 polypeptide of the invention to the lipoparticle. The detection can be by surface plasmon resonance, colorimetric diffraction grating, deflection of micro cantilevers (Weeks B L et al (2003) Scanning 25(6):297-9), or acoustic wave response (Coper M A et al (2001) Nature Biotechnology 19, 833-837). In some examples the CXCR4 binding molecule or polypeptide is attached to a surface that is part of a sensor and this is then contacted with a lipoparticle and the binding is detected. The detection can be by surface plasmon resonance, colorimetric diffraction grating, deflection of microcantilevers, or acoustic wave response. In some examples, the CXCR4 binding molecule or polypeptide and lipoparticle are contacted in solution.

Biosensor devices are designed to measure the interaction between biological molecules. Biosensor devices generally employ an electrode surface in combination with current or impedance measuring elements to be integrated into a device in combination with the assay substrate (such as that described in U.S. Pat. No. 5,567,301). Typically, biosensors measure direct interactions between a protein of interest and potential ligands that may bind to it. Biosensors are typically highly sensitive and can work with and detect even very weak or very small quantity interactions. Biosensor devices have been constructed that consist of optical chips, fiber optics, spectrometer detectors, microchannel chips, nanowells and microcantilevers, and acoustic wave devices. Some forms of biosensors known in the art also rely on surface plasmon resonance to detect protein interactions, whereby a change in the surface plasmon resonance surface of reflection is indicative of a protein binding to a ligand or antibody (U.S. Pat. Nos. 5,485,277 and 5,492,840).

In one example, the lipoparticle is attached to a sensor surface, where a "sensor surface" is any substrate where a change in a property of the substrate mediated by the contacting the surface with a molecule or polypeptide is detected and can be compared to the surface in the absence of such contacting. However, in other examples, the lipoparticle is already attached to a sensor surface. While the sensor surface can be a biosensor chip, the sensor surface also includes any biosensor chip known in the art e.g. Biacore C1 chip, a F1 chip, a glass substrate comprising a coating of e.g. gold.

Biosensors are of particular use in high throughput analysis due to the ease of adapting such systems to micro- or nano-scales. Furthermore, such systems are conveniently adapted to incorporate several detection reagents, allowing for multiplexing of diagnostic reagents in a single biosensor unit. This permits the simultaneous detection of several proteins or peptides in a small amount of body fluids.

The present disclosure also encompasses any assay where the protein of interest is a membrane component (e.g. CXCR4) and where study of the binding of the protein with a binding molecule or polypeptide requires, or is facilitated by presenting the protein in the context of a lipid bilayer and/or attaching the protein to a support or solid substrate. Such assays include assays using a microfluidic device, an optical biosensor, PATIR-FTIR spectroscopy, which is a type of biosensor using total internal reflection Fourier-transform infrared spectroscopy (19998, Chem. Phys. Lipids 96:69-80), CPRW Biosensor (Coupled Plasmon-wavelength resonance (CPWR) spectroscopy as described in Salamon et al (1997) Biophys J 73:2791-2197), multipole coupling spectroscopy (MCS) as described in Signature biosciences, fiber optic biosensors (Illumina) as described in Walt et al (200) Science 287:451-52 and Dickinson et al (1996) Nature 382:697-700, lab-on-α-chip microfluidics as described in Sundberg et al Current Opin in Biotech 11:47-53, micro-channels (Gyros' microchannels etched into a compact disc-based device, Microcantilevers as described in Tamayo et al (2001) Ultramicroscopy 86:167-173, confocal microscopy and nanowell detection as described WO 01/02551 and microwell binding assays. In one example, the sensor surface comprises a 96-well, 384-well, 1536-well a nano-well, optical fiber or slide format.

Imaging Methods

As will be apparent to the skilled artisan from the foregoing, the present disclosure also contemplates imaging methods using a CXCR4 binding molecule or polypeptide of the disclosure. For imaging, a CXCR4 binding molecule or polypeptide is generally conjugated to a detectable label, which can be any molecule or agent that can emit a signal that is detectable by imaging. However, a secondary labelled compound that specifically binds to a CXCR4 binding molecule or polypeptide of the disclosure may also be used. Exemplary detectable labels include a protein, a radioisotope, a fluorophore, a visible light emitting fluorophore, infrared light emitting fluorophore, a metal, a ferromagnetic substance, an electromagnetic emitting substance a substance with a specific magnetic resonance (MR) spectroscopic signature, an X-ray absorbing or reflecting substance, or a sound altering substance.

The CXCR4 binding molecule or polypeptide of the disclosure (and, if used the labelled secondary compound) can be administered either systemically or locally to an organ, or tissue (or tumor, in the case of a cancer) to be imaged, prior to the imaging procedure. Generally, the CXCR4 binding molecule or polypeptide is administered in doses effective to achieve the desired optical image of a tumor, tissue, or organ. Such doses may vary widely, depending upon the particular CXCR4 binding molecule or polypeptide employed, condition to be imaged, tissue, or organ subjected to the imaging procedure, the imaging equipment being used, and the like.

In some examples of the disclosure, the CXCR4 binding molecule or polypeptide is used as in vivo optical imaging agents of tissues and organs in various biomedical applications including, but not limited to, imaging of tumors, tomographic imaging of organs, monitoring of organ functions, coronary angiography, fluorescence endoscopy, laser guided surgery, photoacoustic and sonofluorescence methods, and the like.

Examples of imaging methods include magnetic resonance imaging (MRI), MR spectroscopy, radiography, computerized tomography (CT), ultrasound, planar gamma camera imaging, single-photon emission computed tomography (SPECT), positron emission tomography (PET), other nuclear medicine-based imaging, optical imaging using visible light, optical imaging using luciferase, optical imaging using a fluorophore, other optical imaging, imaging using near infrared light, or imaging using infrared light.

In some examples, an imaging agent is tested using an in vitro or in vivo assay prior to use in humans, e.g., using a model described herein.

Samples

To the extent that a method of the present disclosure is performed in vitro, on an isolated tissue sample, rather than as an in vivo based screen, reference to "sample" should be understood as a reference to any sample of biological material derived from a subject such as, but not limited to, a body fluid (e.g., blood or synovial fluid or cerebrospinal fluid), cellular material (e.g. tissue aspirate), tissue biopsy specimens or surgical specimens.

The sample which is used according to a method of the present disclosure may be used directly or may require some form of treatment prior to use. For example, a biopsy or surgical sample may require homogenization or other form of cellular dispersion prior to use. Furthermore, to the extent that the biological sample is not in liquid form, (if such form is required or desirable) it may require the addition of a reagent, such as a buffer, to mobilize the sample.

As will be apparent from the preceding description, such an assay may require the use of a suitable control, e.g. a normal or healthy individual or a typical population, e.g., for quantification.

A "healthy subject" is one that has not been diagnosed as suffering from a condition, e.g., a CXCR4-related disease or disorder and/or is not at risk of developing the disease or disorder.

Alternatively, or in addition, a suitable control sample is a control data set comprising measurements of the marker being assayed for a typical population of subjects known not to suffer from a condition.

In one example, a reference sample is not included in an assay. Instead, a suitable reference sample is derived from an established data set previously generated from a typical population. Data derived from processing, analyzing and/or assaying a test sample is then compared to data obtained for the sample population.

Pharmaceutical Compositions

CXCR4 binding molecules or polypeptides of the disclosure (syn. active ingredients) are useful for formulations into a pharmaceutical composition for parenteral, topical, oral, or local administration, aerosol administration, or transdermal administration, for prophylactic or for therapeutic treatment. The pharmaceutical compositions can be administered in a variety of unit dosage forms depending upon the method of administration. For example, unit dosage forms suitable for oral administration include powder, tablets, pills, capsules and lozenges.

The pharmaceutical compositions of the present disclosure are useful for parenteral administration, such as intravenous administration or subcutaneous administration or administration into a body cavity or lumen of an organ or joint. The compositions for administration will commonly comprise a solution of the CXCR4 binding molecule or polypeptide of the disclosure dissolved in a pharmaceutically acceptable carrier, such as an aqueous carrier. A variety of aqueous carriers can be used, e.g., buffered saline and the like. The compositions may contain pharmaceutically acceptable carriers as required to approximate physiological conditions such as pH adjusting and buffering agents, toxicity adjusting agents and the like, for example, sodium acetate, sodium chloride, potassium chloride, calcium chloride, sodium lactate and the like. The concentration of binding molecules or polypeptides of the present disclosure in these formulations can vary widely, and will be selected primarily based on fluid volumes, viscosities, body weight and the like in accordance with the particular mode of administration selected and the patient's needs. Exemplary carriers include water, saline, Ringer's solution, dextrose solution, and 5% human serum albumin. Nonaqueous vehicles such as mixed oils and ethyl oleate may also be used. Liposomes may also be used as carriers. The vehicles may contain minor amounts of additives that enhance isotonicity and chemical stability, e.g., buffers and preservatives.

A CXCR4 binding molecule or polypeptide of the disclosure can be formulated for parenteral administration, e.g., formulated for injection via the intravenous, intramuscular, subcutaneous, transdermal, or other such routes, including peristaltic administration and direct instillation into a tumor or disease site (intracavity administration). The preparation of an aqueous composition that contains the compounds of the present disclosure as an active ingredient will be known to those of skill in the art.

Suitable pharmaceutical compositions in accordance with the disclosure will generally include an amount of the CXCR4 binding molecule or polypeptide of the present disclosure mixed with an acceptable pharmaceutical carrier, such as a sterile aqueous solution, to give a range of final concentrations, depending on the intended use. The techniques of preparation are generally known in the art as exemplified by Remington's Pharmaceutical Sciences, 16th Ed. Mack Publishing Company, 1980.

Upon formulation, compounds of the present disclosure will be administered in a manner compatible with the dosage formulation and in such an amount as is therapeutically/prophylactically effective. Suitable dosages of compounds of the present disclosure will vary depending on the specific compound, the condition to be treated and/or the subject being treated. It is within the ability of a skilled physician to determine a suitable dosage, e.g., by commencing with a sub-optimal dosage and incrementally modifying the dosage to determine an optimal or useful dosage.

Exemplary dosages and timings of administration will be apparent to the skilled artisan based on the disclosure herein.

Compositions of the present disclosure can be combined with other therapeutic moieties or imaging/diagnostic moieties. For example, a pharmaceutical composition of the present disclosure may comprise an additional active agent selected from the group consisting of bisphosphonates, active vitamin D3, calcitonin and derivatives thereof, hormone preparations such as estradiol, SERMs (selective estrogen receptor modulators), ipriflavone, vitamin K2 (menatetrenone), calcium preparations, PTH (parathyroid hormone) preparations, nonsteroidal anti-inflammatory agents, soluble TNF receptor preparations, anti-TNF-[alpha] binding molecules, antibodies or functional fragments of the antibodies, anti-PTHrP (parathyroid hormone-related protein) binding molecules, antibodies or functional fragments of the antibodies, IL-1 receptor antagonists, anti-IL-6 receptor binding molecules, antibodies or functional fragments of the antibodies, anti-VEGF-A binding molecules or antibodies anti-CD20 binding molecules or antibodies, anti-PDL-1 or anti-PD1 binding molecules or antibodies, anti-CCL2 binding molecules or antibodies, anti-CCR2 binding molecules or antibodies, anti-RANK-L binding molecules, or functional fragments of the antibodies or i-bodies.

A pharmaceutical composition of the present disclosure also may include a pharmaceutically acceptable anti-oxidant. Examples of pharmaceutically acceptable antioxidants include (1) water soluble antioxidants, such as ascorbic acid, cysteine hydrochloride, sodium bisulfate, sodium metabisulfite, sodium sulfite and the like, (2) oil-soluble antioxidants, such as ascorbyl palmitate, butylated hydroxyanisole (BHA), butylated hydroxytoluene (BHT), lecithin, propyl gallate, alpha-tocopherol, and the like, and (3) metal chelating agents, such as citric acid, ethylenediamine tetraacetic acid (EDTA), sorbitol, tartaric acid, phosphoric acid, and the like.

Pharmaceutical compositions of the present disclosure also can be administered in combination therapy, i.e., combined with other agents. For example, the combination therapy can include a CXCR4 binding molecule or polypeptide of the present disclosure combined with at least one other anti-cancer, anti-inflammatory or immunosuppressant agent.

Examples of anti-cancer or chemotherapeutic agents may include Mitoxantrone, etoposide, Azacitidine, Lenalidomide, Temozolomide, Decitabine, Ganetespib, Clofarabine Cytarabine, Daunorubicin, vinorelbine, azacitidine, sorafenib, rituximab, bevacizumab or bortezomib.

These compositions may also contain adjuvants such as preservatives, wetting agents, emulsifying agents and dispersing agents. Prevention of presence of microorganisms may be ensured both by sterilization procedures, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatine.

The amount of active ingredient which can be combined with a pharmaceutically acceptable carrier to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient (i.e. CXCR4 binding polypeptide), in one example from about 0.1 percent to about 70 percent, in one example from about 1 percent to about 30 percent of active ingredient in combination with a pharmaceutically acceptable carrier. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. "Dosage unit form" as used herein refers to physically discrete units suited as unitary dosages for the subjects to be treated. Each unit contains a predetermined quantity of active compound calculated to produce the desired therapeutic effect in association with the required pharmaceutical carrier. The specification for the dosage unit forms of this disclosure are dictated by and directly dependent on (a) the unique characteristics of the active compound and the particular therapeutic effect to be achieved, and (b) the limitations inherent in the art of compounding such an active compound for the treatment of sensitivity in individuals. For administration of the CXCR4 binding molecule or polypeptide, the dosage ranges from about 0.0001 to 100 mg/kg, and more usually 0.01 to 5 mg/kg, of the host body weight. For example, dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per day, once per week, once every two weeks, once every three weeks, once every four weeks, once a month, once every 3 months or once every three to 6 months. Preferred dosage regimens for a CXCR4 binding molecules or polypeptides of this disclosure include 1 mg/kg body weight or 3 mg/kg body weight via intravenous administration, with the antibody being given using one of the following dosing schedules (i) every four weeks for six dosages, then every three months, (ii) every three weeks, (iii) 3 mg/kg body weight once followed by 1 mg/kg body weight every three weeks.

Actual dosage levels of the active ingredients in the pharmaceutical compositions of the present disclosure may be varied so as to obtain an amount of the active ingredient which is effective to achieve the desired therapeutic response for a particular patient, composition, and mode of administration, without being toxic to the subject. The selected dosage level will depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A "therapeutically effective dosage" of a CXCR4 binding molecule or polypeptide of this disclosure preferably results in a decrease in severity of disease symptoms, an increase in frequency and duration of disease symptom-free periods, or a prevention of impairment or disability due to the disease affliction. For example, for the treatment of CXCR4+ tumors, a "therapeutically effective dosage" preferably inhibits cell growth or tumor growth by at least about 20%, at least about 40%, at least about 60%, or at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit cell growth, such inhibition can be measured in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

Therapeutic compositions can be administered with medical devices known in the art. For example, a therapeutic composition of the present disclosure can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present disclosure include U.S. Pat. No. 4,487,603, which discloses an implantable micro-infusion pump for dispensing medication at a controlled rate, U.S. Pat. No. 4,486,194, which discloses a therapeutic device for administering medicants through the skin, U.S. Pat. No. 4,447,233, which discloses a medication infusion pump for delivering medication at a precise infusion rate, U.S. Pat. No. 4,447,224, which discloses a variable flow implantable infusion apparatus for continuous drug delivery, U.S. Pat. No. 4,439,196, which discloses an osmotic drug delivery system having multi-chamber compartments, and U.S. Pat. No. 4,475,196, which discloses an osmotic drug delivery system. Many other such implants, delivery systems, and modules are known to those skilled in the art.

In one example, the compositions are formulated to be free of pyrogens such that they are capable for administration to human patients.

The present disclosure also contemplates the use of any of the CXCR4 binding polypeptide/i-body compositions of the present disclosure to make a medicament for treating a disorder of the present disclosure. Medicaments can be packaged in a suitable pharmaceutical package with appropriate labels for the distribution to hospitals and clinics according to indication on the label.

Uses of CXCR4 Binding Polypeptides

The CXCR4 binding molecules or polypeptides of the present disclosure have numerous in vitro and in vivo diagnostic and therapeutic utilities involving the diagnosis and treatment of CXCR4 related diseases and disorders. For example, these molecules can be administered to cells in culture, in vitro or ex vivo, or to human subjects, e.g., in vivo, to treat, prevent and to diagnose a variety of disorders. Preferred subjects include human subjects having disorders mediated by or modulated by CXCR4 activity or involving the CXCR4/SDF-1 pathway. When a CXCR4 binding polypeptide is administered together with another agent, the two can be administered in either order or simultaneously. Given the specific binding of the CXCR4 binding molecules or polypeptides of this disclosure for CXCR4, they can be used to specifically detect CXCR4 expression on the surface of cells and, moreover, can be used to purify CXCR4 positive cells via immunoaffinity purification.

Target-specific effector cells, e g, effector cells linked to compositions of this disclosure can also be used as therapeutic agents. Effector cells for targeting can be human leukocytes such as macrophages, neutrophils or monocytes. Other cells include eosinophils, natural killer cells and other IgG- or IgA-receptor bearing cells. If desired, effector cells can be obtained from the subject to be treated. The target-specific effector cells can be administered as a suspension of cells in a physiologically acceptable solution. The number of cells administered will vary depending on the therapeutic purpose. In general, the amount will be sufficient to obtain localization at the target cell, e.g, a tumor cell expressing CXCR4, and to effect cell killing by, e g. phagocytosis.

Therapy with target-specific effector cells can be performed in conjunction with other techniques for removal of targeted cells. For example, anti-tumor therapy using the compositions of the present disclosure and/or effector cells armed with these compositions can be used in conjunction with chemotherapy. Additionally, combination immunotherapy may be used to direct two distinct cytotoxic effector populations toward tumor cell rejection. For example, CXCR4 binding polypeptides linked to anti-Fc-gamma receptor or anti-CD3 may be used in conjunction with IgG- or IgA-receptor specific binding agents. Bispecific and multispecific molecules of the present disclosure can also be used to modulate FcγR or FcγR levels on effector cells, such as by capping and elimination of receptors on the cell surface.

As a co-receptor for HIV entry into T cells, CXCR4 is known to be involved in HIV infection. Additionally, the CXCR4/SDF-1 pathway has been shown to be involved in inflammatory conditions. Still further, the CXCR4/SDF-1 pathway has been shown to be involved in angiogenesis or neovascularisation. Accordingly, the CXCR4 binding polypeptides of the present disclosure can be used to modulate CXCR4 activity in a number of clinical situations, as detailed below.

The present disclosure also provides methods for diagnosing or detecting a CXCR4 related disease or disorder as described herein. Any suitable method for detection and analysis of CXCR4 can be employed. As used herein, the term "sample" refers to a sample from a human, animal, or to a research sample, e.g., a cell, tissue, organ, fluid, gas, aerosol, slurry, colloid, or coagulated material. Samples also include, but are not limited to, protein or membrane extracts of cells, biological fluids such as sputum, blood, serum, plasma, or urine, or biological samples such as formalin-fixed or frozen tissue sections employing antibodies described herein. The term "sample" can also refer to a cell, tissue, organ, or fluid that is freshly taken from a human or animal, or to a cell, tissue, organ, or fluid that is processed or stored. The sample can be tested in vivo, e.g., without removal from the human or animal, or it can be tested in vitro. The sample can be tested after processing, e.g., by histological methods.

Various diagnostic assay techniques known in the art can be used, such as competitive binding assays, direct or indirect sandwich assays and immunoprecipitation assays conducted in either heterogeneous or homogeneous phases (Zola, Monoclonal Antibodies: A Manual of Techniques, CRC Press, Inc. (1987) pp. 147-158). The antibodies used in the diagnostic assays can be labeled with a detectable moiety. The detectable moiety directly or indirectly produces a detectable signal. For example, the detectable moiety can be any of those described herein such as, for example, a radioisotope, such as 3H, 14C, 32P, 35S, or 125I, a fluorescent or chemiluminescent compound, such as fluorescein isothiocyanate (FITC), Texas red, cyanin, photocyan, rhodamine, or luciferin, or an enzyme, such as alkaline phosphatase,/3-galactosidase or horseradish peroxidase. Any method known in the art for conjugating the antibody to the detectable moiety can be employed, including those methods described by Hunter et al., Nature, 144:945 (1962); David et al., Biochemistry, 13:1014 (1974); Pain et al., J. Immunol. Meth., 40:219 (1981); and Nygren, J. Histochem. and Cytochem., 30:407 (1982).

Provided herein is a method of diagnosing a condition associated with CXCR4 comprising assessing a level of CXCR4 and/or SDF-1 in a sample of a subject, wherein a change in level of CXCR4 and/or SDF-1 in the sample in comparison with a reference sample indicates the presence or increase of a tumor or metastasis or fibrosis. In one aspect, the condition associated with CXCR4 or SDF-1 is a tumor, a metastasis, angiogenesis, or fibrosis. An increase in CXCR4 and/or SDF-1 levels in the sample in comparison with a reference sample can indicate the presence of a tumor or metastasis or an increase in tumor or metastatic growth or fibrosis. The reference sample can be a sample taken from the subject at an earlier time point or a sample from another individual. The level of CXCR4 and/or SDF-1 levels in the sample can be detected by contacting the sample with the CXCR4 binding molecule, polypeptide or i-body thereof described herein. In one embodiment, the CXCR4 binding molecule, polypeptide or i-body thereof is detectably labeled.

In another example, a method is provided for diagnosing cancer metastasis in a subject having a tumor, comprising: assessing CXCR4 levels or activity in the tumor, whereby a change in CXCR4 levels or activity in the tumor in comparison with a reference sample indicates the presence of metastatic tumor growth. In some instances, the CXCR4 levels or activities in the tumor can be higher than those when measured earlier, which can indicate that the subject is at a greater risk of cancer metastasis; that the cancer has metastasized; or that cancer metastasis has increased. The reference sample can derive from the same subject, taken from the same tumor at a different time point or from other site of the body, or from another individual.

In another example, a method is provided for diagnosing the level or rate of progression of fibrosis in a subject having fibrosis, comprising: assessing CXCR4 levels or activity in the tissue, blood, plasma or biological fluids, whereby a change in CXCR4 levels in comparison with a reference sample indicates the presence of fibrosis. In some instances, the CXCR4 levels or activities can be higher than those when measured earlier, which can indicate that the subject is at a faster progressor of disease. The reference sample can derive from the same subject, taken from the same tissue, blood, plasma or biological fluids at a different time point or from other site of the body, or from another individual.

Methods of Treatment

Methods are provided herein for treating or preventing a CXCR4 related disease or disorder. The methods comprise administering a therapeutically effective amount of a CXCR4 binding molecule or polypeptide and another therapeutic agent.

CXCR4 has been shown to be expressed by a variety of cancer types and in certain situations an inverse correlation has been established between CXCR4 expression and subject prognosis or survival. Non-limiting examples of cancer types associated with CXCR4 expression include breast, prostate, non-small cell lung, pancreatic, thyroid, nasopharyngeal carcinoma, melanoma, renal cell carcinoma, lymphoma (e.g. non-Hodgkin's lymphoma), neuroblastoma, glioblastoma, rhabdomyosarcoma, colorectal, kidney, osteosarcoma, acute lymphoblastic leukemia, and acute myeloid leukemia.

Thus, in one example according to the present disclosure, a CXCR4 binding molecule or polypeptide of the present disclosure can be used to treat a CXCR4 related disease or disorder, wherein the disease is cancer, and wherein the cancer includes, but is not limited to a cancer selected from the group consisting of bladder cancer, breast cancer, colorectal cancer, endometrial cancer, head & neck cancer, leukemia, lung cancer, lymphoma, melanoma, non-small-cell lung cancer, ovarian cancer, prostate cancer, testicular cancer, uterine cancer, cervical cancer, thyroid cancer, gastric cancer, brain stem glioma, cerebellar astrocytoma, cerebral astrocytoma, ependymoma, Ewing's sarcoma family of tumors, germ cell tumor, extracranial cancer, Hodgkin's disease, leukemia, acute lymphoblastic leukemia, acute myeloid leukemia, liver cancer, medulloblastoma, neuroblastoma, brain tumors generally, non-Hodgkin's lymphoma, osteosarcoma, malignant fibrous histiocytoma of bone, retinoblastoma, rhabdomyosarcoma, soft tissue sarcomas generally, supratentorial primitive neuroectodermal and pineal tumors, visual pathway and hypothalamic glioma, Wilms' tumor, acute lymphocytic leukemia, adult acute myeloid leukemia, adult non-Hodgkin's lymphoma, chronic lymphocytic leukemia, chronic myeloid leukemia, esophageal cancer, hairy cell leukemia, kidney cancer, multiple myeloma, oral cancer, pancreatic cancer, primary central nervous system lymphoma, skin cancer, Myelodysplastic Syndrome and small-cell lung cancer.

In one example according to the present disclosure, a CXCR4 binding molecule or polypeptide of the present disclosure can be used to inhibit metastatic tumour cell growth.

In one example according to the present disclosure a CXCR4 binding molecule or polypeptide of the present disclosure can be used to treat fibrosis.

The CXCR4 binding molecule or polypeptide of the present disclosure can be used alone or in combination other cancer treatments, such as surgery and/or radiation, and/or with other anti-neoplastic agents, such as the anti-neoplastic agents discussed and set forth above, including chemotherapeutic drugs and other anti-tumor antigen antibodies, such as those that bind CD20, Her2, PD-1, PDL-1, IL-2, PSMA, Campath-1, EGFR and the like.

The CXCR4 binding molecule or polypeptide of the present disclosure can be used alone or in combination with other inflammatory and fibrosis treatments.

CXCR4 has been shown to be a coreceptor for HIV entry into T cells and, additionally, certain murine anti-CXCR4 antibodies have been demonstrated to be able to inhibit entry of HIV isolates into T cells (see Hou, T et al. (1998) J Immunol 160 180-188, Carnec, X et al. (2005) J Virol 79 1930-1938). Thus, CXCR4 can be used as a receptor by viruses for entry into the cell and antibodies or other blocking agents can be used to inhibit cell entry of such viruses that use CXCR4 as a receptor. Thus, in one example, the CXCR4 binding molecules or polypeptides of present disclosure can be used to inhibit entry of a virus into a cell, wherein the virus uses CXCR4 as a receptor for cell entry, such that viral infection is inhibited. In one example, the CXCR4 binding molecules or polypeptides are used to inhibit entry of HIV into T cells, e.g, in the treatment or prevention of HIV/AIDS. The CXCR4 binding molecule or polypeptide can be used alone or in combination with other anti-viral agents, such as anti-retroviral drugs such as AZT or protease inhibitors.

CXCR4 has been found to form a heterodimer with CXCR7 and regulated CXCL12-mediated G protein signalling (Levoye A et al (2009) Blood 113(24):6085-6093). The CXCR4/CXCR7 heterodimer has also been shown to recruit beta-arrestin to enhance cell migration (Decaillot F M et al (2011) J Biol Chem 286(37):32188-97). Accordingly, the CXCR4 binding molecules or polypeptides of the present disclosure can be administered alone or together with agents that target the CXCR7 receptor as described in for example, WO 2007/115231, WO 2007/115232, WO 2008/048519, WO 2008/109154, WO 2010/054006. CXCR4 has also been found to form a heterodimer with CCR5 (Sohy et al J Biol Chem. 2009 284; 31270-31279), β$_2$AR (La Rocca et al J Cardiovasc Pharmacol. 2010 56; 548-559) CCR2 (Sohy et al J Biol Chem. 2007 282; 30062-30069), DOR (Delta opiod receptor) (Pello et al Eur. J. Immunol. 2008 38; 537-549) or CCR7. Accordingly, the CXCR4 binding molecules or polypeptides of the present disclosure can be administered alone or together with agents that target these receptors.

The CXCR4/SDF-1 pathway has been shown to play a role in a variety of inflammatory conditions, including but not limited to inflammatory liver disease (Terada, R et al. (2003) Lab. Invest 83:665-672), autoimmune joint inflammation (Matthys, P et al. (2001) J. Immunol 167 4686-4692), allergic airway disease (Gonzalo, J A et al (2000) J. Immunol 165-499-508), and periodontal disease (Hosokawa, Y et al (2005) Clin. Exp. Immunol 4:467-474).

Accordingly, CXCR4 binding molecules or polypeptides of the present disclosure that inhibit binding of SDF-I to CXCR4 can be used to inhibit inflammation, inflammatory disorders, including disorders selected from the group consisting of inflammatory liver disease, autoimmune joint inflammation, allergic airway disease, periodontal disease (induced by *Porphyromonas gingivalis*) (Hajishengallis et al PNAS 2008 105; 13532-13537), rheumatoid arthritis, inflammatory bowel disease, systemic lupus erythematosus, Type I diabetes, inflammatory skin disorders (e.g., psoriasis, lichen planus), skin repair and regeneration (burns, scarring), eye (AMD, uveitis) systemic sclerosis, radiation induced fibrosis, autoimmune thyroid disease, Sjogren's syndrome, pulmonary inflammation (e.g., chronic obstructive pulmonary disease, pulmonary sarcoidosis, lymphocytic alveolitis, idiopathic pulmonary fibrosis), multiple sclerosis (Kohler et al Brain Pathology 2008, 18; 504-516), sepsis (Ding et al Crit Care Med 2006 34; 3011-3017) and inflammatory kidney disease (e.g., IgA nephropathy, glomerulonephritis). The CXCR4 binding polypeptide can be used alone or in combination with other anti-inflammatory agents, such as non-steroidal antiinflammatory drugs (NSAIDs), corticosteroids (e.g., prednisone, hydrocortisone), methotrexate, COX-2 inhibitors, TNF antagonists (e.g., etanercept, infliximab, adalimumab) and immunosuppressants (such as 6-mercaptopurine, azathioprine and cyclosporine A).

Accordingly, CXCR4 binding molecules or polypeptides of the present disclosure that inhibit binding of SDF-I to CXCR4 can be used to inhibit fibrosis, in fibrotic disorders, including disorders selected from the group consisting of lung fibrosis (Idiopathic pulmonary fibrosis, fungal cystic fibrosis (Carevic et al Eur Respir J 2015 46; 395-404), pulmonary arterial hypertension (Farkas et al PLoSONE 2014 9; e89810), radiation induced fibrosis (Shu et al PLoSONE 2013; 8; e79768.) and systemic sclerosis, asthma (Lukacs et al AJP 2012 160; 1353-1360 & Nagase et al J Immunol 2000; 164: 5935-5943)), liver fibrosis (nonalcoholic steatohepatitis (NASH) (Boujedidi et al Clinical Science 2015 128; 257-267)), kidney fibrosis (hypertension and chronic kidney disease (Yuan et al Am J Physiol Renal Physiol. 2014 308; 459-472)), eye fibrosis (proliferative vitroretinopathy, diabetic retinopathy (Butler et al The Journal of Clin Invest 2005 115; 86-93), retinopathy of prematurity (Villalvilla et al Life Sciences 2012 91; 264-270), noninfectious uveitis (Zhang et al Experimental Eye Research 2009 89; 522-531), and wet-AMD (U.S. Pat. No. 7,964,191)), cardiac fibrosis (hypertension, ischemic cardiomyopathy, endomyocardial fibrosis, arterial fibrosis (Chu et al Circ Heart Fail. 2011 4; 651-658)), skin fibrosis (hypertrophic scarring (Ding et al Wound Rep and Reg 2014 22; 622-630), burn related scarring (Avniel et al Journal of Investigative Dermatology 2006 126; 468-476), diabetic wounds, scleroderma or systemic sclerosis (Tourkina et al Fibrogenesis & Tissue Repair 2011, 4; 10.1186/1755-1536-4-15)). The CXCR4 binding molecules or polypeptides of the current invention can be used alone or in combination with other anti-fibrotic agents, for example Pirfenidone or Nintedanib.

It has been demonstrated that SDF-1 induces neovascularization through recruitment of CXCR4-expressing hemangiocytes (Jin, D. K. et al. (2006) Nat Med. 12:557-567). CXCR4 has also been found to be essential for vascularisation of the gastrointestinal tract (Tachibana et al. (1998) Nature 393(6685):591-4). Moreover, blockade of the SDF-1/CXCR4 pathway can attenuate in vivo tumor growth by inhibiting angiogenesis in a VEGF-independent manner (Guleng, B. et al. (2005) Cancer Res. 65:5864-58-71). Accordingly, the CXCR4 binding molecules or polypeptides of the present disclosure that inhibit binding of SDF-I to CXCR4 can be used to inhibit angiogenesis by interfering with the SDF-1/CXCR4 pathway. Inhibition of angiogenesis can be used, for example, to inhibit tumor growth or tumor metastasis (regardless of whether the tumor is CXCR4*). The CXCR4 binding molecule or polypeptide can be used alone or in combination with other anti-angiogenic agents, such as anti-VEGF (Grunewald M et al (2006) Cell 124(1): 175-89) or PDGF-D antibodies or fragments of antibodies.

Lack of Mobilisation of Stem Cells by the i-Bodies of the Present Disclosure-Potential Applications Various cytokines, chemokines and adhesion molecules have been implicated in the regulation CD34$^+$ stem cell mobilisation (reviewed in Gazitt, Y. (2001). J Hematother. Stem Cell Res. 10:229-236), including the interaction of CXCR4 and SDF-I. Moreover, a small molecule CXCR4 antagonist has been demonstrated to stimulate rapid mobilization of CD34$^+$ stem cells from the bone marrow to the periphery (see e.g, Devine, S M et al. (2004) J. Clin. Oncol 22 1095-1 102; Broxmeyer, H E et al. (2005) J. Exp. Med 201:1307-1318, Flomenberg, N et al (2005) Blood 106: 1867-1874).

In contrast, some of the i-bodies of the present disclosure were found to lack stem cell mobilisation ability. There are several studies that indicate that CXCR4 inhibitors/antagonists that do not mobilise stem cells, such as the i-bodies described herein, will be useful in long-term studies and treatment of chronic diseases.

i) Fibrosis Treatment

The response to injury involves the activation of adaptive mechanisms designed not only to maintain homeostasis but also to induce tissue repair. This potential for regenerative repair is evident in humans in certain circumstances such as following hepatic resection or acute tubular necrosis. However, in the presence of chronic or repeated injury, the response mostly involves a combination of disordered parenchymal cell regeneration in conjunction with the production of large quantities of ECM, eventually leading to the formation of a connective tissue scar. While this repair by connective tissue clearly assists in the maintenance of organ integrity following, for instance, a skin wound, its presence in the other organs such as the heart, kidney and lungs is often detrimental (Wynn et al Nat Med (2012) 18: 1028-1040).

There is an unmet clinical need for the treatment of fibrosis (Luppi et al Curr Respir Care Rep (2012) 1:216-223, Friedman et al Sci Transl Med. (2013) 5:167sr1). Importantly, there are no current therapeutic strategies that target the pro-fibrotic inflammatory processes and hence indicate a clear unmet clinical need to develop new therapeutic agents. Accordingly, strategies that inhibit pro-inflammatory cytokine activation and pathological accumulation of ECM provide a potential therapeutic target for prevention of pathological organ fibrosis.

(a) Lung Fibrosis: Idiopathic Pulmonary Fibrosis (IPF)

Idiopathic pulmonary fibrosis (IPF) is an interstitial inflammatory disease characterized by scarring and fibrosis of the lungs ultimately resulting in terminal respiratory insufficiency. Recent studies present evidence that circulating fibrocytes that express CXCR4 contribute to the pathogenesis of pulmonary fibrosis (Phillips et al J Clin Invest (2004) 114: 438-446.). This and other recent studies suggest that blocking the activity of the CXCR4 on these fibrocytes might be useful approach for therapy in patients with various types of fibrosis, including fibrosis associated with pulmonary disease, diabetes and cardiovascular disease.

b) Occular Fibrosis

The pathological growth of new blood vessels in the posterior eye is a devastating consequence of a number of diseases including Age related Macular Degeneration, proliferative diabetic retinopathy and Retinopathy of Prematurity. Advanced, vision threatening, Age Related Macular Degeneration (referred to as Wet AMD) affects 5.7% of all people over 85 years. Diabetic retinopathy is the most feared complication of diabetes affecting approximately 40% of those with Type II diabetes and 86% of those with type I diabetes (Cheung et al Lancet 2010; 376: 124-36). Another retinal vascular disease, called Retinopathy of Prematurity, is a devastating consequence of premature birth, and remains the leading cause of childhood blindness in the Western world. A common feature of these conditions is the abnormal growth of blood vessels and subsequent scar formation that is the crucial event leading to blindness. In order to prevent blindness from these diseases, treatments that target both abnormal growth of retinal blood vessels as well as subsequent scarring are necessary Wet AMD is currently treated with a monthly or bimonthly injection into the eye of a humanized antibody or antibody fragment that blocks the action of the angiogenic growth factor, Vascular Endothelial Growth Factor (VEGF). These new treatments have transformed the clinical care of those with Wet AMD and prevents the sudden loss of vision in a majority of patients (Rosenfeld et al N Engl J Med 2006; 355: 1419-31; Brown et al N Engl J Med 2006; 355: 1432-44). The CXCR4 binding molecule or polypeptides of the current invention can be used for the treatment of scaring and fibrotic related disorders of the eye including vitreoretinopathy, diabetic retinopathy and retinopathy of prematurity.

ii) Atherosclerosis Treatment

Zernecke and colleagues (Zernecke et al (2008) Circulation Research 102:09-217) provide evidence that the CXCL12/CXCR4 axis is protective in atherosclerosis and this protective effect is due to the control of myeloid cell homeostasis. These studies show that long-term inhibition of the CXCR4 by the small molecule antagonist AMD3465 aggravated diet-induced atherosclerotic lesion development in two different mouse strains (Apoe$^{-/-}$ mice and Ldlr$^{-/-}$). CXCR4 antagonism with AMD3465 has been shown to be 10-fold more effective than AMD3100 at releasing neutrophils from the bone marrow (Hatse et al. Biochem Pharmacol. 2005; 70:752-761). Zernecke et al also demonstrated that prolonged treatment with AMD3465 led to an expansion of myeloid neutrophils and a slight increase in monocytes, which appeared to correlate with a reduction of lymphocytes in the bone marrow. They concluded that "caution seems warranted when attempting therapy with CXCR4 antagonists, which can mobilize hematopoietic cells but may inhibit the recruitment of plaque-stabilizing progenitor subsets and may thus promote atherosclerosis". Thus, agents that lack the ability to mobilise hematopoietic cells may be useful in the treatment of atherosclerosis. The CXCR4 binding molecule or polypeptides of the current invention have the ability to have anti-atheroscerotic effects while not increasing stem cell mobilization.

iii) Kidney Disease

A study by Zuk et al (2014) Am J Physiol Renal Physiol October 1; 307(7):F783-97, provides compelling evidence that CXCR4 inhibition ameliorates acute kidney injury by inhibiting leukocyte infiltration and expression of pro-inflammatory cytokines rather than via any effect on hematopoetic stem cells or their mobilisation. Thus, the CXCR4 binding molecules or polypeptides of the present disclosure may be useful in the treatment of kidney disease.

iv) Angiogenesis

SDF-1 and its receptor, CXCR4 have been implicated in angiogenesis and scar formation (fibrosis)(Ferrara et al Nature 2005; 438: 967-74). Indeed, SDF-1 is increased in the vitreous of those with wet AMD, proliferative diabetic retinopathy and retinopathy of prematurity (Scotti et al Retina 2014; 34: 1802-10, Butler et al J Clin Invest 2005; 115: 86-93, Sonmez et al Ophthalmology 2008; 115: 1065-1070). Its receptor, CXCR4, is localized to the growing tips of pathologically growing blood vessels. Moreover, inhibition of CXCR4 has been shown to prevent the abnormal growth of vessels in a rodent model of choroidal neovascularization and retinopathy of prematurity (Lima e Silva et al FASEB J 2007; 21: 3219-30). Another study has shown that circulating fibrocytes may function as precursors of myofibroblasts in Proliferative vitreoretinopathy (PVR) membranes. In PVR epiretinal membranes, there were high numbers of cells expressing CXCL12 and CXCR4 and suggested that the CXCL12/CXCR4 chemokine axis appears to be predominant for the recruitment of fibrocytes into the eye in patients with PVR (Abu El-Asar et al Br J Ophthalmol 2008; 92:699-704).

In order to improve the clinical management of these vascular diseases, a treatment is needed that targets both angiogenesis and subsequent fibrosis. The novel polypeptides or i-bodies of the present disclosure are useful for such treatment.

Thus, the CXCR4 binding molecules, polypeptides or i-bodies of the present disclosure could be effective in reducing angiogenesis and subsequent scarring in models of vascular disease of the posterior eye in AMD, proliferative diabetic retinopathy, retinopathy of prematurity, proliferative vitreoretinopathy, uveitis, corneal angiogenesis.

Inflammatory Models

The ability of the CXCR4 binding molecules or polypeptides of the present disclosure to inhibit inflammation can be examined in inflammatory mouse models. These models include the murine experimental colitis model, the carrageenan-induced paw edema model and the bleomycin-induce lung fibrosis model as described in Liang Zhongxing et al (2012) PLoS ONE 7(4): e34038.doi:10.1371.

Fibrotic Models

The ability of the CXCR4 binding molecules or polypeptides of the present disclosure to inhibit fibrosis can be examined in the bleomycin rodent model. In the rodent bleomycin model, which is used frequently to mimic idiopathic pulmonary fibrosis (IPF), SDF-1 levels are increased in serum and bronchial alveolar lavage fluid. Moreover, neutralizing antibodies to CXCR4 and the small molecule CXCR4 antagonist, AMD3100, were found to reduce lung eosinophilia, indicating that CXCR4-mediated signals contribute to lung inflammation in a mouse model of allergic airway disease (Gonzalo et al J Immunol. 2000; 165:499-508, Lukacs et al Am J Pathol. 2002; 160:1353-60). These data strongly indicate that CXCR4 has a prominent role in promoting fibrosis than re-epithelialisation. The CXCR4 binding molecule or polypeptides of the current invention can be used as an anti-fibrotic agent.

To date, several CXCR4 antagonists have been developed (Tsutsumi et al Biopolymers. 2007; 88: 279-289). Blocking CXCR4 using an antagonist such as TN14003, MSX-122 or AMD3100 has been shown to effectively alleviate bleomycin induced pulmonary fibrosis (Xu et al Cell Mol Biol. 2007; 37: 291-299). AMD3100 (Plerixafor), an FDA-approved small molecule CXCR4 antagonist, has also been tested on bleomycin treated mice. While AMD3100 is effective at blocking stem cell homing, it also increases stem cell mobilization, which has led to its use for increasing stem cell yields in preparation for autotransplantation. TN14003, a 14-mer peptide, blocks development of pulmonary fibrosis in bleomycin-treated mice, while MSX-122, a small molecule has also demonstrated superiority over TN14003 and AMD3100 in completely preventing bleomycin-induced lung fibrosis (Xu et al Cell Mol Biol. 2007; 37: 291-299) and irradiated mice that received MSX-122 had significant reductions in development of pulmonary fibrosis while AMD3100 did not significantly suppress this fibrotic process (Shu et al PLoS ONE 2013; 8(11): e79768.). The CXCR4 binding molecule or polypeptides of the current invention have the ability to block stem cell homing while not increasing stem cell mobilization.

An alternative technique to elucidate the role of novel targets in the pathogenesis of IPF involves isolation of fibroblasts from patients with the disease and comparing mediator release to fibroblasts from healthy subjects. In this process, cells are exposed to pharmacologic agonists and antagonists. The fibroblasts can be embedded and cultured in three-dimensional matrices and cocultured with other cell types. The ability of the CXCR4 binding molecules or polypeptides of the present disclosure to inhibit fibrosis can be examined with the human patient fibroblasts.

Yet another translational model is the implantation of fibroblasts from patients with IPF into immunodeficient mice. The ability of the CXCR4 binding molecules or polypeptides of the present disclosure to inhibit fibrosis can be examined in this animal model of fibrosis (Murray et al, American Journal of Respiratory Cell and Molecular Biology Volume 50 Number 5, May 2014).

Cancer/Metastasis Models

The ability of the CXCR4 binding molecules or polypeptides of the present disclosure to inhibit metastasis can be examined in mouse models. These models include the breast cancer model (via administration of MDA-MB-231 cells), the head and neck cancer animal model (via administration of 686LN-Ms cells) and the uveal melanoma micrometastasis model as described in Liang Zhongxing et al (2012) PLoS ONE 7(4): e34038.doi:10.1371.

In Vivo Angiogenesis Assay

The ability of the CXCR4 binding molecules to inhibit angiogenesis can be examined in a mouse model. These models are described in Liang et al, (2007) Biochem Biophys Res Commun. August 3; 359(3): 716-722, whereby MDA-MB-231 cells are implanted subcutaneously into the flanks of nude mice.

Kits

In some examples, the CXCR4 binding molecule or polypeptides may be provided in a kit or pharmaceutical package.

In one example, the present disclosure relates to kits for carrying out the administration of a CXCR4 binding molecule described herein.

Pharmaceutical packages and kits can additionally include an excipient, a carrier, a buffering agent, a preservative or a stabilizing agent in a pharmaceutical formulation. Each component of the kit can be enclosed within an individual container and all of the various containers can be within a single package. Invention kits can be designed for room temperature or cold storage. Additionally, the preparations can contain stabilisers to increase shelf life of the kits and include, for example bovine serum albumin (BSA) or other known conventional stabilizers. Where the compositions are lyophilized, the kit can contain further preparations of solutions to reconstitute the preparations. Acceptable solutions are well known in the art and include, for example, pharmaceutically acceptable phosphate buffered saline (PBS).

Additionally, the pharmaceutical packages or kits provided herein can further include any of the other moieties provided herein such as, for example, a chemotherapeutic agent as described elsewhere in more detail.

Pharmaceutical packages and kits of the present invention can further include the components for an assay provided herein, such as, for example, an ELISA assay. Alternatively, preparations of the kits are used in immunoassays, such as immunohistochemistry to test patient tissue biopsy sections.

Pharmaceutical packages and kits of the present invention can further include a label specifying, for example, a product description, mode of administration and indication of treatment. Pharmaceutical packages provided herein can include any of the compositions as described herein. The pharmaceutical package can further include a label for preventing, reducing the risk of, or treating any of the disease indications described herein.

Kits of the present disclosure can additionally include labels or instructions for using the kit components in any method of the invention. A kit can include an i-body compound of the present disclosure in a pack, or dispenser together with instructions for administering the compound in a method of the disclosure. Instructions can include instructions for practicing any of the methods of the disclosure described herein including treatment, detection, monitoring or diagnostic methods. Instructions may additionally include indications of a satisfactory clinical endpoint or any adverse symptoms that may occur, or additional information required by regulatory agencies such as the Food and Drug Administration for use on a human subject.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive. The present disclosure includes the following non-limiting examples.

General Methods

Biacore Assay (FIG. 2, 5, 11, 17) Kinetic binding analysis of selected i-bodies with immobilized CXCR4 lipoparticles were performed at 25° C. using Biacore T200 instrument (GE Healthcare, Uppsala, Sweden). Streptavidin immobilization was performed in 1×HBS-P+ running buffer (10 mM HEPES, 150 mM NaCl, 0.05% [v/v] Tween-20). Amine coupling kit (GE Healthcare) and the instructions therein were utilized for the attachment of Streptavidin (Sigma; diluted to 100 pg/mL in 10 mM sodium acetate buffer pH 4.5) in all four channels on the sensor chip surface simultaneously, resulting in >6,000 RU of Streptavidin being coupled (1 RU=1 pg protein/mm$^2$). All binding experiments involving lipoparticles were performed with 1×HBS/BSA (10 mM HEPES, 150 mM NaCl, 1 mg/mL BSA) as instrument running buffer. Biotinylated CXCR4 lipoparticles (Integral Molecular, Cat # LEV-101B; 3.6 U/mL as described in WO 2005/042695) were typically diluted 1 in 20 in the running buffer and immobilized onto a Streptavidin containing channel by injecting at 2 µL/mL for 1,800 sec resulting in captured response levels of greater than 2,500 RU. Biotinylated CCR5 and null lipoparticles, used as off-target controls, were immobilized in a similar manner. In order to determine binding kinetics, serial dilutions (three-fold) of i-bodies diluted in 1×HBS/BSA were injected over immobilized lipoparticles with the association and dissociation phases monitored for 60 sec and 600 sec, respectively. A control measurement of the instrument running buffer ("zero-buffer" blank) solution was also included for double referencing purposes. Collected experimental data were processed using Scrubber software (www.biologic.com.au). Kinetic parameters (ka=association and kd=dissociation rate constants) and equilibrium dissociation constant (KD=kd/ka) were derived by fitting each set of experimental data to a Langmuir 1:1 binding model. All interaction measurements were performed in triplicate and the derived binding parameters reported as averaged values±standard deviation.

Figure 14:
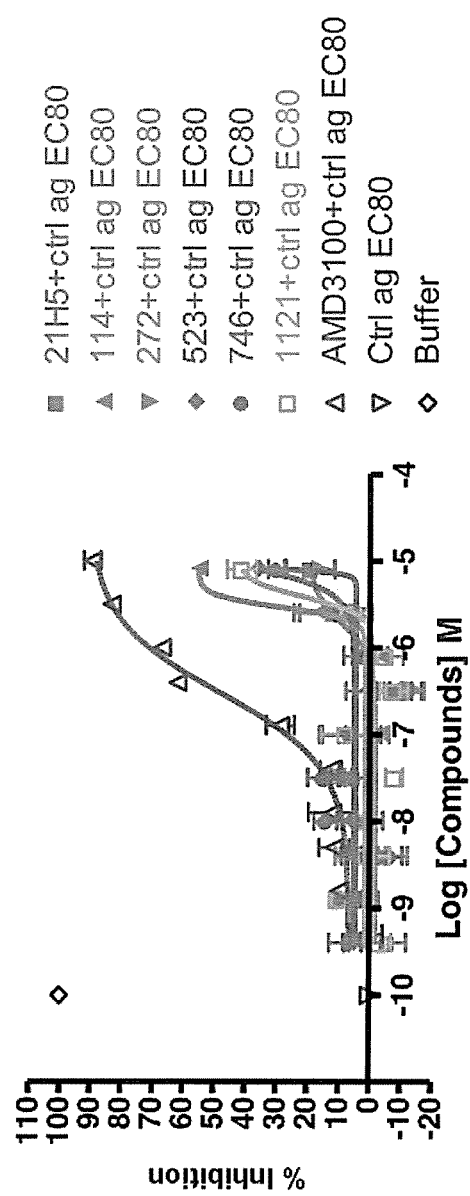
FIG. 14 shows the percent inhibition of Calcium flux measured by the Quest™ Fluo-8 kit for i-bodies AM3-114, AM4-272, AM3-523, AM4-746, and AM4-1121, control Ag (SDF-1), 21H5 negative control i-body and AMD3100 positive control (effective concentration $EC_{80}$)).

Beta-Arrestin (BRET) Assay (FIGS. 3 and 14) BRET was used in this study to assess the real-time kinetic profiles resulting from any consequent increase in proximity, building upon the previously validated monitoring of GPCR/β-arrestin interactions utilizing BRET. BRET occurs between a complementary *Renilla* luciferase (Rluc) variant as donor and green fluorescent protein variant as acceptor. Upon Rluc-catalyzed oxidation of the coelenterazine substrate (such as coelenterazine h for first generation BRET (BRET) or EnduRen for extended BRET (eBRET), energy is transferred to the acceptor if within 10 nm, resulting in acceptor light emission peaking at a characteristic wavelength. BRET β-arrestin assays were carried out as described previously (See, H. B., Seeber, R. M., Kocan, M., Eidne, K. A. and Pfleger, K. D. (2011) 'Application of G protein-coupled receptor-heteromer identification technology to monitor beta-arrestin recruitment to G protein-coupled receptor heteromers', Assay Drug Dev Technol, 9(1), 21-30, 10.1089/adt.2010.0336). CXCR4/Rluc8 cDNA constructs were generated from plasmids containing the respective receptor cDNA tagged with Rluc kindly provided by Aron Chakera (Oxford University, United Kingdom). The β-arrestin 2/Venus cDNA construct was prepared previously from pCS2-Venus kindly provided by Atsushi Miyawaki (RIKEN Brain Science Institute, Wako-city, Japan). BRET technology in cells transiently expressing CXCR4/Rluc8 and β-arrestin2/Venus in the presence of 100 nM SDF-1 agonist was evaluated in the presence of the CXCR4 agonist SDF-1/CXCL12 and the i-bodies. HEK293FT cells were maintained at 37° C., 5% CO$_2$ in Complete Media (Dulbecco's modified Eagle's medium containing 0.3 mg/mL glutamine, 100 IU/mL penicillin, and 100 mg/mL streptomycin; Gibco) supplemented with 10% fetal calf serum (FCS) and 400 mg/mL Geneticin (Gibco). Transfections were carried out 24 h after seeding using Genejuice (Novagen) according to manufacturer's instructions. Cells were harvested with 0.05% Trypsin-EDTA (Gibco). HEK293FT cells were transfected using FuGene6 (Promega). 5 µM coelenterazine h (Promega) in HBSS was used as the luciferase substrate solution. Cells were harvested 24 h post-transfection in HEPES-buffered phenol red-free Complete Medium containing 5% FCS and added to a poly-L-lysine-coated white 96-well plate (Nunc). Dose-response curves were generated using BRET, with medium in the plate being replaced with PBS containing 5 mM coelenterazine h (Molecular Probes) and assays carried out immediately. For these assays, 48 h post-transfection, the plate was incubated at 378C., 5% $CO_2$ for 2 h with 30 mM EnduRen (Promega) to ensure substrate equilibrium was reached. All BRET measurements were taken at 37° C. using the VICTOR Light plate reader with Wallac 1420 software (PerkinElmer). Filtered light emissions were sequentially measured at 400-475 and 520-540 nm. The BRET signal was calculated by subtracting the ratio of 520-540 nm emission over 400-475 nm emission for a vehicle-treated cell sample from the same ratio for a second aliquot of the same cells treated with agonist (in this instance in the presence of SDF-1 or CXCL12) and i-body (ADCX-99, ADCX-272, ACDX-6, ACDX-306, ADCX-668) at various concentrations. Data are mean±S.E.M. of four independent experiments carried out in duplicate.

(FIG. 9) The PathHunter® β-Arrestin assay (DiscoveRx) was performed according to the manufacturer's protocol. Cells were seeded into white walled, 384-well tissue culture-treated microplates (Corning) and normalized at 5,000 cells (or 10,000 cells for CXCR4) in a total volume of 20 μL. Cell growth was at 37° C. (5% $CO_2$, 95% relative humidity). I-bodies or AMD3100 (Tocris Bioscience) (5 μL at 0.5-3.8 μM) were added to singlicate wells and the plates were incubated at 37° C. for 30 min. Agonists were then added at the EC80 concentration and incubation was continued at 37° C. for 90 min (or 180 min for CCR1). Assay signal was generated through a single addition of 15 μL (50% v/v) of PathHunter Detection reagent cocktail, followed by 1 h incubation at room temperature. Microplates were read following signal generation with a PerkinElmer Envision instrument for chemiluminescent signal detection of relative light units (RLU). Compound activity was analyzed using the CBIS data analysis suite (ChemInnovation). % inhibition=100%×[1−(mean RLU of test sample−mean RLU of vehicle control)/(mean RLU of EC80 control−mean RLU of vehicle control)].

Im7-FH corresponds to an N-terminal solubility and purification tag wherein Im7 is an *E. coli* protein (Hosse R J et al (2009) Anal Biochem 15; 385(2):346-57 and FH is flag+6 Histidine residues.

Example 1—Identification of CXCR4 Blocking i-Bodies

The principles learnt from shark IgNAR antibody structures can be successfully applied to the generation of binding repertoires of human I-set domains from the immunoglobulin superfamily, which is further described in WO 2005/118629. Shark IgNAR antibodies are structurally close to the immunoglobulin superfamily of I-set domains such as Domain 1 of NCAM. The modified Domain 1 of NCAM is referred to as the i-body scaffold. Using this scaffold, a library of polypeptides is created and displayed on phage for screening against particular targets for specific binders to that target. Such libraries are anticipated to primarily contain variability in the CDR1 and CDR3 analogous regions.

An i-body library was created which had a random amino acid sequence in the CDR1 region (represented by XXXXXX in FIG. 1B) and in the CDR3 region (represented by Y'n in FIG. 1B), wherein n (the number of amino acids in the random CDR3 sequence) is varied randomly between 10 and 20 amino acids in length and sequence as per SEQ ID NO:2. The i-bodies of the disclosure comprise a scaffold region which corresponds to amino acid residues 1 to 26, 33 to 79 and 88 to 97 of SEQ ID NO:1 or a sequence at least 60% identical thereto or otherwise may comprise between one and five amino acid additions or substitutions. In one example, the scaffold region comprises the sequence set forth in SEQ ID NO:2 or the sequence set forth in SEQ ID NO:2 comprising between 1 and 5 amino acid additions or substitutions.

The complementarity determining regions (CDR1 and CDR3) of SEQ ID NO:2 are modified by amino acid addition and/or substitution relative to the corresponding CDR1 and/or CDR3 regions in SEQ ID NO:1 represented by amino acid positions 27 to 32 and 80 to 86 in SEQ ID NO:1 respectively. The resulting i-body polypeptides are able to bind to human CXCR4 with an affinity of less than 50 μM.

In one example A' and B' in SEQ ID NO:2 are any amino acid residue.

In one example, A' in SEQ ID NO:2 is amino acid Q or K and B' in SEQ ID NO:2 is amino acid residue V or A. In a further example, A' is Q and B' is V or A in SEQ ID NO:2.

Sequence ID NO:2 may further comprise between 1 and 4 consecutive N-terminal amino acid residues selected from the group consisting of M, EAEA, MA, or MP.

I-bodies displayed on phage were selected against human CXCR4 (hCXCR4) displayed in a lipoparticle or expressed in a HEK cell line, following incubation of the i-body library and hCXCR4 lipoparticle captured on plates or beads or with CXCR4 positive cells in solution. Extensive washing was completed to remove non-specific binders in either format. Enrichment to the hCXCR4 positive lipoparticles or cells was observed and single colonies were picked and grown. The sequence of the i-body scaffold remains the same except for the specific regions of the CDR1 and CDR3 regions. The CDR1 and CDR3 sequences of the single colonies that specifically bound to hCXCR4 are detailed in Table 1. The affinities of the i-bodies to CXCR4 are described in Table 1 and FIG. 5 for ADCX-99 and FIG. 2 for i-bodies ADCX-306, ADCX-272 and ADCX-668.

Figure 3:
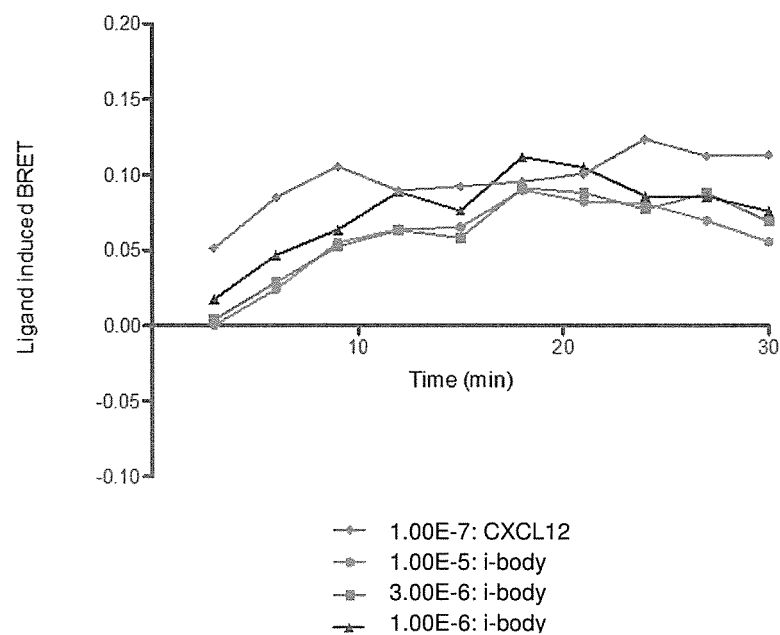
Figure 1:
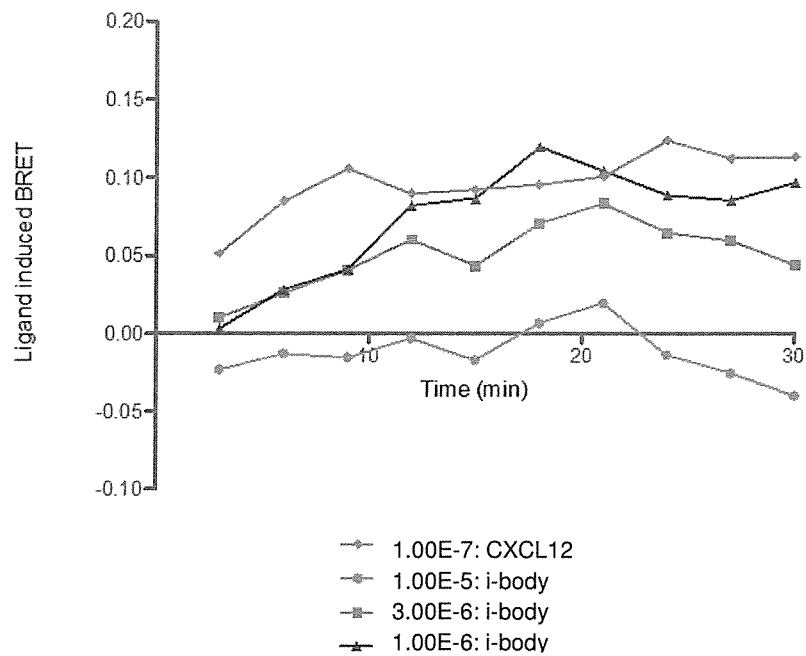
Figure 3:
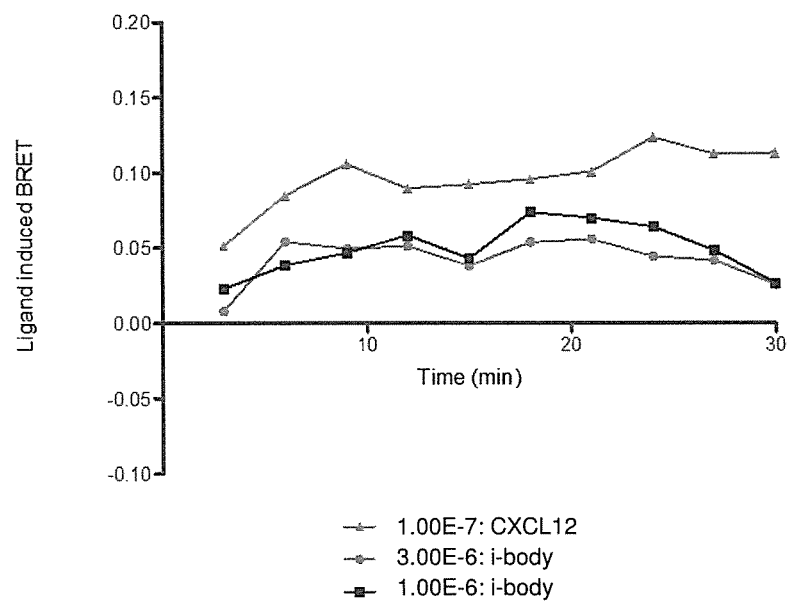
Figure 2:
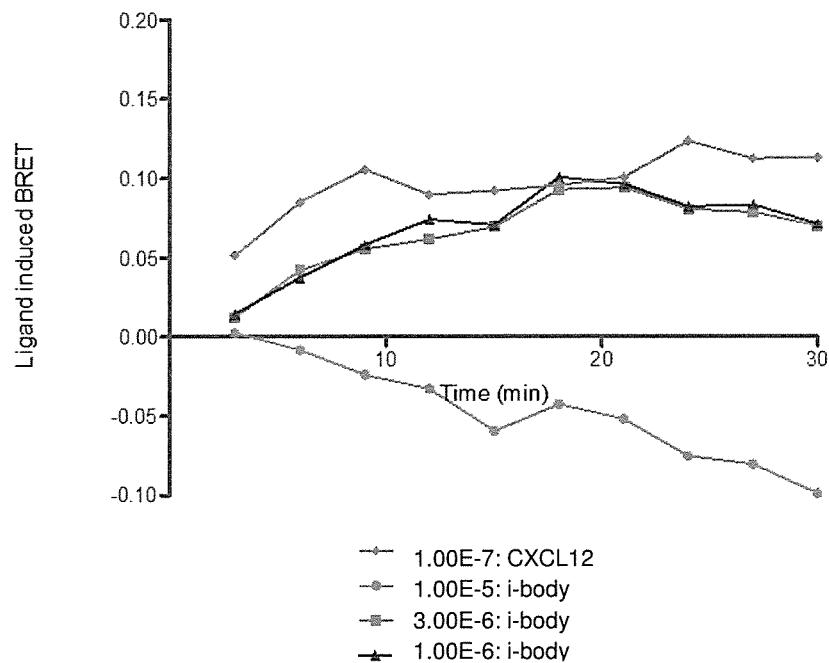
Figure 3:
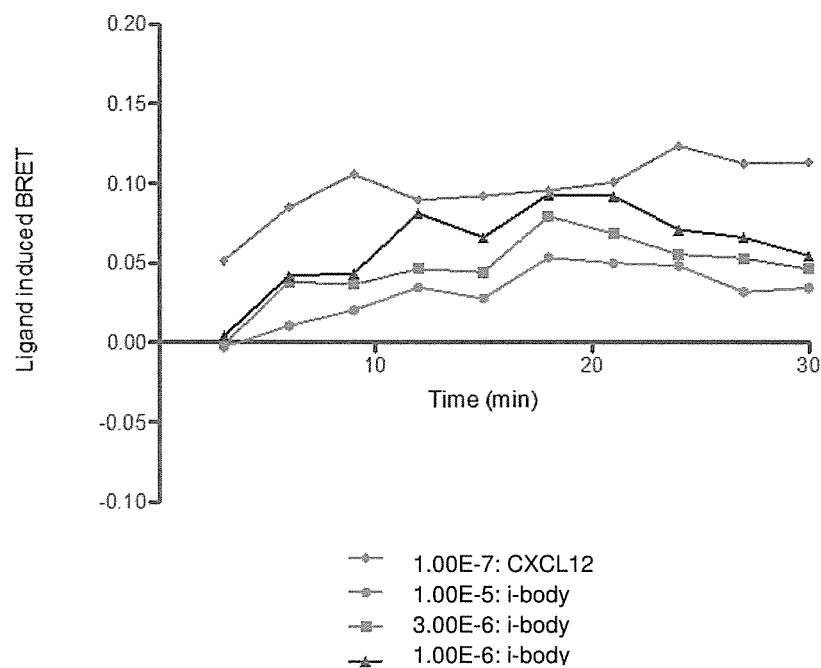
Figure 3:
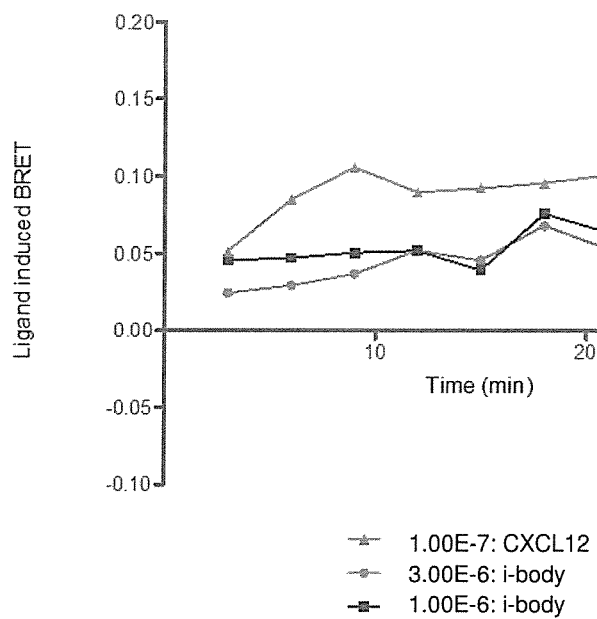

The ability of i-body binders ADCX-99, ADCX-272, ADCX-6, ADCX-306, and ADCX-668 to modulate β-arrestin is also demonstrated in FIG. 3.

TABLE 1

Panel of i-bodies identified to hCXCR4

| Name | CDR1 Sequence | CDR3 Sequence | SEQ ID NO. of i-body | $K_D$ (μM) |
| --- | --- | --- | --- | --- |
| ADCX-99 | SGSDIR (SEQ ID NO: 12) | YRTGGYRHRALVLG (SEQ ID NO: 13) | 11 | 0.7 |
| ADCX-272 | HLEVRS (SEQ ID NO: 15) | EQRGRSQSYFS (SEQ ID NO: 16) | 14 | 1.6 |
| ADCX-6 | LTSLEG (SEQ ID NO: 18) | EDHPQYSKME (SEQ ID NO: 19) | 17 | ND |

TABLE 1-continued

Panel of i-bodies identified to hCXCR4

| Name | CDR1 Sequence | CDR3 Sequence | SEQ ID NO. of i-body | $K_D$ (µM) |
|---|---|---|---|---|
| ADCX-54 | RTIIVE (SEQ ID NO: 21) | VLSIRGKWEL (SEQ ID NO: 22) | 20 | ND |
| ADCX-LS | IAEFST (SEQ ID NO: 24) | QVSDHPEAGILWRG (SEQ ID NO: 25) | 23 | ND |
| ADCX-668 | TIWYEQ (SEQ ID NO: 27) | WTRPVTSSMH (SEQ ID NO: 28) | 26 | 42 |
| ADCX-306 | FQEWVN (SEQ ID NO: 30) | TMPHTLNNLDVRT (SEQ ID NO: 31) | 29 | 22 |

ND = not determined.

In addition, a control i-body was generated, designated 21H5 which does not bind to CXCR4. This was used as an isotype control. The sequence of this i-body is shown below:

(SEQ ID NO: 82)
LQVDIVPSQGEISVGESKFFLCQVAGDAKDKDISWFSPNGEKLTPNQ

QRISVVWNDDSSSTLTIYNANIDDAGIYKCVVTGSDAMSNYSYPISE

SEATVNVKIFQ

Example 2—Characterisation of CXCR4 Blocking i-Bodies 2.1 I-Body Expression and Purification in *E. coli*

Figure 4:
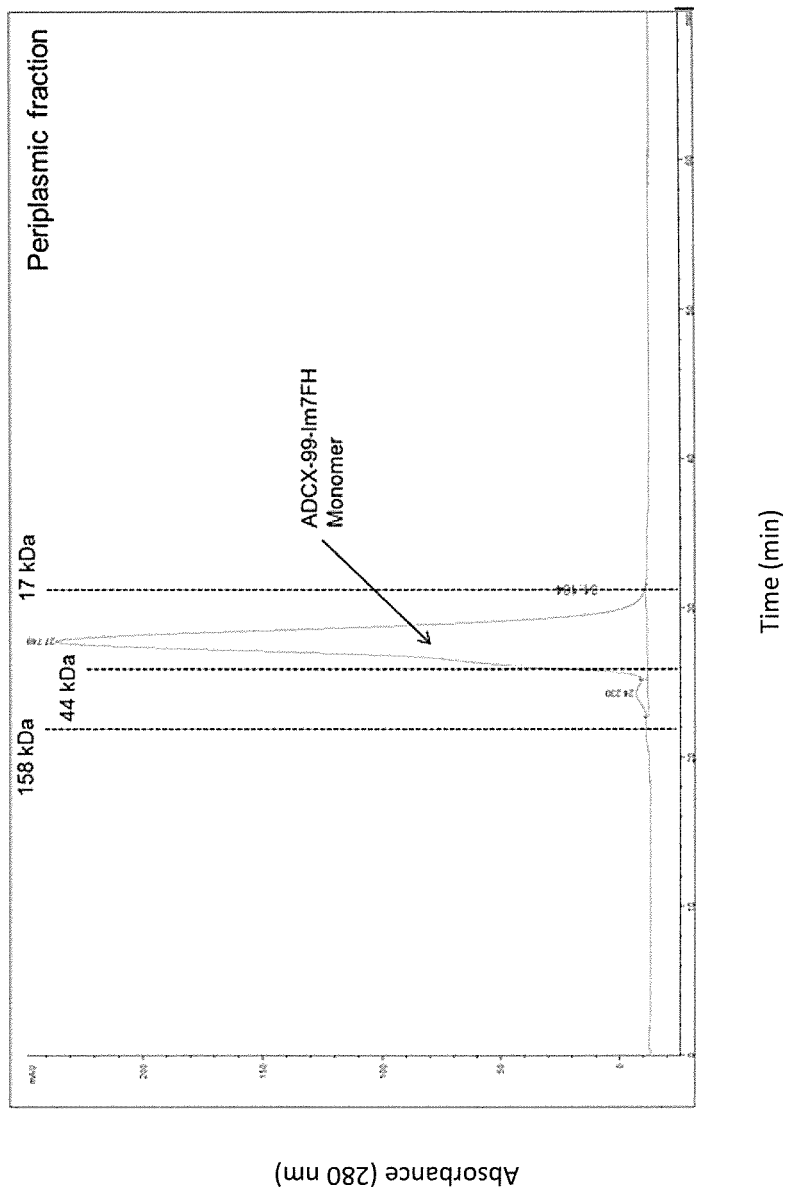
FIG. 4 shows size exclusion chromatography (SEC) results for i-body ADCX-99 protein (conjugated to IM7-FH (IM7 flag histidine tagged immunity protein) purified from the periplasmic fraction. SEC was conducted using a Superdex 75 column.

I-bodies were expressed and purified using an *E. coli* expression system. I-bodies were expressed with various affinity tags including *E coli*. immunity protein (Im7) FLAG and 6×HIS (designated Im7-FH in FIG. 4). I-bodies were purified from the periplasmic fraction and the cytoplasm using the various tags using anti-FLAG resin or Ni-NTA resin respectively. The results of size exclusion chromatography are shown in FIG. 4.

2.2 i-Body Expression and Purification in *Pichia*

Genes for the i-bodies were cloned into a *Pichia* expression vector. After some optimisation of clone selection, the protein titres ranged from 3-9 mg/L at the small (2 ml scale). At the fermentation scale the yields were between 26-150 mg/L. Further parameters such as (temperature, pH, feed rate and feed strategy) could be optimised at the fermentation level to improve yields. After large-scale expression and purification the i-bodies were characterised by SDS-PAGE and they have been shown to be essentially intact as they migrate at the appropriate size (Figure not shown).

2.3 Affinity and Specificity of i-Body Binding to CXCR4

Figure 5:
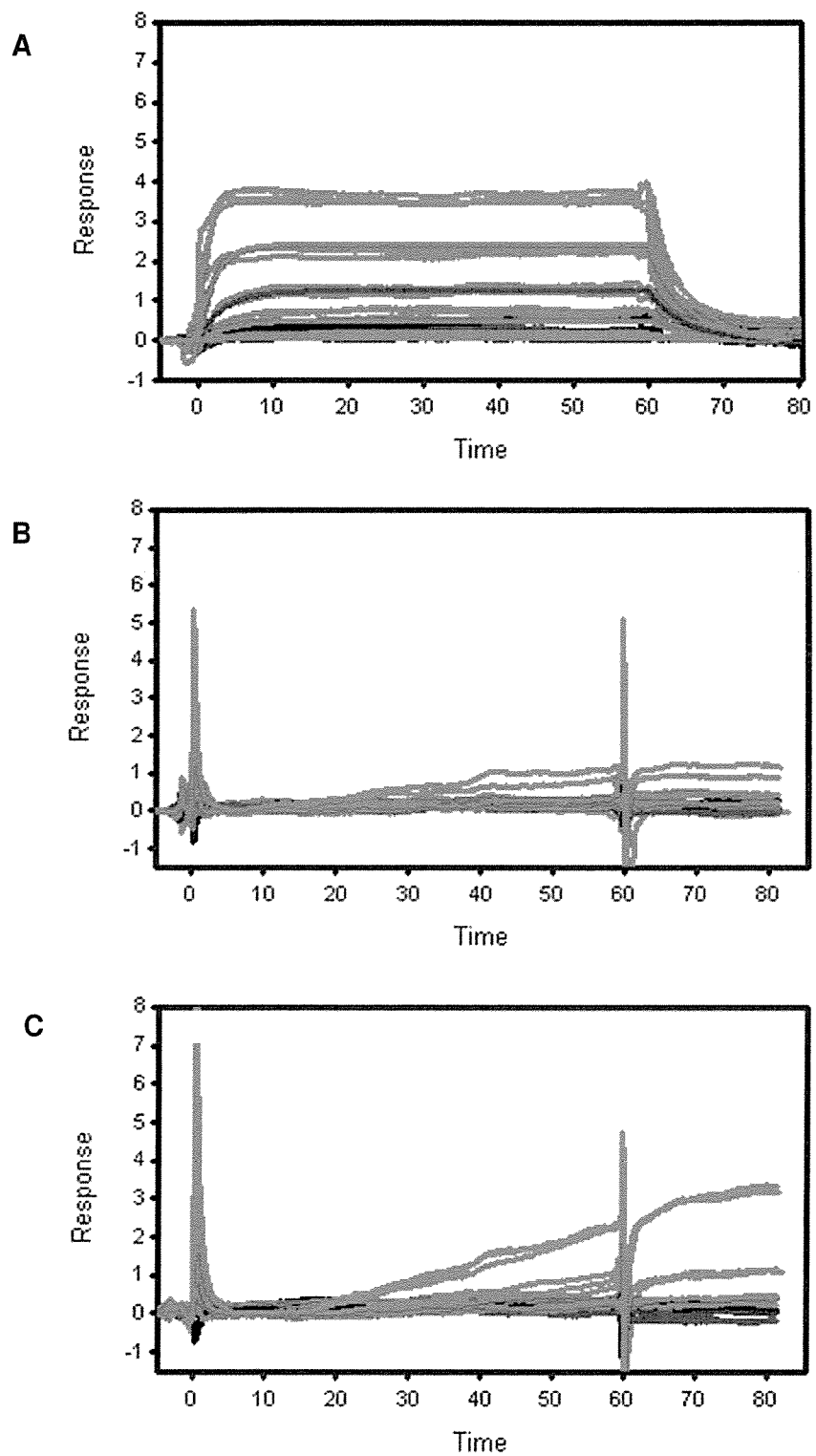
FIG. 5 shows surface plasmon resonance (SPR; BIAcore) of i-body ADCX-99 for binding to immobilised CXCR4 positive lipoparticles (A). ADCX-99 did not bind to null lipoparticles (B) or to CCR5 positive lipoparticles (C).

The i-body ADCX-99 was shown in a BIAcore assay to bind to immobilised CXCR4 positive lipoparticles (A), but showed very little binding to null lipoparticles (B) or to lipoparticles that were positive for the GPCR CCR5 (C), demonstrating the specificity of the i-body ADCX-99 to CXCR4 (FIG. 5).

The affinity of one CXCR4 i-body identified, ADCX-99 was approximately $K_D$ of 600 nM (622.877 nM) to the CXCR4 positive lipoparticles determined by Biacore assay in FIG. 5.

The i-body ADCX-272 was shown in a BIAcore assay to bind to CXCR4 positive lipoparticles (FIG. 2), but showed very little binding to null lipoparticles or to lipoparticles that were positive for the GPCR CCR5 via ELISA (FIG. 7B), demonstrating the specificity of the i-body ADCX-272 to CXCR4.

The affinity of CXCR4 i-body ADCX-272 was determined to be approximately $K_D$ 1.6 uM to the CXCR4 positive lipoparticles determined by Biacore (FIG. 2B).

Example 3—Affinity Maturation of i-Bodies

The i-body ADCX-99 was affinity matured using error prone PCR. This was carried out in two ways; either by creating a library of random mutations directed to the CDR1 and CDR3 or using an average of 2-3 nucleotide mutations anywhere in the sequence. The library was panned according to Henderson et al. (2007) Structure 15:1452-66. Using this strategy, the i-body ADCX-99 was modified in the CDR1 and/or the CDR3 regions to improve the affinity or expression to create a library of mutants.

3.1 Improvement to Expression Levels, Affinity and Specificity of i-Bodies

Figure 6:
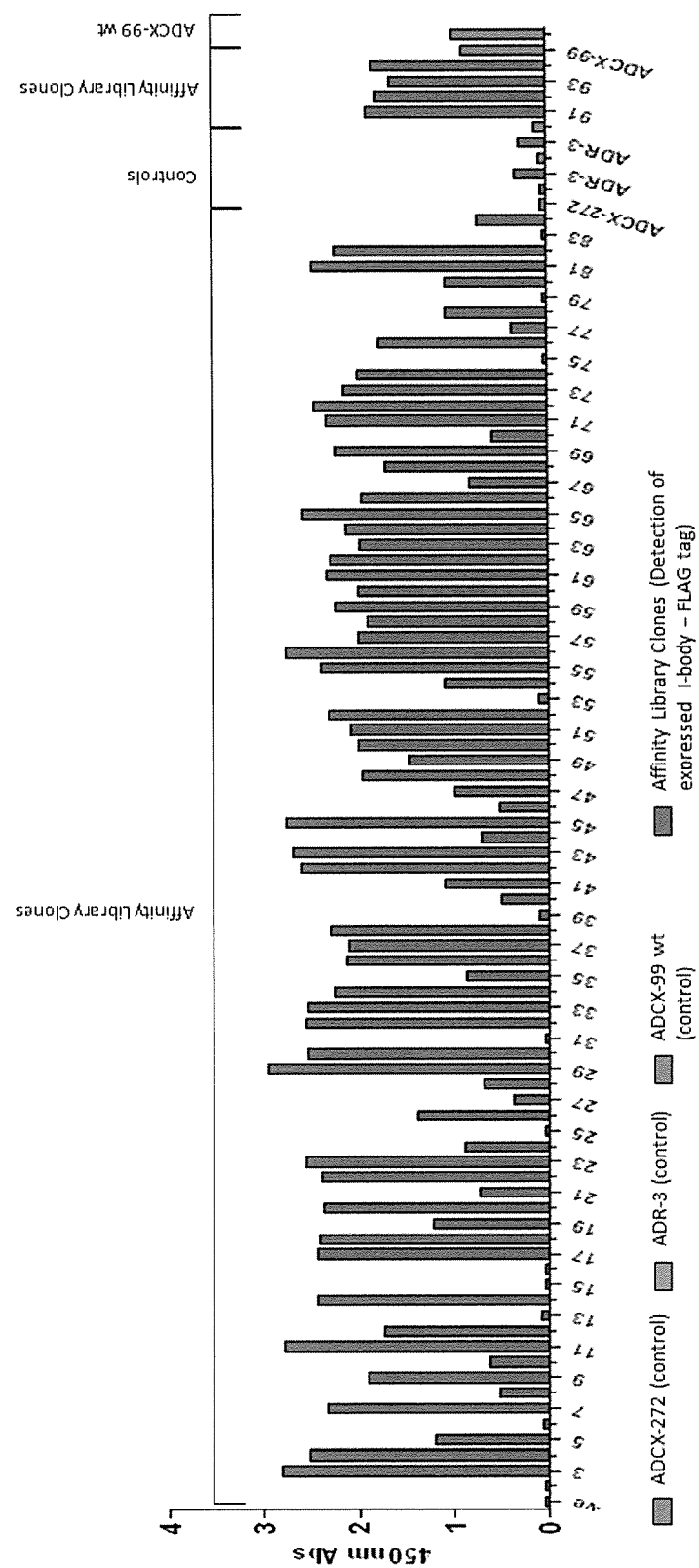
FIG. 6 shows 90 individual i-bodies from an affinity-matured mutant library derived from i-body ADCX-99. The affinity-matured i-bodies were tested for expression by binding of anti-FLAG antibody compared to negative controls ADCX-272 and ADR-3 and the wildtype i-body ADCX-99, which were grown under the same conditions and is provided in the last two columns.

Ninety random mutant i-bodies of the affinity matured ADCX-99 were cultured in a 96 well plate. Analysis of periplasmic fractions showed protein expression and affinity levels varied significantly among the mutant clones. By comparison with ADCX-99, several mutant clones were better expressers than the wild-type ADCX-99 i-body (FIG. 6).

Figure 1:
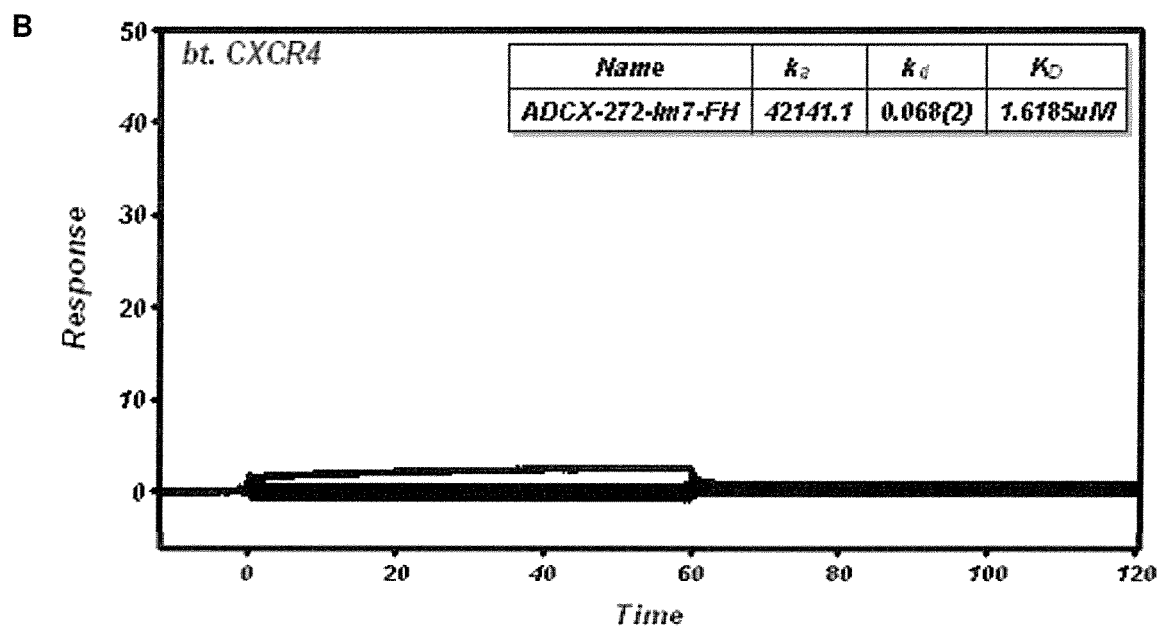
FIG. 1 is a diagrammatic representation showing the sequence of the human NCAM domain 1 (A); the i-body scaffold and CDR1 (represented by XXXXXX) and CDR3 (represented by Yn) (B); sequence of a specific CXCR4 binder, ADCX-99 (C) and consensus sequence for affinity matured binders of ACDX-99 (D). X and Y are any amino acid, n is a number between 10 and 20 inclusive. A', B' is any amino acid. Z is absent or amino acids M, EAEA, MA or MP.
Figure 2:
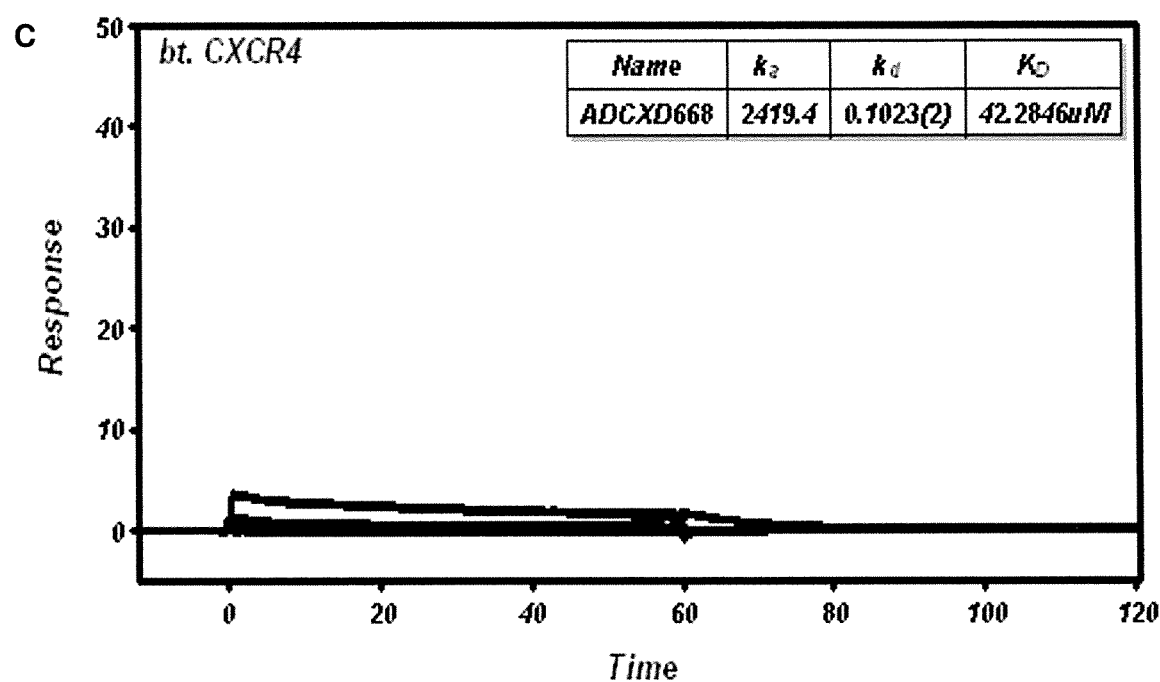
Figures 1, 7:
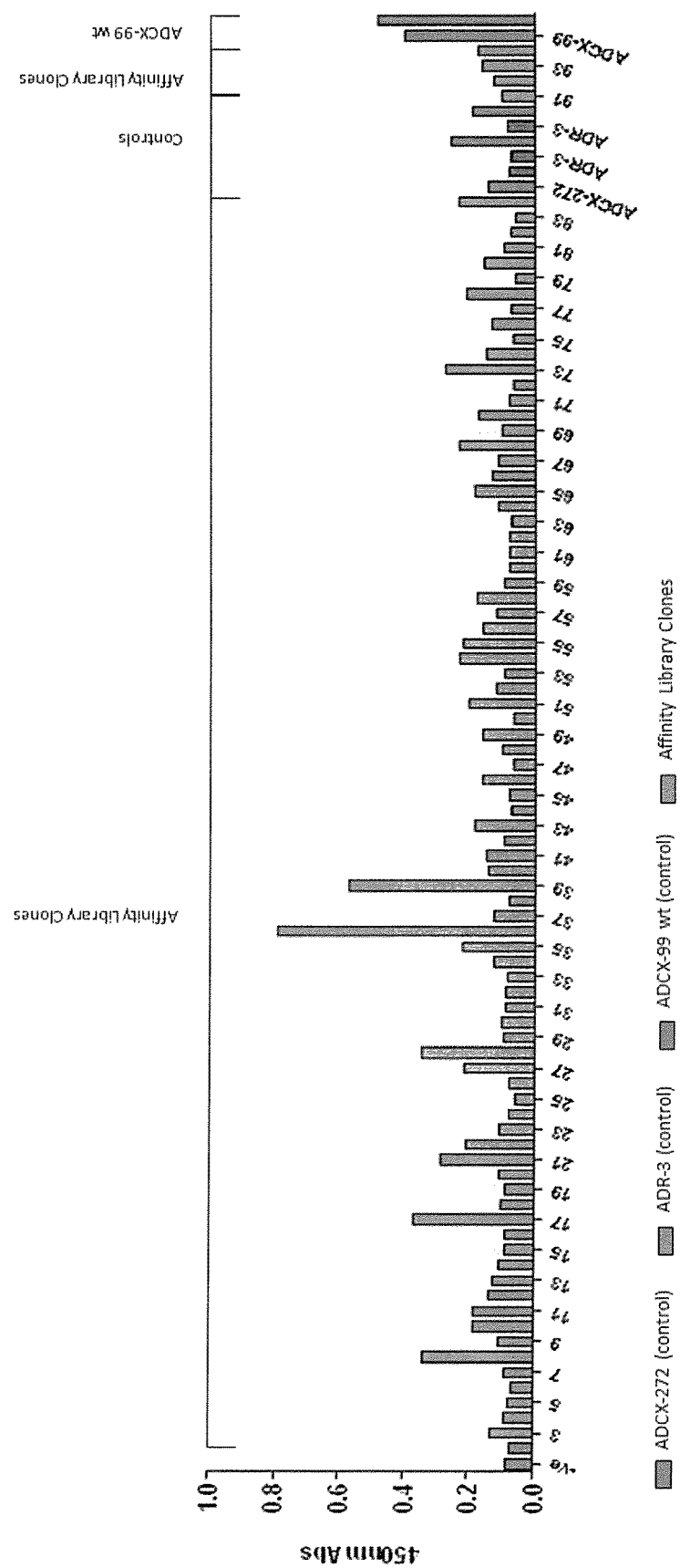
Figures 2, 7:
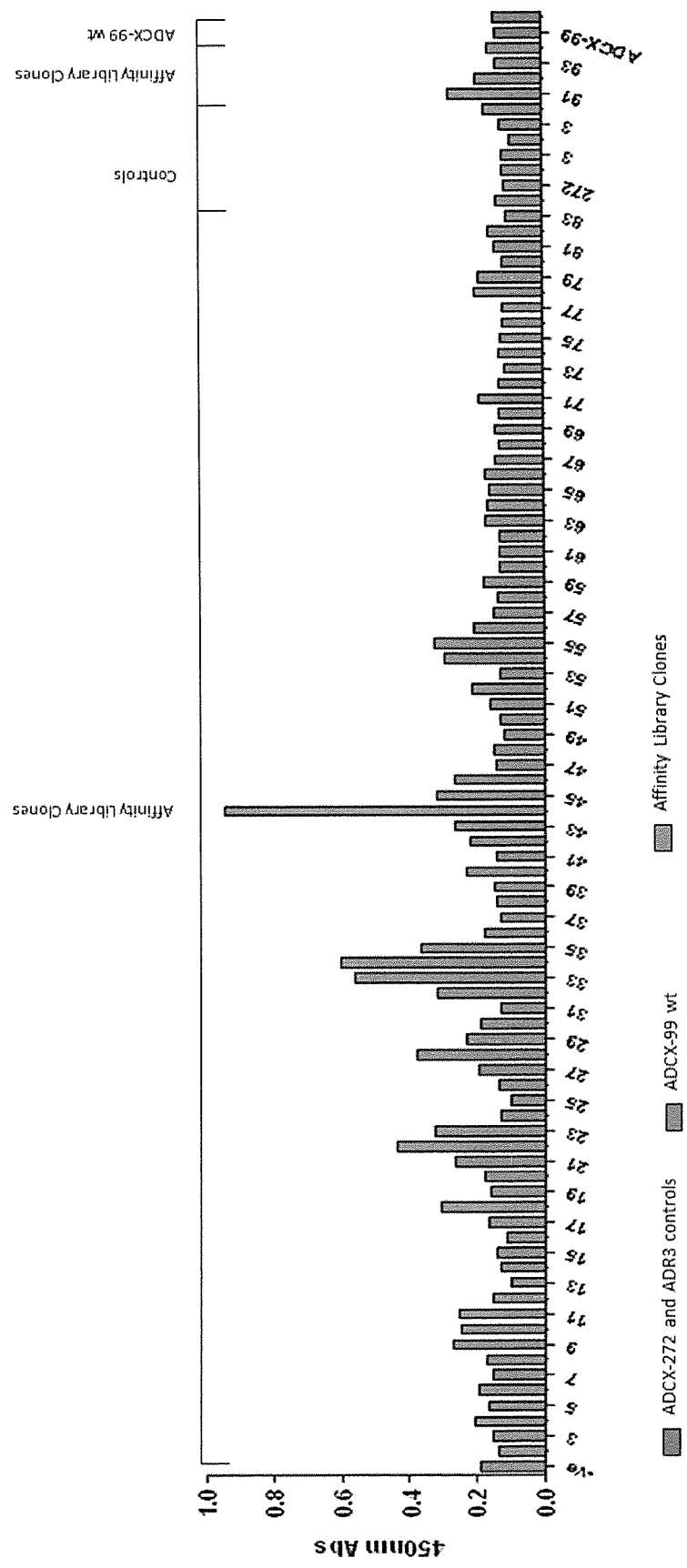

When the same ninety clones were then examined for binding to CXCR4 positive lipoparticles it was observed that, although most of the clones had lower affinity for CXCR4 positive lipoparticles, several clones showed higher affinity (FIG. 7-1). Mutant i-body clones 36 and 39 appeared to have higher binding to CXCR4 positive lipoparticles in this assay compared to the wild-type ADCX-99 i-body. The mutant i-body clones were also examined for binding to CCR5 positive lipoparticles (FIG. 7-2). I-body mutant clones 36 and 39 had the same low binding for CCR5 as the wild-type ADCX-99 (FIG. 7-2) demonstrating specificity for CXCR4.

The mutant clones of ADCX-99 were subject to a further round of affinity maturation and over 1000 mutant clones examined for improved affinity and expression.

The consensus sequence of the affinity matured i-bodies is shown in FIG. 1D (SEQ ID NO:39). The CD1 and CDR3 regions are represented by $SX_1SX_2X_3R$ and $Y'_1RY'_2GY'_3YRHRY'_4LY'_5LG$ respectively.

The affinity matured i-bodies of the disclosure comprise a scaffold region which corresponds to amino acid residues 1 to 26, 33 to 79 and 88 to 97 of SEQ ID NO:1 or a sequence at least 60% identical thereto or otherwise may comprise between one and five amino acid additions or substitutions. In one example, the polypeptide comprises the sequence set forth in SEQ ID NO:2 or the sequence set forth in SEQ ID NO:2 comprising between 1 and 5 amino acid additions or substitutions.

In one example A' and B' in SEQ ID NO:39 are any amino acid residue.

In one example, A' in SEQ ID NO:39 is amino acid Q or K and B' in SEQ ID NO:39 is amino acid residue V or A. In a further example, A' is Q and B' is V or A in SEQ ID NO:39.

In one example, Z is absent or an amino acid selected from M, EAEA, MA or MP. A summary of the affinity matured sequences with improvements is described in Table 2.

TABLE 2

Summary of sequences derived from ADCX-99 generated by two rounds of affinity maturation Original CXCR i-body Binder ADCX-99   LQVDIVPSQGEISVGESKFFLCQVAG<u>SGSDIR</u>IS
          WFSPNGEKLTPNQQRISVVWNDDSSSTLTIYNAN
          IDDAGIYKCVV<u>YRTGGYRHRALVLG</u>EATVNVKIF
          Q (SEQ ID NO: 11)

Affinity Maturation Round 2 Sequences

AM3-114   LQVDIVPYQGEISVGESKFFLCQVAG<u>SLSGIR</u>IS
          WFSPNGEKLTPNQQRISVVWNDDSSSTLTIYNAN
          IDDAGIYKCVV<u>WRTGGYRHRYLVLG</u>EATVNVKIF
          Q (SEQ ID NO: 40)

AM3-920   LQVDIVPSQGEISVGESKFFLCQVAG<u>SGSGIR</u>IS
          WFSPNGEKLTPNQQRISVVWNDDSSSTLTIYNAN
          IDDAGIYKCVV<u>WRTGGYRHRYLVLG</u>EATVNVKIF
          Q (SEQ ID NO: 44)

AM4-1121  LQVDIVPSQGEISVGESKFFLCQVAG<u>SKSGIR</u>IS
          WFSPNGEKLTPNQQRISVVWNDDSSSTLTIYNAN
          IDDAGIYKCVV<u>YRTGGYRHRYLRLG</u>EATVNVKIF
          Q (SEQ ID NO: 48)

AM4-613   LQVDIVPSQGEISVGESKFFLCQVAG<u>SKSDVR</u>IS
          WFSPNGEKLTPNQQRISVVWNDDSSSTLTIYNAN
          IDDAGIYKCVV<u>WRTGGYRHRYLVLG</u>EATVNVKIF
          Q (SEQ ID NO: 52)

AM3-523   LQVDIVPSQGEISVGESKFFLCQVAG<u>SGSHMR</u>IS
          WFSPNGEKLTPNQQRISVVWNDDSSSTLTIYNAN
          IDDAGIYKCVV<u>WRVGGYRHRALVLG</u>EATVNVKIF
          Q (SEQ ID NO: 56)

AM4-661   LQVDIVPSQGEISVGESKFFLCQVAG<u>SKSDFR</u>IS
          WFSPNGEKLTPNQQRISVVWNDDSSSTLTIYNAN
          IDDAGIYKCVV<u>YRTGGYRHRYLVLG</u>EATVNVKIF
          Q (SEQ ID NO: 60)

AM3-466   LQVDIVPSQGEISVGESKFFLCQVAG<u>SGSHQR</u>IS
          WFSPNGEKLTPNQQRISVVWNDDSSSTLTIYNAN
          IDDAGIYKCVV<u>WRTGAYRHRALVLG</u>EATVNVKIF
          Q (SEQ ID NO: 64)

AM5-245   LQVDIVPSQGEISVGESKFFLCQAAG<u>SGSHIR</u>IS
          WFSPNGEKLTPNQQRISVVWNDDSSSTLTIYNAN
          IDDAGIYKCVV<u>WRTGGYRHRALVLG</u>EATVNVKIF
          Q (SEQ ID NO: 68)

AM4-272   LQVDIVPSQGEISVGESKFFLCQVAG<u>SYSDYR</u>IS
          WFSPNGEKLTPNQQRISVVWNDDSSSTLTIYNAN
          IDDAGIYKCVV<u>YRIGGYRHRYLVLG</u>EATVNVKIF
          Q (SEQ ID NO: 72)

TABLE 2-continued

Summary of sequences derived from ADCX-99 generated by two rounds of affinity maturation AM4-746   LQVDIVPSQGEISVGESKFFLCQVAG<u>SKSNIR</u>IS
          WFSPNGEKLTPNQQRISVVWNDDSSSTLTIYNAN
          IDDAGIYKCVV<u>YRTGGYRHRYLKLG</u>EATVNVKIF
          Q (SEQ ID NO: 76)

Figure 8:
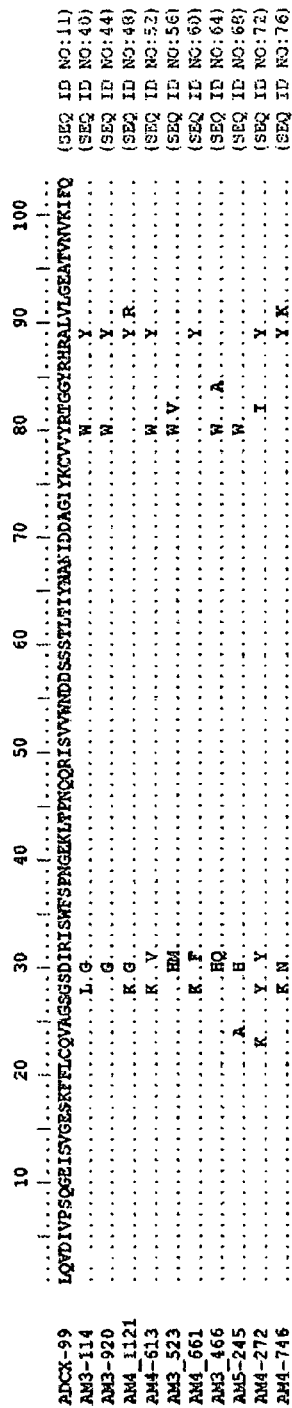
FIG. 8 shows the sequence alignment of the affinity matured i-bodies relative to starting sequence ADCX-99.

A summary of the amino acid positions modified relative to the consensus sequence of ADCX-99 (SEQ ID NO: 2 and 39) is shown in FIG. 1. FIG. 8 indicates the particular amino acid residue substitutions corresponding to each affinity matured i-body. Underlining corresponds to the CDR1 and CDR3 regions in each sequence.

Table 3 summarises improvements in relation to the off-rates of the top twenty affinity matured i-bodies for CXCR4 expressed on lipoparticles.

TABLE 3

Kd values for twenty affinity matured i-bodies

| | Amino acid change compared to ADCX99 | | |
|---|---|---|---|
| | CDR1 | CDR3 | Kd |
| AM3-114 (SEQ ID 40) | SLSGIR (SEQ ID NO: 41) | WRTGGYRHRYLVLG (SEQ ID NO: 42) | 0.0066 |
| AM3-466 (SEQ ID 64) | SGSHQR (SEQ ID NO: 65) | WRTGAYRHRALVLG (SEQ ID NO: 66) | 0.00784 |
| AM3-920 (SEQ ID 44) | SGSGIR (SEQ ID NO: 45) | WRTGGYRHRYLVLG (SEQ ID NO: 46) | 0.00817 |
| AM4-661 (SEQ ID 60) | SKSDFR (SEQ ID NO: 61) | YRTGGYRHRYLVLG (SEQ ID NO: 62) | 0.00955 |
| AM3-523 (SEQ ID 56) | SGSHMR (SEQ ID NO: 57) | WRVGGYRHRALVLG (SEQ ID NO: 58) | 0.00998 |
| AM4-774 | SKSVIR (SEQ ID NO: 83) | YRTGGYRHRYLVLG (SEQ ID NO: 84) | 0.0105 |
| AM4-1121 (SEQ ID 48) | SKSGIR (SEQ ID NO: 49) | YRTGGYRHRYLRLG (SEQ ID NO: 50) | 0.1153 |
| AM4-613 (SEQ ID 52) | SKSDVR (SEQ ID NO: 53) | WRTGGYRHRYLVLG (SEQ ID NO: 54) | 0.01236 |
| AM4-208 | SKSEIR (SEQ ID NO: 85) | YRTGGYRHRYLVLG (SEQ ID NO: 86) | 0.01283 |
| AM4-1088 | SKSDFR (SEQ ID NO: 87) | RTGGYRHRYLKLG (SEQ ID NO: 88) | 0.01349 |
| AM4-239 | AYSDIR (SEQ ID NO: 89) | YRTGGYRHRYLVLG (SEQ ID NO: 90) | 0.01356 |
| AM3-32 | SGSGIT (SEQ ID NO: 91) | WRTGVYRHRALVLG (SEQ ID NO: 92) | 0.0136 |
| AM5-245 (SEQ ID 68) | SGSHIR (SEQ ID NO: 69) | WRTGGYRHRALVLG (SEQ ID NO: 70) | 0.01445 |
| AM4-757 | SKSAIR (SEQ ID NO: 93) | YRTGSYRHRYLVLG (SEQ ID NO: 94) | 0.01488 |

TABLE 3-continued

Kd values for twenty affinity matured i-bodies

| | Amino acid change compared to ADCX99 | | |
|---|---|---|---|
| | CDR1 | CDR3 | Kd |
| AM4-386 | ITSEGH (SEQ ID NO: 95) | ETTVFNEVMRLGNG AHVY (SEQ ID NO: 96) | 0.015 |
| AM4-352 | SKDDIR (SEQ ID NO: 97) | YRTGGYRHRYLVLG (SEQ ID NO: 98) | 0.0152 |
| AM3-182 | VGNHIR (SEQ ID NO: 99) | WRAGGYRHRALVLG (SEQ ID NO: 100) | 0.01562 |
| AM4-203 | SYGDIR (SEQ ID NO: 101) | YRTGGWRHRYLVLG (SEQ ID NO: 102) | 0.01621 |
| AM4-272 (SEQ ID 72) | SYSDYR (SEQ ID NO: 73) | YRIGGYRHRYLVLG (SEQ ID NO: 74) | 0.01631 |
| AM5-95 | SGSHIR (SEQ ID NO: 103) | WRTGGYRHRALVLG (SEQ ID NO: 104) | 0.01663 |

Table 4 summarises the affinity (Ka, Kd and $K_D$) of the top twenty affinity matured i-bodies for CXCR4 expressed on lipoparticles.

TABLE 4

Affinity of CXCR4 binding polypeptides for CXCR4 expressed on lipoparticles

| Binding polypeptide | Affinity to CXCR4 expressed on lipoparticles | | |
|---|---|---|---|
| | Ka ($M^{-1} s^{-1}$) | Kd ($M^{-1} s^{-1}$) | KD (nM) |
| AM3-114 | $1.297 \times 10^6$ | $6.29 \times 10^3$ | 4.85 |
| | $1.9 \times 10^6$ | $6.34 \times 10^3$ | 3.33 |
| AM3-523 | $1.003 \times 10^6$ | $8.61 \times 10^3$ | 8.53 |
| | $9.65 \times 10^5$ | $9.15 \times 10^3$ | 9.47 |
| AM3-466 | $4.65 \times 10^5$ | $6.43 \times 10^3$ | 13.83 |
| | $4.26 \times 10^5$ | $6.67 \times 10^3$ | 15.7 |
| AM3-920 | $1.117 \times 10^6$ | $8.02 \times 10^3$ | 7.18 |
| | $1.26 \times 10^6$ | $7.41 \times 10^3$ | 5.87 |
| AM4-613 | $1.334 \times 10^6$ | $10.44 \times 10^3$ | 7.83 |
| AM4-1121 | $1.289 \times 10^6$ | $9.29 \times 10^3$ | 7.21 |
| | $1.42 \times 10^6$ | $9.54 \times 10^3$ | 6.7 |
| AM4-661 | $9.66 \times 10^5$ | $9.21 \times 10^3$ | 9.53 |
| | $9.83 \times 10^5$ | $9.5 \times 10^3$ | 9.66 |
| AM5-245 | $8.13 \times 10^5$ | $12.1 \times 10^3$ | 14.88 |
| | $7.71 \times 10^5$ | $12.3 \times 10^3$ | 15.9 |
| AM4-272 | $8.06 \times 10^6$ | $13.08 \times 10^3$ | 1.6 |
| AM4-746 | $2.5 \times 10^6$ | $13.39 \times 10^3$ | 5.36 |

Figure 9:
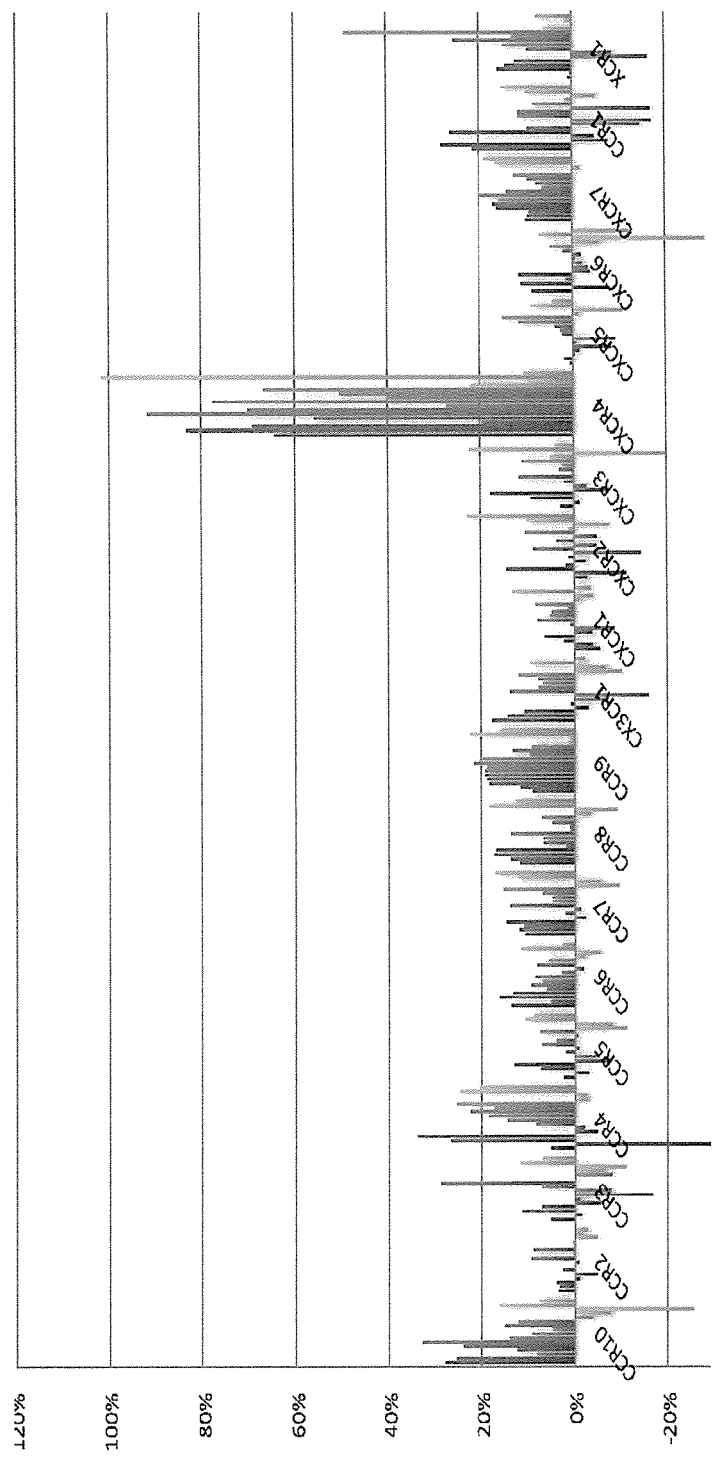
FIG. 9 shows specificity of i-bodies (of Table 4) acting as antagonists against a number of chemokine receptors expressed on cells and measured by β-arrestin assay.

The specificity of the affinity matured binders in Table 4 was determined against a number of chemokines and is shown in FIG. 9 demonstrating high specificity for the target CXCR4 and limited binding to other chemokine G-protein coupled receptors (GPCRs).

Figure 10:
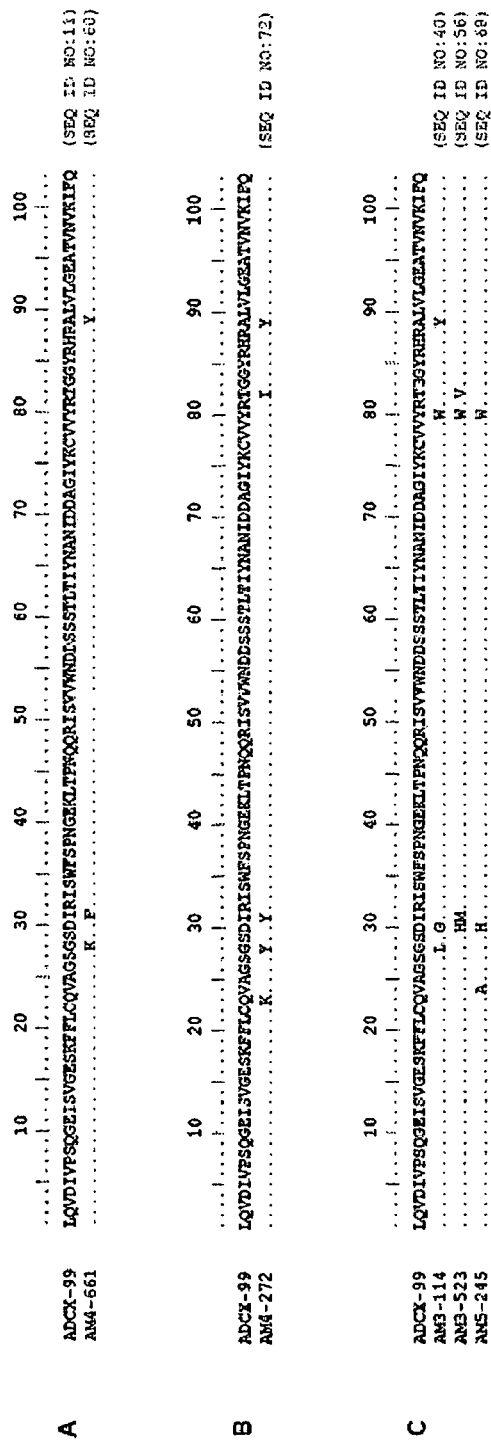
FIG. 10 shows individual sequence alignments for i-bodies AM4-661 (A), AM4-272 (B) and AM3-114, AM3-523 and AM5-245 relative to ADCX-99 (C).

3.2 Improvement to Expression Levels, Affinity and Specificity of Affinity Matured i-Bodies Improvement in expression from 10 mg/L to 14 mg/L was observed when a G>K amino acid substitution at position 28 and an I>F amino acid substitution at position 31 were made to (designated $X_1$ and $X_3$ respectively in FIG. 1D) within the CDR1 of ADCX-99 and an A>Y amino acid substitution was made at position 89 (designated $Y_4$ in FIG. 1D) within the CDR3 of the ADCX-99 sequence. This is represented by the sequence corresponding to AM4-661. The alignment of AM4-661 against ADXC-99 is shown in FIG. 10A.

An improvement in affinity for CXCR4 from >700 nM to 1 nM was seen when a G>Y substitution at position 28 (designated $X_1$ in FIG. 1D), and I>Y substitution at position 31 (designated $X_3$ in FIG. 1D) were made in the CDR1 of ADCX-99, and a T>I (designated $Y_2$ in FIG. 1D) in position 82 and A>Y substitution at position 89 (designated $Y_4$ in FIG. 1D) were made in the CDR3 of ADCX-99, as evidenced by sequence corresponding to AM4-272. The alignment is shown in FIG. 10B.

An improvement in specificity for CXCR4 was observed for polypeptides AM3-114, AM5-245 and AM3-523. CCR4 activity (determined by DiscoverX β-arrestin assay) of 34% for ADCX-99 was reduced to −3%, −5% and −2% for AM3-114, AM5-245 and AM3-523 respectively. All three polypeptides had a Y>W substitution at position 80 (designated $Y_1$ in FIG. 1D) in the CDR3 of ADCX-99 and a D>G or H substitution at position 30 (designated $X_2$ in FIG. 1D) in the CDR1 of ADCX-99. The alignment is shown in FIG. 10C.

Example 4—Half-Life Improvement of i-Bodies 4.1 Dual Specificity to CXCR4 and Human Serum Albumin A dual specificity i-body was generated by conjugating an 18-residue human serum albumin (HAS) binding peptide (N-terminus)-RLIEDICLPRWGCLWEDD-(C-terminus) (described in US 20100104588; Dennis M S et al (2002) J. Biol. Chem. 277, 35035-35043) to the C-terminus of AM3-114 to generate AM3-114-Im7-SA21 (SEQ ID NO: 80). The Im7 protein was used to facilitate detection of the conjugate.

Figure 11:
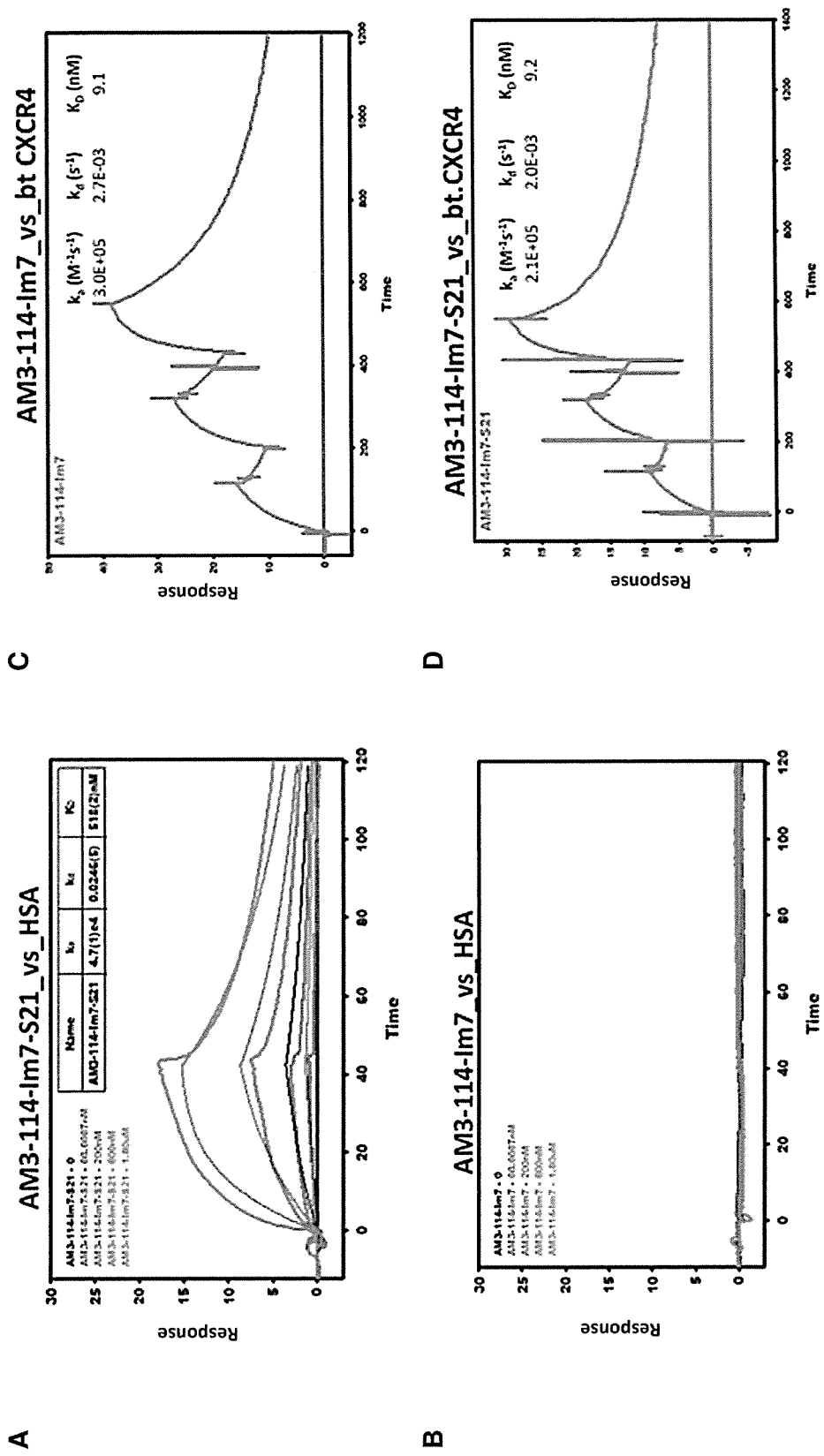
FIG. 11 shows surface plasmon resonance (SPR; BIAcore) of bi-specific AM3-114-Im7-S21 binding to both CXCR4 and Human Serum Albumin (HSA). (A) binding of bi-specific i-body AM3-114-Im7-S21 to HSA by SA21 peptide ($K_D$ 518 (+/−2) nM) at various concentrations 60 nM, 200 nM, 600 nM and 1.00 µM, (B) lack of binding by i-body AM3-114 to HSA at various concentrations 60 nM, 200 nM, 600 nM and 1.00 µM, (C) binding of i-body AM3-114 to CXCR4 ($K_D$ 9 nM) and (D) binding of bi-specific AM3-114-Im7-S21 to CXCR4 ($K_D$ 9 nM).

Affinity for CXCR4 and HSA was measured by surface plasmon resonanceas shown in FIG. 11. The bi-specific CXCR4 and HSA binder AM3-114-Im7-SA21 demonstrated approximately 5-10 nM affinity for CXCR4 and approximately 500 nM affinity for human serum albumin (HSA) (FIG. 11A). The affinity to CXCR4 was unchanged with and without the additional of the 18 residue HSA peptide SA21 (FIGS. 11C and D respectively). The i-body AM3-114 did not bind to HSA without the addition of the 18 residue HSA peptide SA21 (FIG. 11B). Accordingly, the conjugate demonstrating specific binding to both CXCR4 and HSA.

4.2 PEGylation of i-Bodies

AM3-114-Im7-FH and AM4-746-Im7-FH [Im7-FH corresponds to an N-terminal solubility and purification tag wherein Im7 is an *E. coli* protein (Hosse R J et al (2009) Anal Biochem 15; 385(2):346-57 and FH is flag+6 His] were conjugated to 30K linear or 2×20K branched PEG using a site-specific conjugation approach (HiPEG™ technology, PolyTherics, UK) in order to increase the hydrodynamic radius of the i-body molecules and thus reduce renal and hepatic elimination (Konterman et al 2011 Curr Opin Biotech 22:868-8760).

4.3 Evaluation of Half-Life Extended i-Bodies

The PEGylated material (AM3-114-30K PEG, AM3-114-2×20K PEG, AM4-746-2×20K PEG) and one HSA peptide conjugate (AM3-114-Im7-FH-SA21) were evaluated in a preclinical pharmacokinetic study in mice alongside control i-bodies ADCX99-9H (9 histidine tag) and AM3-114-Im7-FH (containing both the Im7 protein and FLAG+6 His tag). The test items were administered to groups of mice once by intravenous injection administration as described in Table 4 below:

TABLE 4

Test items administered to mice

| Group Numbers | Treatment | Dose Level (mg/kg) | Dose Concentration (mg/mL) | Dose volume (mL/kg) | Number of Animals (Males) |
|---|---|---|---|---|---|
| 1 | ADCX99-9H | 3 | 1 | 3.0 | 9 |
| 2 | AM3-114-IM7-FH | 3 | 1 | 3.0 | 9 |
| 3 | AM3-114-Im7-FH-SA21 | 2 | 1 | 2.0 | 9 |
| 4 | AM4-746-2x20K PEG | 1.25 | 1 | 1.25 | 12 |
| 5 | AM3-114-30K PEG | 3 | 1 | 3.0 | 9 |
| 6 | AM3-114-2x20K PEG | 1.25 | 1 | 1.25 | 12 |

The dose volume administered to animals in groups 1, 2 and 5 was 3 mL/kg.
The dose volume administered to animals in group 3 was 2 mL/kg.
The dose volume administered to animals in groups 4 and 6 was 1.25 mL/kg.
A series of blood samples from all mice (0.3 mL, 2 time point/mouse 3/group/time point) were collected following dosing as follows:

TABLE 5

Timing of blood sampling from mice

| Group Number | Timepoints |
|---|---|
| 1 | 5, 15, 45, 60 and 90 minutes |
| 2 | 5, 15, 45, 60 and 90 minutes |
| 3 | 5 minutes and 2, 6, 12 hours and 1 and 3 days |
| 4 | 5 minutes and 2, 6, 12 hours and 1 and 3, 5 and 6 days |
| 5 | 5 minutes and 2, 6, 12 hours, 1 and 3 days |
| 6 | 5 minutes and 2, 6, 12 hours and 1, 3, 5 and 6 days |

For this purpose, each mouse (CD-1 mouse) was bled via the saphenous vein or under isoflurane anaesthesia by cardiac puncture and the samples collected into tubes containing the anticoagulant, $K_2$-EDTA. Tubes were placed on wet ice pending processing. Following its last blood sampling, each animal was euthanized by cervical dislocation and discarded without further examination.

Following collection, the samples were centrifuged (approximately 4° C.) and the resulting plasma was recovered in two separate aliquots and stored frozen (≤60° C.) in labeled Protein LoBind 1.5 mL tubes (Eppendorf, cat no. 022431081). The ADCX99-9H, AM3-114-1M7-FH, AM3-114-Im7-FH-SA21, AM4-746-2×20K PEG, AM3-114-30K PEG and AM3-114-2×20K PEG concentrations were determined by an LC-MS/MS assay method. Sample pre-treatment involved the direct tryptic digestion of ADCX99-9H, AM3-114-IM7-FH, AM3-114-Im7-FH-SA21, AM4-746-2×20K PEG, AM3-114-30K PEG and AM3-114-2×20K PEG to a signature peptide (sPeptide) from CD-1 mouse plasma; GEKLTPNQQRIG was used as the internal standard. The compounds were identified and quantified over a theoretical concentration range of 0.500 µg/mL to 100.000 µg/mL for ADCX99-9H, AM3-114-IM7-FH, AM3-114-Im7-FH-SA21, AM3-114-30K PEG and AM3-114-2×20K PEG and 0.083 µg/mL to 16.667 µg/mL for AM4-746-2×20K PEG. Stock solutions of ADCX99-9H, AM3-114-IM7-FH, AM3-114-Im7-FH-SA21, AM4-746-2×20K PEG, AM3-114-30K PEG and AM3-114-2×20K PEG were stored at −80° C. nominal and GEKLTPNQQRIG internal standard was stored at 4° C.

An AB Sciex API 5000 or QTRAP 5500 quadrupole mass spectrometer using a Turbo ionspray was used for the detection of ADCX99-9H, AM3-114-IM7-FH, AM3-114-Im7-FH-SA21, AM4-746-2×20K PEG, AM3-114-30K PEG and AM3-114-2×20K PEG.

Figure 12:
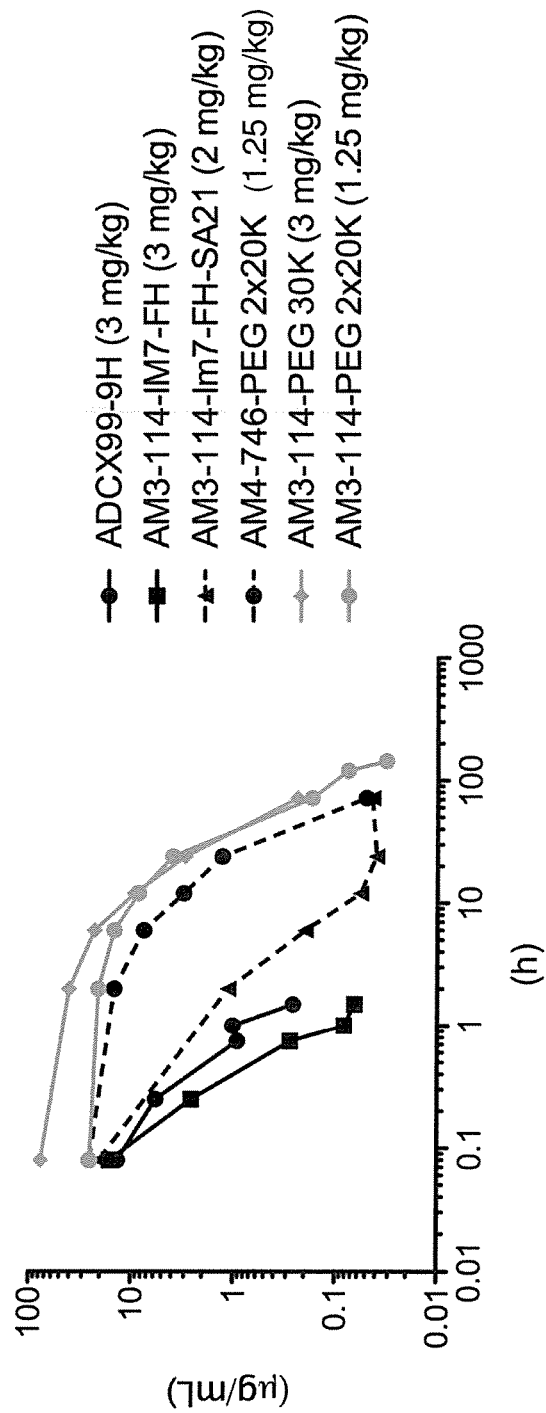
FIG. 12 shows the profile of i-body concentration following intravenous injection of mice, as determined by quantitative mass-spectrometry. I-bodies (AM3-114, AM4-746) were conjugated to either IM7-FH, IM7-FH-SA21 or PEG (30K or 2×20K), and were compared to the unconjugated control, ADCX99-9×His.

The half-life of the AM3-114 i-body was extended by the addition of both the SA21 HSA-binding peptide and by the addition of PEG 30K and PEG 2×20K as demonstrated in FIG. 12, and Table 6A and 6B.

TABLE 6A

Pharmacokinetic Parameters Following Intravenous Injection in CD-1 Mice, AAT-M4-438 (1 of 2)

| Formulation | Gender | $C_0$ (ug/mL) | $T_{max}$ (h) | $C_{max}$ (ug/mL) | $C_{max}$ (SE) (ug/mL) | $AUC_{0-T}$ (ug * h/mL) | $AUC_{0-T}$ (SE) (ug * h/mL) |
|---|---|---|---|---|---|---|---|
| ADCX99-9H/3 mg/kg | Male | 20.871 | 0.08 | 13.611 | 3.083 | 5.318 | 0.403 |
| AM3-114-IM7-FH/3 mg/kg | Male | 40.820 | 0.08 | 16.275 | 2.107 | 4.750 | 0.297 |
| AM3-114-Im7-FH-SA21/2 mg/kg | Male | 23.284 | 0.08 | 20.531 | 1.024 | 25.266 | 1.114 |
| AM4-746-2 × 20K PEG/1.25 mg/kg | Male | 26.168 | 0.08 | 25.559 | 2.023 | 175.057 | 8.650 |
| AM3-114-30K PEG/3 mg/kg | Male | 78.799 | 0.08 | 76.652 | 1.508 | 495.670 | 16.804 |
| AM3-114-2 × 20K PEG/1.25 mg/kg | Male | 25.652 | 0.08 | 25.442 | 2.267 | 380.960 | 23.559 |

TABLE 6B

Pharmacokinetic Parameters Following Intravenous Injection in CD-1 Mice, AAT-M4-438 (2 of 2)

| Formulation | Gender | $AUC_{0-\infty}$ (ug * h/mL) | $T_{last}$ (h) | $\lambda_Z$ (1/h) | $T_{half}$ (h) | $V_D$ (mL/kg) | $Cl_{TOT}$ (mL/h/kg) |
|---|---|---|---|---|---|---|---|
| ADCX99-9H (6H)/3 mg/kg | Male | 5.417 | 1.50 | 2.6660 | 0.26 | 207.739 | 553.838 |
| AM3-114-IM7-FH/3 mg/kg | Male | 4.767 | 1.50 | 3.8809 | 0.18 | 162.155 | 629.303 |

TABLE 6B-continued

Pharmacokinetic Parameters Following Intravenous
Injection in CD-1 Mice, AAT-M4-438 (2 of 2)

| Formulation | Gender | $AUC_{0-\infty}$ (ug * h/mL) | $T_{last}$ (h) | $\lambda_Z$ (1/h) | $T_{half}$ (h) | $V_D$ (mL/kg) | $Cl_{TOT}$ (mL/h/kg) |
|---|---|---|---|---|---|---|---|
| AM3-114-Im7-FH-SA21/2 mg/kg | Male | 25.544 | 6.00 | 0.7279 | 0.95 | 107.571 | 78.296 |
| AM4-746-2 × 20K PEG/1.25 mg/kg | Male | 175.834 | 72.00 | 0.0674 | 10.29 | 105.535 | 7.109 |
| AM3-114-30K PEG/3 mg/kg | Male | 499.831 | 72.00 | 0.0585 | 11.85 | 102.618 | 6.002 |
| AM3-114-2 × 20K PEG/1.25 mg/kg | Male | 381.849 | 144.00 | 0.0360 | 19.24 | 90.854 | 3.274 |

4.4 Fusion of XTEN Protein Sequence with i-Bodies

As an alternative to PEGylation the inventors examined the utility of the XTEN approach which utilises the addition of roughly 400 residues of quasi-repeat sequence to the i-body, to increase the half-life of i-body in vivo, followed by a C-terminal His tag for purification/detection. The XTEN sequence is engineered to be intrinsically unstructured and therefore non-immunogenic, and is also highly hydrophilic which should aid with the solubility and stability of the i-bodies during expression/purification/downstream applications (Schellenberger et al, (2009) Nature Biotech; 27(12): 1186-1190).

AM3-114 was cloned into a bacterial expression vector (pET26) and initial expression trials were performed. Western blotting shows a band that was reactive to anti-His antibody, which is not present in the non-induced control, strongly suggesting that the AM3-114-XTEN construct is indeed being expressed. The predicted MW of the AM3-114-XTEN construct is roughly 50 kDa, whereas the band of interest is at an apparent MW of just over 100 kDa (data not shown). This is consistent with the expected mobility shift due to the highly unstructured and acidic XTEN group causing a significant decrease in the electrophoretic mobility of the ibody, a phenomenon that has previously been observed for other unstructured proteins.

This material was tested for binding to CXCR4 on RAMOS cells by Flow Cytometry and shown to bind in a dose dependant fashion. Binding was only slightly less than for the AM3-114 i-body, indicating that the 114-XTEN was active. AM3-114-XTEN was tested in SPR and found that it still retained binding to CXCR4 on lipoparticles albeit at a slightly reduced affinity. Interestingly the lower affinity appears to be due primarily to the on rate as the off rate is similar to the i-body without XTEN (data not shown).

4.5 PASylation of i-Bodies

Another method of extending the half-life of the i-body is to use the PASylation technology. The i-body will be genetically fused with a polypeptide sequence that consists of several hundred residues of the small amino acids proline, alanine, and/or serine ("PAS"). These PAS sequences, particularly the PAS(400) and PAS(600) adopt a random coil structure in aqueous solution thus generating a large hydrodynamic volume that allows for extension of the half-life of the protein in blood, proteins fused with these sequences have also reported to have very low immunogenicity and toxicity, (Schlapschy et al. Protein Eng Des Sel (2013) 26:489). These sequences when fused to a target protein have been shown to extend the half-life in mice, and to improve the drug like qualities of the target protein.

The i-body will be fused to the PAS sequence at the C-terminus and protein expressed in E. Coli.

Example 5—Functional Characteristics of the i-Bodies 5.1 Modulation of cAMP on CXCR4 Transfected Cells DiscoveRx has developed a panel of cell lines stably expressing non-tagged GPCRs that signal through cAMP. Hit Hunter® cAMP assays monitor the activation of a GPCR via an inhibitory regulative G-protein (Gi) and a stimulative regulative G-protein (Gs) secondary messenger signaling in a homogenous, non-imaging assay format using a technology developed by DiscoveRx called Enzyme Fragment Complementation (EFC) with β-galactosidase (β-Gal) as the functional reporter. The enzyme is split into two complementary portions: EA for Enzyme Acceptor and ED for Enzyme Donor. ED is fused to cAMP and in the assay competes with cAMP generated by cells for binding to a cAMP-specific antibody. Active β-Gal is formed by complementation of exogenous EA to any unbound ED-cAMP. Active enzyme can then convert a chemiluminescent substrate, generating an output signal detectable on a standard microplate reader.

Methods

Cell Handling

CAMP Hunter cell lines were expanded from freezer stocks according to standard procedures. The cells were then seeded in a total volume of 20 μL into white walled, 384-well microplates and incubated at 37° C. for the appropriate time prior to testing. cAMP modulation was determined using the DiscoveRx HitHunter cAMP XS+assay according to manufacturer's instructions.

Antagonist Format

For antagonist determination, the Hunter cells which express CXCR4 were pre-incubated with sample followed by agonist challenge at the EC80 concentration. (For Gi cAMP assays, a forskolin concentration of 15 μM was used). Media was aspirated from cells and replaced with 10 μL 1:1 HBSS/Hepes:cAMP XS+Ab reagent. 5 μL of 4× stock of AMD3100 or i-bodies to CXCR4 were added to the cells and incubated at 37 t or room temperature for 30 minutes. 5 μL of 4×EC80 agonist SDF-1 was added to cells and incubated at 37° C. or room temperature for 30 or 60 minutes. For Gi coupled GPCRs, EC80 forksolin was included (a forskolin concentration of 15 μM was used).

Signal Detection

After appropriate compound incubation, assay signal was generated through incubation with 20 μL cAMP XS+ED/CL lysis cocktail for one hour followed by incubation with 20 μL cAMP XS+EA reagent for three hours at room temperature. Microplates were read following signal generation with a PerkinElmer Envision™ instrument for chemiluminescent signal detection.

Results

Figure 13:
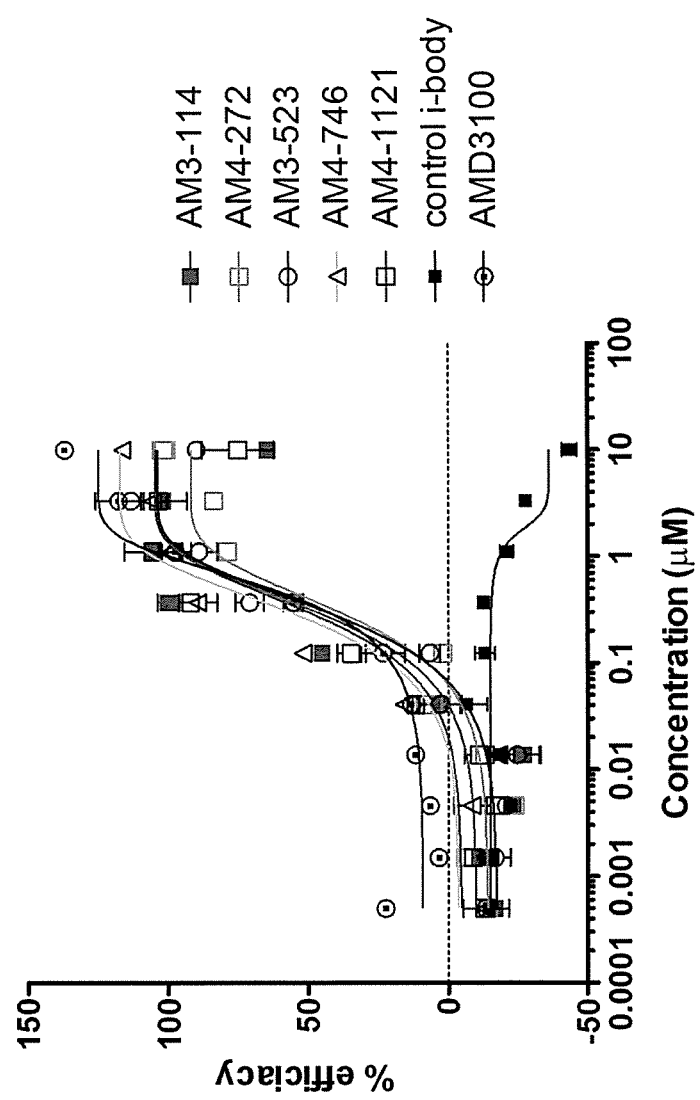
FIG. 13 shows chemiluminescent signal detection of CXCR4 for i-bodies AM3-114, AM4-272, AM3-523, AM4-746 and AM4-1121, positive control AMD3100 and negative control i-body as measured by cAMP assay.

Inhibition of CAMP by control i-body (21H5), AMD3100 and i-bodies AM3-114, AM4-272, AM3-523, AM4-746, AM4-1121 (IC50) was then determined. The data is show in Table 7 and FIG. 13. Chemokine receptors such as CXCR4 are primarily Gαi-coupled and therefore, signal via 2nd messenger cAMP. Regulation of cyclic AMP (cAMP) might be important for interactions between SDF-1 and various cellualar signalling. The panel of CXCR4 i-bodies was examined for the ability to modulate cAMP levels in vitro. The previously described antagonist AMD3100 displayed a dose-dependent effect inhibition of cAMP with an expected IC50 of 615 nM. The i-bodies were very effective at blocking the SDF-1 induced decrease in cAMP in these cells. Indeed, all i-bodies had IC50 values lower than AMD3100. Based on the IC50 results, the CXCR4-binding i-body AM3-114 is a potent inhibitor of cAMP.

These data suggest that the i-bodies can bind to CXCR4 and inhibit key functional signalling such as Gai-signaling pathway, which controls cAMP modulation without blocking the Gq-pathway that influences calcium flux. This could be the reason why the i-bodies could block inflammation and fibrosis but not mobilise stem cells which would be an advantage when used in long term therapy.

TABLE 7

$IC_{50}$ of compounds to CXCR4 determined by cAMP assay in antagonist mode

| Sample | cAMP inhibition IC50 (nM) |
|---|---|
| 21H5 (control i-body) | >10 uM |
| AMD3100 | 615 |
| AM3-114 | 99 |
| AM4-1121 | 125 |
| AM3-523 | 225 |
| AM4-746 | 115 |
| AM4-272 | 300 |

5.2 Modulation of Calcium on CXCR4 Transfected Cells

CXCR4 transfected cells were treated with i-bodies or AMD3100 for 30 min, then stimulated with 100 ng/ml of SDF-1 for 30 min. Inhibition of Ca2+ influx by controls or i-bodies ($IC_{50}$) was then determined.

Materials
Cells

Mammalian cells stably expressing human CXCR4 receptor were produced in-house by Multispan, Inc (catalog no. C1004-1). Control agonist used was SDF-1 (Peprotech, Cat #300-28A).

Compounds 7 compounds/i-bodies (21H5, AM3-114, AM4-272, AM3-523, AM4-746, AM4-1121, and AMD3100) were tested in liquid form at 40 uM or 10 mM. AMD3100 (also known as plerixafor or Mozobil) is a small molecule antagonist of CXCR4 and is available commercially. It was used as a positive control.

Calcium Assay Kit

Screen Quest™ Fluo-8 No Wash kit (AAT Bioquest, Cat #36315)

Instruments

FLIPR 384 (Molecular Devices)

Methods
Calcium Assay

Cells were seeded in 384-well plate at an appropriate density and cultured overnight. Calcium assay was conducted according to the manufacturer's protocols. The calcium dye loading buffer was added to the cells and incubated for one hour at 37° C. Calcium flux was monitored for 120 seconds with compound injected into the wells at 19th second. In antagonist mode, carrier or compounds were preincubated with the cells for 30 minutes before calcium flux measurement with the control agonist at EC80 concentration obtained from dose-response curve. The data are shown in Table 8 and FIG. 14. Since Calcium flux is directed by the Gq pathway, this results suggests that all i-bodies tested do not significantly modulate the Gq pathway. Accordingly, the i-bodies do not modulate calcium flux.

TABLE 8

Calcium Inhibition Assay

| | Calcium Inhibition EC50 (nM) |
|---|---|
| 21H5 | >10 uM |
| AMD3100 | 500 nM |
| AM3-114 | uM |
| AM4-1121 | uM |
| AM3-523 | uM |
| AM4-746 | uM |
| AM4-272 | uM |

5.3 Modulation of β-Arrestin on CXCR4 Transfected Cells

Binding of the i-bodies to CXCR4 were examined in a β-Arrestin BRET assay as described in See, Heng B et al (2011) Assay and Drug Development Technologies 9(1):21-30. The i-bodes were examined at ten concentrations with and without 100 nM SDF-1 with the addition of 'vehicle' and 'SDF-1+ vehicle' controls in order to characterise if the i-bodies are agonist or antagonists of CXCR4 activity.

Figure 15:
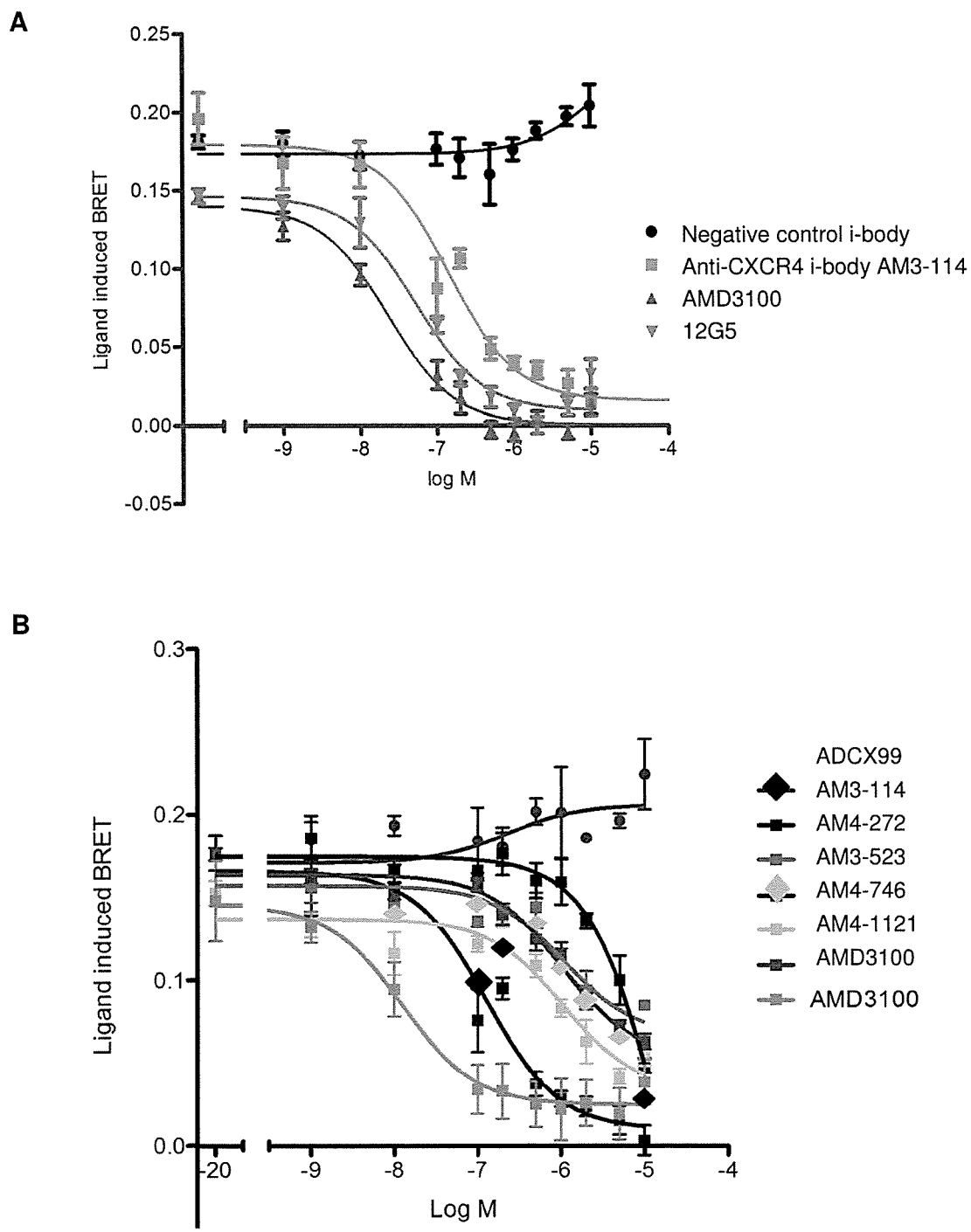
FIG. 15 shows the results of the BRET β-arrestin assay for (A) anti-CXCR4 i-body AM3-114 compared with two positive controls (small molecule AMD3100 and MAb12G5) and a negative control i-body; and (B) anti-CXCR4 i-bodies AM3-114, AM4-272, AM3-523, AM4-746, and AM4-1121, positive control (AMD3100) and ADCX-99.

The results of the β-Arrestin BRET assay for each binder is provided in Table 9 and in FIG. 15. AMD3100 had an IC50 of 18 nM whilst the parent CXCR4 i-body, ADCX-99, had a very weak effect on β-arrestin recruitment, probably due to the low affinity (643 nM) for CXCR4 as shown by SPR. The i-body panel IC50 values ranged between 164 nM for AM3-114 and 127, 13 nM for AM3-523. These changes in β-arrestin recruitment are as a result of changing 1-10 amino acids in the binding regions.

TABLE 9

Affinity of i-bodies determined by β-Arrestin assay

| Protein | IC50 (nM) in β-Arrestin BRET assay (Antagonist mode in the presence of 100 nM SDF-1) |
|---|---|
| 23B2 | No activity |
| AMD3100 | 18 |
| mAb-12G5 | 64 |
| SDF-1 | NA |
| ADCX-99 | No activity |
| AM1-126 | 610 |
| AM1-320 | 1419 |
| AM3-114 | 164 |
| AM3-920 | ~uM |
| AM4-1121 | 796 |
| AM4-613 | 1826 |
| AM3-523 | 12713 |
| AM4-661 | 1544 |
| Am3-466 | 6322 |
| AM5-245 | ~uM |
| AM4-272 | 861 |
| AM4-746 | 741 |

Example 6—Binding Characteristics of the i-Bodies

Any cell that expresses human CXCR4 on the surface can be used to examine the ability of the CXCR4 binding molecules or polypeptides (i-bodies) described herein to bind native, cell surface CXCR4. Examples of such cell lines include the human T cell line, CEM, as well as other cell lines such as Ramos, Raji, Namalwa, L540, DMS79, MDA-MB-231, MDA-MB-361, MDA-MB-549, MOLT-4, DU-4475, DU-145, PC3, LNcaP, SW480, HT29, NCI-H69 and HL60.

6.2 In Vitro Binding Affinity of i-Bodies by Flow Cytometry Analysis

Cells were treated with i-bodies AM3-114, AM4-272, AM3-523, AM4-746 and AM4-1121 (10 µM, 1 µM and 0.001 µM), and the staining intensities were evaluated by flow cytometry analysis. Cell lines tested were T47D (CXCR4 negative), MDA-MB-231 (low CXCR4 expression) and Namalwa, NCI-H69, Jurkat, CCRF-CEM, A498, Ramos (high CXCR4 expression).

Method

Cell Lines were harvested and transferred cells to 96-well tissue culture plates ($2 \times 10^5$ cells/well). The culture plate was then centrifuged at 1000 rpm, 4° C. for 5 min. Cells were resuspended with 100 uL of PBS buffer containing test antibody and incubated at 4° C. for 60 min. Cells were washed with 300 ul ice-cold FACS buffer twice, 1000 rpm, 5 min and resuspended with 100 ul of PBS buffer containing anti-His-PE antibody (for i-bodies) and incubated at 4° C. for 40 min in dark. Cells were then washed with 300 uL ice-cold FACS buffer×2, 1000 rpm, 5 min and the cells resuspended with 300 ul of suspension buffer and subject to FACS analysis according to standard methods.

Figures 1, 16:
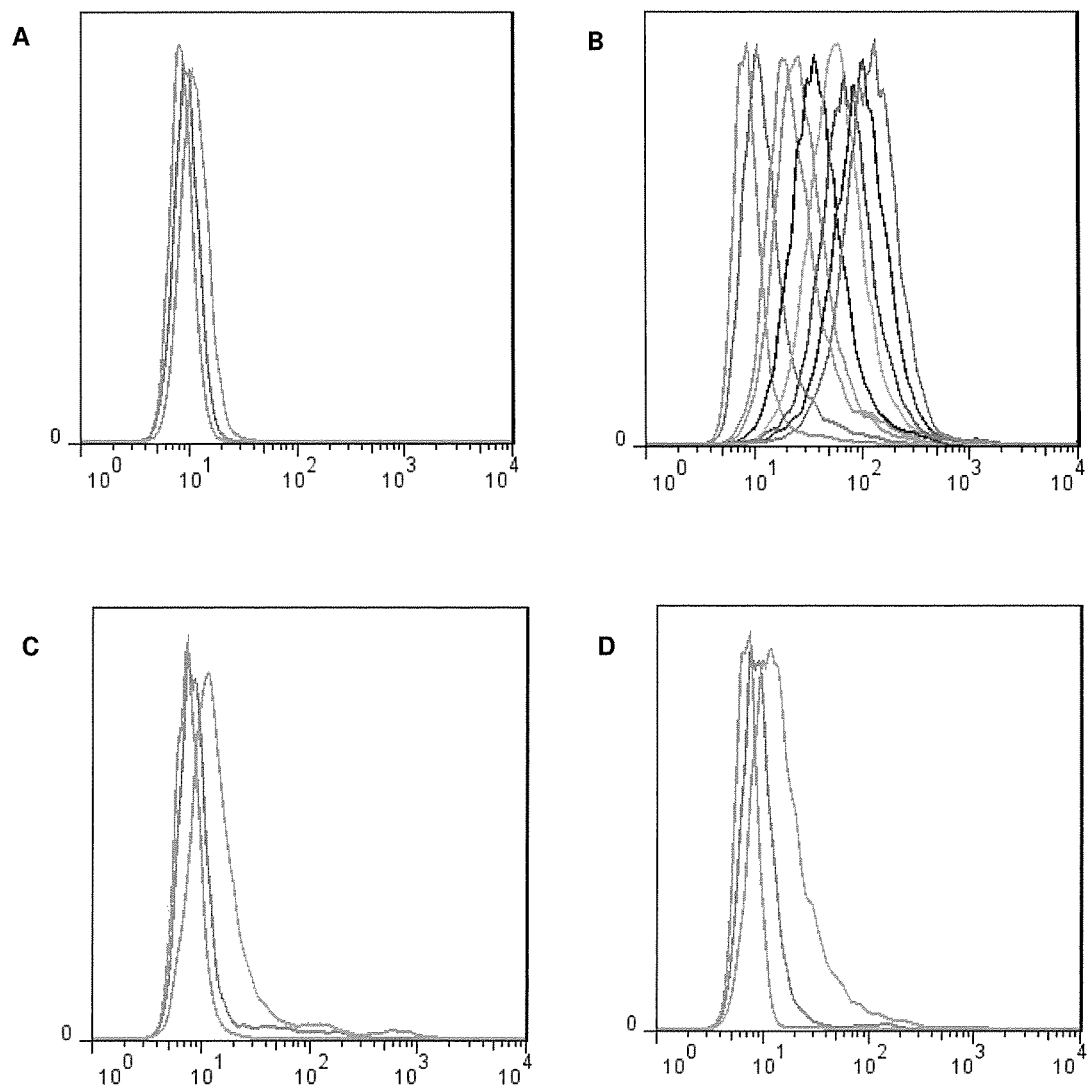
Figures 2, 16:
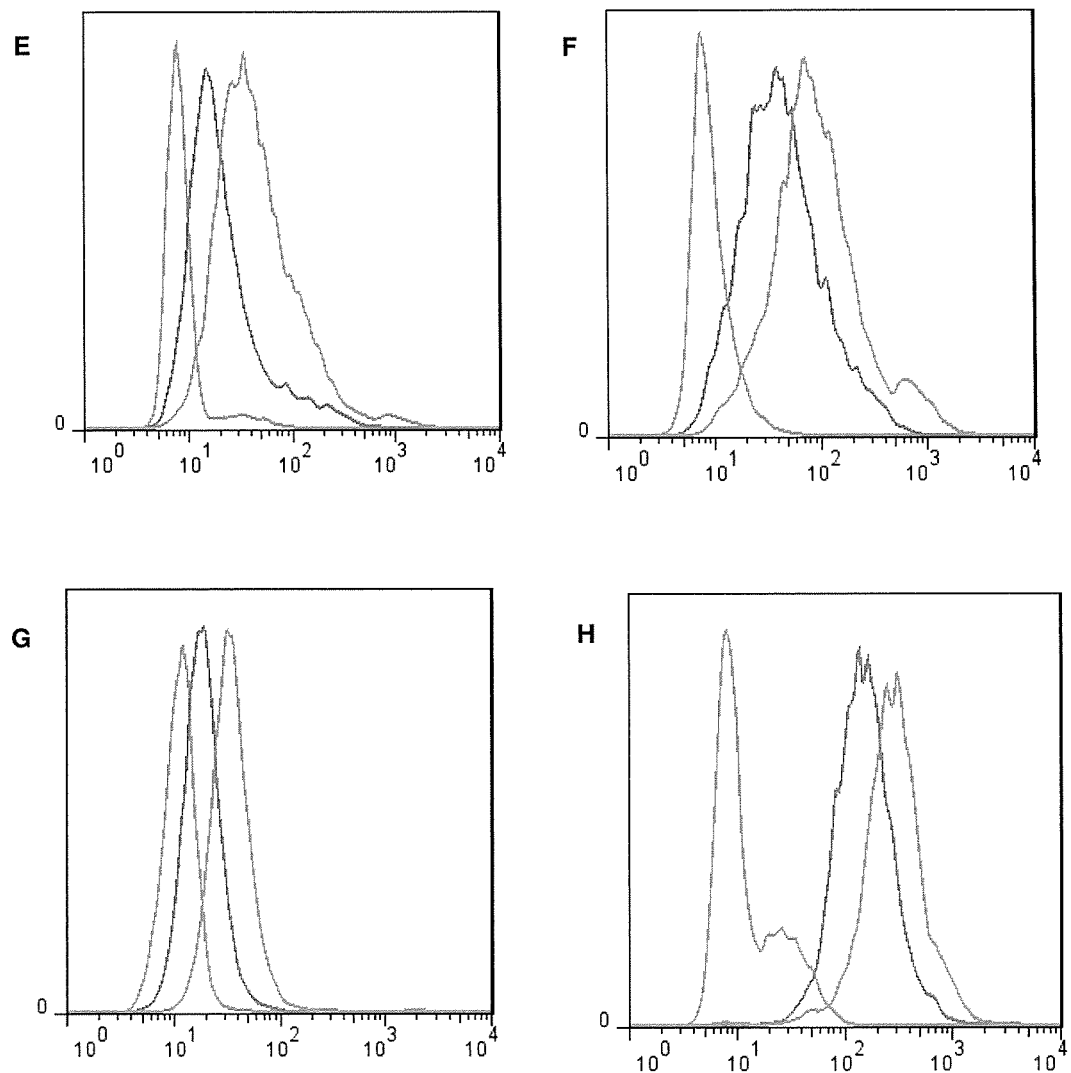
Figures 3, 16:
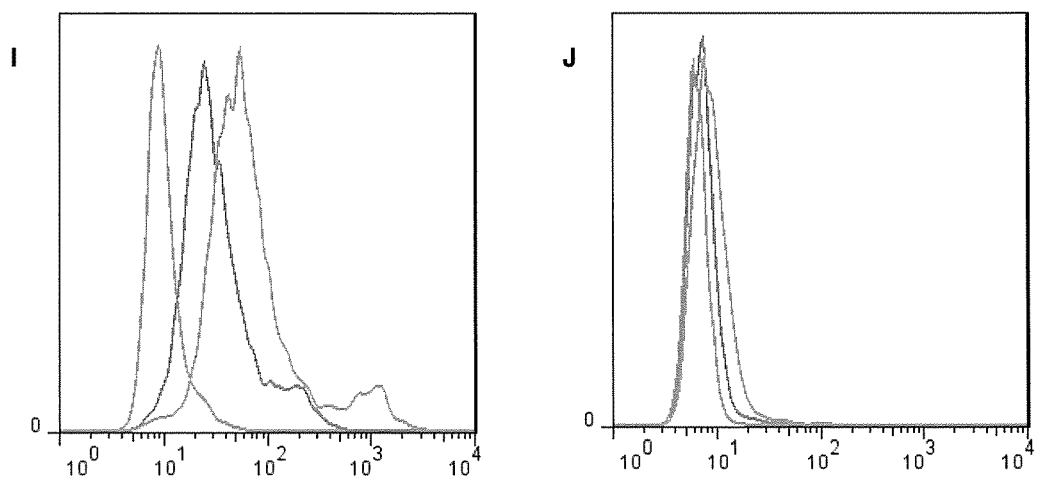

Binding affinity for CXCR4 demonstrated by flow cytometry analysis is shown in FIGS. 16-1 to 16-3 for representative i-body AM3-114 on T47D cells (A), Namalwa cells (B), MOLP8 (C), MOLT4 (D), Jurkat cells (E), CCRF-CEM (F), A498 (G), Ramos (H), NCI-H69 (I), and HL-60 (J). Cell lines were tested with three i-body concentrations, (10 µM, 1 µM and 0.001 µM) with the exception of Namalwa cells which were also tested with i-bodies at 4.7, 2.1, 0.47, 0.21, 0.1 and 0.01 µM.

Example 7—Competition with SDF-1 Binding to CXCR4 by the i-Bodies 7.1 SPR Assay of Competition for i-Bodies Binding to CXCR4

Competition studies were performed to determine the ability of the i-bodies to inhibit binding of SDF-1 to CXCR4 utilising CXCR4 containing lipoproteins (IntegraMolecular) as described in WO 2005/042695.

Figure 17:
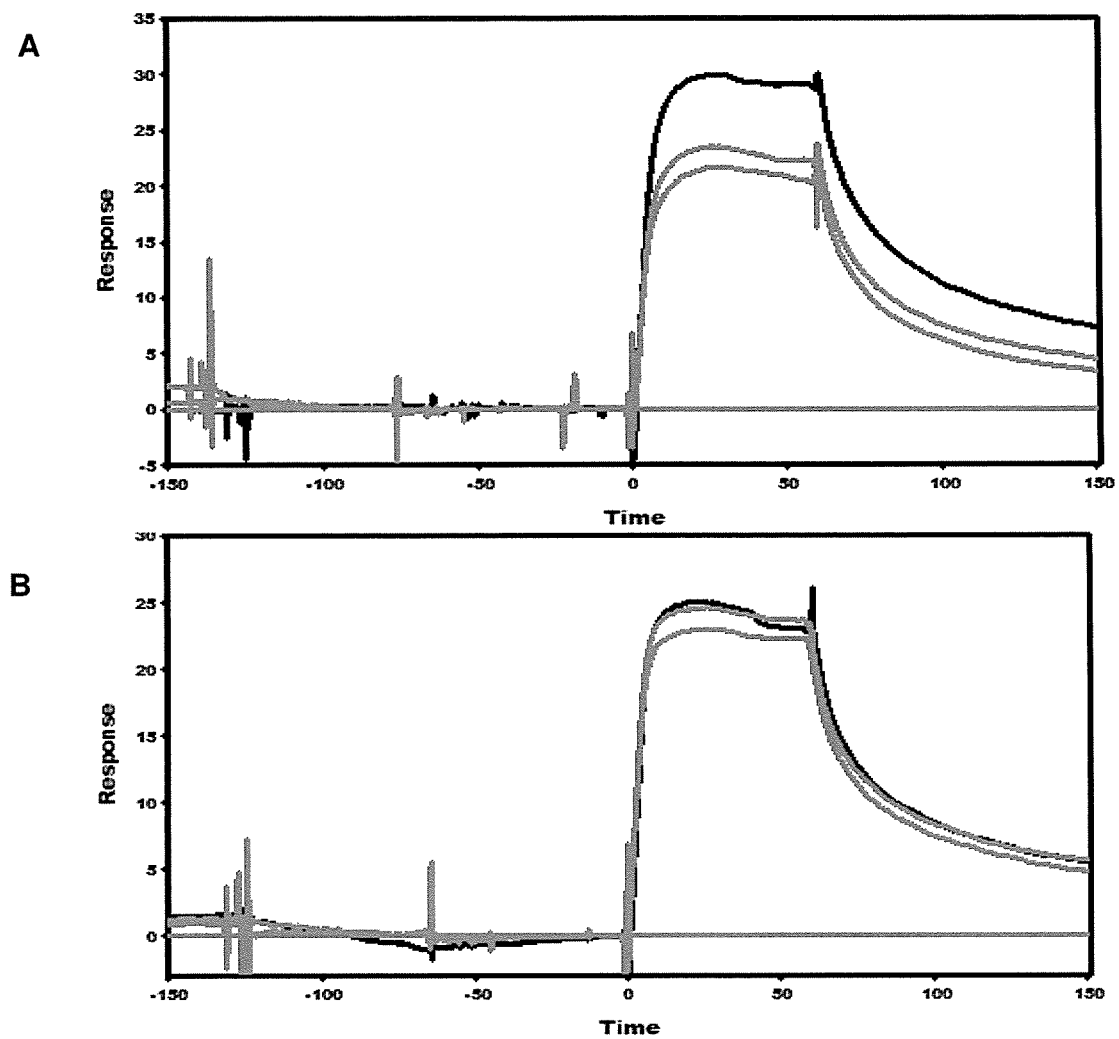
FIG. 17 shows competition of CXCR4 i-bodies with SDF-1 for binding to CXCR4 positive lipoparticles measured by surface plasmon resonance (SPR; BIAcore). Data shown for i-body AM3-114 (A) and AM4-272 (B).

A panel of CXCR4 i-bodies were tested by surface plasmon resonance (SPR) for their ability to compete with the ligand SDF-1. FIG. 17 shows an example of two i-bodies, one which competed with SDF-1 in a dose dependant manner (AM3-114 FIG. 17A) and one which did not compete well (AM4-272 FIG. 17B). CXCR4 lipoparticles were co-injected with i-body and SDF-1 at 2 nM 50 nM and 200 nM.

Table 12 shows the extent (indicated by +) of each i-body to compete with SDF-1 for binding to CXCR4 positive lipoparticles.

TABLE 12

Extent of competition with SDF-1 for binding to CXCR4 positive lipoparticles

| i-body | Competition with SDF-1 |
| --- | --- |
| AM4-661 | + |
| AM3-466 | ++ |
| AM3-114 | +++ |
| AM4-272 | +/− |

TABLE 12-continued

Extent of competition with SDF-1 for binding to CXCR4 positive lipoparticles

| i-body | Competition with SDF-1 |
| --- | --- |
| AM3-523 | ++ |
| AM4-746 | ++ |
| AM4-1121 | ++ |
| AM3-920 | ++ |
| AM3-126 | − |

Figure 18:
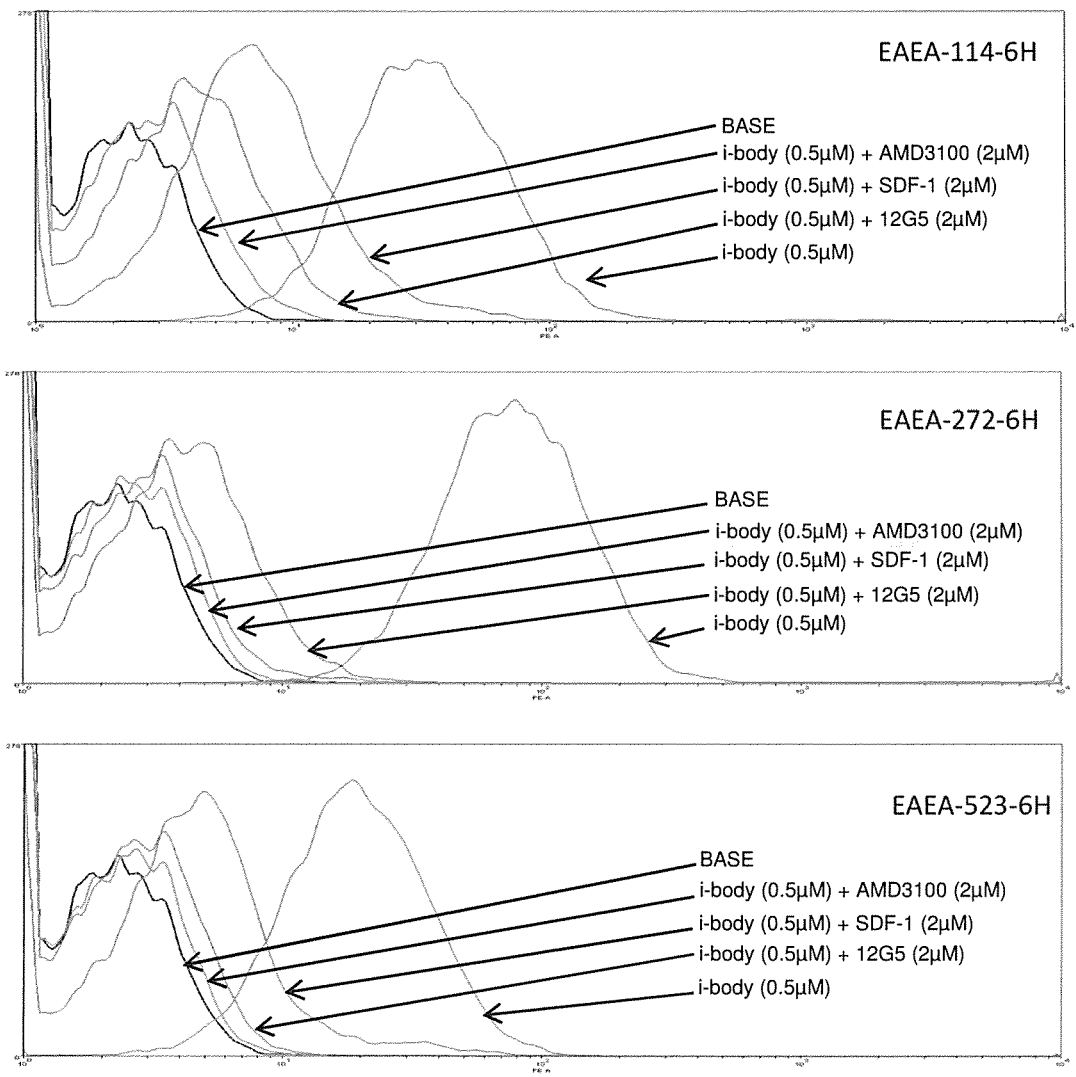
FIG. 18 shows competition of CXCR4 i-body binding to Ramos cells with various molecules. AM3-114 (top panel), AM4-272 (middle panel), AM3-523 (bottom panel) i-bodies bound to Ramos cells and this binding was reduced to varying degrees upon the addition of AMD3100, MAb12G5 and the natural ligand SDF-1.

7.2 Flow Cytometry Assay of Competition for i-Bodies Binding to CXCR4 by Various CXCR4 Binding Molecules The binding of CXCR4 i-bodies (AM3-114-6H, AM4-272-6H and AM3-523-6H) containing the N-terminal sequence EAEA to CXCR4 expressed on the surface of cells and the ability of SDF-1 to compete for the binding was assessed using flow cytometry. The i-bodies were incubated with Ramos cells in 100 µl of FACS buffer (1×PBS & 2% FCS) at 4° C. for 60 minutes. After washing twice with 2 ml of ice cold FACS buffer, cells were centrifuged at 1,500 rpm for 5 mins, cells were resuspend in 100 µl of FACS buffer containing the anti-His-PE antibody (MACS Molecular, Order no: 130-092-691) and incubated at 4° C. for 40 mins in the dark. This assay is robust and can be used to examine competition between the i-bodies and SDF-1 and other antagonists. In this case each i-body (0.5 µM) is incubated with the cells either alone or in the presence of an excess of SDF-1 (2 µM), MAb12G5 (2 µM), and AMD3100 (2 µM). The binding of all three i-bodies was reduced upon the addition of 2 µM AMD3100 (FIG. 18). SDF-1 was able to compete well with AM4-272 but only partially with AM3-114 and AM3-523. All three i-bodies were competed with AMD3100 indicating that there is similarity between the binding site for the i-bodies and this small molecule. The anti-CXCR4 MAb 12G5, was able to reduce the binding of 523 almost completely and to partially block the binding of AM3-114 and AM4-272.

Example 8—Inhibition of Migration of CXCR4 Expressing Cells by the i-Bodies

The ability of the CXCR4 binding molecules or polypeptides disclosed herein (i-bodies) to inhibit migration induced by SDF-1 can be examined using breast cancer cells line MDA-MB-468 and prostate cancer cell line PC3 which are well characterised in terms of their metastatic potential and properties both in vitro and in vivo (Kaighn et al 1979 *Invest Urol.* 17(1):16-23. Yoneda et al 2000 Cancer 88:2979-88). MDA-MB-468 cells are invasive and metastasise to lung from the primary mammary fat pad tumours of nude mice. The method is described in Byeong-Chel Lee et al (2004) Mol Cancer Res 2; 327. Briefly, the cells are added to fibronectin (50 µg/mL)-coated transwell inserts (Costar Corp., Cambridge, Mass.). The MDA-MB-468 cells and PC3 cells are then starved overnight in serum-free media and would then be incubated with the anti-CXCR4 i-body before their application to 8-µm-pore-size transwell inserts. Cells are suspended into the upper chamber at a final concentration of $7 \times 10^4$/mL in 500 µL of RPMI 1640. Serially diluted recombinant SDF-1 is added to the lower chamber. After 3 to 9 hours of incubation, the cells on the upper surface of the filters are removed by wiping with cotton swabs, and the migrated cells on the lower chamber are fixed and stained using a Hema3 kit (Biochemical Sciences Inc., Swedesboro, N.J.), according to the manufacturer's instructions. Cellular transmigration is then enumerated in four separate microscopic fields per field (Kashima et al Cancer Sci 105 (2014) 1343-1350; Zhu et al Molecular Cancer Research (2013) 11(1) 86-94).

Example 9—Inhibition of Angiogenesis by the i-Bodies

Inactivation of surface SDF-1 or CXCR4 in HUVECs impairs the ability of HUVECs to align into tubular structures on Matrigel-coated surfaces. The i-bodes of the present disclosure can be tested for their effects on the ability of HUVECs to form Matrigel-dependent tubular structures as per Liang et al, Biochem Biophys Res Commun. 2007 August 3; 359(3): 716-722. To perform the capillary tube formation assay, CXCR4 i-body antagonist is pre-incubated with human umbilical vein endothelial cells (HUVEC) at 100 nM, 5 µM, and 1 µg/ml concentrations, respectively, for 10 min at room temperature before seeding. The cells are then plated onto the layer of Matrigel at a density of $1\times10^5$ cells/ml of M199 medium with 1% FBS and 200 ng/ml of SDF-1. After 18 hrs, the wells are photographed at 4× magnification in five randomized fields and the number of their tubular networks is counted.

Example 10—Inhibition of Tumor Cell Proliferation In Vitro by i-Bodies

The ability of the CXCR4 molecules or polypeptides disclosed herein (i-bodies) to inhibit proliferation of Ramos tumor cells, a human Burkitt's lymphoma cell line expressing CXCR4 mentioned above, in vitro was examined in a MTT cell proliferation assay as described in (Lapteva (2005) Cancer Gene Therapy 12, 84-89). Cells were grown in a 96-well tissue culture plate and treated with a vehicle or the anti-CXCR4 i-body. The cells were then incubated with the MTT solution for approximately 4 hours. After this incubation period, a water-insoluble formazan dye is formed. After solubilization, the formazan dye is quantitated using a scanning multi-well spectrophotometer (ELISA reader). The absorbance revealed directly correlates to the cell number.

It was found that i-body AM3-114 at 10 µM was able to substantially inhibit the growth of RAMOS cells. This effect was particularly obvious between 24 and 48 hrs after addition of the i-body, although there was still substantial inhibition of cells at 72 hrs after i-body addition. As expected AMD3100 was also able to inhibit cell growth in this time frame. Two control i-bodies (21H5 and AM8-7) had little effect on cell growth. There was a small inhibitory effect of i-body AM4-272 but AM3-523 had no observable effect in this assay. The i-bodies had no effect on normal HEK cells.

Example 11—Induction of Apoptosis by the i-Bodies

Figures 1, 19:
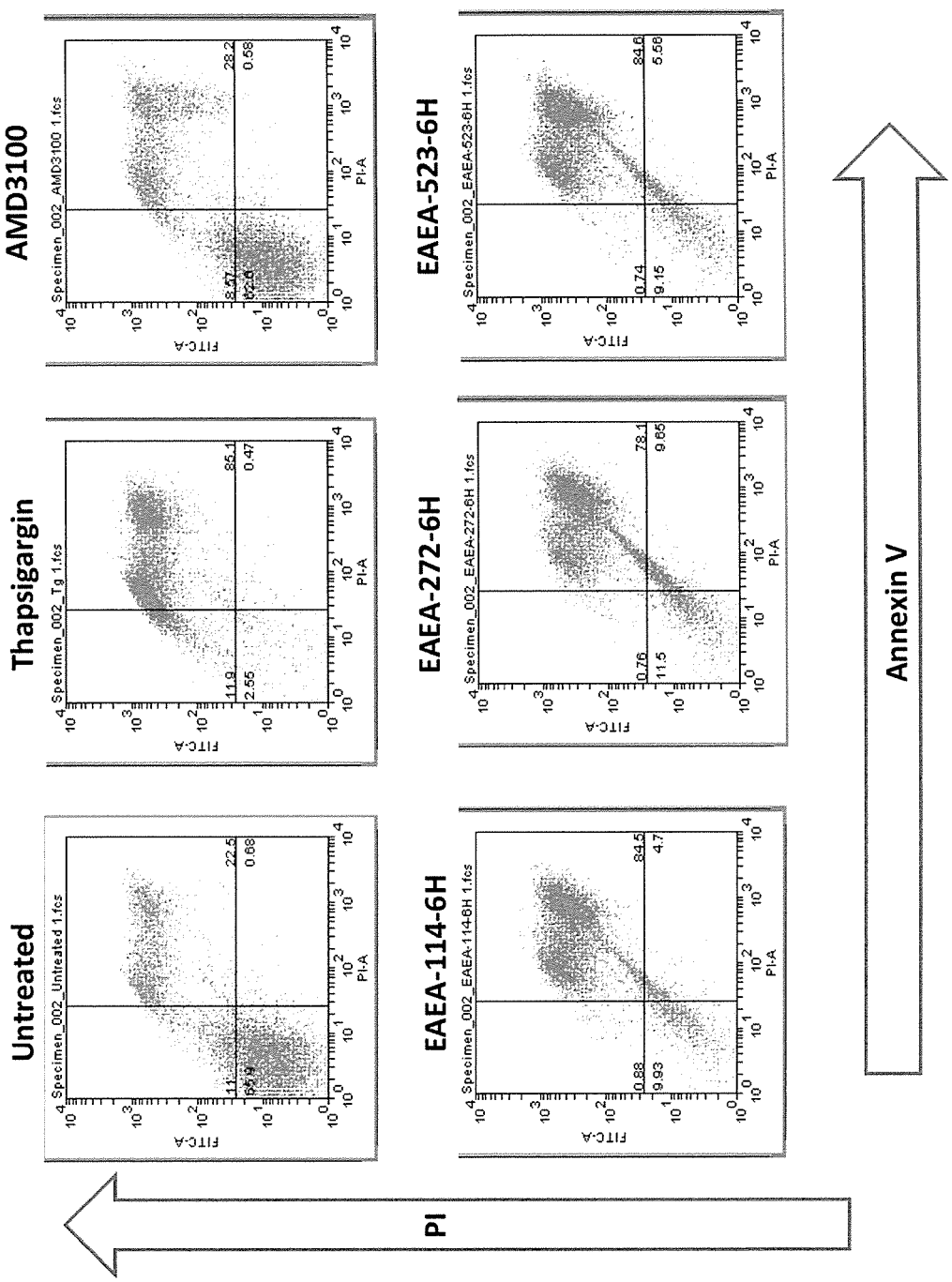
Figures 2, 19:
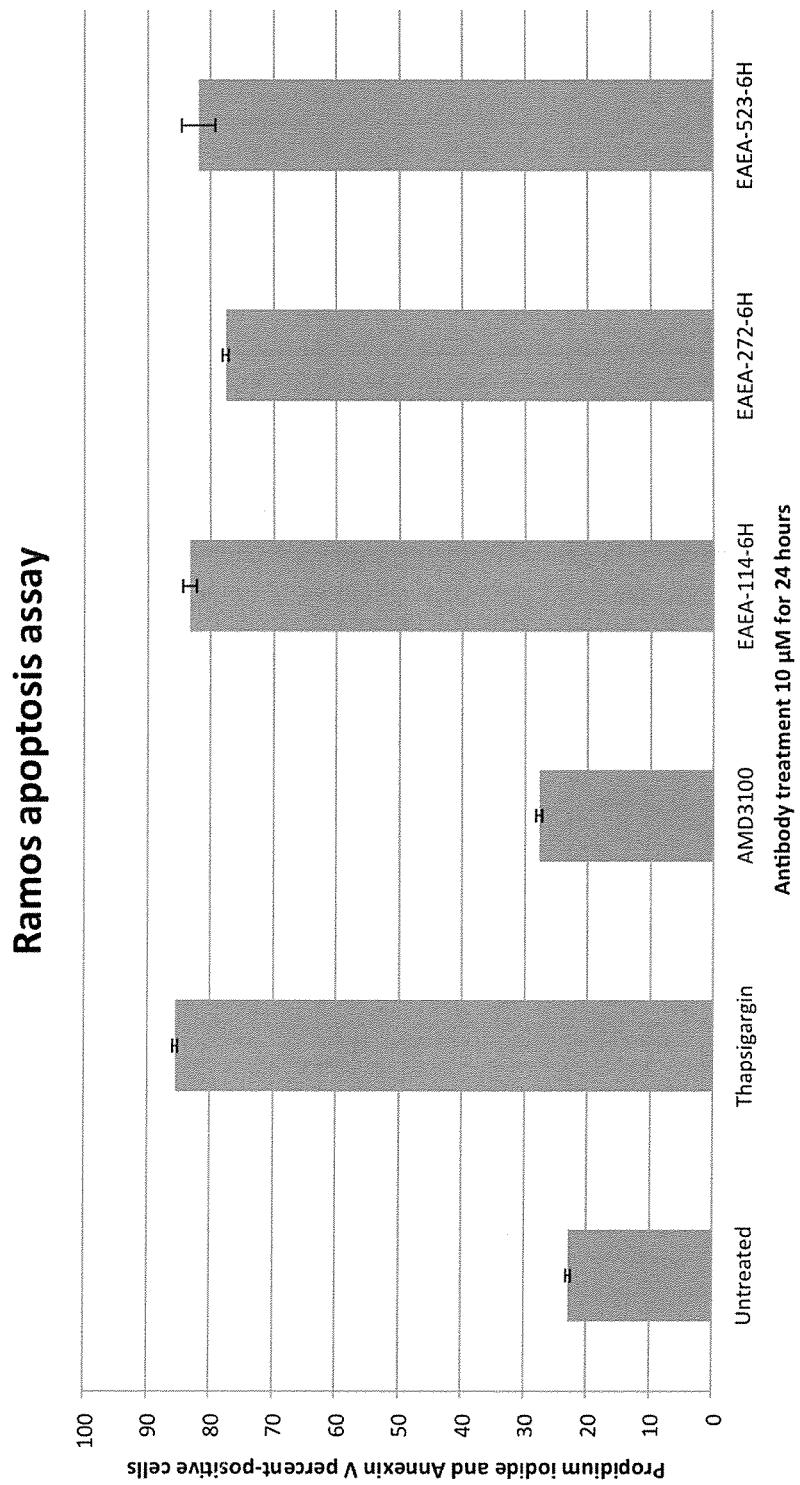

The ability of an i-body of the invention to induce apoptosis in Ramos tumor cells (a human Burkitt's lymphoma cell line) was examined in an apoptosis assay according to the methods as described in Mishra M et al (2011) J Cell Mol Med 15(11):2462-77. I-bodies were incubated with Ramos cells and examined by flow cytometry after 24 or 72 hours. The cells were stained for annexin V and propidium iodide which are classic markers for apoptosis. Cells which were double positive were assessed to have become apoptotic. The three CXCR4 bodies (AM3-114-6H, AM4-272-6H and AM3-523-6H) were able to strongly induce apoptosis (FIG. 19). Untreated cells acted a negative control to show that the cells were otherwise healthy. Thapsigargin is a well-described inducer of apoptosis, and shows the expected level of apoptosis. AMD3100 does not induce significant apoptosis in Ramos cells. This is consistent with a previous report showing that the human anti-CXCR4 mAb MDX-1338 was able to induce apoptosis in Ramos cells but AMD3100 was not (Kuhne et al Clin Cancer Res (2013) 19(2): 357-66).

Example 12—Binding of the i-Bodies to Tumours In Vivo 12.1—i-Body Staining of Tumours in the Spleens and Livers of SCID/bg Mice that had been Intravenously Injected with CCRF-CEM Cells Immunohistochemistry staining using the anti CXCR4 i-bodies (AM3-114-6H, AM4-272-6H and AM3-523-6H) at 130 µg/ml was carried out on the spleens and livers of SCID/bg mice that had been intravenously injected with CCRF-CEM cells and sacrificed after 27 days. Tissues were fixed in 10% neutral buffered formalin overnight and subsequently transferred into tissue cassettes and placed in 70% ethanol. The tissues were then paraffin embedded. Slides containing 4 µm sections were deparaffinized and hydrated by incubating them in two changes of xylene for five min each, followed by two changes of 100% ethanol for 3 min each, 70% ethanol for 2 min, 50% ethanol for 2 min, and distilled water for 5 min. Antigen retrieval was performed by incubating the slides in 10 mM Citric acid solution (pH 6.0) in an 80° C. oven overnight. The slides were subsequently washed in PBS and permeabilized in 10% methanol containing 0.4% $H_2O_2$ for 30 min. After permeabilization, slides were stained with CXCR4 specific iBodies (AM3-114-6H, AM4-272-6H, or AM3-523-6H) and a control iBody (21H5-6H) overnight at 4° C. All slides were subsequently stained with biotinylated anti-His tag antibodies (Miltenyi Biotech) and developed using an HRP-DAB cell and tissue staining kit according to the manufacturer's instructions (R&D systems).

130 µg/ml of AM3-114-6H and AM4272-6H stained CCRF-CEM cells in the spleen and liver of the immunocompromised mice challenged with these cells (Figure not shown).

12.2—Solid Tumors

The ability of the CXCR4 binding molecules or polypeptides (i-bodies) to inhibit proliferation of an established solid tumor in vivo can be examined using a Ramos subcutaneous tumor cell model (or Namawala cells or MDA-MB-231 or MDA-MB-468 or PC3 cells). In this assay, $10\times10^6$ cells/mouse are implanted into the flank region of each mouse and allowed to grow to a mean size of 40 mm³, calculated by length×width×height/2 of the tumors. The mice then receive an intraperitoneal (ip) injection of a first dose of i-body (designated as day 0 of treatment) and a second ip dose of antibody on day 7. Groups of mice are treated with either (i) vehicle (ii) i-body or (iii) anti-CD20 positive control. Tumor volume and mouse body weight are measured at regular intervals (approximately 2-3 times/week) between day 0 and day 30 post dosing.

This assay model can also be used to assess the ability of the i-bodes to increase survival time of the mice.

12.3—Metastasis

The anti-metastatic efficacy of the i-bodies of the present disclosure can be tested in animal models. For breast cancer metastasis, MDA-MB-231 cells are injected intravenously to generate an experimental metastasis model. Six- to eightweek-old female nude mice are given injections of 1.5×10⁶ MDA-MB-231 breast cancer cells mixed with the i-body (1 mM, less than 5 min preincubation) through the tail vein (10/group). From the following day, mice in the treated group are given 4 mg/kg of the i-body daily by i.p. injection. The animals are sacrificed 35 days after the tumor cell injection. Whole lung tissues are harvested and sectioned for real-time RT-PCR for human CXCR4 and H&E histostaining to evaluate the metastatic tumor area in five fields per section microscopically.

For the head and neck cancer animal model, metastatic subclones of 686LN-Ms cells are injected in the same way as MDA-MB-231 cells as described (Yoon Y et al., (2007) Cancer Res 67:7518-7524).

For the uveal melanoma micrometastasis mouse model, on day 0, each mouse is inoculated with 1×10⁶ wild-type OMM2.3 cells expressing HGF/TGF-b/CXCR4/MMP2 into the posterior chamber of right eye. On day 3, mice are treated with the i-body of the invention daily by i.p. injection, whereas the control mice are injected with 0.1 mL 45% (2-hydroxypropyl)-beta cyclodextrin. On day 7, eyes with tumor are enucleated. The growth of tumor is checked by histological methods. On day 28, hepatic tissues are collected and fixed in 10% formalin, processed, H&E stained, and the number of hepatic micrometastases counted under microscope. Six sections through the center of the liver are microscopically examined for the presence of micrometastases (100 mm diameter) and the average number of micrometastases per section determined (Liang et al PLoS One. 2012; 7(4): e34038).

Example 13—Inhibition of HIV Invasion by i-Bodies

Figure 20:
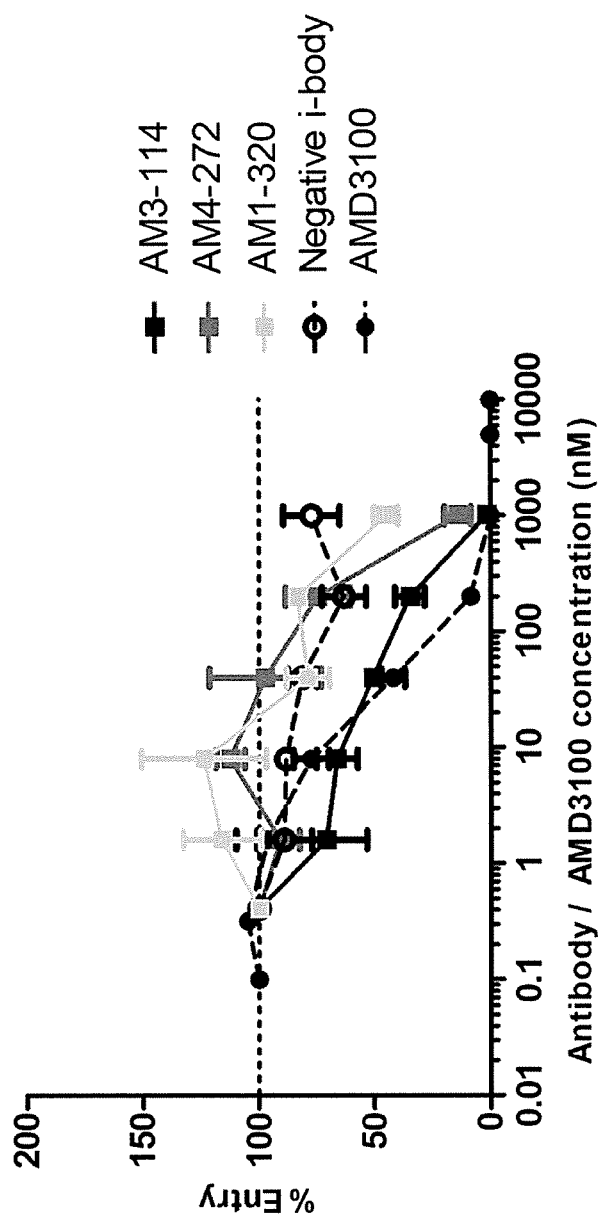
FIG. 20 shows the results of an HIV inhibition assay for i-bodies AM3-272, AM3-114 and AM1-320 relative to a negative control i-body and the positive control small molecule AMD3100.

An in vitro HIV inhibition assay was used to demonstrate the ability of i-bodes to inhibit HIV entry into CXCR4 expressing T-cells. AM3-114 was able to block HIV entry into CXCR4 expressing T-cells with a similar efficacy as AMD3100 as shown in FIG. 20. AM3-114 and AMD-3100 had an $IC_{50}$ of 50 nM, whereas the negative control i-body (21H5) had no effect in the inhibition assay as expected.

Cell Viability

In a second experiment it was demonstrated that the i-bodies did not cause loss in viability of the cells used for HIV infection.

Method

Figure 21:
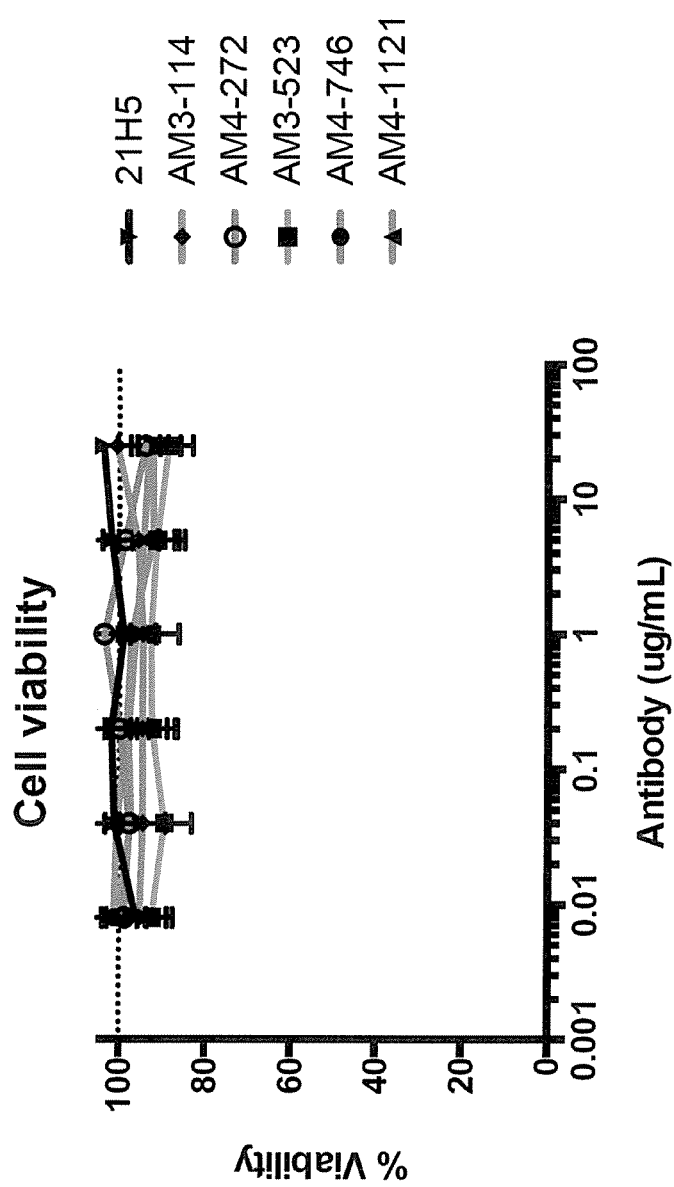
FIG. 21 shows NP2-CD4/CXCR4 cell viability of i-bodies AM3-114, AM4-272, AM3-523, AM4-746 and AM4-1121 and control 21H5 measured using a FLUOStar microplate reader.

For the HIV inhibition assay, NP2-CD4/CXCR4 cells (1×10⁴ in 100 µl) were seeded in flat-bottom 96-well plates 24 h prior to addition of i-body (negative control i-body 21H5, and anti-CXCR4 i-bodies AM3-114, AM4-272, AM3-523, AM4-746 or AM4-1121). Media was then removed from the cells and replaced with 100 µl of fresh media with five-fold dilutions of i-body for 16 hr at 37° C. The concentration range for the CXCR4 i-bodies was 25 µg/ml to 0.008 ug/ml. The concentration of PBS (5.8%, vol/vol) was maintained in the untreated wells. Following this, the media was removed and replaced with fresh media. The i-body concentrations were maintained throughout the subsequent culture period. NP2-CD4/CXCR4 cells were incubated at 37° C. for a total of 72 h. The cell viability in each well was assessed using the CellTitre-Glo Luminescent Cell Viability Assay (Promega) according to the manufacturer's protocol. Luminescence was measured using a FLUOStar microplate reader (BMG). To determine the percentage cell viability in the presence of antibody, the amount of luciferase in cells treated with the antibody was expressed as a percentage of that in untreated cells. The results are presented in FIG. 21.

Inhibition of Virus Entry

Figure 22:
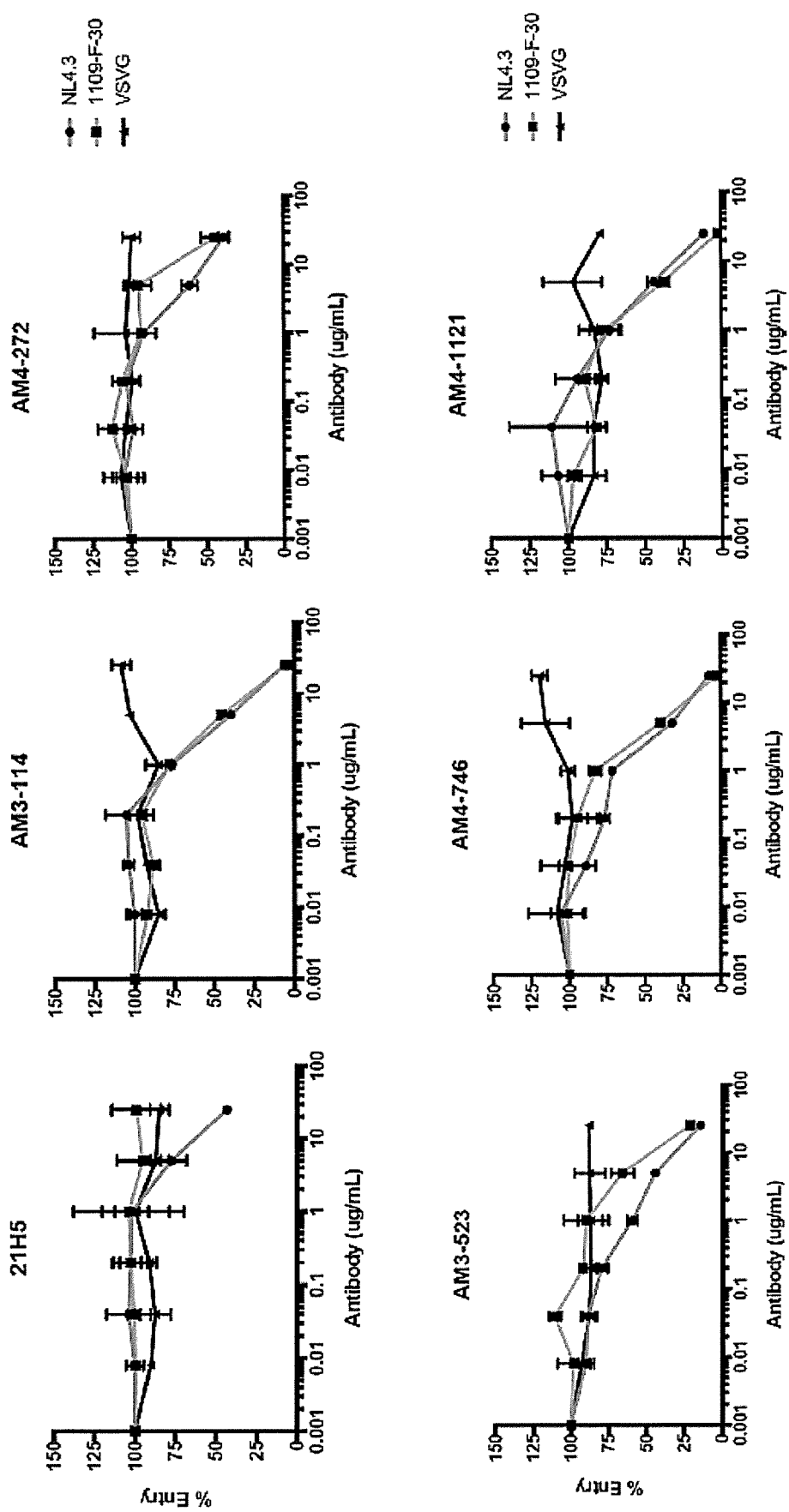
FIG. 22 shows inhibition of HIV strains (NL4.3 and 1109-F-30) with various i-bodies AM3-114, AM4-272, AM3-523, AM4-746 and AM4-1121 relative to a negative control i-body 21H5. CXCR4 i-bodies block infection of HIV in a dose dependent manner. VSVG is the Envelope from the Vesicular stomatitis virus that undergoes endocytosis after binding to an unrelated receptor.

All of the CXCR4 i-bodies appear to cause significant levels of inhibition of two HIV-1 CXCR4-using envelope strains NL4.3 and 1109-F-30. NL4.3 is a lab adapted Envelope whilst 1109-F-30 is a subtype C clinical Envelope from a chronically infected individual. The i-bodies did not inhibit entry of an unrelated virus, VSVG, which is the Envelope from the Vesicular stomatitis virus which undergoes endocytosis after binding to an unrelated receptor. The results are presented in FIG. 22.

The negative control i-body, 21H5, had little effect on strain 1109-F-30 but some invasion effect on strain NL4.3. By comparison, i-bodies AM3-114, AM4-746 and AM4-1121 all inhibited both HIV strains very well with an $IC_{50}$ of around 80 nM. Furthermore, when i-bodies AM3-114 and AM4-746 were conjugated to PEG sized 30K (linear) and 2×20K (branched) the $IC_{50}$s remained consistently around 80 nM. Also consistent with the earlier experiment, AM4-272 was the least effective at blocking HIV infection.

PEGylated i-bodies were assayed for their ability to block HIV infection into host cells. AM3-114 conjugated with 20K PEG, AM3-114 conjugated with 30K PEG and AM4-746 conjugated with 30K PEG were assayed for the ability to block HIV invasion of three different virus strains. These were compared with the non-PEGylated versions of the i-body. Both AM3-114 and AM4-746 were able to block HIV invasion in a similar fashion to the non-PEGylated versions, with only a slight reduction in the potency of the PEGylated i-bodies compared to the non-PEgylated i-bodies (FIG. 23-1)

Figures 1, 23:
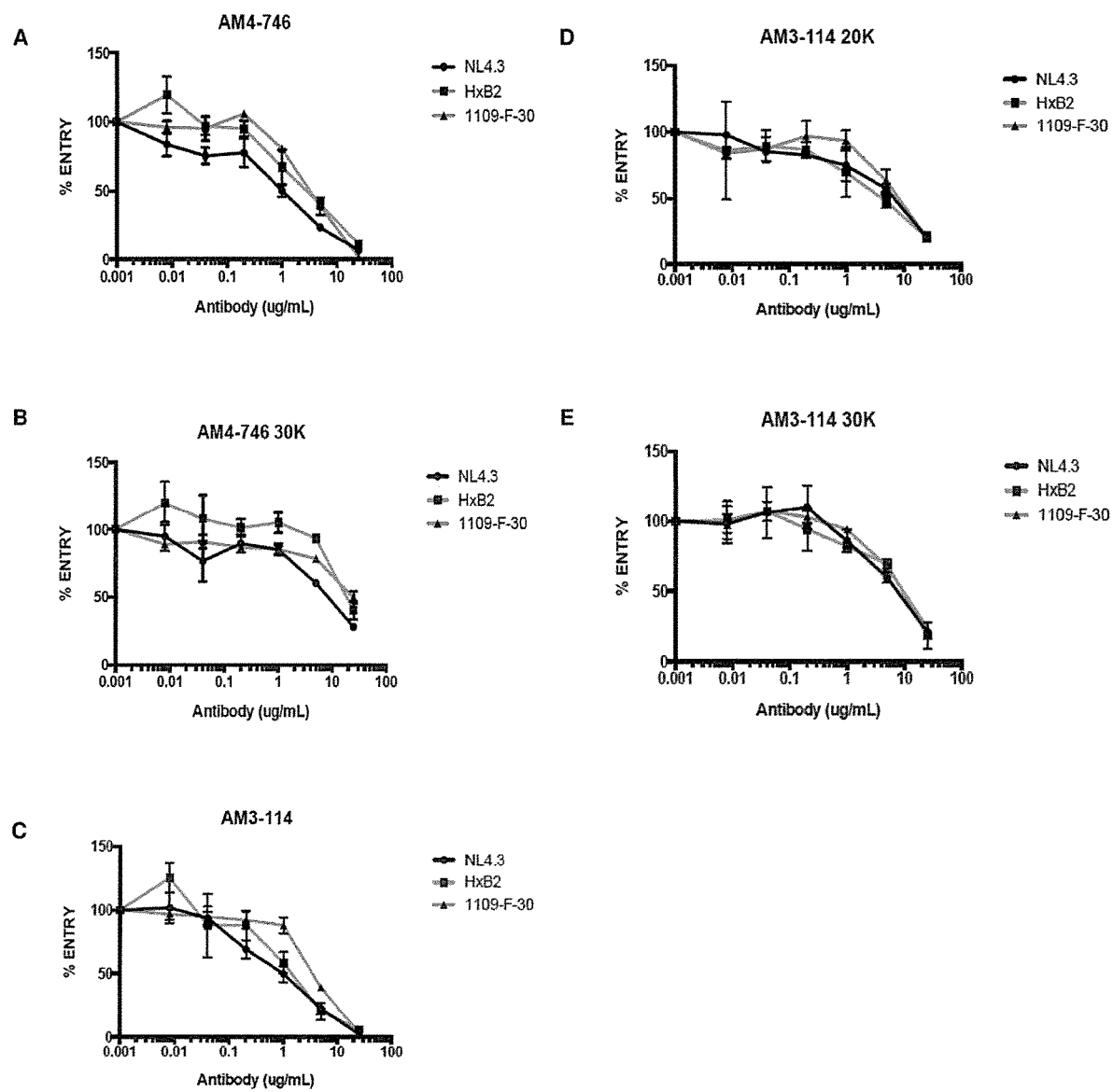
Figures 2, 23:
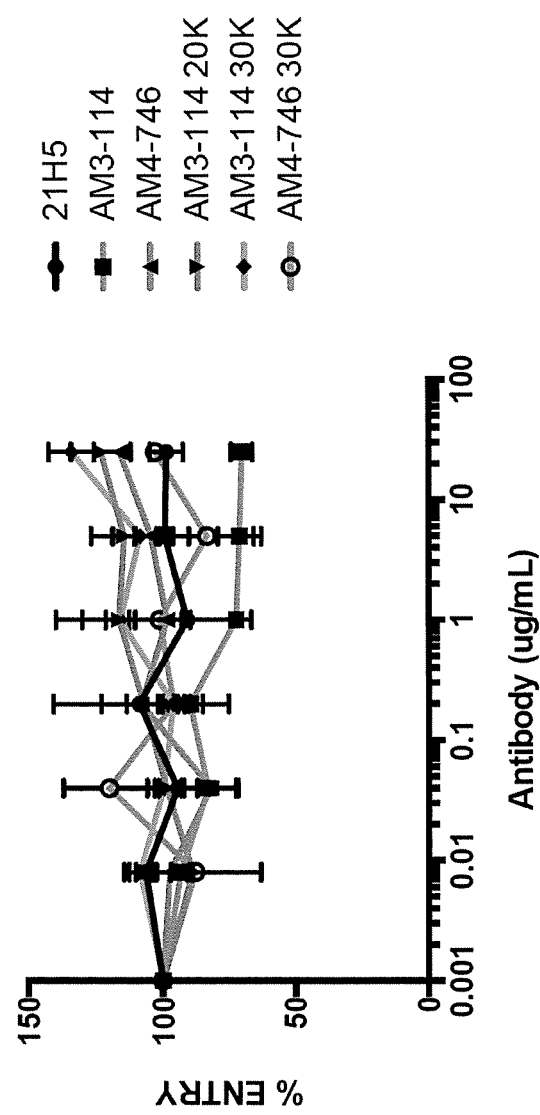

The PEGylated i-bodies and non-PEGylated ibodies are not able to block HIV entry into host cells by a strain of HIV (YU-2) that relies on CCR5 for entry (FIG. 23-2). This demonstrates that the anti-CXCR4 activity of the i-bodies are critical for blocking HIV entry.

Method

NP2-CD4/CXCR4 cells (1×10⁴ in 100 µl) were seeded in flat-bottom 96-well plates 24 h prior to infection. The anti-CXCR4 antibodies were resuspended in phosphate buffered saline (PBS). Prior to infection the media was removed from cells and replaced with 100 µl of fresh media with five-fold dilutions of i-body (at a ×2 concentration) for 30 min at 37° C. The concentration range for the CXCR4 antibodies was 25 µg/ml to 0.008 ug/ml. The concentration of PBS (5.8%, vol/vol) was maintained in the untreated wells. NP2-CD4/CXCR4 cells were infected with 200 TCID50 of Env-pseudotyped luciferase reporter viruses in 100 µl for 12 h at 37° C. Following this, the inoculum was removed and replaced with fresh media. The i-body concentrations were maintained throughout the subsequent culture period. NP2-CD4/CXCR4 were incubated at 37° C. for a total of 72 h. The level of HIV-1 entry was measured by luciferase activity in cell lysates (Promega) according to the manufacturers protocol. Luminescence was measured using a FLUOStar microplate reader (BMG). Background activity was assessed by mock-infected cells and was subtracted from all wells. To calculate the percentage of HIV-1 entry in the presence of i-body, the amount of luciferase in cells treated with an i-body was expressed as a percentage of that in untreated cells.

Example 14—Lack of Stem Cell Mobilisation by i-Bodies

Plerixafor or AMD3100 is a small molecule bicyclam CXCR4 inhibitor, which has been approved for use in combination with G-CSF for HSC mobilisation. CXCR4 inhibitors of the prior art are known to cause stem cell mobilisation. As demonstrated in the experiments shown in this Example, i-bodies of the present disclosure lack the ability to cause mobilisation of stem cells.

14.1 Assessment of Specificity of CXCR4 Antibodies to Various Haemopoietic Cells.

To confirm direct binding of CXCR4 antibodies (FLAG-tagged) to various haemopoietic cell populations, bone marrow cells harvested from C57/BL6 mice were stained with a cocktail of five CXCR4 i-bodies (AM4-272, AM4-746, AM4-1121, AM3-114 or AM3-523) and then secondarily labelled with a fluorescent anti-FLAG antibody. These cells were stained for lineage, progenitor and HSC markers and CXCR4 expression assessed on various haemopoietic cell populations. The results of this experiment validate CXCR4 i-body activity on primary mouse haemopoietic cells. The same experiment was performed on bone marrow cells harvested from humanised NSG mice to validate CXCR4 i-body activity on primary human haemopoietic cell populations (data not shown).

The i-bodies were all able to bind to bone marrow cells and human cord blood, which were $CD34^+$ and $CD38^-$.

14.2 Mobilisation of Mouse LSK and LSKSLAM Cells

Figure 24:
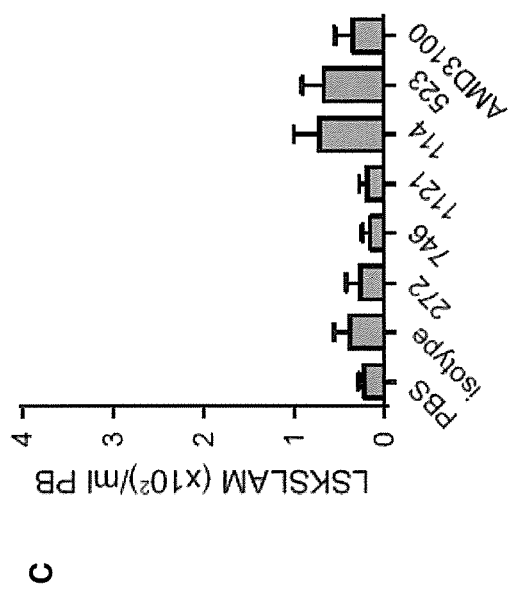
FIG. 24 shows white blood cell count (A) of peripheral blood (PB) of mice injected with i-bodies AM4-272, AM4-746, AM4-1121, AM3-114, AM3-523, or negative controls saline, isotype control i-body (21H5) or positive control AMD3100; lack of mobilisation of LSK cells by the i-bodies is shown in (B) and lack of mobilisation of LSKSLAM cells by the i-bodies is shown in (C).
Figure 24:
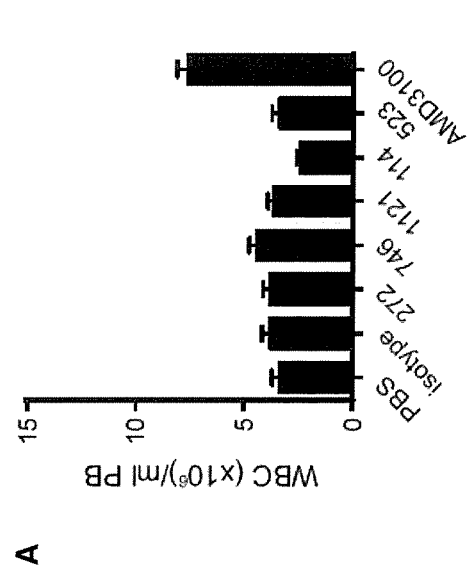
Figure 24:
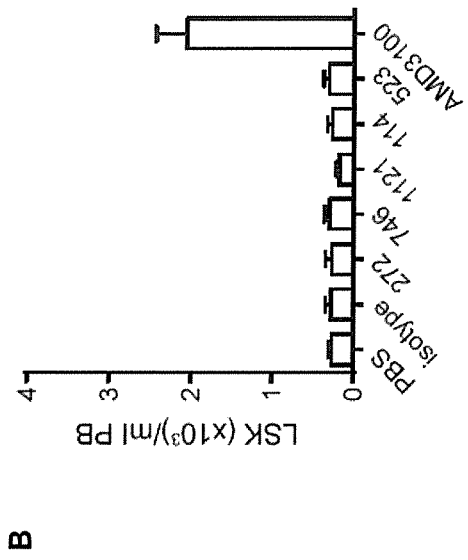

To acquire evidence of haemopoietic stem cell mobilisation using CXCR4 i-bodies, mice were injected with a CXCR4 i-body (AM4-272, AM4-746, AM4-1121, AM3-114 or AM3-523) by i.v. injection (5 mice/group). After 1 and 3 hours, mice were euthanized and peripheral blood (PB) harvested. Spleens were harvested and weighed to assess for splenomegaly (enlargement of the spleen). PB was counted to assess white blood cell content as shown in FIG. 24A. Samples were lysed to remove red blood cells and 4000 cells plated for LPP (low-proliferative potential) and CFU-HPP (colony forming unit-high proliferative potential) colonies (colony counting 7 days post-plating). The remaining cells were stained with an antibody cocktail to assess lineage-committed, stem and progenitor cell content. Flow cytometric analysis was used to calculate numbers of lineage-committed cells, haemopoietic stem and progenitor cells as well as enriched HSC per volume of PB. No mobilisation of white blood cells was detected with any of the i-bodies (AM4-272, AM4-746, AM4-1121, AM3-114 or AM3-523 FIG. 24A) compared to the positive control AMD3100. Lack of mobilisation of murine $Lin^-$, $Sca-1^+$, $c-Kit^+$ (LSK cells) is shown in FIG. 24B against a positive control AMD3100. No mobilisation of LSK cells was achieved by the i-bodies when compared to positive control AMD3100.

FIG. 24C shows lack of mobilisation of $Lin^-$, $Sca-1^+$, $c-Kit^+$, $CD150^+$, $CD48^-$, ($CD34^-$) LSKSLAM cells by i-bodies. Again, no mobilisation was observed for all i-bodies.

14.3 Mobilisation of Human CD34+ Cells

To acquire evidence of mobilisation of human $CD34^+$ stem and progenitor cells using CXCR4 i-bodies, the above mobilisation experiment was conducted in humanized NODSIL2Rγ (NSG) mice. NSG mice are severely immunodeficient and lack mature T cells, B-cells and NK cells and have severely defective innate immunity, which allows engraftment of human cells without subsequent rejection. NSG mice were transplanted with freshly sorted $CD34^+$ cord blood cells and upon confirmation of positive human CD45/CD34 engraftment (~4-5 weeks) were used as a mouse model for human stem cell mobilisation.

Humanised NSG mice were treated with 21H5 i-body, CXCR4 i-bodies (AM3-114 and AM3-523) and positive control AMD3100, which has previously demonstrated to give significant mobilisation of CD34+ cells in this model.

Mobilised peripheral blood was harvested and assessed for $CD34^+$ (human stem and progenitors).

Figure 25:
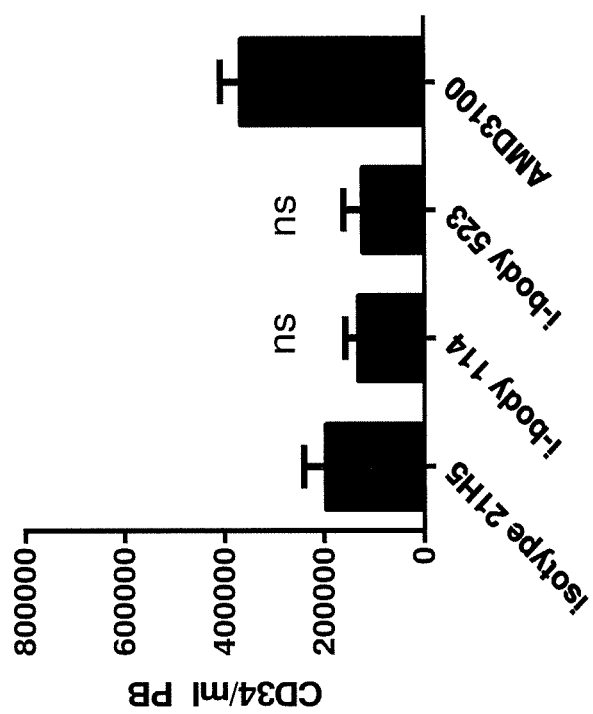
FIG. 25 shows i-bodies AM3-114 and AM4-523 and negative control i-body 21H5 do not mobilise stem cells compared to the positive control AMD3100 in a humanised NODSIL2Rγ (NSG) mouse model. ns=not statistically significant.

Preliminary experiments with i-bodies AM3-114 and AM4-523 as shown in FIG. 25 demonstrate that these i-bodies do not mobilise stem cells compared to the positive control AMD3100 in a humanised NODSIL2Rγ (NSG) mouse model. This finding is significant and represents a departure from CXCR4 inhibitors of the prior art which are known to cause stem cell mobilisation.

14.4 Confirmation of Binding of i-Bodies to Stem Cells

To determine whether CXCR4 i-bodies bind HSC, in vitro binding analysis to human $CD34+CD38^-$ cells was assessed. Umbilical cord blood (CB) and human bone marrow (BM) were collected as previously described (Nilsson S K et al, 2005 15; 106(4):1232-9; Grassinger, 2009 2; 114(1):49-59). Enriched human BM $CD34^+$ cells and purified CB CD34+ cells were isolated as previously described (Grassinger, 2009). Human CB and BM CD34+ cells and huNSG BM were stained sequentially with CXCR4 i-bodies (10 µg/ml), anti-His-PE and an antibody cocktail containing CD34-FITC (BD Biocences #348053) and CD38-BV421 (BD Horizon #562444), washed with PBS (0.5% BSA) and analysed by flow cytometry on a Cytopeia Influx (BD) as previously described (Grassinger, 2009). For analysis of human and murine BM and PB, up to $5 \times 10^6$ cells were analyzed at 10-20,000 cells/sec. Data were analyzed using FlowJo 10 software (FlowJo, LLC). For analysis of huNSG BM, huCD45-PECy7 (BD Biosciences #557748) and muCD45-BUV395 (BD Biosciences #564279) were also included in the antibody cocktail. HSC from human CB and BM were defined as CD34+CD38− and HSC from huNSG mice were defined as $muCD45^-huCD45^+CD34^+CD38^-$. CB and BM samples from 3 individual donors and BM from 3 individual huNSG mice were assessed.

Figure 26:
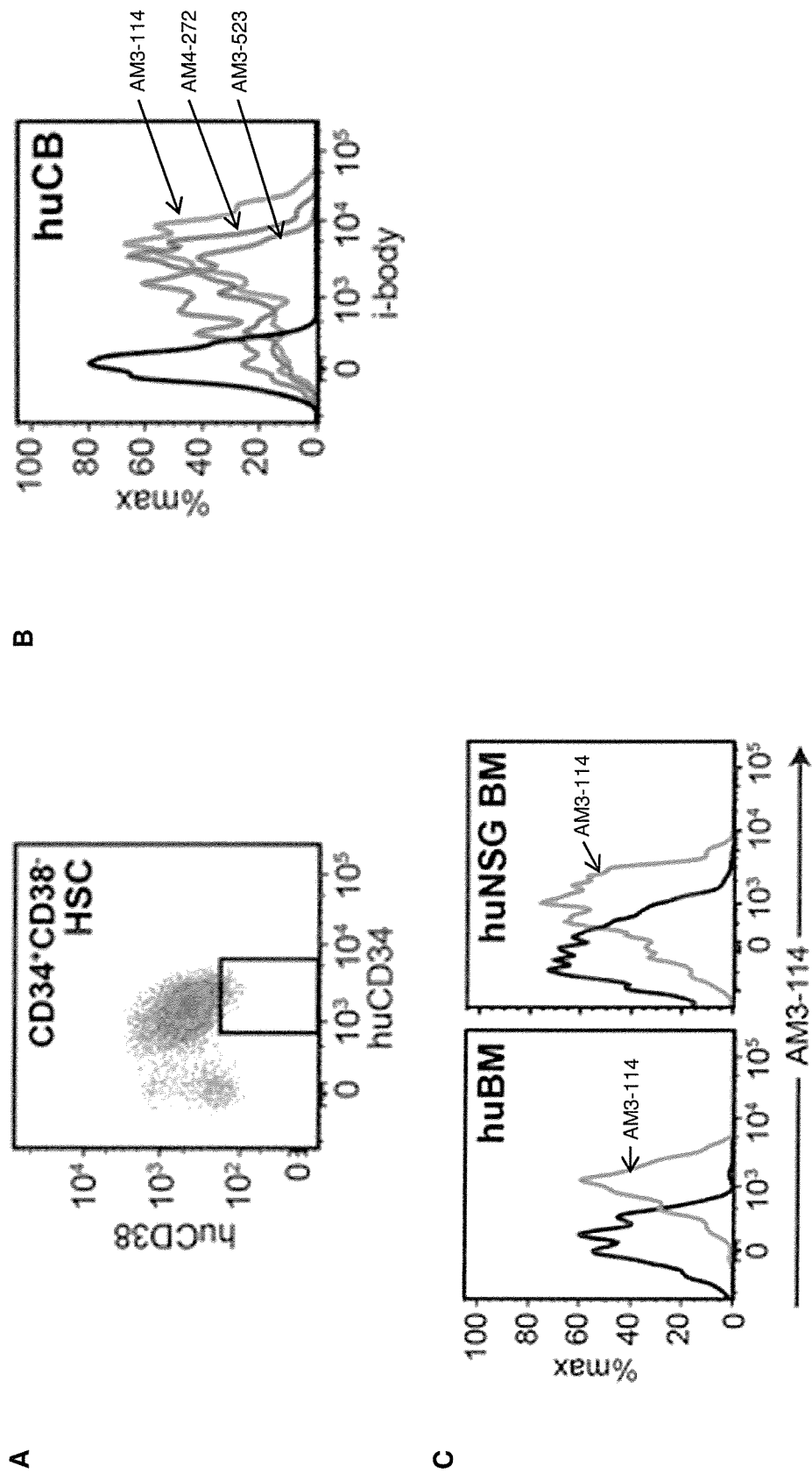
FIG. 26 shows CXCR4 i-bodies do not mobilize human stem and progenitors. In vitro binding experiments on sorted CD34$^+$CD38$^-$HSC (A) Representative dot plot of human CD34$^+$CD38$^-$ HSC. (B) Representative flow cytometric histogram of i-body binding to human cord blood (CB) CD34$^+$CD38$^-$HSC with AM3-114, AM4-272 and AM3-523 as indicated by arrows (C) Representative histogram of AM3-114 binding to human BM CD34$^+$CD38$^-$HSC and muCD45$^-$huCD45$^+$CD34$^+$CD38$^-$HSC from huNSG BM relative to control i-body (21H5).

I-bodies AM3-114, AM4-272 and AM3-523 effectively bound human Cord Blood HSC in decreasing avidity (FIG. 26). AM3-114 also effectively bound to human Bone Marrow HSC and Bone Marrow harvested from humanized NODSCIDIL2Rγ$^{-/-}$ (huNSG) mice (FIG. 26).

Example 15—Prevention of Fibrosis by i-Bodies 15.1 Corneal Alkali Burn Model

Fibrosis induction (corneal neovascularisation (NV)) by the i-bodies can be examined using the corneal alkali burn model as described in Cai X et al (2014) PLoS ONE 9(2):e88176. The method involves anesthetising rats (e.g. Sprague Dawley) with an intraperitoneal injection of 60 mg/kg of Nembutal and the topical administration of a drop of tetracaine. A corneal alkali-wound is made by placing a 1.5 mm diameter circular piece of filter paper, soaked in 1 N naOH, in contact with the central cornea on the right eye for 40 sec. Immediately after alkali exposure, the ocular surface is rinsed with PBS for 60 sec. The rats are randomly divided into 2 groups (n=15): Group 1 comprising rats subjected to alkali burn with normal saline treatment (10 µl, 4 times per day), and Group 2 comprising rats subjected to alkali burn with TMP treatment (1.5 mg/ml in a volume of 10 ml, 4 times per day). All eyes are then observed on day 28 using slit lamp microscopy for the evaluation of corneal NV.

15.2 Evaluation of NV in the Cornea

Corneal NV (NV) can be quantified as described in Zhang Z et al (2005) Invest Ophthalmol Vis Sci 46:4062-4071 doi:10.1167/iovs.04-1330. Briefly, an ophthalmologist blinded to the study conditions examines all eyes under a slit lamp microscope on days 1, 2, 5 and 8 after alkali burn. The corneal image is divided into 4 quarters. The vessel length of each quarter (Li, i=1-4) is measured using a Vernier caliper. The corneal NV area (A) is calculated using the following equation: $A = \Sigma i = 1\text{-}4\ 3.1416 \times \{R2 - (R - Li)2\}$ (R is the radius of the rat cornea. R=3.5 mm, as calculated from the measurement of 15 rat corneas.

15.3 Choroidal Neovascularisation

The laser induced choroidal neovascularisation (CNV) is a well characterised and accepted model of choroidal neovascularisation (Fletcher E L et al. (2011) Prog Mol Biol Transl Sci 100:211-286). It is also a rapid method for determining the efficacy of potential treatments that target angiogenesis and fibrosis. Briefly, up to four laser spots are applied to the posterior eye using a continuous wave photocoagulation laser (532 nM diode). The laser energy is high enough to create a break in Bruch's membrane. During the following 7-14 days, growth of blood vessels from the choroid into the retina occurs, and is quantified either immunocytochemically, or using fluorescein angiography.

Briefly, a total of twenty (20) Dark agouti rats or C57BL/6 mice housed in a Biomedical Animal Facility in a cyclic light environment (12 hours on, 12 hours off, at an in-cage luminance of <350 lux) for 10 days or more before use are anaesthetised and treated with a 532 nm continuous wave thermal laser applied as 4 spots around the optic nerve. Immediately following laser treatment, animals are treated with the highest dose of i-body (concentration at the retina being 20 mg/ml).

The structure of the retina of all rats is examined with a dedicated rodent fundus camera/OCT (Micron III, Phoenix Instruments), and the integrity of the vascular quantified using fluorescein angiography. The size (diameter and area) of all fluorescent lesions is then quantified to provide a measure of the extent of angiogenesis.

Following imaging, the animals are killed by anaesthetic overdose and the posterior eye cups fixed in 4% paraformaldehyde for 30 mins. Retinal whole mounts are then processed for IB4 labelling to assess the extent of the growth of choroidal vessels into the subretinal space. The diameter and area of the lesion provides an assessment of the extent of neovascularisation.

In addition, the level of scarring that develops as a consequence of invasion of choroidal blood vessels is quantified by immunolabeling for the gliotic marker GFAP.

In addition retinal contraction, lesion size, alteration in microglia and glial response and pro-fibrotic gene expression in the treated retinas following laser treatment is also examined to evaluate fibrosis.

The anti-CXCR4 i-body AM3-114-6H (plus a control i-body) reduces pathological angiogenesis or lesion characteristics in a mouse model of choroidal neovascularization. The levels of CXCR4 have been examined in the eye following laser treatment (PCR fibrosis array; SABiosciences) and were shown to be dysregulated. The upregulation of CXCR4 in this setting suggests that treatment with CXCR4 antagonist i-bodies could have a beneficial effect. Mice were treated as below:

Group 1 (n=10): laser both eyes-vehicle in one eye; i-body in the other
Group 2 (n=10): Laser one eye (no i-body); other eye unlasered.

The i-body drug was injected intravitreally in 1 µl volume at a concentration up to 20 mg/ml.

Data of the effects of the i-bodies on the retinal contraction, lesion size and gene expression in the treated retinas following laser treatment was obtained. There was a dramatic contraction of the retina following laser treatment compared with unlasered regions in the same eye. Treatment with both AM3-114 and AM4-272 resulted in significant reduction in the contraction of the lasered regions. One confounding factor was that the vehicle controls also seem to have a very significant reduction in the ratio of contraction. Since the vehicle consists of only a single injection of TBS it is unlikely that this would have such an effect. The more likely explanation is that i-body has actually escaped from the treated eye and entered the circulation perhaps blocking inflammatory cells from infiltrating the vehicle treated eye. There was also a reduction of the lesion size upon administration of the i-body AM3-114.

Figure 27:
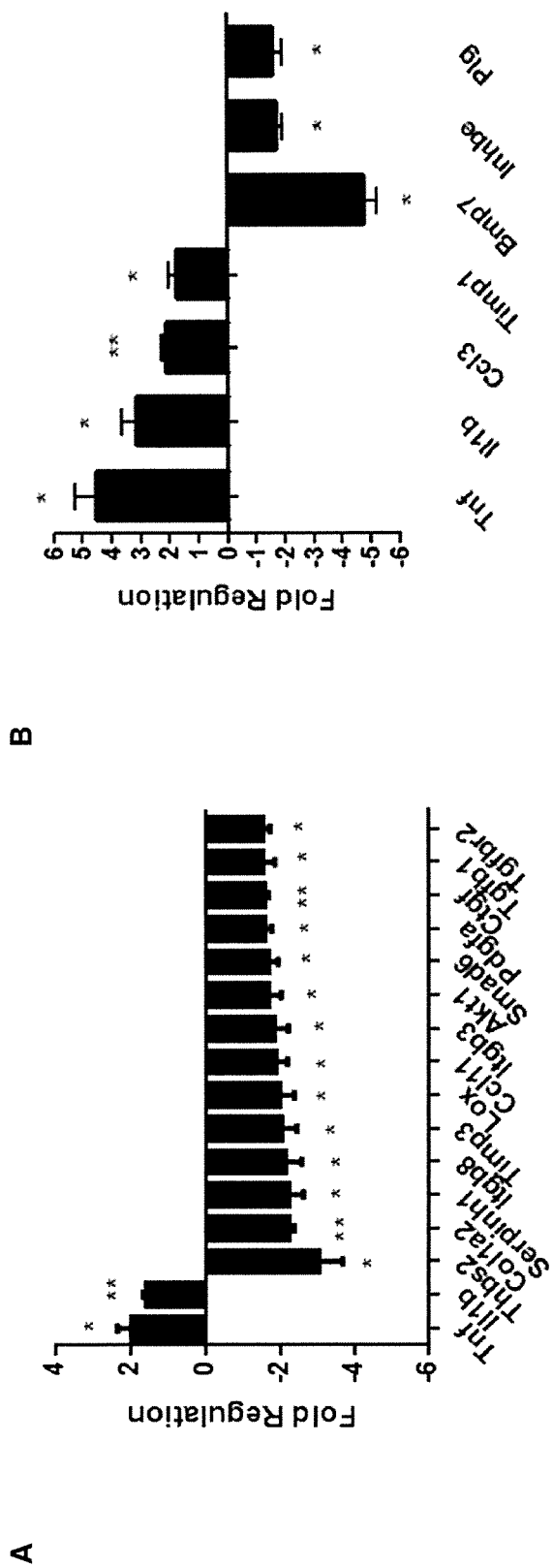
FIG. 27 shows effect of i-bodies AM3-114 (A) and AM4-272 (B) on pro-fibrotic gene expression in laser treated mice. A panel of 85 profibrotic genes were tested for mRNA levels in i-body treated mice.

The expression of genes associated with angiogenesis and fibrosis was examined. Total RNA was isolated from the retina and RPE/choroidal samples using commercial spin columns (RNeasy, Qiagen, Valencia Calif.). A PCR gene array was used to assess the expression of 84 genes involved angiogenesis or fibrosis (Qiagen). Briefly, total RNA samples from untreated, laser treated eyes and untreated fellow eyes (n=9 each group, each 25ng) were pooled within their respective treatment groups (3 independent experiments containing 3 pooled samples), reversed transcribed (RT2 first strand, Qiagen) and then underwent pre-amplification of the cDNA target templates (RT2 pre-AMP, Qiagen). Samples were added to a commercial mastermix (RT2 SYBR green mastermix, Qiagen) and amplified for 40 cycles (ABI 7900HT, Life Technologies, Grand Island N.Y.). Three independent arrays were performed for each treatment group. The data were analysed using delta delta Ct ($\Delta\Delta$Ct), expressed as fold change and regulation assessed using an unpaired t-test. This gene expression data from both AM3-114 and AM4-272 treated eyes which indicates that there is extensive down regulation of pro fibrotic genes such as Col1A2, TGF-b1, connective tissue growth factor (CTGF) and Tissue inhibitor of metalloproteinase (TIMP3), Thrombospondin 2 (Thbs2), serine peptidase inhibitor (SerpinH1), Integrin β8 subunit (ITGB8), Lysyl oxidase (LOX), Eotaxin (CCL11), β3 integrin (ITGB3), serine-threonine protein kinase (Akt1), SMAD family member 6 (SMAD6), Platelet-Derived Growth Factor Alpha Polypeptide (PDFGA), Transforming Growth Factor, Beta Receptor II (Tgfbr2), Bone Morphogenetic Protein 7 (Bmp7), (FIG. 27).

Example 16—Binding of i-Bodies to Fibrocytes

Circulating bone-derived mesenchymal cells that have the potential to develop into fibrocytes and can play a critical role in the pathogenesis of fibrosis (Strieter R M, Keeley E C, Burdick M D and Mehrad B. The Role of Circulating Mesenchymal Progenitor Cells, Fibrocytes, in Promoting Pulmonary Fibrosis. Trans Am Clin Climatol Assoc 2009; 120; 49-59) and that cells expressing CD45 and CXCR4 are circulating fibrocytes that can migrate in response to SDF-1 and traffic to the lungs in a murine model of bleomycin-induced pulmonary fibrosis (Phillips R J, Burdick M D, Hong K, Lutz M A, Murray L A et al. Circulating fibrocytes traffic to the lungs in response to CXCL12 and mediate fibrosis. J Clin Invest (2004) 114: 438-44).

Double labeling of i-body (AM3-114) and CD-45 was performed as follows. I-body AM3-114 was incubated with isolated human PBMCs at room temperature for 4 hours. PBMCs were smeared on a microscope slide and fixed with acetone at 4° C. for 10 minutes. Following three times washing and rehydration with PBS the slides were incubated with mouse antiFLAG 1:100 dilution over night at 4° C. After washing the slides were incubated with Goat anti-mouse Alex Fluor 568 (to detect i-body by binding anti FLAG) at room temperature for 1 hour. The slides were then washed and incubated with Mouse anti-CD-45 FITC labeled antibody over night at 4° C. After further washing the slides were and mounted with ProLong Gold antifade mountant containing DAPI. Images were captured by using Nikon A1 confocal microscope.

Figure 28:
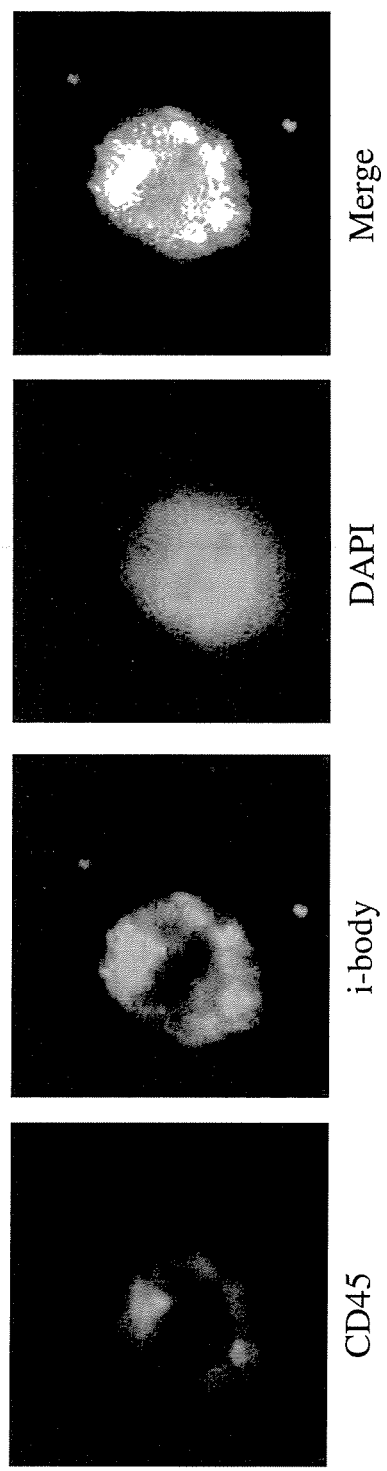
FIG. 28 shows binding of AM3-114 i-body to human fibrocytes. Human fibrocytes were identified by staining with an antibody to CD45. Binding of i-body AM3-114 was identified by an anti-FLAG antibody to the C-terminal tag. DAPI was used to stain the nucleus of the cells. The final panel is a merged image of all three stains.

Human fibrocytes were identified by staining with an antibody to CD45. Binding of i-body AM3-114 was identified by an anti-FLAG antibody to the C-terminal tag. DAPI was used to stain the nucleus of the cells. The results are presented in FIG. 28. The results show that i-body AM3-114 was capable of binding to human fibrocytes.

Example 17—In Vivo Murine Air-Pouch Model

The ability of i-bodies to block inflammation was evaluated in an in vivo murine air pouch model. The subcutaneous (s.c.) air pouch is an in vivo model used to study acute and chronic inflammation (Durate et al, Models of Inflammation: Carrageenan Air Pouch, Current Protocols in Pharmacology 5.6.1-5.6.8, March 2012). Injection of irritants into an air pouch in rats or mice induces an inflammatory response that can be quantified by the volume of exudate produced, the infiltration of cells, and the release of inflammatory mediators. An air pouch, is generated by injection of sterile air under the skin of the back of the mouse. The mouse is pretreated with either the anti-inflammatory compound or test article (i-bodies or AMD3100), and secondarily treated with SDF-1, the inducer of inflammation. Air pouch lavage fluid is then analyzed for cell trafficking and cytokine release.

The air pouch assay was performed on 7-week-old BALB/c mice. On days 1 and 3, 0.2 ml/g initial body weight (IBW) of sterile air was injected under the back skin to create the pouch. On day 6, mice were divided in groups and received an intraperitoneal injection of 0.5 ml of PBS containing or not containing the i-body (AM3-114, AM4-272, AM3-523, AM4-746 or AM4-1121) or AMD3100 (10 mg/kg). Thirty minutes later, SDF-1 (6 µg) was injected into the pouch. Four hours later, the mice were killed in a $CO_2$ chamber and the air pouch was washed. Cells were collected, counted, and characterized by flow cytometry.

Figure 29:
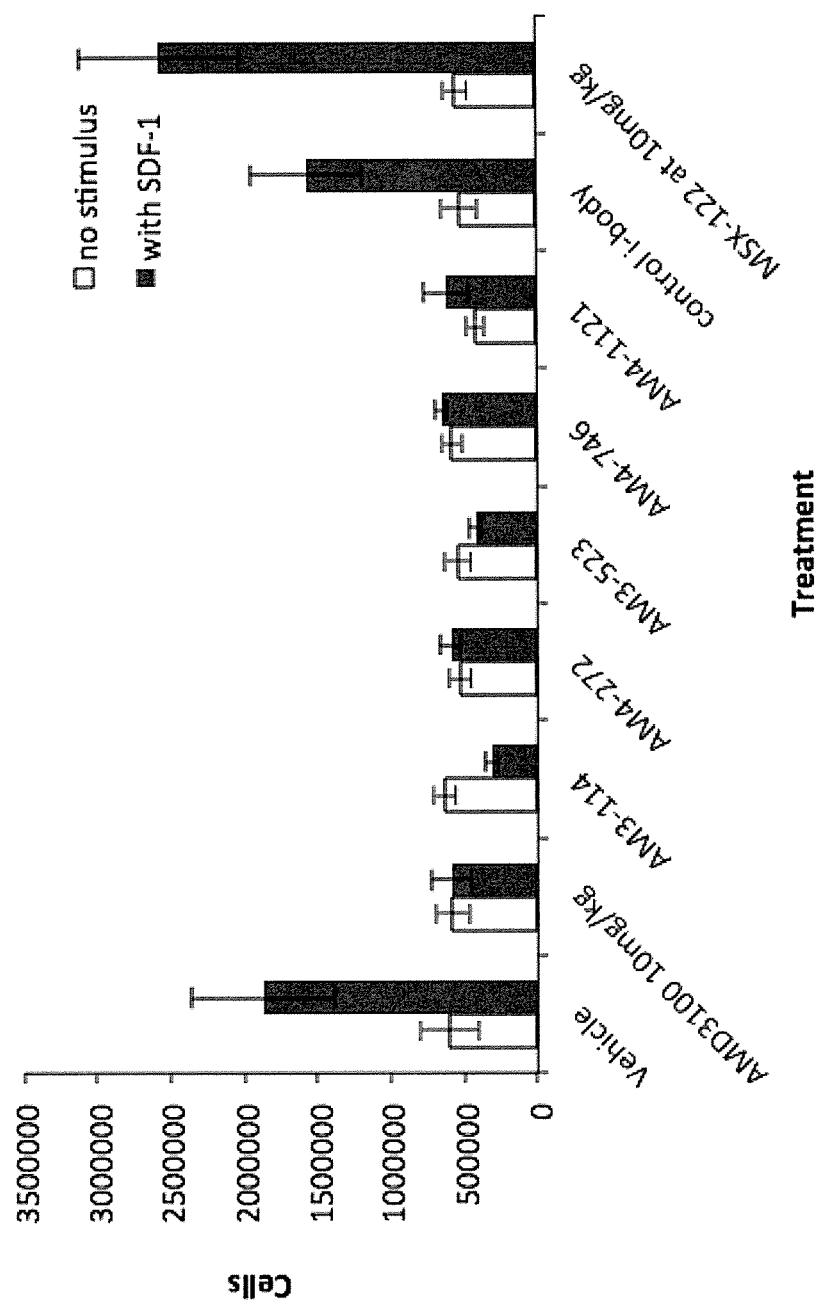
FIG. 29 shows i-bodies AM3-114, AM4-272, AM3-523, AM4-746 and AM4-1121 inhibiting leukocyte infiltration into a murine air pouch loaded with SDF-1 compared with a negative control i-body (which does not bind to CXCR4), positive controls AMD3100 and MSX-122 and a vehicle only control.

Total cells in the air pouch demonstrate that the test articles inhibit the migration of cells into the airpouch/site of inflammation. The i-bodies AM3-114, AM4-272, AM3-523, AM4-746 and AM4-1121 inhibited cell migration to the airpouch (similar to AMD3100) however the negative control i-body (21H5) did not inhibit cell migration. I-bodies injected into the mouse without the inflammatory stimulant had no effect on migration of cells to the air pouch (FIG. 29).

Example 18—Prevention of Idiopathic Pulmonary Fibrosis (IPF) in a Bleomycin Mouse Model The ability of the CXCR4 binding molecules (i-bodies) to inhibit pulmonary fibrosis was examined in a mouse model of disease. Bleomycin, an antibiotic and anti-tumour agent, is widely used in experimental models of human disease resembling IPF. Bleomycin is able to cause cell damage independent from its effect on DNA by inducing lipid peroxidation. The precise nature of the interaction between bleomycin and the lung that leads to collagen deposition is uncertain. However, over-activation of cytokines and growth factors such as IL-1, IL-6, TNF-alpha, PDGF and TGF-beta has been consistently implicated in the disease progression. Recent evidence suggests that antagonising CXCR4 is effective in preventing the pulmonary fibrosis in the bleomycin mouse model.

The mouse IPF model is a validated model of inflammation and fibrosis, with initial (within 48 hours) lung injury characterised histologically, by perivascular oedema, capillary congestion and alveolar wall thickening associated with intra-alveolar haemorrhage and inflammatory cell infiltrate in the alveolar walls as well as in the spaces. Focal peribronchial and subpleural collagen deposition usually follows within a week after bleomycin administration in this model.

The optimal dose of Bleomycin is 2 U/mouse and the optimal time for assessing fibrocyte recruitment was confirmed at day 4. At days 4 bronchoalvelolar lavage (BAL) fluids were collected for analysis of SDF-1 concentration. One half of the lung tissue was used to make single cell suspensions of the lung and the cells used for flow cytometry and assayed for CD45+, CXCR4+ and Collagen1+(fibrocytes). The other half of the lung tissue was Sircol stained for the presence of collagen 1 and RNA will be tested for Col-1, Col-3 and SDF-1.

Using 2 U Bleomycin/mouse (10 per group) mice were dosed with i-bodies, negative control i-body 21H5 at 30 mg/kg and anti-CXCR4 i-bodies, AM3-114, AM4-272, AM3-523 at 1, 10 and 30 mg/kg. SDF-1, fibrocytes and collagen deposition were monitored at Day 4. Groups were dosed with the i-body just prior to administration with Bleomycin. One half of the lung tissue was minced and washed in PBS and used to make single cell suspensions of the lung with Collagenase A and disperse treatment. The cells were then used for flow cytometry and assayed for CD45+, CXCR4+ and Collagen1+fibrocytes.

Figure 30:
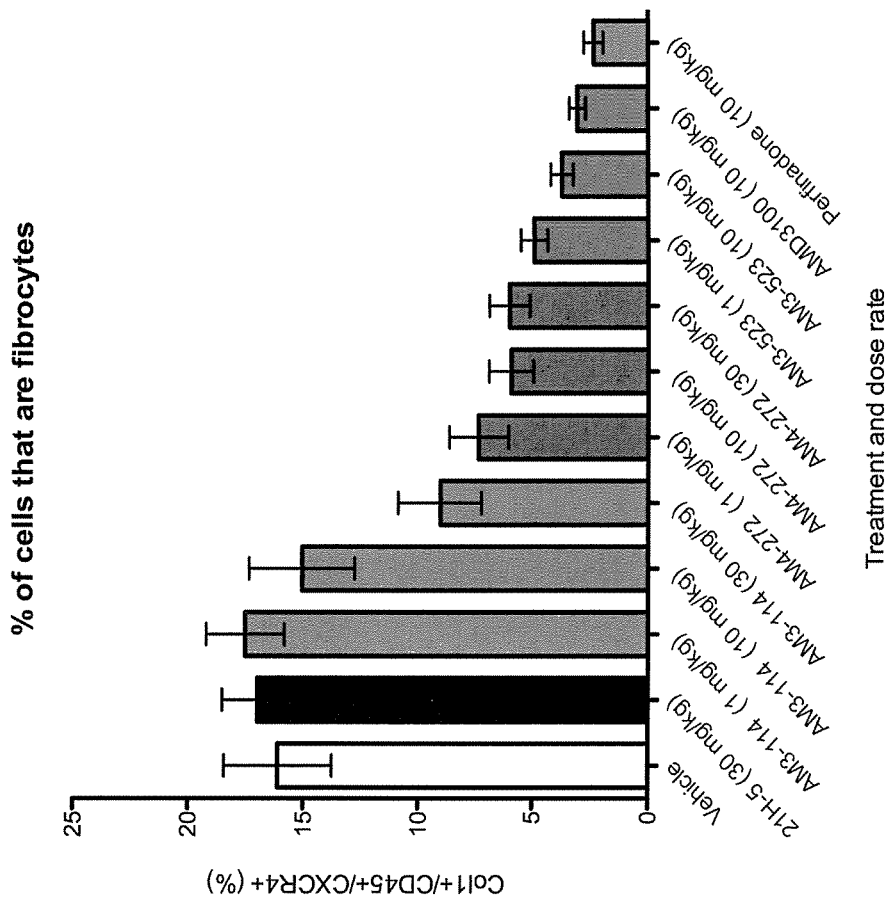
FIG. 30 shows the effect of i-bodies (AM3-114, AM4-272, AM3-523) at different doses on intrapulmonary fibrocyte recruitment after bleomycin injury compared to positive controls AMD3100 and Pirfenidone and negative control i-body (21H5). Fibrocytes were measured by staining the lung tissue from Bleomycin treated mice for CD45+ CXCR4+Col 1+ cells. Percentage of cells that are fibrocytes is indicated on the Y axis.

Administration of i-body AM3-114 at 30 mg/kg was able to dramatically attenuate the recruitment of fibrocytes into the lungs of mice with Bleomycin induced fibrosis. It was also evident that i-bodies AM4-272 and AM3-523 were able to significantly attenuate the recruitment of fibrocytes into the lungs of these mice. I-bodies AM4-272 and AM3-523 were able to block recruitment of fibrocytes even at 1 mg/Kg. As expected, AMD3100 and Perfenidone were also able to block recruitment of fibrocytes. Neither the vehicle alone nor the negative control i-body affected recruitment of fibrocytes into the lungs of mice with Bleomycin induced fibrosis (FIG. 30).

The lung tissue was examined using the Sircol staining assay (Biocolour Ltd., Carrickfergus, Northern Ireland) according to the manufacturer's protocol, to determine the presence of the extracellular matrix protein collagen. i-body AM3-114 at 30 mg/kg, i-body AM4-272 at 10 mg/kg and i-body AM-3523 at 30 mg/kg all reduced the collagen content of the lung as compared to the vehicle alone or the negative control i-body (21H5). A reduction in collagen was also seen for AMD3100 and Pirfenidone.

A Bleomycin pulmonary fibrosis experiment in mice was performed over 21 days to assess the effect of PEGylated i-body. Administration of PEGylated i-body AM4-272 at 10 mg/Kg was able to attenuate the recruitment of fibrocytes into the lungs of mice with Bleomycin induced fibrosis at day 7. AM4-272-PEG decreased fibrocytes at day 7 to about the same extent as AMD3100 and Pirfenidone.

Subsequently the remaining lung tissue was used to analyse the RNA from each sample for CXCL12, Col1a1 and Col3a1 gene expression as per Phillips et al (2004) J Clin Invest 114, 438.

Example 19 Epitope Mapping

Shotgun mutagenesis (Integral Molecular) was used to evaluate anti-CXCR4 i-bodies AM3-114, AM4-272 and AM3-523 binding to wild-type and mutated human CXCR4. The i-bodies were tested against HEK-293 T cells expressing CXCR4. Optimal screening conditions were determined for the immunodetection and epitope mapping of i-bodies AM3-114 (1 µg/ml), AM4-272 (2 µg/ml) and AM3-523 (1 µg/ml) which gave a high signal-to-background value. The mean i-body reactivities (and ranges) are shown in Table 13 for all critical residues identified in the screen. Control antibodies were anti-flag and 12G5 which are commercially available.

TABLE 13

Critical residues for binding of i-bodies AM3-114, AM4-272 and AM3-523 to CXCR4

| Mutation in CXCR4 | Binding reactivity (% WT) | | | | |
|---|---|---|---|---|---|
| | i-body AM3-114 | i-body AM4-272 | i-body AM3-523 | anti-Flag | 12G5 |
| E32K | 58.8 | 38.1 | 6.6 | 71.1 | 58.3 |
| Y184S | 96.1 | 61.7 | 12.6 | 147.7 | 106.8 |
| F189L | 26.1 | 21.8 | 45.5 | 115.7 | 153.2 |
| W195R | 28.8 | 84.8 | 57.6 | 87.6 | 101.1 |
| D262G | 30.2 | 26.7 | 12.5 | 74.4 | 97.4 |
| L266H | 23 | 60.6 | 60.4 | 105.1 | 127.3 |
| C28W | 15.9 | 28 | 75 | 121.7 | 46.6 |
| V112A | 63.6 | 109 | 7.6 | 61.7 | 95 |
| P191T | 66 | 55 | 42.3 | 116 | 154 |
| D193G | 38 | 80 | 78.6 | 116 | 108.5 |
| E268 | 104.4 | 56.6 | 44.4 | 138 | 149 |
| E288 | 54.6 | 80.6 | 91.5 | 78.8 | 163 |

Critical residues of the CXCR4 protein for i-body binding (grey) were identified as those that were negative for i-body binding (<30% WT for AM3-114 and AM4-272; <15% for AM3-523) but positive for the anti-Flag mAb (>70% WT), and also positive for an additional control mAb 12G5 (>50% WT).

All three i-bodies had residue D262 in common which AMD3100 also binds (Haste et al., (2001) Molecular Pharmacology 60:164-173). All critical amino acids identified by the epitope mapping are conserved between human and mouse CXCR4 except for F189. No binding agents have been previously identified that bind to residues E32 or L266 of CXCR4.

An additional set of residues also had an effect on the binding of some i-bodies they are; C28, V112, D193, P191, E268 and E288

Example 20—i-Body Binding to CXCR4 in Human Patient Tissues with Idiopathic Pulmonary Fibrosis (IPF)

To further confirm the expression of CXCR4 in normal and IPF lungs, negative control i-body 21H5, CXCR4-specific iBodies (AM3-114, AM4-272 and AM3-523) were utilized in Immunohistochemical (IHC) analysis (data not shown). Few CXCR4 expressing cells were detected in normal and slow-IPF lung biopsies. CXCR4 expressing cells were readily detected in rapid-IPF lung biopsies. Finally, CXCR4 was detected with the i-bodies in interstitial cells present in fibrotic regions of rapid-IPF lung biopsies. The i-bodies of the present disclosure were able to bind to the fibroblasts from IPF patient lung biopsies (both rapid and slow processors) but did not bind to lung biopsies from normal lung tissue.

Example 21—Reduction of Human Lung Fibroblast Invasion from Idiopathic Pulmonary Patient Tissue Several reports have shown evidence for a role of CXCL12 and CXCR4 in lung invasion (Li et al Cancer Lett 2012 322; 169-176 & Krook et al Mol Cancer Res 2014 12; 953-964). Lovgren, A et al have shown that β-arrestin plays an important role in lung fibroblast invasion (Lovgren et al Sci Transl Med 2011 3; 74ra23). Further, several reports have shown that CXCR4 delivers CXCL12 to CXCR7, leading to the activation of the β-arrestin pathway, suggesting that CXCR4 may promote invasion of lung fibroblasts (Coggins et al. 2014 PLoS One 9, e98328, Decaillot et al. J Biol Chem 2011 286; 32188 32197, & Rajagopal et al PNAS 2010 107; 628-632).

To determine the role of CXCR4 and CXCL12 in fibroblast invasion, normal and IPF lung fibroblasts were utilized in a wound healing invasion assay. ImageLock 96 well plates (Essen Bioscience) were coated with 50 µg/ml of Basement membrane extract (BME; Trevigen) for one hour at room temperature. Normal, and fibroblasts generated from lung biopsies of idiopathic pulmonary fibrosis (IPF) patients showing slow progression or rapid progression of the disease were plated (36,000 cells per well) on the BME-coated plates and incubated overnight. The following day, cells were scratched using a Woundmaker™ (Essen Bioscience), washed with DPBS treated with negative control i-body 21h5, CXCR4-specific iBodies (AM3-114, AM4-272; 130 µg/ml) or AMD3100 (12 NM) in a 2 mg/ml BME solution. The BME was allowed to polymerize by incubating the plate at 37° C. for 15 minutes. The plates were then inserted into an IncuCyte Zoom imaging system and images were acquired every 2 hours for approximately 50 hours. Invasion was quantified using IncuCyte software (Essen Bioscience).

Figures 1, 31:
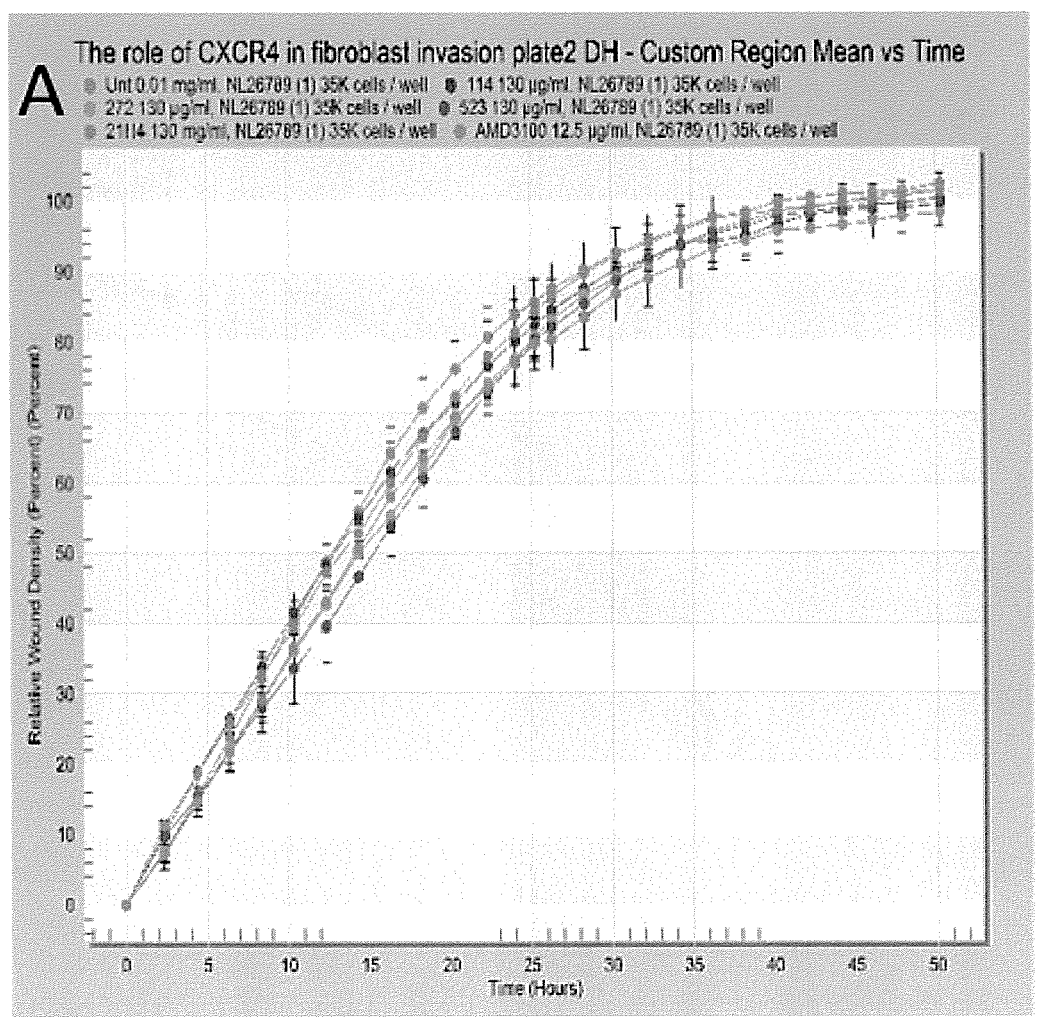
Figures 2, 31:
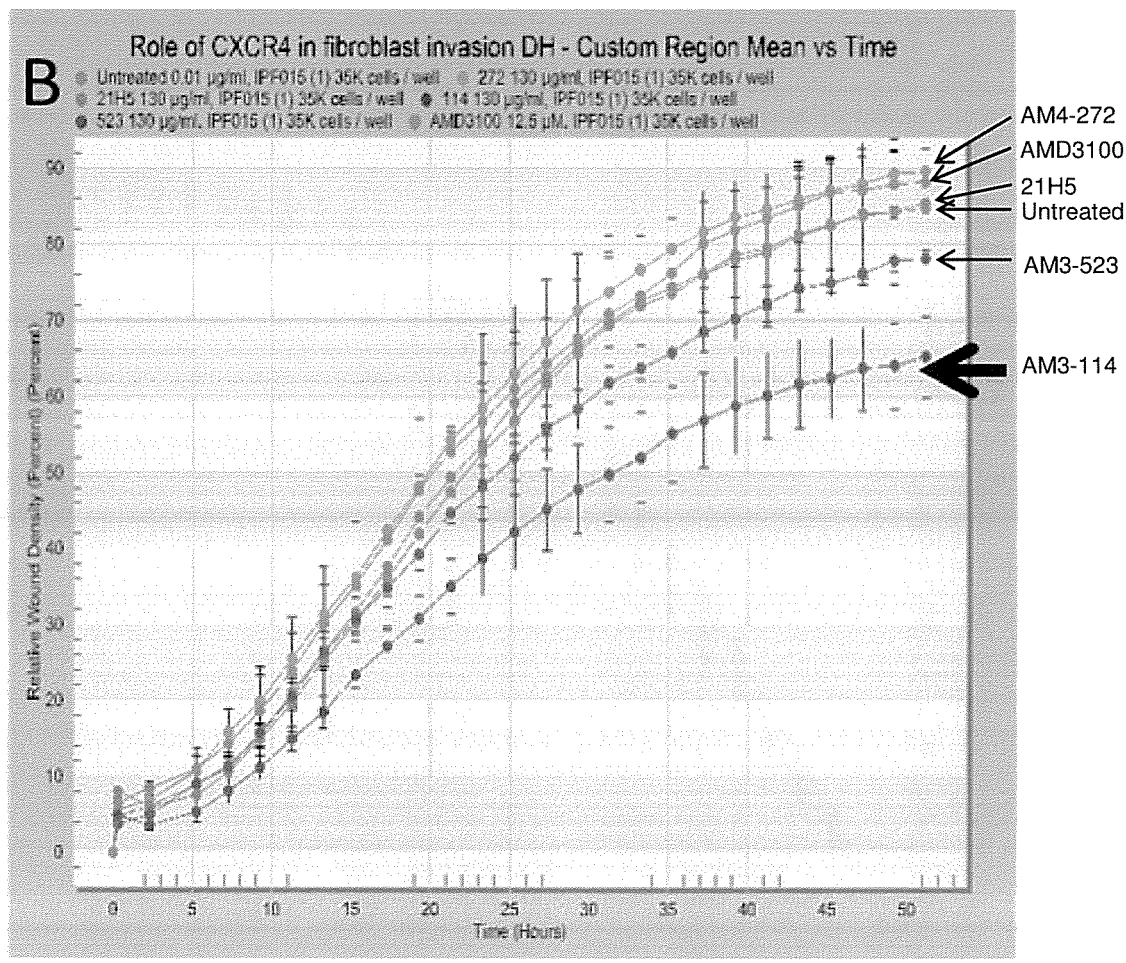
Figures 3, 31:
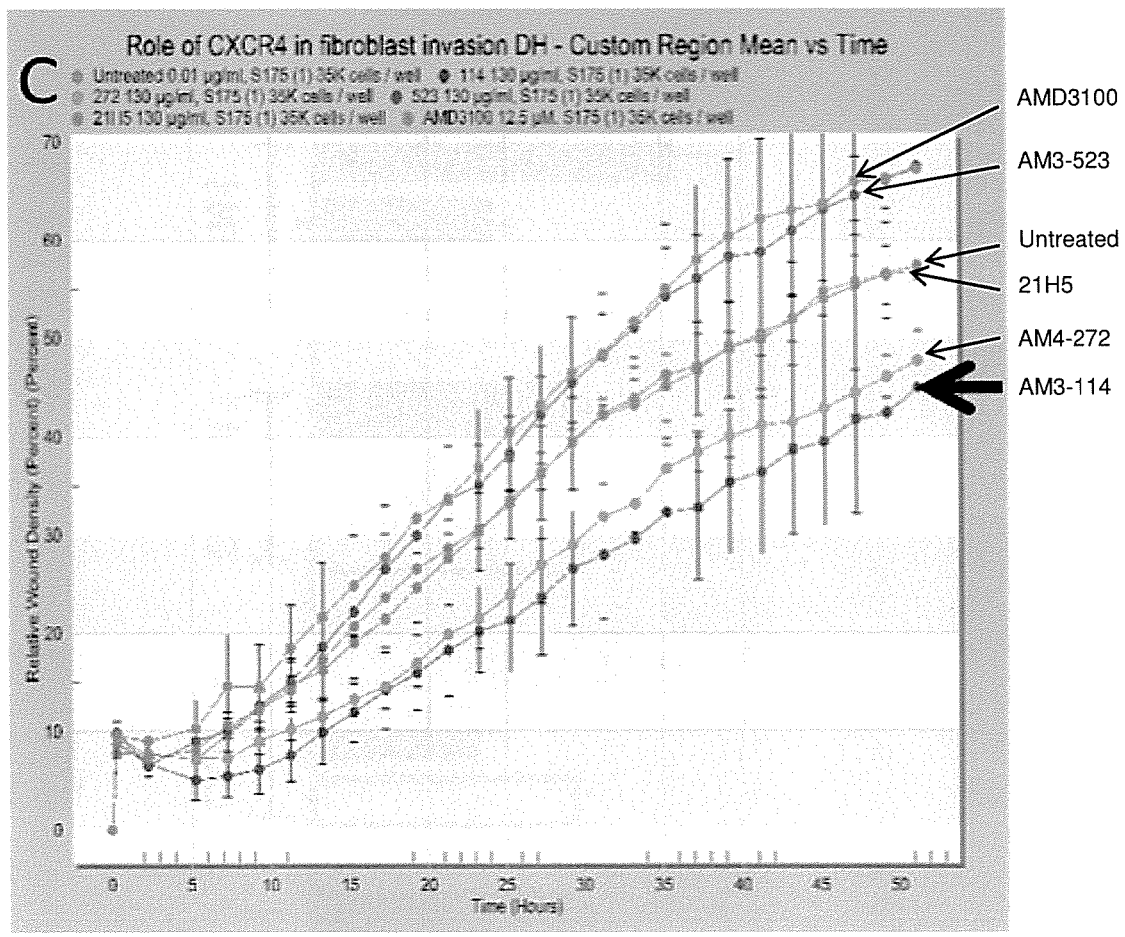

BIBF-1120, a multiple receptor tyrosine kinase inhibitor currently approved for the treatment of IPF, effectively inhibited both normal and IPF fibroblast motility. CXCR4 specific iBodies AM3-114-6H and AM4-272-6H inhibited invasion in slow-IPF and two out three rapid-IPF but not normal lung fibroblasts (FIGS. 31-1 to 31-3 shows representative examples of fibroblasts form normal, slow and fast IPF patients).

Example 22—i-Bodies Exhibit Anti-Fibrotic Properties In Vitro

Figure 32:
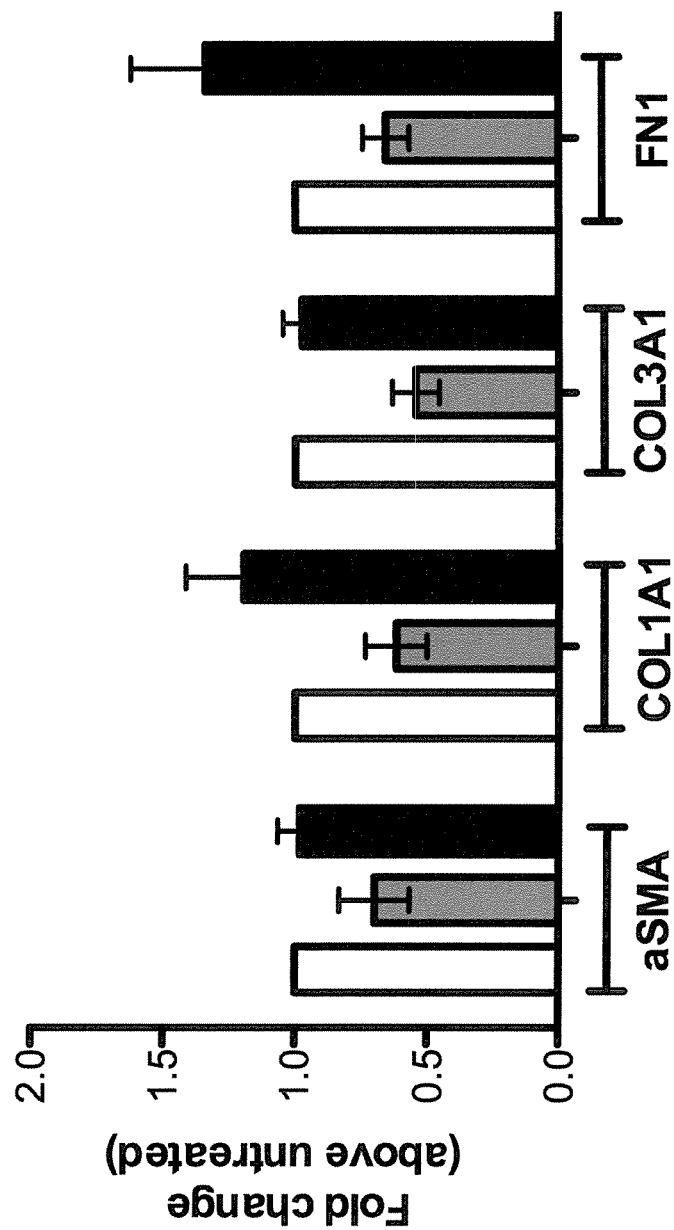
FIG. 32 shows that AM3-114-6H i-body markedly reduced ACTA2, COL1A1, COL3A1 and FN1 transcript expression in slow-IPF lung fibroblasts. Slow lung fibroblasts were plated on BME and treated with 2 mg/ml of BME alone (open bars) and containing i-body AM3-114-6H (grey bars) or AMD3100 (black bars). RNA was extracted and qPCR analysis was performed for pro-fibrotic transcripts. Depicted is the average transcript expression of alpha SMA, COL1A1, COL3A1, and FN1 in slowlung fibroblasts (n=3/group).

To determine potential roles for CXCR4 in lung fibroblast activation and extracellular matrix generation fibroblasts were treated with CXCR4 specific i-bodies (AM3-114-6H, AM4-272-6H, AM3-523-6H), negative control-iBody (21H5) or AMD3100 for 48 hours after which RNA was extracted and qPCR analysis was performed for ACTA2, COL1A1, COL3A1 and FN1 transcripts. The qPCR method was as follows: Fibroblasts were plated on 50 µg/ml of BME and treated with 130 µg/ml of iBodies or 12 µM of AMD3100. After 48 hours, RNA was extracted using Trizol reagent and reverse transcribed into cDNA using superscript II reverse transcriptase (Life technology) as previously described (Trujillo et al Sci Transl Med 2010 2; 57ra82). Complementary DNA (cDNA) was subsequently loaded into a Taqman plate and gene expression analysis were performed using predesigned primers for COL1A1, COL3A1, FN1, and αSMA. All Taqman analysis was performed using an Applied Bio system's Viia 7 instrument (Life technology). The results were then exported, normalized to 18s RNA expression and fold change analysis were calculated using Data Assist software (Life technologies). CXCR4 specific AM3-114-6H markedly reduced pro-fibrotic gene transcript expression of ACTA2, COL1A1, COL3A1 and FN1 in Slow-IPF but not normal lung fibroblasts (FIG. 32).

In order to examine whether the i-bodies could modulate soluble collagen in IPF lung fibroblasts an ELISA was used. Collagen 1 was detected using a direct ELISA. Briefly, purified collagen 1 protein and conditioned supernatants were coated on maxi-sorb ELISA plates overnight at 4° C. The next morning, plates were washed, blocked with 1% BSA for one hour and then incubated with a biotinylated anti-Collagen 1 antibody (Abcam) for 2 hours on a rotating shaker at room temperature. Plates were then washed and HRP-conjugated strepdavidin was added to the wells for 20 minutes. After 20 minutes, the plates were washed and developed with TMB substrate for 20 minutes after which a stop solution was added and the absorbance was acquired at 450 nm using a Synergy H1 microplate reader (Biotek).

The CXCR4 specific iBody, AM4-272-6H, markedly reduced soluble collagen protein in conditioned supernatants of fibroblast 48 hours post treatment with the iBody.

Example 23—i-Bodies Modulate Various Signalling Partners

Various reports indicate that CXCR4 signals in conjunction with other chemokine receptors, including CCR2. To determine whether CXCR4 specific iBodies may modulate potential CXCR4 signaling partners, conditioned supernatants were collected from normal, slow- and rapid-IPF lung fibroblast culture 48 hours post iBody (AM3-114-6H or AM4-272-6H), AMD3100 or BIBF-1120 treatment and CCL2, CCL5 and CXCL12 were detected in fibroblast-conditioned supernatants using commercial ELISA kits as recommended by the manufacturer (R&D Systems). The CXCR4 targeting iBodies, AM3-114-6H and AM4-272-6H, AMD3100 and BIBF-1120 markedly increased CCL2 protein in IPF but not normal fibroblast conditioned supernatants, which was evident in rapid-IPF lung fibroblast conditioned supernatants. The CXCR4 targeting iBody, AM4-272-6H, increased CCL5 levels in some IPF lung fibroblasts; however, this effect was not consistent and was observed in one slow-IPF lung fibroblast line treated with the control iBody, 21H5-6H.

Example 24—i-Bodies Block Platelet Aggregation

Figure 33:
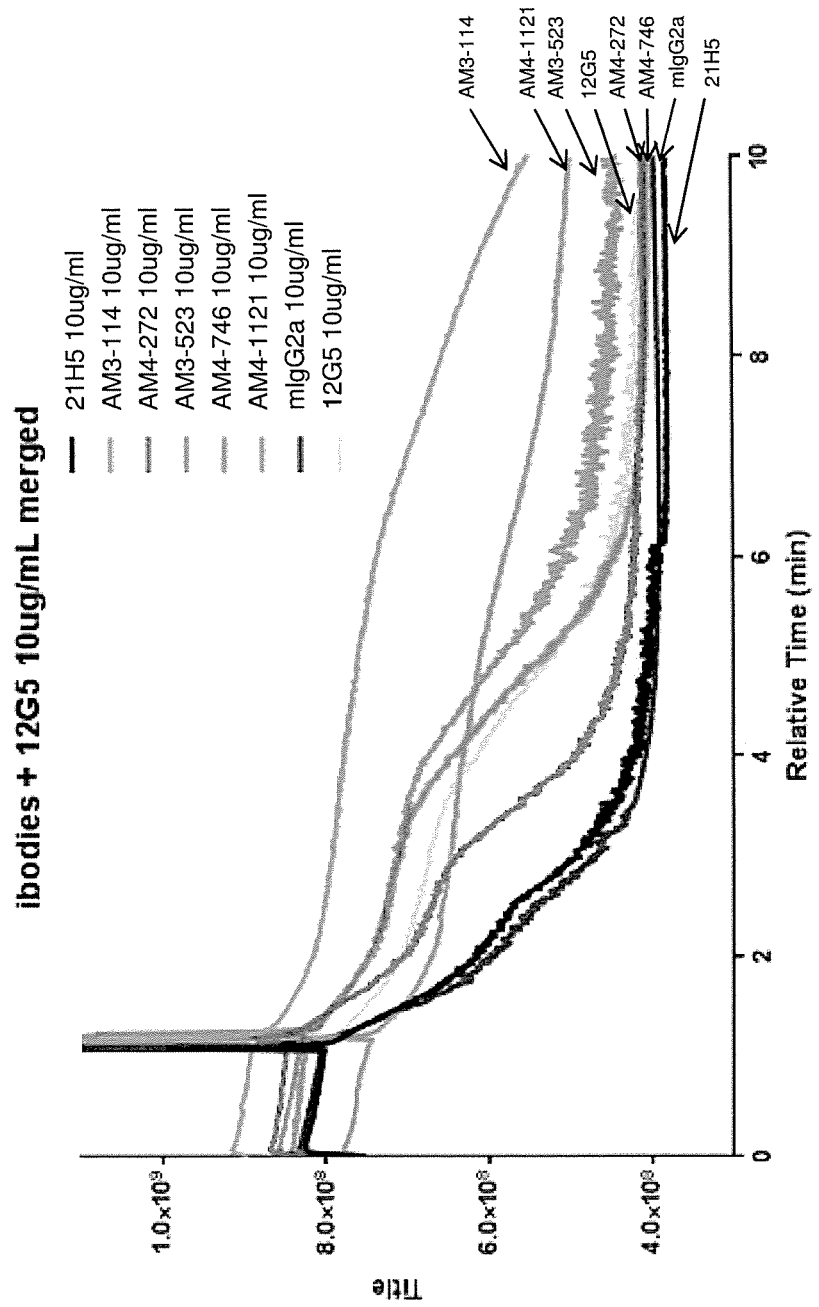
FIG. 33 shows the ability of i-bodies to block platelet aggregation. AM4-272, AM4-746, AM4-1121, AM3-114, AM3-523 and MAb12G5 as well as a negative control i-body (21H5) and a negative control MAB (mIgG2a) were tested for blocking SDF-1α induced platelet aggregation. Under these conditions i-bodies AM3-114 and AM4-1121 were the most effective at blocking this aggregation.

Experiments were carried out to examine whether the i-bodies could block platelet aggregation induced by SDF-1α. Human platelet rich plasma suspensions were pre-incubated with the i-bodies AM3-114, AM3-523, AM4-746 or AM4-1121 (or 12G5 postive control anti-CXCR4 Mab) at 10 or 20 ug/mL for 10 min, followed by stimulation with 100 nM SDF-1 alpha. In the presence of negative control i-body 21H5 (or the isotype control for 12G5: mouse IgG2a). SDF-1 induced a robust and reproducible aggregation (the descending black curves, which indicate an increase in light transmission), which matches with what has been previously published. All the i-bodies as well as 12G5 had an inhibitory effect with AM3-114 and AM4-1121 being the most efficient (FIG. 33). These i-bodies showed a strong and sustained blocking of aggregation. AM3-523 and AM4-746 blocked aggregation to the same extent as the MAb12G5, and AM4-272 blocked aggregation only weakly. Neither the negative control i-body nor the control MAb had any effect on platelet aggregation.

Example 25—Anti CXCR4 i-Body is Active in a Mouse Model of Multiple Scelerosis (Experimental Autoimmune Encephalomyelitis)

Figure 34:
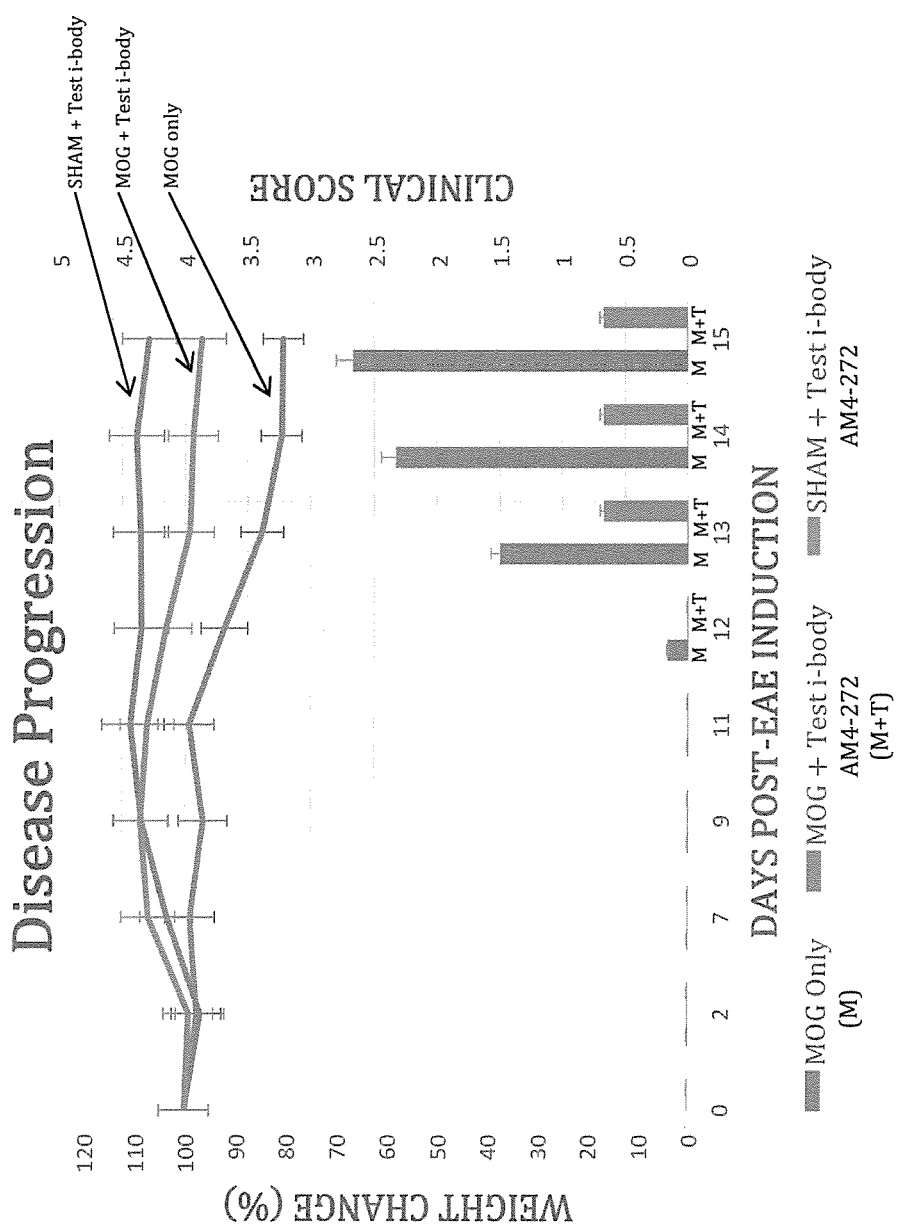
FIG. 34 shows the effect of i-body AM4-272 on clinical scores and body weight of mice with induced EAE. The lines represent body weights of the mice in the groups with MOG induced experimental autoimmune encephalomyelitis (EAE) and various treatments. The bars represent clinical scores of the mice in the various groups. I-body AM4-272 reduces the clinical scores and prevents the bodyweight loss seen in MOG induced EAE animals.

Holman et al (Biochimica et Biophysica Acta 2011) There have been a some publications suggesting demosntrated that CXCL12 is responsible for recruiting CXCR4 positive cells across the blood brain barrier around the day 8-12 time points in Experimental autoimmune encephalomyelitis (EAE), mouse model of multiple sclerosis. In addition recent studies demonstrated that CXCR4 antagonists showed efficacy in EAE (Hanes et al JBC Vol 290(37):22385-22397 (2015), Kohler et al Brain Pathology 2008, 18; 504-516). The inventors induced EAE in a small number of animals (n=3 per group) by injection of myelin oligodendrocyte protein (MOG) at day 0 and treated them with i-body AM4-272 intravenously at 4 mg/Kg between day 7-10 (one injection/day for 4 days). This is the time that has been reported to be critical for infiltration of inflammatory cells across the blood brain barrier. It was noted that of the three mice injected with the AM4-272 i-body, one progressed to the disease whereas the other 2 were almost disease free. The bodyweights of the animals treated with i-body at day 15 is significantly different from disease animals or those injected with negative control i-body 21H5. In addition, the clinical scores were dramatically improved by injection with i-body as compared to disease animals or those injected with control i-body at both day 14 and day 15 (FIG. 34). These data suggest that the i-bodies of the current invention can bind to CXCR4 on the inflammatory cells and inhibit their migration form the peripheral blood system into the brain. It appears that blocking this migration can alleviate the symptoms of EAE.

Immunohistochemistry of the brains of the experimental mice was performed. A large amount of inflammatory cell staining was seen in the white matter of the brains of diseased animals (MOG only) and in the symptomatic mouse given the AM4-272 i-body. Whereas there was very little inflammatory T-cell staining in the vehicle control or in the asymptomatic mice given AM4-272 i-body.

Initial Hematoxylin and eosin staining has been carried out on the brain tissue of EAE mice with and without i-body (AM4-272) treatment to highlight T-cell infiltration into the white matter. Dramatic T-cell infiltration was observed in the MOG mice treated with the control i-body 21H5 but not in the mice treated with the AM4-272 i-body.

The invention claimed is:

1. A polypeptide which binds to human C-X-C chemokine receptor type 4 (CXCR4), comprising a scaffold region and binding loop regions contained therein, the scaffold region comprising a sequence which has at least 90% identity to the scaffold region defined by amino acids 1 to 26, 33 to 79 and 88 to 97 of SEQ ID NO:1; and wherein the first binding loop region comprises a sequence represented by the formula $SX_1SX_2X_3R$ wherein $X_1$ is G, K, L or Y;
$X_2$ is D, H, G or N; and
$X_3$ is I, V, M, F, Q or Y; or
a conservative amino acid substitution thereof
and/or
wherein the second binding loop region comprises a sequence represented by the formula $Y'_1RY'_2GY'_3YRHRY'_4LY'_5LG$ wherein
$Y'_1$ is Y or W;
$Y'_2$ is T, V or I;
$Y'_3$ is G or A;
$Y'_4$ is A or Y; and
$Y'_5$ is V, R or K; or
a conservative amino acid substitution thereof.

2. The polypeptide according to claim 1, wherein the first binding loop region comprises or consists of the sequence set forth in any one of SEQ ID NO: 41, SEQ ID NO: 45, SEQ ID NO: 49, SEQ ID NO: 53, SEQ ID NO:57, SEQ ID NO:61, SEQ ID NO:65, SEQ ID NO:69, SEQ ID NO: 73, or SEQ ID NO:77; and/or
wherein the second binding loop region comprises or consists of the sequence set forth in any one of SEQ ID NO: 42, SEQ ID NO: 46, SEQ ID NO: 50, SEQ ID NO: 54, SEQ ID NO: 58, SEQ ID NO:62, SEQ ID NO:66, SEQ ID NO:70, SEQ ID NO: 74, or SEQ ID NO:78.

3. The polypeptide according to claim 1 or 2:
(i) comprising a sequence at least 90% identical to the sequence selected from the group consisting of SEQ ID NO: 40, SEQ ID NO: 44, SEQ ID NO: 48, SEQ ID NO: 52, SEQ ID NO: 56, SEQ ID NO: 60, SEQ ID NO: 64, SEQ ID NO: 68, SEQ ID NO: 72 or SEQ ID NO: 76; or
(ii) comprising or consisting of the sequence set forth in any one of SEQ ID NO: 40, SEQ ID NO: 44, SEQ ID NO: 48, SEQ ID NO: 52, SEQ ID NO: 56, SEQ ID NO: 60, SEQ ID NO: 64, SEQ ID NO: 68, SEQ ID NO: 72 or SEQ ID NO: 76.

4. The polypeptide according to claim 1 which binds to one or more residues of CXCR4 selected from the group consisting of C28, E32, V112, Y184, F189, P191, D193, W195, D262, L266, E268 and E288 of human CXCR4 (SEQ ID NO:105).

5. A conjugate comprising a polypeptide according to claim 1 and an agent selected from a therapeutic agent, a toxin, a detectable label or an agent which extends the half-life of the polypeptide.

6. A polypeptide according to claim 1, or the conjugate of claim 5, for use in the treatment or to reduce the likelihood of occurrence of a CXCR4-related disease or disorder, wherein the disease or disorder is selected from the group consisting of cancer, inflammatory disease and fibrosis.

7. A pharmaceutical composition comprising the polypeptide according to claim 1 and an acceptable carrier.

8. An expression construct comprising the nucleic acid molecule encoding the polypeptide according to claim 1.

9. A method of reducing the likelihood of occurrence of or treating a CXCR4-related disease or disorder wherein the disease or disorder is selected from the group consisting of cancer, inflammatory diseases and fibrosis comprising administering to a subject in need thereof a polypeptide according to claim 1.

10. A method for localizing and/or detecting and/or diagnosing a CXCR4-related disease or disorder, the method comprising detecting in vivo the polypeptide according to claim 1 bound to CXCR4, if present, wherein the polypeptide is conjugated to a detectable tag.

* * * * *